US011659987B2

(12) United States Patent
Abou Shousha et al.

(10) Patent No.: US 11,659,987 B2
(45) Date of Patent: *May 30, 2023

(54) VISION TESTING VIA PREDICTION-BASED SETTING OF INITIAL STIMULI CHARACTERISTICS FOR USER INTERFACE LOCATIONS

(71) Applicant: UNIVERSITY OF MIAMI, Miami, FL (US)

(72) Inventors: Mohamed Abou Shousha, Fort Lauderdale, FL (US); Amr Saad Mohamed Elsawy, Miami, FL (US)

(73) Assignee: University of Miami, Miami, FL (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/343,292

(22) Filed: Jun. 9, 2021

(65) Prior Publication Data
US 2022/0125295 A1    Apr. 28, 2022

Related U.S. Application Data

(63) Continuation of application No. 17/083,043, filed on Oct. 28, 2020, now Pat. No. 11,039,742.

(51) Int. Cl.
*A61B 3/024*    (2006.01)
*G16H 50/30*    (2018.01)
(Continued)

(52) U.S. Cl.
CPC .............. *A61B 3/024* (2013.01); *A61B 3/022* (2013.01); *A61B 3/028* (2013.01); *A61B 3/06* (2013.01);
(Continued)

(58) Field of Classification Search
CPC ......... A61B 3/024; A61B 3/022; A61B 3/028; A61B 3/06; A61B 3/103; A61B 3/10;
(Continued)

(56) References Cited

U.S. PATENT DOCUMENTS 11,039,742 B1 * 6/2021 Abou Shousha ...... G06N 3/084
2016/0198950 A1   7/2016 Gross et al.
(Continued)

OTHER PUBLICATIONS

International Search Report and Written Opinion issued in corresponding International Application No. PCT/US2021/055167 dated Feb. 9, 2022 (9 pages).

*Primary Examiner* — Mohammed A Hasan
(74) *Attorney, Agent, or Firm* — Perkins Coie LLP

(57) ABSTRACT

In some embodiments, initial feedback indicating threshold characteristics (under which a user sees initial stimuli presented on a user interface) may be provided to a prediction model, and a set of predicted characteristics (for a set of locations of the user interface) and a set of confidence scores associated with the set of locations may be obtained via the prediction model. Based on the set of confidence scores, one or more locations may be selected to be tested during a visual test presentation. As an example, the locations may be selected over one or more other locations of the set of locations based on the set of confidence scores. Based on predicted characteristics associated with the selected locations, stimuli may be presented at the selected locations during the visual test presentation. Visual defect information for the user may be generated based on feedback from the visual test presentation.

20 Claims, 66 Drawing Sheets

(51) Int. Cl.
  *G16H 50/20* (2018.01)
  *A61B 3/028* (2006.01)
  *G06N 3/02* (2006.01)
  *A61B 3/02* (2006.01)
  *A61B 3/06* (2006.01)

(52) U.S. Cl.
  CPC ............... *G06N 3/02* (2013.01); *G16H 50/20* (2018.01); *G16H 50/30* (2018.01)

(58) Field of Classification Search
  CPC ........ G06N 3/02; G06N 3/0454; G06N 3/084; G06N 20/00; G16H 50/20; G16H 50/30; G16H 30/40
  See application file for complete search history.

(56) References Cited

U.S. PATENT DOCUMENTS

2020/0073476 A1    3/2020    Tiwari et al.
2022/0125296 A1*   4/2022    Abou Shousha .... G06N 3/0454

* cited by examiner

Centroid of largest component

Any point between the centroid of largest component and the closet to the center Center of largest inscribed circle Any point between the center of the circle and the closet to the center Center of largest inscribed square Any point between the center of the square and the closet to the center

VISION TESTING VIA PREDICTION-BASED SETTING OF INITIAL STIMULI CHARACTERISTICS FOR USER INTERFACE LOCATIONS

CROSS REFERENCE TO RELATED APPLICATIONS

This application is a continuation of U.S. patent application Ser. No. 17/083,043, filed on Oct. 28, 2020, the contents of which are hereby incorporated by reference in its entirety.

FIELD OF THE INVENTION

The invention relates to facilitating vision testing and vision defect determination therefrom.

BACKGROUND

Current vision defect determination requires the testing of many locations of a user's field of view. Oftentimes, each location may be tested over a series of characteristics, making the testing process slow and inefficient. For example, a vision test may include testing up to several thousand combinations (e.g., over 70 locations of the user's field of view under a series of 50 different characteristics or other combinations). These and other drawbacks exist.

SUMMARY

Aspects of the invention relate to methods, apparatuses, and/or systems for facilitating vision testing via confidence-based selection of a testing location subset.

In some embodiments, initial feedback indicating threshold characteristics (under which a user sees initial stimuli presented on a user interface) may be provided to a prediction model, and a set of predicted characteristics (for a set of locations of the user interface) and a set of confidence scores associated with the set of locations may be obtained via the prediction model. Based on the set of confidence scores, one or more locations may be selected to be tested during a visual test presentation. As an example, the locations may be selected over one or more other locations of the set of locations based on the set of confidence scores. Based on predicted characteristics associated with the selected locations, stimuli may be presented at the selected locations during the visual test presentation. Visual defect information for the user may be generated based on feedback from the visual test presentation.

Various other aspects, features, and advantages of the invention will be apparent through the detailed description of the invention and the drawings attached hereto. It is also to be understood that both the foregoing general description and the following detailed description are exemplary and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise.

DETAILED DESCRIPTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

Figure 1A:
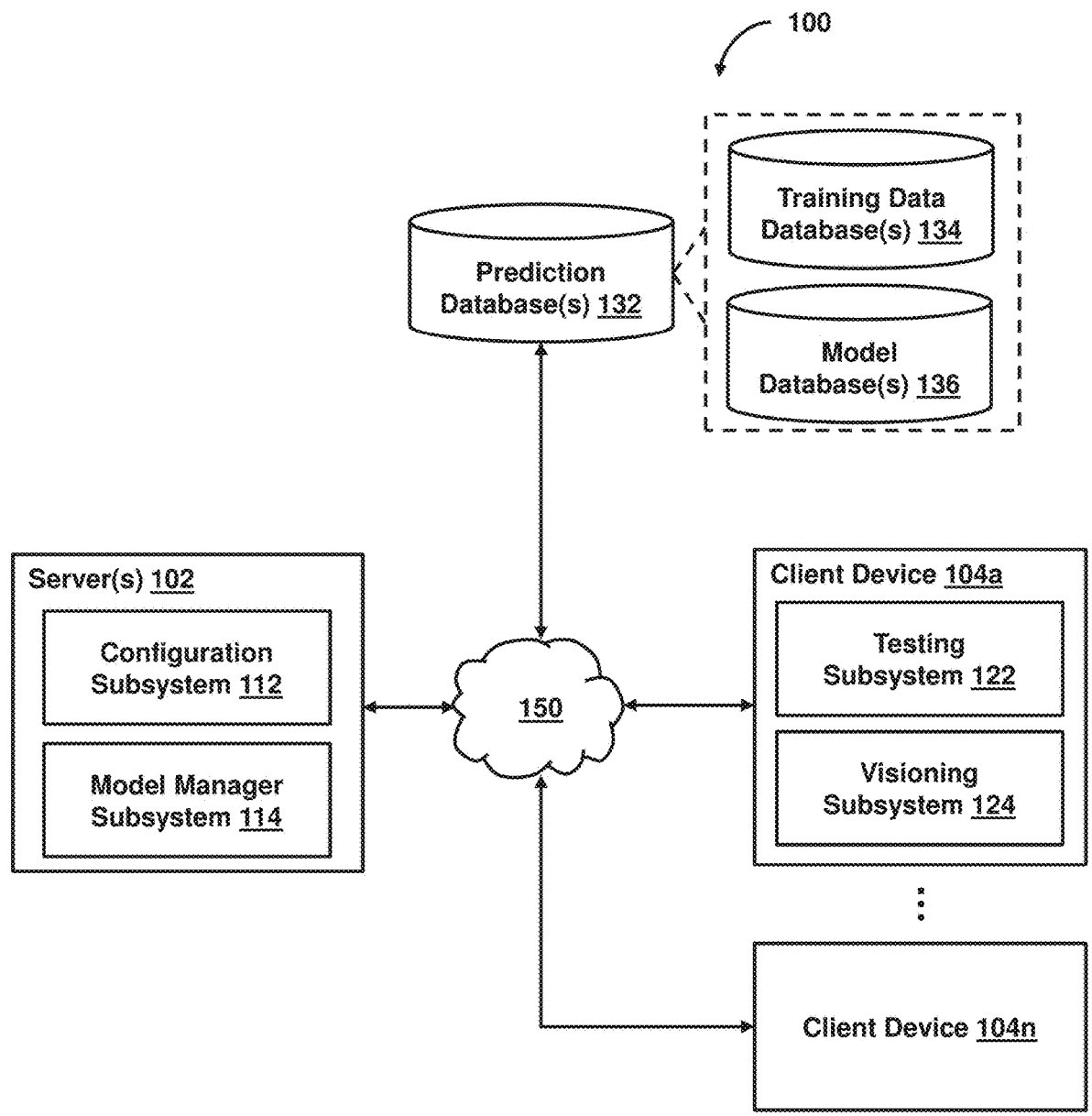
FIG. 1A illustrates a system for facilitating vision testing, vision defect determination, or modification related to a vision of a user, in accordance with one or more embodiments.

FIG. 1A shows a system 100 for facilitating vision testing, vision defect determination, or modification related to a vision of a user, in accordance with one or more embodiments. As shown in FIG. 1A, system 100 may include server(s) 102, client device 104 (or client devices 104a-104n), or other components. Server 102 may include configuration subsystem 112, model manager subsystem 114, or other components. Client device 104 may include testing subsystem 122, visioning subsystem 124, or other components. Each client device 104 may include any type of mobile terminal, fixed terminal, or other device. By way of example, client device 104 may include a desktop computer, a notebook computer, a tablet computer, a smartphone, a wearable device, or other client device. Users may, for instance, utilize one or more client devices 104 to interact with one another, one or more servers, or other components of system 100. Additionally, or alternatively, system 100 may comprise one or more components described in U.S. patent application Ser. No. 17/082,983, entitled "Systems and Methods for Visual Field Testing in Head-Mounted Displays" and filed Oct. 28, 2020, the contents of which are hereby incorporated by reference in its entirety.

It should be noted that, while one or more operations are described herein as being performed by particular components of client device 104, those operations may, in some embodiments, be performed by other components of client device 104 or other components of system 100. As an example, while one or more operations are described herein as being performed by components of client device 104, those operations may, in some embodiments, be performed by components of server 102. It should also be noted that, while one or more operations are described herein as being performed by particular components of server 102, those operations may, in some embodiments, be performed by other components of server 102 or other components of system 100. As an example, while one or more operations are described herein as being performed by components of server 102, those operations may, in some embodiments, be performed by components of client device 104. It should further be noted that, although some embodiments are described herein with respect to machine learning models, other prediction models (e.g., statistical models or other analytics models) may be used in lieu of or in addition to machine learning models in other embodiments (e.g., a statistical model replacing a machine learning model and a non-statistical model replacing a non-machine-learning model in one or more embodiments).

In some embodiments, system 100 may provide a visual test presentation to a user, where the presentation including a set of stimuli (e.g., light stimuli, text, or images displayed to the user). During the presentation (or after the presentation), system 100 may obtain feedback related to the set of stimuli (e.g., feedback indicating whether or how the user sees one or more stimuli of the set). As an example, the feedback may include an indication of a response of the user to one or more stimuli (of the set of stimuli) or an indication of a lack of response of the user to such stimuli. The response (or lack thereof) may relate to an eye movement, a gaze direction, a pupil size change, or a user modification of one or more stimuli or other user input (e.g., the user's reaction or other response to the stimuli). As another example, the feedback may include an eye image captured during the visual test presentation. The eye image may be an image of a retina of the eye (e.g., the overall retina or a portion thereof), an image of a cornea of the eye (e.g., the overall cornea or a portion thereof), or other eye image.

In some embodiments, system 100 may determine one or more defective visual field portions of a visual field of a user (e.g., an automatic determination based on feedback related to a set of stimuli displayed to the user or other feedback). As an example, a defective visual field portion may be one of the visual field portions of the user's visual field that fails to satisfy one or more vision criteria (e.g., whether or an extent to which the user senses one or more stimuli, an extent of light sensitivity, distortion, or other aberration, or other criteria). In some embodiments, system 100 may provide an enhanced image or adjust one or more configurations of a wearable device based on the determination of the defective visual field portions. As an example, the enhanced image may be generated or displayed to the user such that one or more given portions of the enhanced image (e.g., a region of the enhanced image that corresponds to a macular region of the visual field of an eye of the user or to a region within the macular region of the eye) are outside of the defective visual field portion. As another example, a position, shape, or size of one or more display portions of the wearable device, a brightness, contrast, saturation, or sharpness level of such display portions, a transparency of such display portions, or other configuration of the wearable device may be adjusted based on the determined defective visual field portions.

In some embodiments, one or more prediction models may be used to facilitate determination of vision defects (e.g., light sensitivities, distortions, or other aberrations), determination of modification profiles (e.g., correction/enhancement profiles that include modification parameters or functions) to be used to correct or enhance a user's vision, generation of enhanced images (e.g., derived from live image data), or other operations. In some embodiments, the prediction models may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

Figure 1B:
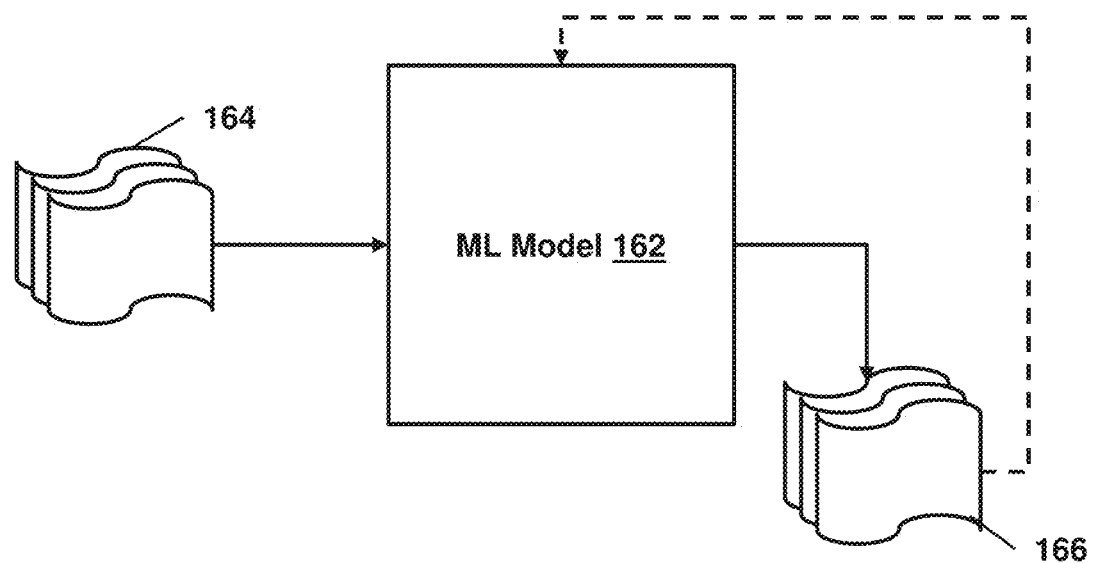
FIG. 1B illustrates a system implementing a machine learning model to facilitate vision testing, vision defect determination, or modification related to a vision of a user, in accordance with one or more embodiments.

As an example, with respect to FIG. 1B, machine learning model 162 may take inputs 164 and provide outputs 166. In one use case, outputs 166 may be fed back to machine learning model 162 as input to train machine learning model 162 (e.g., alone or in conjunction with user indications of the accuracy of outputs 166, labels associated with the inputs, or with other reference feedback information). In another use case, machine learning model 162 may update its configurations (e.g., weights, biases, or other parameters) based on its assessment of its prediction (e.g., outputs 166) and reference feedback information (e.g., user indication of accuracy, reference labels, or other information). In another use case, where machine learning model 162 is a neural network, connection weights may be adjusted to reconcile differences between the neural network's prediction and the reference feedback. In a further use case, one or more neurons (or nodes) of the neural network may require that their respective errors be sent backward through the neural network to them to facilitate the update process (e.g., backpropagation of error). Updates to the connection weights may, for example, be reflective of the magnitude of error propagated backward after a forward pass has been completed. In this way, for example, the prediction model may be trained to generate better predictions.

In some embodiments, upon obtaining feedback related to a set of stimuli (displayed to a user), feedback related to one or more eyes of the user, feedback related to an environment of the user, or other feedback, system 100 may provide the feedback to a prediction model, and the prediction model may be configured based on the feedback. As an example, the prediction model may be automatically configured for the user based on (i) an indication of a response of the user to one or more stimuli (of the set of stimuli), (ii) an indication of a lack of response of the user to such stimuli, (iii) an eye image captured during the visual test presentation, or other feedback (e.g., the prediction model may be personalized toward the user based on the feedback from the visual test presentation). As another example, the prediction model may be trained based on such feedback and other feedback from other users to improve accuracy of results provided by the prediction model. In some embodiments, upon the prediction model being configured (e.g., for the user), system 100 may provide live image data or other data to the prediction model to obtain an enhanced image (derived from the live image data) and cause the enhanced image to be displayed. As an example, a wearable device of system 100 may obtain a live video stream from one or more cameras of the wearable device and cause the enhanced image to be displayed on one or more displays of the wearable device. In some embodiments, the wearable device may obtain the enhanced image (e.g., a file or other data structure representing the enhanced image) from the prediction model. In some embodiments, the wearable device may obtain a modification profile (e.g., modification parameters or functions) from the prediction model, and generate the enhanced image based on the live video stream and the modification profile. In one use case, the modification profile may include modification parameters or functions used to generate the enhanced image from the live image data (e.g., parameters of functions used to transform or modify the live image data into the enhanced image). Additionally, or alternatively, the modification profile may include modification parameters or functions to dynamically configure one or more display portions (e.g., dynamic adjustment of transparent or opaque portions of a transparent display, dynamic adjustment of projecting portions of a projector, etc.).

In some embodiments, system 100 may facilitate enhancement of a field of view of a user via one or more dynamic display portions (e.g., transparent display portions on a transparent display, projecting portions of a projector, etc.). As an example, with respect to a transparent display, the dynamic display portions may include one or more transparent display portions and one or more other display portions (e.g., of a wearable device or other device). System 100 may cause one or more images to be displayed on the other display portions. As an example, a user may see through the transparent display portions of a transparent display, but may not be able to see through the other display portions and instead sees the image presentation on the other display portions (e.g., around or proximate the transparent display portions) of the transparent display. In one use case, live image data may be obtained via the wearable device, and an enhanced image may be generated based on the live image data and displayed on the other display portions of the wearable device. In some embodiments, system 100 may monitor one or more changes related to one or more eyes of the user and cause, based on the monitoring, an adjustment of the transparent display portions of the transparent display. As an example, the monitored changes may include an eye movement, a change in gaze direction, a pupil size change, or other changes. One or more positions, shapes, sizes, transparencies, or other aspects of the transparent display portions of the wearable device may be automatically adjusted based on the monitored changes. In this way, for example, system 100 may improve mobility without restriction (or at least reducing restrictions) on eye movements, gaze direction, pupil responses, or other changes related to the eye.

In some embodiments, system 100 may facilitate an increase in a field of view of a user via combination of portions of multiple images of a scene (e.g., based on feedback related to a set of stimuli displayed to the user or other feedback), system 100 may obtain a plurality of images of a scene. System 100 may determine a region common to the images, and, for each image of the images, determine a region of the image divergent from a corresponding region of at least another image of the images. In some embodiments, system 100 may generate or display an enhanced image to a user based on the common region and the divergent regions. As an example, the common region and the divergent regions may be combined to generate the enhanced image to include a representation of the common region and representations of the divergent regions. The common region may correspond to respective portions of the images that have the same or similar characteristics as one another, and each divergent region may correspond to a portion of one of the images that is distinct from all the other corresponding portions of the other images. In one scenario, a distinct portion of one image may include a part of the scene that is not represented in the other images. In this way, for example, the combination of the common region and the divergent region into an enhanced image increase the field of view otherwise provided by each of the images, and the enhanced image may be used to augment the user's vision.

In some embodiments, system 100 may generate a prediction indicating that an object will come in physical contact with a user and cause an alert to be displayed based on the physical contact prediction (e.g., an alert related to the object is displayed on a wearable device of the user). In some embodiments, system 100 may detect an object in a defective visual field portion of a visual field of a user and cause the alert to be displayed based on (i) the object being in the defective visual field portion, (ii) the physical contact prediction, or (iii) other information. In some embodiments, system 100 may determine whether the object is outside (or not sufficiently in) any image portion of an enhanced image (displayed to the user) that corresponds to at least one visual field portions satisfying one or more vision criteria. In one use case, no alert may be displayed (or a lesser-priority alert may be displayed) when the object is determined to be within (or sufficiently in) an image portion of the enhanced image that corresponds to the user's intact visual field portion (e.g., even if the object is predicted to come in physical contact with the user). On the other hand, if the object in the defective visual field portion is predicted to come in physical contact with the user, and it is determined that the object is outside (or not sufficiently in) the user's intact visual field portion, an alert may be displayed on the user's wearable device. In this way, for example, the user can rely on the user's own intact visual field to avoid incoming objects within the user's intact visual field, thereby mitigating the risk of dependence on the wearable device (e.g., through habit forming) for avoidance of such incoming objects. It should be noted, however, that, in other use cases, an alert related to the object may be displayed based on the physical contact prediction regardless of whether the object is within the user's intact visual field.

Figure 1C:
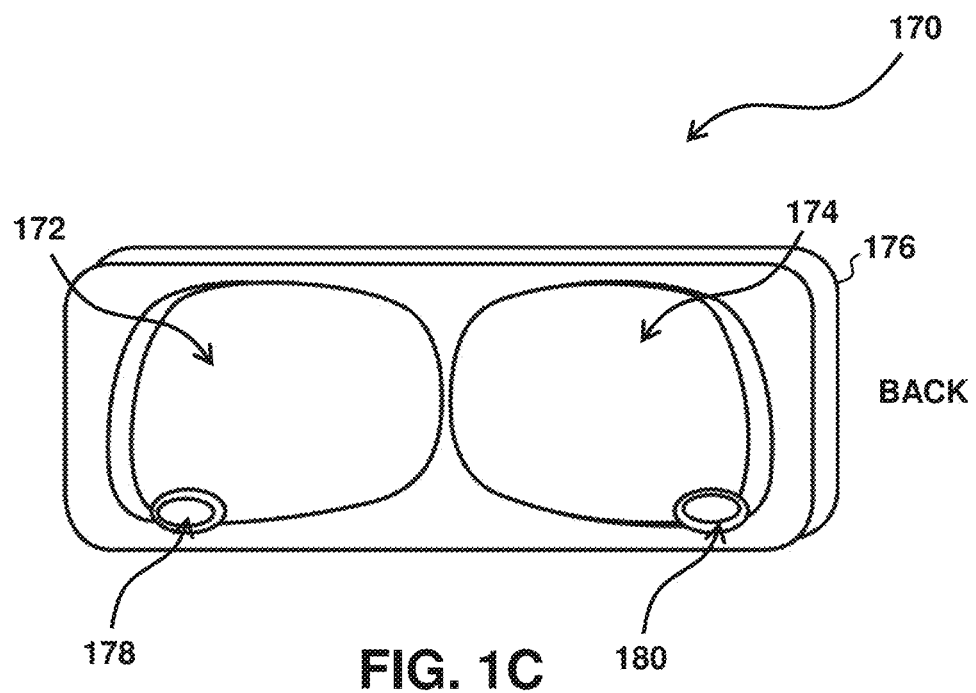
FIGS. 1C-1F illustrate views of example spectacles devices, in accordance with one or more embodiments.

In some embodiments, with respect to FIG. 1C, client device 104 may include a spectacles device 170 forming a wearable device for a subject. In some embodiments, the spectacles device 170 may be a part of a visioning system as described herein. The spectacles device 170 includes a left eyepiece 172 and a right eyepiece 174. Each eyepiece 172 and 174 may contain and/or associate with a digital monitor configured to display (e.g., provide on a screen or project onto an eye) recreated images to a respective eye of the subject. In various embodiments, digital monitors may include a display screen, projectors, and/or hardware to generate the image display on the display screen or project images onto an eye (e.g., a retina of the eye). It will be appreciated that digital monitors comprising projectors may be positioned at other locations to project images onto an eye of the subject or onto an eyepiece comprising a screen, glass, or other surface onto which images may be projected. In one embodiment, the left eyepiece 172 and right eyepiece 174 may be positioned with respect to the housing 176 to fit an orbital area on the subject such that each eyepiece 172, 174 is able to collect data and display/project image data, which in a further example includes displaying/projecting image data to a different eye.

Each eyepiece 172, 174 may further includes one or more inward directed sensors 178, 180, which may be inward directed image sensors. In an example, inward directed sensors 178, 180 may include infrared cameras, photodetectors, or other infrared sensors, configured to track pupil movement and to determine and track visual axes of the subject. The inward directed sensors 178, 180 (e.g., comprising infrared cameras) may be located in lower portions relative to the eyepieces 172, 174, so as to not block the visual field of the subject, neither their real visual field nor a visual field displayed or projected to the subject. The inward directed sensors 178, 180 may be directionally aligned to point toward a presumed pupil region for better pupil and/or line of sight tracking. In some examples, the inward directed sensors 178, 180 may be embedded within the eyepieces 172, 174 to provide a continuous interior surface.

Figure 1D:
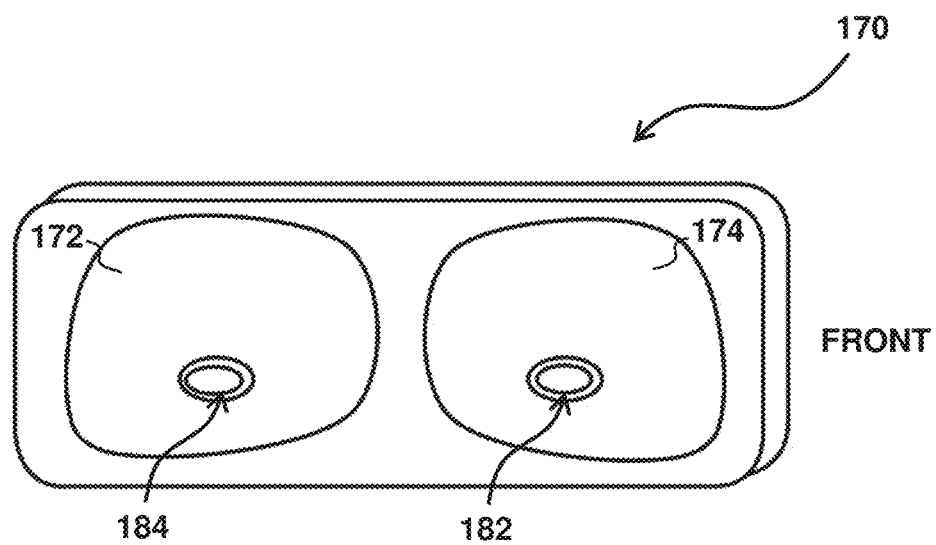

FIG. 1D illustrates a front view of the spectacles device 170, showing the front view of the eyepieces 172, 174, where respective outward directed image sensors 182, 184 comprising field of vision cameras are positioned. In other embodiments, fewer or additional outward directed image sensors 182, 184 may be provided. The outward directed image sensors 182, 184 may be configured to capture continuous images. The spectacles device 170 or associated vision system may be further configured to then correct and/or enhance the images, which may be in a customized manner based on the optical pathologies of the subject. The spectacles device 170 may further be configured to display the corrected and/or enhanced image to the subject via the monitors in a visioning mode. For example, the spectacles device may generate the corrected and/or enhanced image on a display screen associated with the eyepiece or adjacent region, project the image onto a display screen associated with the eyepiece or adjacent region, or project the image onto one or more eyes of the subject.

Figure 1E:
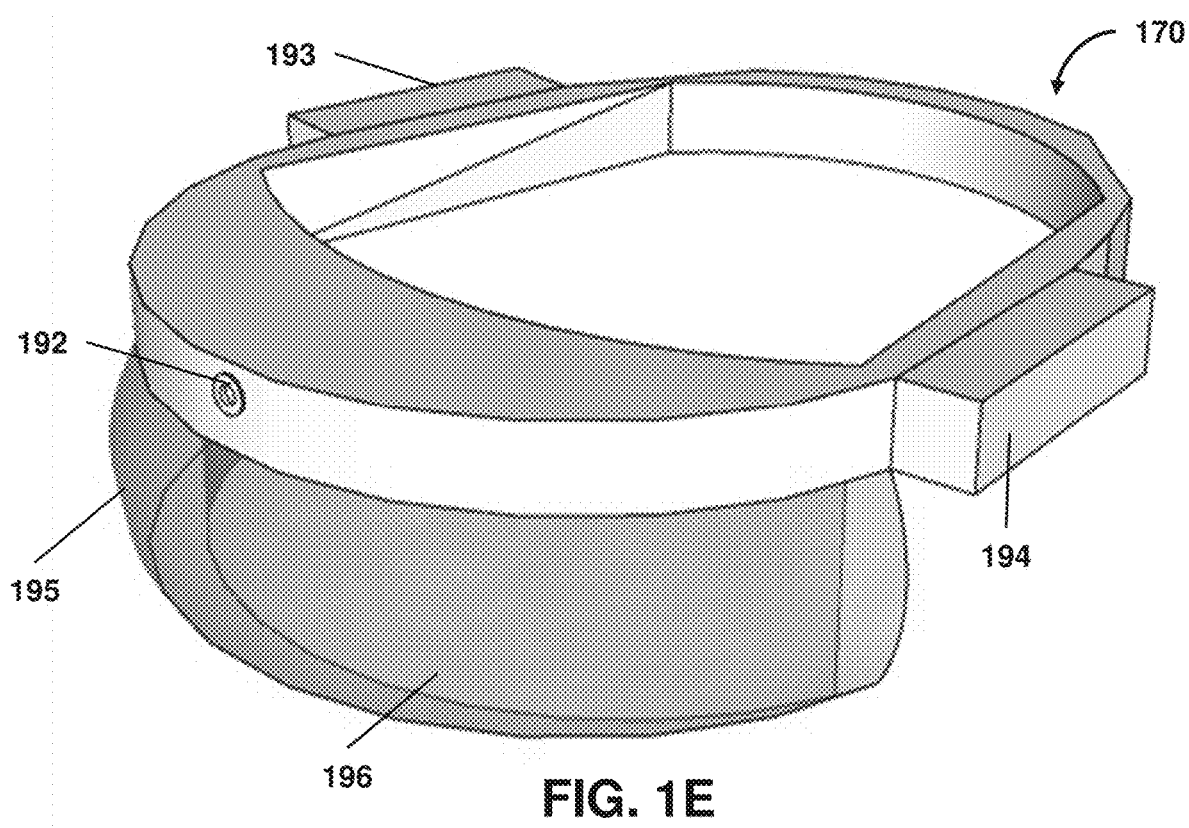
Figure 1F:
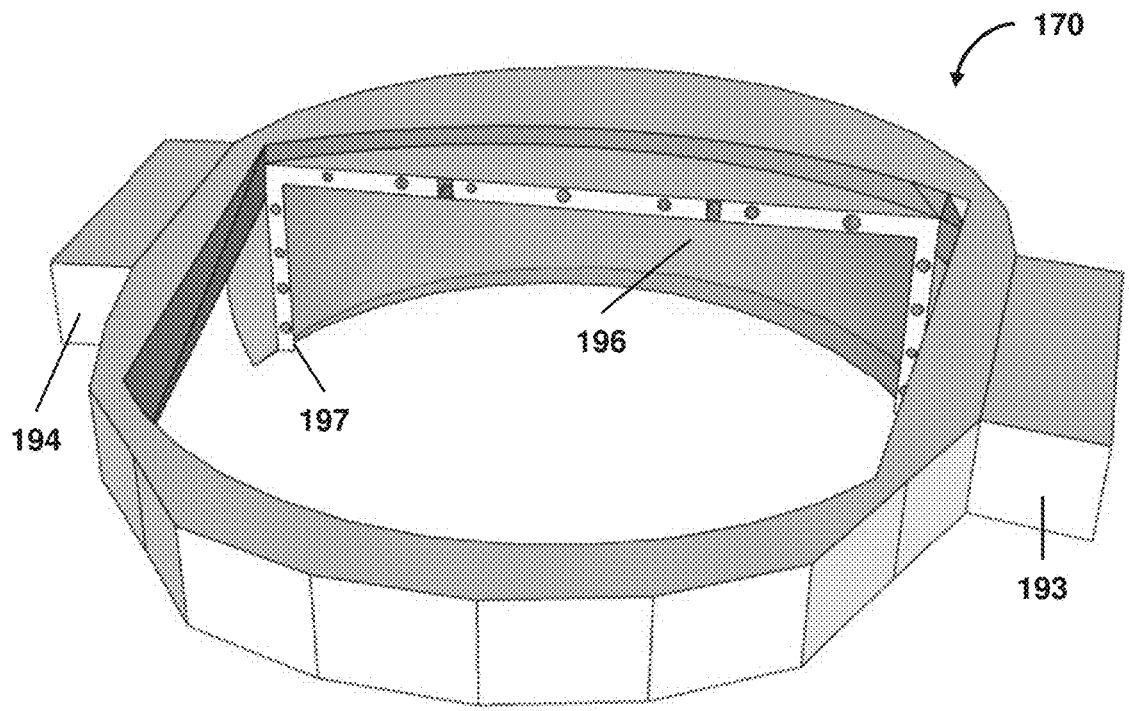

FIGS. 1E-1F illustrate other examples of spectacles device 170. With respect to FIGS. 1E-1F, spectacles device 170 includes a high-resolution camera (or cameras) 192, a power unit 193, a processing unit 194, a glass screen 195, a see-through display 196 (e.g., a transparent display), an eye tracking system 197, and other components.

In some embodiments, the spectacles device 170 may include a testing mode. In an example testing mode, the inward directed sensors 178, 180 track pupil movement and perform visual axis tracking (e.g., line of sight) in response to a testing protocol. In this or another example, the inward directed sensors 178, 180 may be configured to capture a reflection of a pattern reflected on the cornea and/or retina to detect distortions and irregularities of the cornea or the ocular optical system.

Testing mode may be used to perform a visual assessments to identify ocular pathologies, such as, high and/or low order aberrations, pathologies of the optic nerve such as glaucoma, optic neuritis, and optic neuropathies, pathologies of the retina such as macular degeneration, retinitis pigmentosa, pathologies of the visual pathway as microvascular strokes and tumors and other conditions such as presbyopia, strabismus, high and low optical aberrations, monocular vision, anisometropia and aniseikonia, light sensitivity, anisocorian refractive errors, and astigmatism. In the testing mode, data may be collected for the particular subject and used to correct captured images before those images are displayed, which may include projected as described herein, to the subject by the monitors.

In some examples, external sensors may be used to provide further data for assessing visual field of the subject. For example, data used to correct the captured image may be obtained from external testing devices, such as visual field testing devices, aberrometers, electro-oculograms, or visual evoked potential devices. Data obtained from those devices may be combined with pupil or line of sight tracking for visual axis determinations to create one or more modification profiles used to modify the images being projected or displayed to a user (e.g., correction profiles, enhancement profiles, etc., used to correct or enhance such images).

The spectacles device 170 may include a visioning mode, which may be in addition to or instead of a testing mode. In visioning mode, one or more outward directed image sensors 182, 184 capture images that are transmitted to an imaging processor for real-time image processing. The image processor may be embedded with the spectacles device 170 or may be external thereto, such as associated with an external image processing device. The imaging processor may be a component of a visioning module and/or include a scene processing module as described elsewhere herein.

The spectacles device 170 may be communicatively coupled with one or more imaging processor through wired or wireless communications, such as through a wireless transceiver embedded within the spectacles device 170. An external imaging processor may include a computer such as a laptop computer, tablet, mobile phone, network server, or other computer processing devices, centralized or distributed, and may be characterized by one or more processors and one or more memories. In the discussed example, the captured images are processed in this external image processing device; however, in other examples, the captured images may be processed by an imaging processor embedded within the digital spectacles. The processed images (e.g., enhanced to improve functional visual field or other vision aspects and/or enhanced to correct for the visual field pathologies of the subject) are then transmitted to the spectacles device 170 and displayed by the monitors for viewing by the subject.

In an example operation of a vision system including the spectacles device, real-time image processing of captured images may be executed by an imaging processor (e.g., using a custom-built MATLAB (MathWorks, Natick, Mass.) code) that runs on a miniature computer embedded in the spectacles device. In other examples, the code may be run on an external image processing device or other computer wirelessly networked to communicate with the spectacles device. In one embodiment, the vision system, including the spectacles device, image processor, and associated instructions for executing visioning and/or testing modes, which may be embodied on the spectacles device alone or in combination with one or more external devices (e.g., laptop computer) may be operated in two modes, a visioning mode and a separate testing mode.

Figure 2:
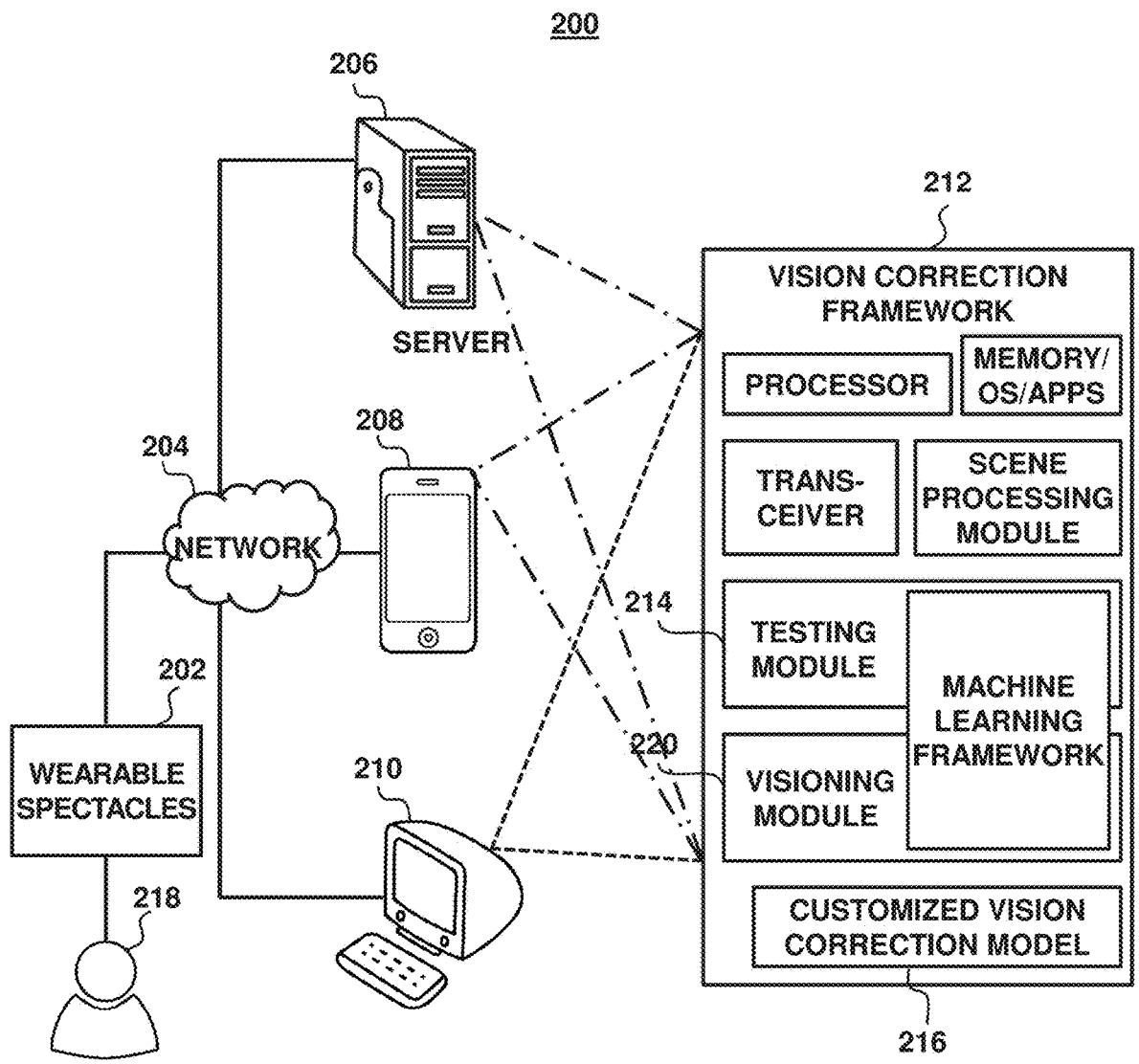
FIG. 2 illustrates an example vision system, in accordance with one or more embodiments.

In some embodiments, with respect to FIG. 2, system 100 may include vision system 200, which includes a spectacles device 202 communicatively coupled to a network 204 for communicating with a server 206, mobile cellular phone 208, or personal computer 210, any of which may contain a visional correction framework 212 for implementing the processing techniques herein, such as image processing techniques, which may include those with respect to the testing mode and/or visioning mode. In the illustrated example, the visional correction framework 212 includes a processor and a memory storing an operating system and applications for implementing the techniques herein, along with a transceiver for communicating with the spectacles device 202 over the network 204. The framework 212 contains a testing module 214, which includes a machine learning framework in the present example. The machine learning framework may be used along with a testing protocol executed by the testing module, to adaptively adjust the testing mode to more accurately assess ocular pathologies, in either a supervised or unsupervised manner. The result of the testing module operation may include development of a customized vision correction model 216 for a subject 218.

A visioning module 220, which in some embodiments may also include a machine learning framework having accessed customized vision correction models, to generate corrected visual images for display by the spectacles device 202. The vision correction framework 212 may also include a scene processing module which may process images for use during testing mode and/or visioning mode operations and may include operations described above and elsewhere herein with respect to a processing module. As described above and elsewhere herein, in some embodiments, the spectacles device 202 may include all or a portion of the vision correction framework 212.

In the testing mode, the spectacles device 170 or 202, and in particular the inward directed image sensors comprising tracking cameras, which may be positioned along an interior of the spectacles device 170 or 202, may be used to capture pupil and visual axis tracking data that is used to accurately register the processed images on the subject's pupil and visual axis.

Figure 3:
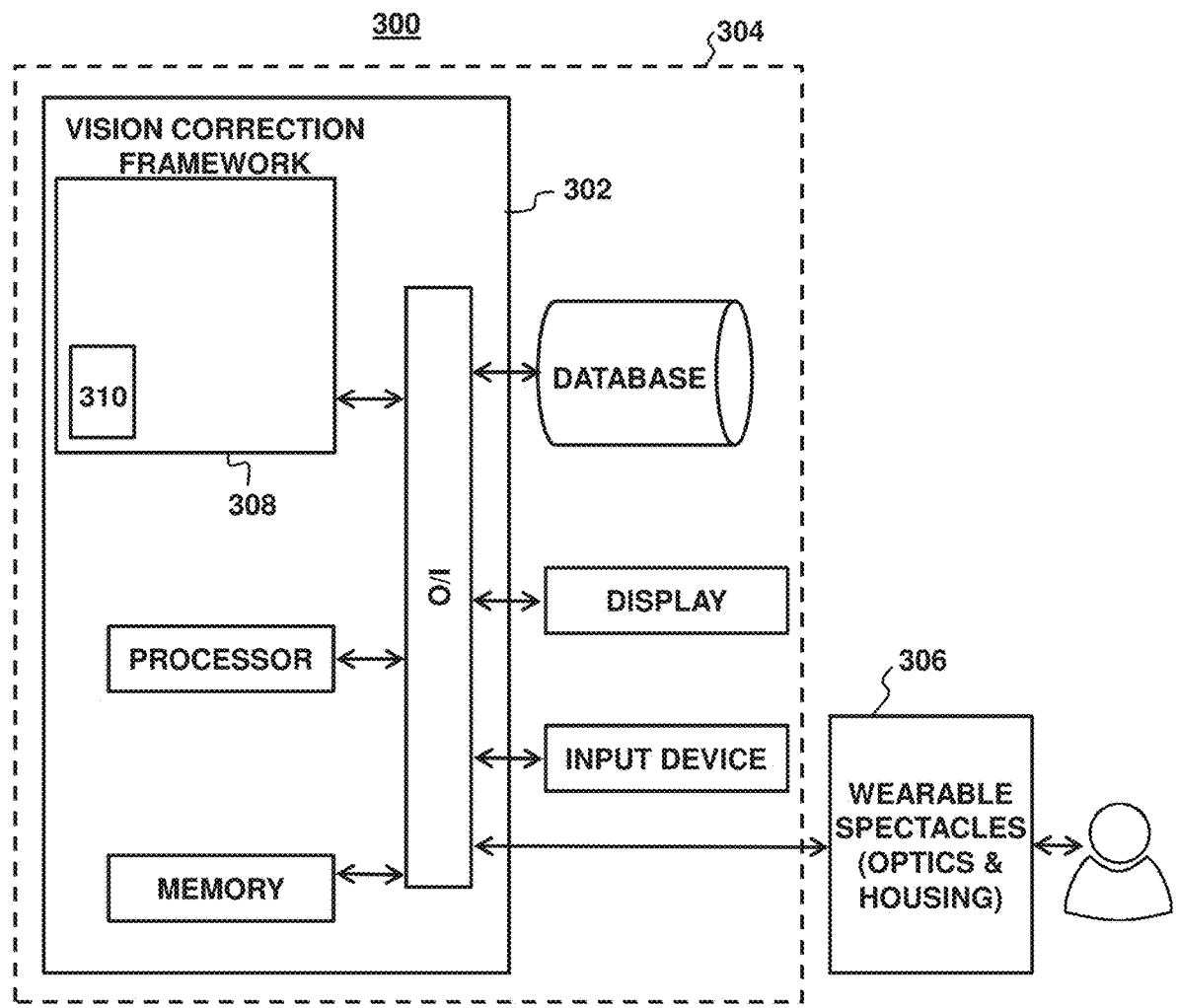
FIG. 3 illustrates a device with a vision correction framework implemented on an image processing device and a wearable spectacles device, in accordance with one or more embodiments.

In some embodiments, with respect to FIG. 3, system 100 may include a vision system 300, which includes a vision correction framework 302. The vision correction framework 302 may be implemented on an image processing device 304 and a spectacles device 306 for placing on a subject. The image processing device 304 may be contained entirely in an external image processing device or other computer, while in other examples all or part of the image processing device 304 may be implemented within the spectacles device 306.

The image processing device 304 may include a memory 308 storing instructions 310 for executing the testing and/or visioning modes described herein, which may include instructions for collecting high-resolution images of a subject from the spectacles device 306. In the visioning mode, the spectacles device 306 may capture real-time visual field image data as raw data, processed data, or pre-processed data. In the testing mode, the spectacles device may project testing images (such as the letters "text" or images of a vehicle or other object) for testing aspects of a visual field of a subject.

The spectacles device 306 may be communicatively connected to the image processing device 304 through a wired or wireless link. The link may be through a Universal Serial Bus (USB), IEEE 1394 (Firewire), Ethernet, or other wired communication protocol device. The wireless connection can be through any suitable wireless communication protocol, such as, WiFi, NFC, iBeacon, Bluetooth, Bluetooth low energy, etc.

In various embodiments, the image processing device 304 may have a controller operatively connected to a database via a link connected to an input/output (I/O) circuit. Additional databases may be linked to the controller in a known manner. The controller includes a program memory, the processor (may be called a microcontroller or a microprocessor), a random-access memory (RAM), and the input/output (I/O) circuit, all of which may be interconnected via an address/data bus. It should be appreciated that although only one microprocessor is described, the controller may include multiple microprocessors. Similarly, the memory of the controller may include multiple RAMs and multiple program memories. The RAM(s) and the program memories may be implemented as semiconductor memories, magnetically readable memories, and/or optically readable memories. The link may operatively connect the controller to the capture device, through the I/O circuit.

The program memory and/or the RAM may store various applications (i.e., machine readable instructions) for execution by the microprocessor. For example, an operating system may generally control the operation of the vision system 300 such as operations of the spectacles device 306 and/or image processing device 304 and, in some embodiments, may provide a user interface to the device to implement the processes described herein. The program memory and/or the RAM may also store a variety of subroutines for accessing specific functions of the image processing device 304 described herein. By way of example, and without limitation, the subroutines may include, among other things: obtaining, from a spectacles device, high-resolution images of a visual field; enhancing and/or correcting the images; and providing the enhanced and/or corrected images for display to the subject by the spectacles device 306.

In addition to the foregoing, the image processing device 304 may include other hardware resources. The device may also include various types of input/output hardware such as a visual display and input device(s) (e.g., keypad, keyboard, etc.). In an embodiment, the display is touch-sensitive, and may cooperate with a software keyboard routine as one of the software routines to accept user input. It may be advantageous for the image processing device 304 to communicate with a broader network (not shown) through any of a number of known networking devices and techniques (e.g., through a computer network such as an intranet, the Internet, etc.). For example, the device may be connected to a database of aberration data.

In some embodiments, system 100 may store prediction models, modification profiles, visual defect information (e.g., indicating detected visual defects of a user), feedback information (e.g., feedback related to stimuli displayed to users or other feedback), or other information at one or more remote databases (e.g., in the cloud). In some embodiments, the feedback information, the visual defect information, the modification profiles, or other information associated with multiple users (e.g., two or more users, ten or more users, a hundred or more users, a thousand or more users, a million or more users, or other number of users) may be used to train one or more prediction models. In some embodiments, one or more prediction models may be trained or configured for a user or a type of device (e.g., a device of a particular brand, a device of a particular brand and model, a device having a certain set of features, etc.) and may be stored in association with the user or the device type. As an example, instances of a prediction model associated with the user or the device type may be stored locally (e.g., at a wearable device of the user or other user device) and remotely (e.g., in the cloud), and such instances of the prediction model may be automatically or manually synced across one or more user devices and the cloud such that the user has access to the latest configuration of the prediction model across any of the user devices or the cloud. In some embodiments, multiple modification profiles may be associated with the user or the device type. In some embodiments, each of the modification profiles may include a set of modification parameters or functions to be applied to live image data for a given context to generate an enhanced presentation of the live image data. As an example, the user may have a modification profile for each set of eye characteristics (e.g., a range of gaze directions, pupil sizes, limbus positions, or other characteristics). As further example, the user may additionally or alternatively have a modification profile for each set of environmental characteristics (e.g., a range of brightness levels of the environment, temperatures of the environment, or other characteristics). Based on the eye characteristics or environmental characteristics currently detected, the corresponding set of modification parameters or functions may be obtained and used to generate the enhanced presentation of the live image data.

Subsystems 112-124

In some embodiments, with respect to FIG. 1A, testing subsystem 122 may provide a visual test presentation to a user. As an example, the presentation may include a set of stimuli. During the presentation (or after the presentation), testing subsystem 122 may obtain feedback related to the set of stimuli (e.g., feedback indicating whether or how the user sees one or more stimuli of the set). As an example, the feedback may include an indication of a response of the user to one or more stimuli (of the set of stimuli) or an indication of a lack of response of the user to such stimuli. The response (or lack thereof) may relate to an eye movement, a gaze direction, a pupil size change, or a user modification of one or more stimuli or other user input (e.g., the user's reaction or other response to the stimuli). As another example, the feedback may include an eye image captured during the visual test presentation. The eye image may be an image of a retina of the eye (e.g., the overall retina or a portion thereof), an image of a cornea of the eye (e.g., the overall cornea or a portion thereof), or other eye image. In some embodiments, testing subsystem 122 may generate one or more results based on the feedback, such as affected portions of a visual field of the user, an extent of the affected portions, vision pathologies of the user, modification profiles to correct for the foregoing issues, or other results.

Figure 31A:
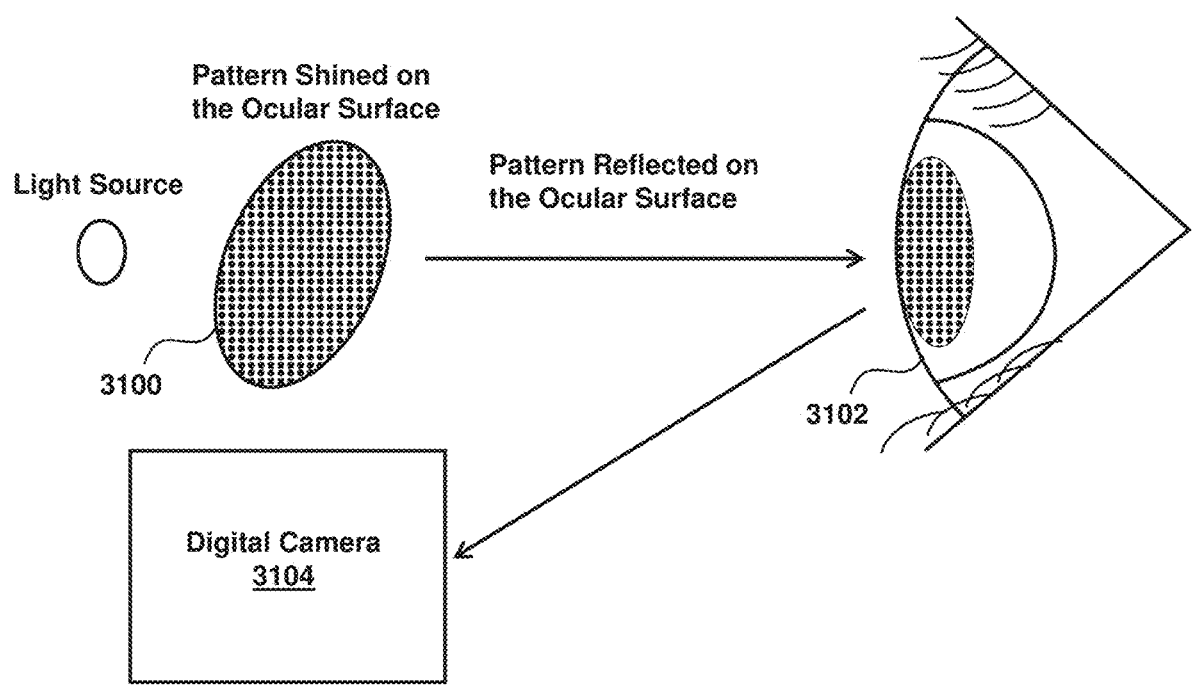
FIG. 31A illustrates a technique for assessing dry eye and corneal irregularities including projecting a pattern onto the corneal surface and imaging the corneal surface reflecting the pattern, in accordance with one or more embodiments.
Figure 33:
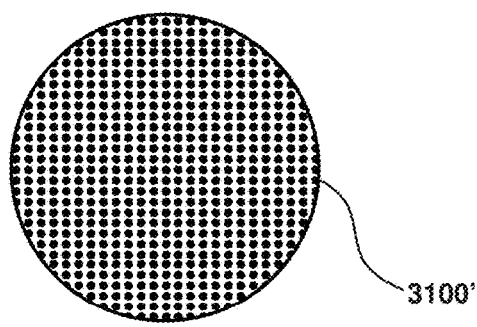
FIG. 33 illustrates an example of a normal pattern reflection, in accordance with one or more embodiments.
Figure 34:
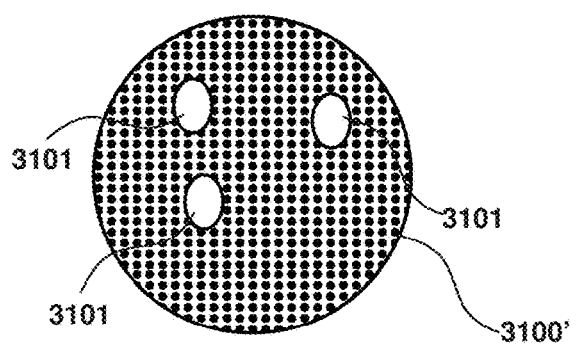
FIG. 34 illustrates an example of an abnormal pattern reflection, in accordance with one or more embodiments.
Figure 32:
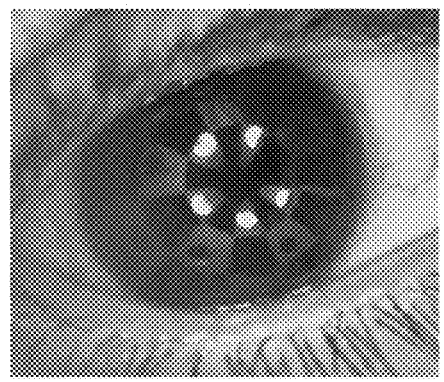
FIG. 32 is an image of a corneal surface reflecting a pattern projected onto the corneal surface, in accordance with one or more embodiments.

In some embodiments, based on feedback related to a set of stimuli (displayed to a user during a visual test presentation) or other feedback, testing subsystem 122 may determine light sensitivity, distortions, or other aberrations related to one or more eyes of the user. In some embodiments, the set of stimuli may include a pattern, and testing subsystem 122 may cause the pattern to be projected onto one or more eyes of the user (e.g., using a projection-based wearable spectacles device). As an example, the pattern may be projected onto a retina or a cornea of the user to determine defects affecting the retina or the cornea. In one use case, the projection pattern can be used to assess correct for dysmorphopsia in age-related macular degeneration and other retinal pathologies. As shown in FIG. 31A, a digital projection of a pattern 3100 may be projected onto a subject's eye 3102. The pattern may be digitally generated on a projector positioned on an interior of a spectacles device. A digital camera 3104 (e.g., an inward directed image sensor) may also be positioned on an interior side of the spectacles device to capture an image of the pattern 3100 reflected from the eye 3102. For example, the image capture may be captured from the corneal surface of the eye, as shown in FIG. 32. From the captured image of the pattern 3100, testing subsystem 122 may determine if the pattern looks normal (e.g., as depicted in FIG. 33) or exhibits anomalies (e.g., as depicted in FIG. 34 (3101)). The anomalies may be assessed and corrected for using one of the techniques described herein.

In some embodiments, testing subsystem 122 may cause a set of stimuli to be displayed to a user, obtain an image of one or more of the user's eyes (e.g., at least a portion of a retina or cornea of the user) as feedback related to the set of stimuli, and determine one or more modification parameters or functions to address light sensitivity, distortions, or other aberrations related to the user's eyes (e.g., lower or higher order aberrations, static or dynamic aberrations, etc.). Such modifications may include transformations (e.g., rotation, reflection, translation/shifting, resizing, etc.), image parameter adjustments (e.g., brightness, contrast, saturation, sharpness, etc.), or other modifications. As an example, when a pattern (e.g., an Amsler grid or other pattern) is projected onto a retina or cornea of the user, the obtained image may include a reflection of the projected pattern with the aberrations (e.g., reflected from the retina or cornea). Testing subsystem 122 may automatically determine the modification parameters or functions to be applied to the pattern such that, when the modified pattern is projected onto the retina or cornea, an image of the retina or cornea (subsequently obtained) is a version of the pre-modified-pattern image without one or more of the aberrations. In one use case, with respect FIG. 31C, when the pattern 3100 is projected onto a retina of the user, the obtained image may include the pattern 3100 with distortions (e.g., an inverse of the distortions depicted in modified pattern 3100' of FIG. 31D). A function (or parameters for such a function, e.g., that inverses the distortions in the obtained image) may be determined and applied to the pattern 3100 to generate the modified pattern 3100'. When the modified pattern 3100' is projected onto the user's retina, the reflection of the modified pattern 3100' from the user's retina will include the pattern 3100 of FIG. 31C without the prior distortions. To the extent that the reflection still includes distortions, testing subsystem 122 may automatically update the modified parameters or functions to be applied to the pattern to further mitigate the distortions (e.g., shown in the reflection of the retina).

In another use case, the eye image (e.g., the image of one or more of the user's eyes) capturing the projected stimuli (e.g., pattern or other stimuli) reflected from a retina or cornea may be used to determine a function (or parameters for the function) to correct for one or more other aberrations. Upon applying a determined function or parameters to the projected stimuli, and to the extent that the reflection of the modified stimuli still includes aberrations, testing subsystem 122 may automatically update the modified parameters or functions to be applied to the stimuli to further mitigate the aberrations (e.g., shown in the reflection). In a further use case, the foregoing automated determinations of the parameters or functions may be performed for each eye of the user. In this way, for example, the appropriate parameters or functions for each eye may be used to provide correction for Anisometropia or other conditions in which each eye has different aberrations. With respect to Anisometropia, for example, typical corrective glass spectacles cannot correct for the unequal refractive power of both eyes. That is because the corrective glass spectacles produced two images (e.g., one to each eye) with unequal sizes (aniseikonia) and the brain could not fuse those two images into a binocular single vision, resulting in visual confusion. That problem is simply because the lenses of glass spectacles are either convex, magnify the image or concave, minify the image. The amount of magnification or minification depends on the amount of correction. Given that the appropriate parameters or functions may be determined for each eye, the foregoing operations (or other techniques described herein) can will correct for Anisometropia (along with other conditions in which each eye has different aberrations), thereby avoiding visual confusion or other issues related to such conditions.

In some embodiments, with respect to FIG. 1A, testing subsystem 122 may cause a set of stimuli to be displayed to a user and determine one or more modification parameters or functions (to address light sensitivity, distortions, or other aberrations related to the user's eyes) based on the user's modifications to the set of stimuli or other user inputs. In some scenarios, with respect to FIG. 31C, the pattern 3100 may be a grid (e.g., an Amsler grid) or any known reference shape designed to allow for detecting a transformation needed to treat one or more ocular anomalies. That transformation may then be used to reverse-distort the image in real-time to allow better vision. In an example implementation of FIG. 8, a vision system 800 may include a testing module 802. The testing module 802 may be associated with wearable spectacles or may be executed in combination with an external device as described elsewhere herein. The testing module 802 may present testing stimuli comprising an Amsler grid to a subject 806. The subject, via the user device 808 or other input device, may manipulate the image of the grid to improve distortions (e.g., by dragging or moving one or more portions of the lines of the grid). The vision correction framework 810 may present the Amsler grid for further correction by the subject. When the subject has completed their manual corrections (e.g., resulting in modified pattern 3100'), the vision correction framework 810 may generate the modification profile of the subject to apply to visual scenes when they are using the spectacles device. As an example, the vision correction framework 810 may generate an inverse function (or parameters for such a function) that outputs the modified pattern 3100' when the pattern 3100 is provided as input the function. The described workflow of vision system 800 may similarly be applicable to other testing mode operations described herein.

Figure 31B:
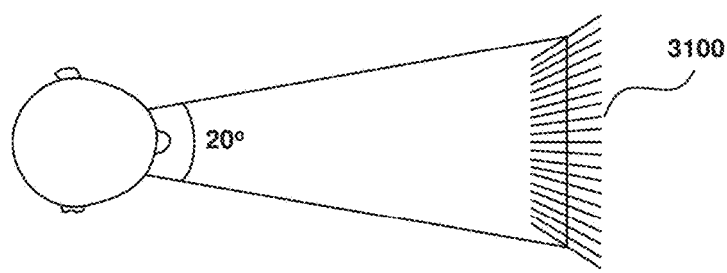
FIG. 31B schematically illustrates presentation of a reference image comprising a grid displayed to a subject or projected onto a cornea or retina of the subject via wearable spectacles, in accordance with one or more embodiments.
Figure 31C:
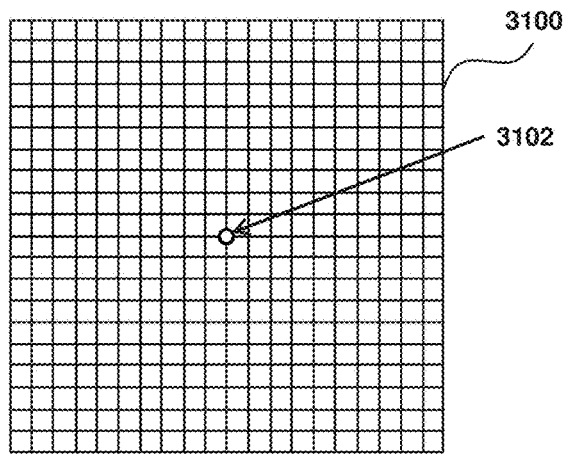
FIG. 31C illustrates an example grid for manipulation by a subject, in accordance with one or more embodiments.
Figure 31D:
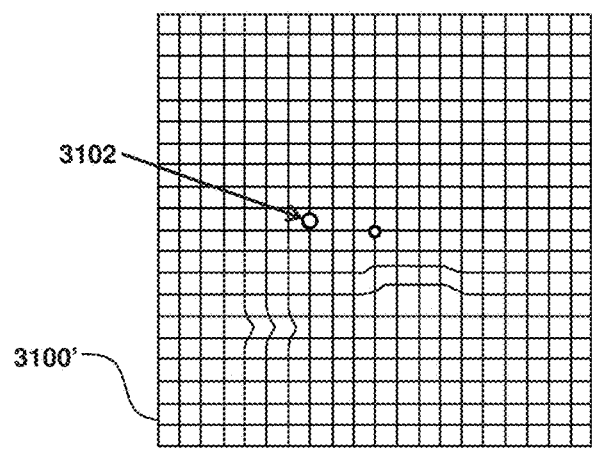
FIG. 31D illustrates an example manipulation of the grid illustrated in FIG. 31C, in accordance with one or more embodiments.

FIG. 31B is a schematic illustration of the presentation of an Amsler grid 3100 (e.g., an example reference image) displayed as an image on a wearable spectacle (e.g., VR or AR headset). The Amsler grid 3100 may be displayed to or projected onto a cornea and/or retina of the subject. An example standard grid 3100 is shown in FIG. 31C. The same grid pattern may be displayed on a user device. The subject may manipulate the lines of the grid pattern, particularly the lines that appear curved, utilizing a keyboard, mouse, touch screen, or other input on a user device, which may include a user interface. The subject can specify an anchor point 3102 from which to manipulate the image. After specifying the anchor point, the subject can use the user device (e.g., arrow keys) to adjust the specified line, correcting the perceived distortion caused by their damaged macula. This procedure may be performed on each eye independently, providing a set of two modified grids.

Figure 31E:
FIG. 31E illustrates a scene as it should be perceived by the subject, in accordance with one or more embodiments.
Figure 31F:
FIG. 31F illustrates an example corrected visual field that when provided to a subject with a visual distortion determined by the grid technique results in that subject perceiving the visual field as shown FIG. 31E, in accordance with one or more embodiments.

Once the subject completes the modification of the lines to appear straight, a vision correction framework takes the new grids and generate meshes of vertices corresponding to the applied distortions. These meshes, resulting from the testing mode, are applied to an arbitrary image to compensate for the subject's abnormalities. For example, each eye may be shown the modified image corresponding to the appropriate mesh, as part of confirmation of the testing mode. The subject can then indicate on the user device if the corrected images appear faultless which, if true, would indicate that the corrections were successful. For example, FIG. 31E illustrates an actual scene, as it should be perceived by the user. FIG. 31F illustrates a corrected visual field that when provided to a subject with a visual distortion determined by the Amsler grid technique, results in that subject seeing the visual field of FIG. 31F as the actual visual field of FIG. 31E.

Such correction may be performed in real time on live images to present the subject with a continuously corrected visual scene. The correction may be achieved real-time whether the spectacles device includes displays that generate the capture visual field or whether the spectacles device is custom-reality based and uses a correction layer to adjust for the distortion, as both cases may utilize the determined corrective meshes.

Figure 31G:
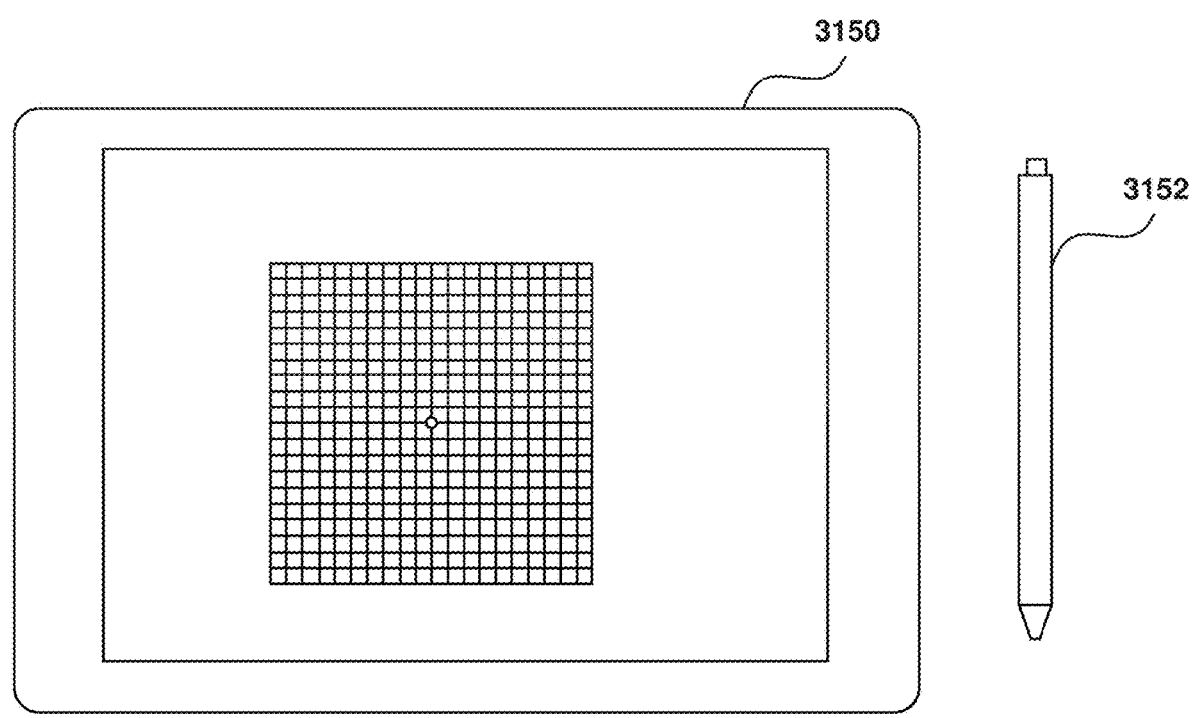
FIG. 31G illustrates a display including a manipulatable grid onto which a subject may communicate distortions within a visual field, in accordance with one or more embodiments.

In some examples, a reference image such as the Amsler pattern may be presented directly on a touch screen or tablet PC, such as 3150 (e.g., a tablet PC) shown in FIG. 31G. The Amsler pattern is presented on a display of the device 3150, and the subject may manipulate the lines that appear curved using a stylus 3152 to draw the corrections that are to be applied to the lines to make them appear straight. During the testing mode, after each modification, the grid may be redrawn to reflect the latest edit. This procedure may be performed on each eye independently, providing us a set of two modified grids. After the subject completes the testing mode modification, the tablet PC executes an application that creates and sends the mesh data to an accompanying application on the spectacles device to process images that apply the determined meshes.

Once the spectacles device receives the results of the testing mode modification, the spectacles device may apply them to an arbitrary image to compensate for the subject's abnormalities. The images that result from this correction may then be displayed. The display may be via an VR/AR headset. In one example, the display presents the images to the user via the headset in a holographical way. Each displayed image may correspond to the mesh created for each eye. If the corrected images seem faultless to the subject, the corrections may be considered successful and may be retained for future image processing. In some embodiments of the testing mode, instead of or in addition to presenting a single image modified according to the modified grids, a video incorporating the modifications may be presented. In one example, the video includes a stream of a camera's live video feed through the correction, which is shown to the subject.

In some embodiments, with respect to FIG. 1A, testing subsystem 122 may determine one or more defective visual field portions of a visual field of a user (e.g., an automatic determination based on feedback related to a set of stimuli displayed to the user or other feedback). As an example, a defective visual field portion may be one of the visual field portions of the user's visual field that fails to satisfy one or more vision criteria (e.g., whether or an extent to which the user senses one or more stimuli, an extent of light sensitivity, distortion, or other aberration, or other criteria). In some cases, the set of stimuli displayed to the user includes at least one testing image of text or of an object. Defective visual field portions may include regions of reduced vision sensitivity, regions of higher or lower optical aberrations, regions of reduced brightness, or other defective visual field portions. In some cases, the set of stimuli may differ in contrast levels with respect to each other and with respect to a baseline contrast level by at least 20 dB. In some cases, the set of stimuli may differ in contrast levels with respect to each other and with respect to a baseline contrast level by at least 30 dB. In some cases, testing subsystem 122 may, in the testing mode, instruct a wearable spectacles device to display the set of testing stimuli to the user in a descending or ascending contrast.

In one use case, testing was performed on 4 subjects. A testing protocol included a display of text at different locations one or more display monitors of the spectacles device. To assess the subject's visual field of impaired regions, the word "text" was displayed on the spectacle monitors for each eye, and the subject was asked to identify the "text." Initially the "xt" part of the word "text" was placed intentionally by the operator on the blind spot of the subject. All 4 subjects reported only seeing "te" part of the word. The letters were then moved using software to control the display, specifically. The text "text" was moved away from the blind spot of the subject who was again asked to read the word. Subjects were able to read "text" stating that now the "xt" part of the word has appeared.

Figures 6A, 6B, 6C:
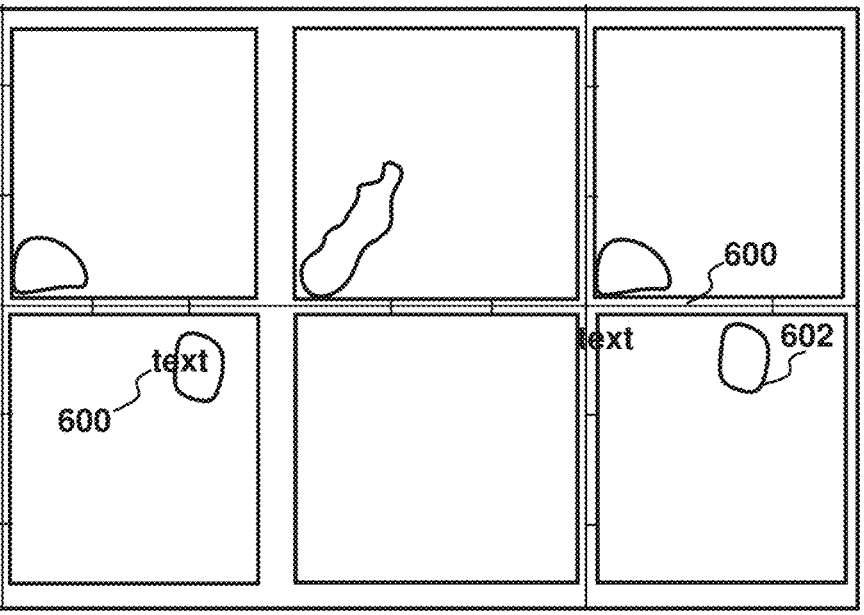
FIGS. 6A-6C illustrate an example assessment protocol for a testing mode process including pupil tracking, in accordance with one or more embodiments.

An example of this assessment protocol of a testing mode is shown in FIGS. 6A-6C. As shown in FIGS. 6A-6B, the code automatically detects the blind spots on a Humphrey visual field. The word "text" 600 is projected so that "xt" part of the word is in a blind spot 602 (FIG. 6A). The subject was asked to read the word. The word "text" 600 was then moved away from the blind spot 602 (FIG. 6B) and the subject was asked to read it again. The word "text" 600 can be displayed at different coordinates of the visual field of the subject, with the visual field divided into 4 coordinates in the illustrated example. This protocol allows for identification of multiple blind spots, including peripheral blind spot 604. The text may be moved around over the entire visual field of the subject, with the subject being asked to identify when all or portions of the text is not visible or partially visible or visible with a reduced intensity.

The pupil tracking functionalities described herein may include pupil physical condition (e.g., visual axis, pupil size, and/or limbus), alignment, dilation, and/or line of sight. Line of sight, also known as the visual axis, is a goal that can be achieved by one or more of tracking the pupil, the limbus (which is the edge between the cornea and the sclera), or even track blood vessel on the surface of the eye or inside the eye. Thus, pupil tracking may similarly include limbus or blood vessel tracking. The pupil tracking may be performed utilizing one or more inward facing image sensors as described herein. In various embodiments, pupil tracking functionalities may be used for determination of parameters for registering the projected image on the visual field of the subject (FIG. 6C).

With respect to FIG. 6C, a GUI 606 display may be displayed to an operator. The GUI 606 may provide information related to the testing. For example, the GUI 606 shows measured visual field defects and the relative location of the image to the defects. The GUI 606 may be operable to allow automatic distribution of the images to the functional part of the visual field but may include buttons to allow the operator to override the automatic mode. The external image processing device may be configured to determine where this assessment text is to be displayed and may wirelessly communicate instructions to the digital spectacles to display the text at the various locations in the testing mode.

Figure 7A:
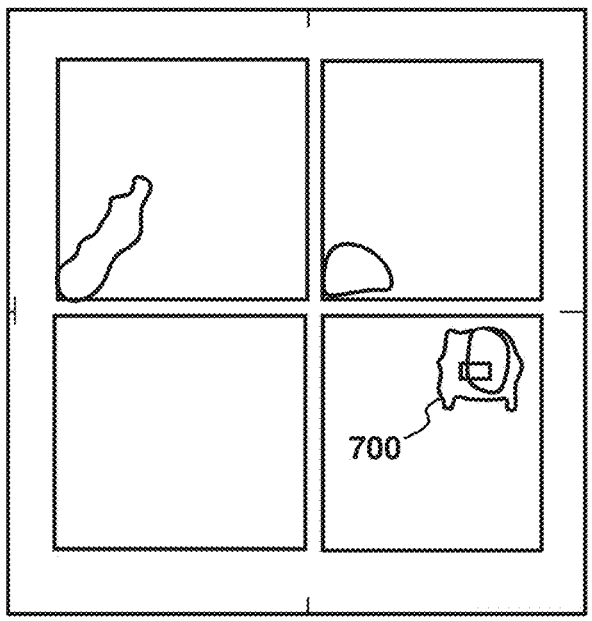
FIGS. 7A-7C illustrate an example assessment protocol for a testing mode process including pupil tracking, in accordance with one or more embodiments.
Figure 7B:
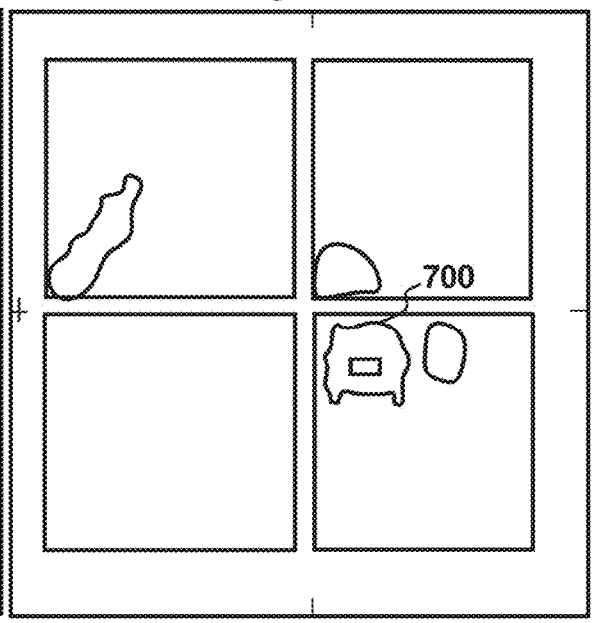
Figure 7C:
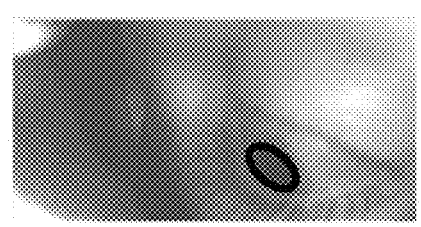

In another use case, with respect to FIGS. 7A-7C, instead of "text" being used, the subject was tested to determine whether they could see a car 700 placed in different portions of the visual field, for pupil tracking and affected region determination. The pupil tracking functionality allows the vision system to register the projected image on the visual field of the subject.

In some embodiments, with respect to FIG. 1A, testing subsystem 122 may determine one or more defective visual field portions of a visual field of a user based on a response of the user's eyes to a set of stimuli displayed to the user or lack of response of the user's eyes to the set of stimuli (e.g., eye movement response, pupil size response, etc.). In some embodiments, one or more stimuli may be dynamically displayed to the user as part of a visual test presentation, and the responses or lack of responses to a stimulus may be recorded and used to determine which part of the user's visual field is intact. As an example, if an eye of the user responds to a displayed stimulus (e.g., by changing its gaze direction toward the displayed stimulus's location), the eye's response may be used as an indication that the eye can see the displayed stimulus (e.g., and that a corresponding portion of the user's visual field is part of the user's intact visual field). On the other hand, if an eye of the user does not respond to a displayed stimulus (e.g., its gaze direction does not move toward the displayed stimulus's location), the eye's lack of response may be used as an indication that the eye cannot see the displayed stimulus (e.g., and that a corresponding portion of the user's visual field is a defective visual field portion). Based on the foregoing indications, testing subsystem 122 may automatically determine the defective visual field portions of the user's visual field.

In some embodiment, the set of stimuli displayed to the user may include stimuli of different brightness, contrast, saturation, or sharpness levels, and the responses or lack of responses to a stimulus having a particular brightness, contrast, saturation, or sharpness level may provide an indication of whether a portion of the user's visual field (corresponding to the location of the displayed stimuli) has an issue related to brightness, contrast, saturation, or sharpness. As an example, if an eye of the user responds to a displayed stimulus having a certain brightness level, the eye's response may be used as an indication that the eye can see the displayed stimulus (e.g., and that a corresponding portion of the user's visual field is part of the user's intact visual field). On the other hand, if an eye of the user does not respond to a stimulus having a lower brightness level (e.g., that a normal eye would respond to) at the same location, the eye's lack of response may be used as an indication that a corresponding portion of the user's visual field has reduced brightness. In some cases, the brightness level for the stimulus may be incrementally increased until the user's eye responds to the stimulus or until a certain brightness level threshold is reached. If the user's eye eventually reacts to the stimulus, the current brightness level may be used to determine a level of light sensitivity for that corresponding virtual field portion. If the brightness level threshold is reached and the user's eye does not react to the stimulus, it may be determined that the corresponding virtual field portion is a blind spot (e.g., if the corresponding changes to one or more of contrast, saturation, sharpness, etc., to the stimulus also does not trigger an eye response). Based on the foregoing indications, testing subsystem 122 may automatically determine the defective visual field portions of the user's visual field.

In some embodiment, a fixation point for a visual test presentation may be dynamically determined. In some embodiments, a location of a fixation point and locations of the stimuli to be displayed to the user may be dynamically determined based on gaze direction or other aspect of the user's eyes. As an example, during a visual test presentation, both the fixation points and stimuli locations are dynamically represented to a patient relative to the patient's eye movement. In one use case, the current fixation point may be set to a location of the visual test presentation that the patient is currently looking at a particular instance, and a test stimulus may be displayed relative to that fixation point. In this way, for example, the patient is not required to fix his attention to a certain predefined fixation location. This allows the visual test presentation to be more objective, interactive, and reduce stress caused by prolonged fixation on a fixed point. The use of dynamic fixation points also eliminates patient errors related to fixation points (e.g., if the patient forgets to focus on a static fixation point).

Figure 35A:
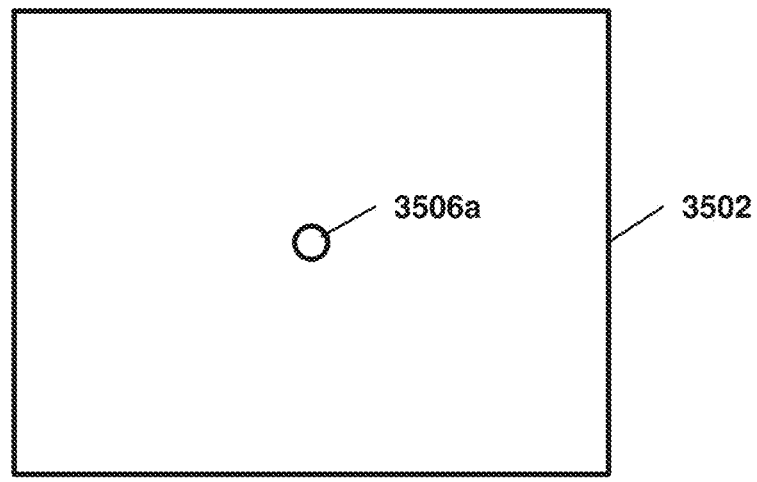
FIGS. 35A-35E illustrates a visual test presentation using a dynamic fixation point, in accordance with one or more embodiments.
Figure 35A:
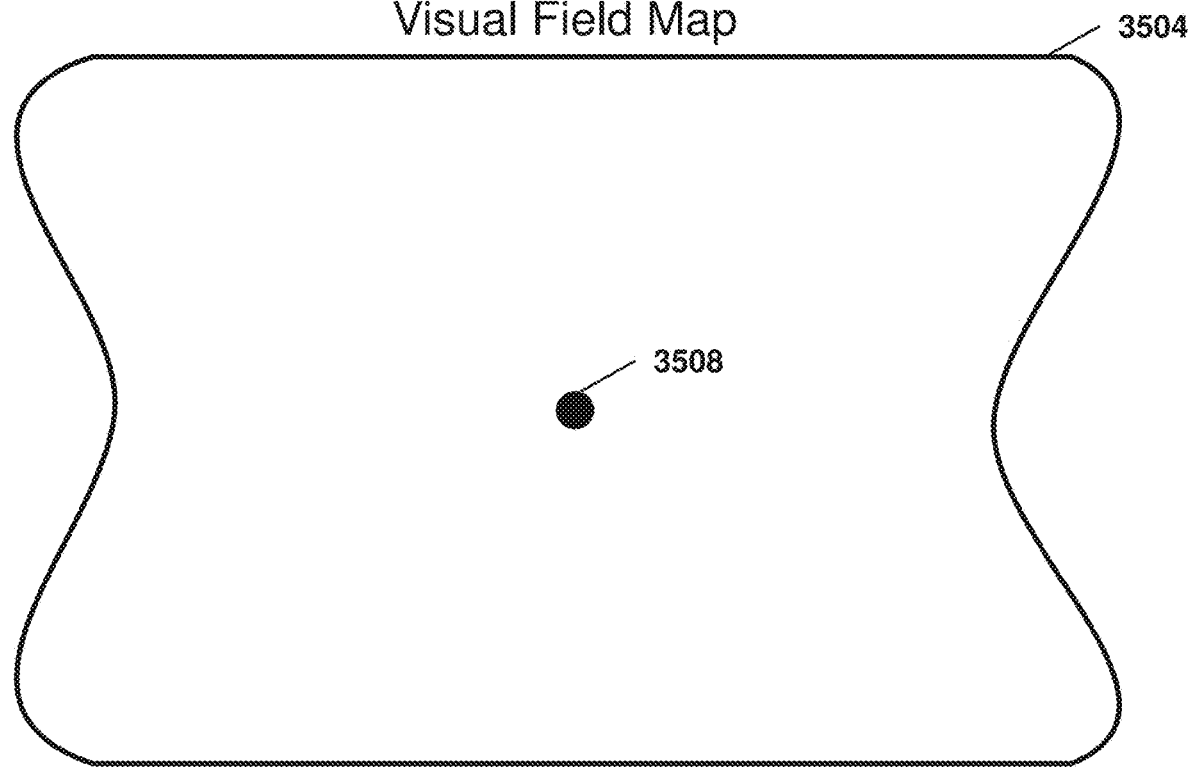
Figure 35B:
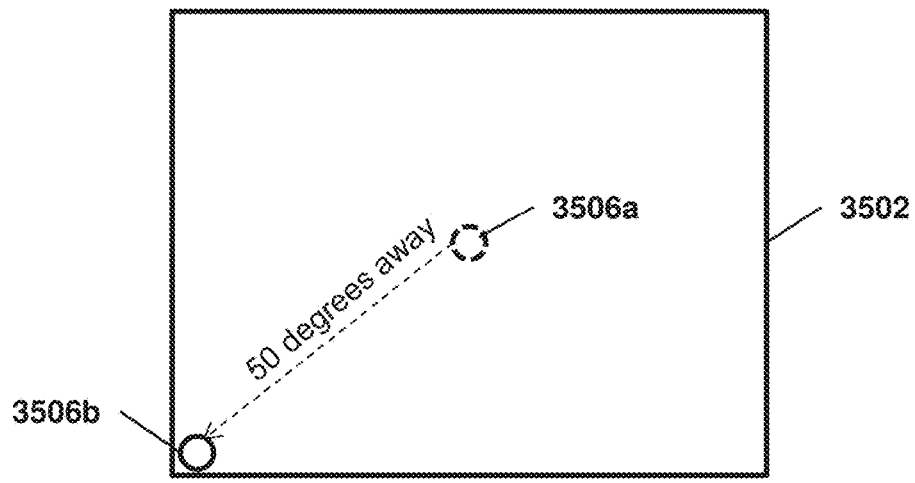
Figure 35B:
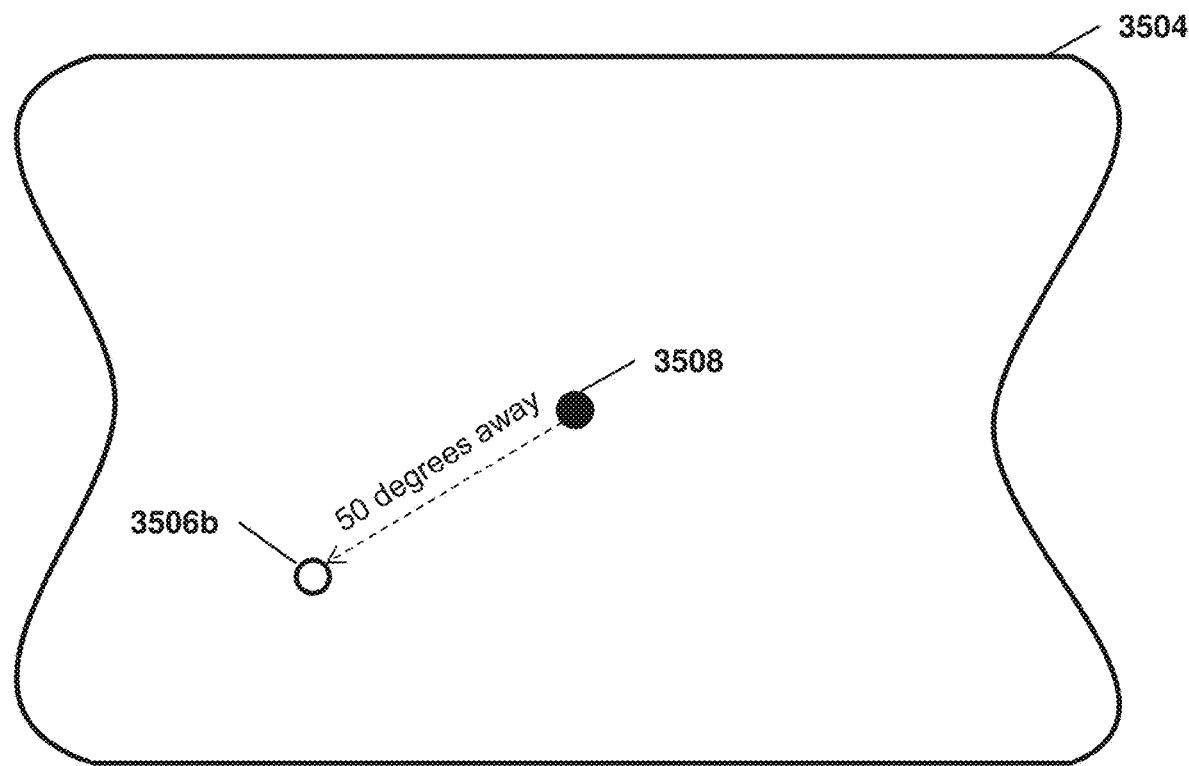
Figure 35C:
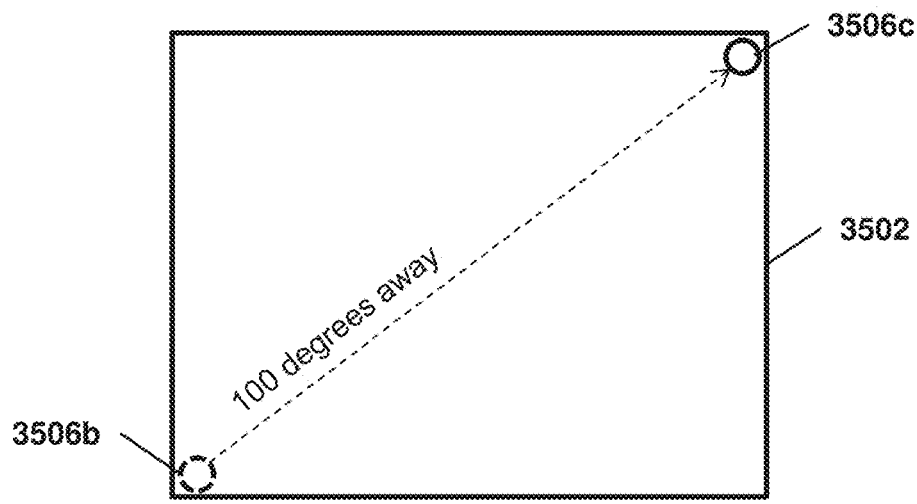
Figure 35C:
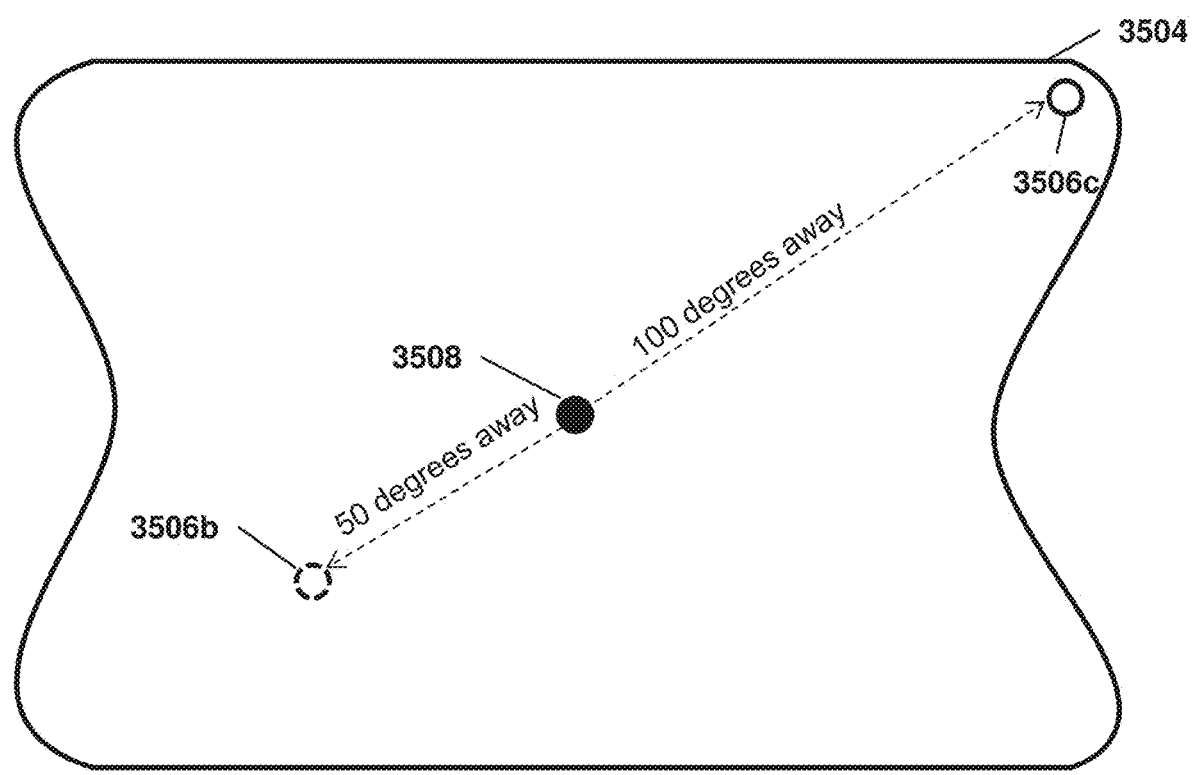
Figure 35D:
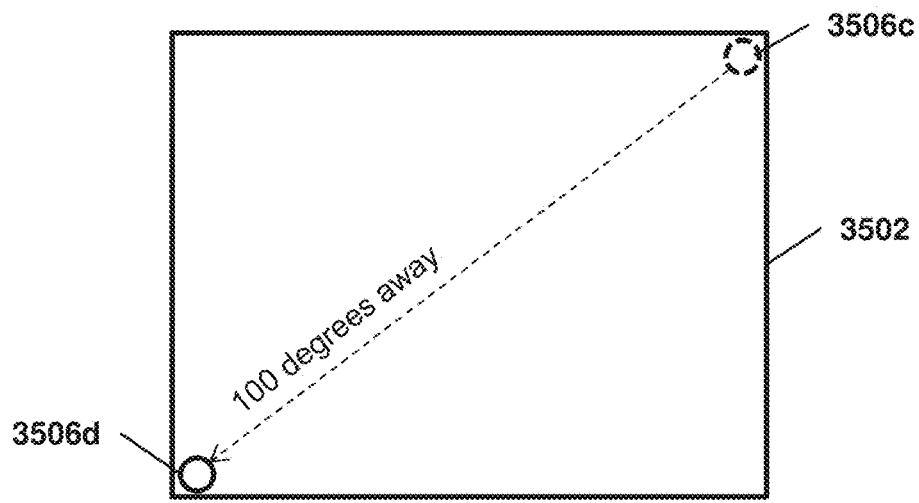
Figure 35D:
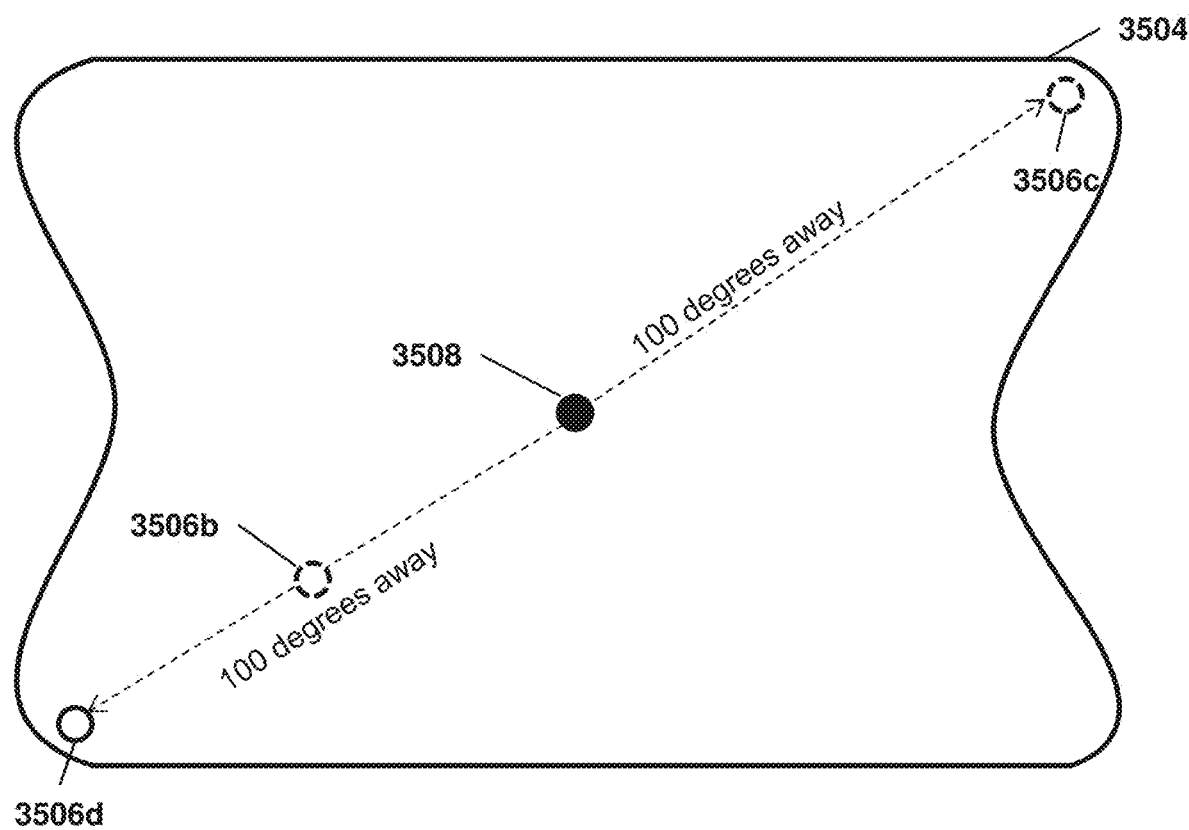
Figure 35E:
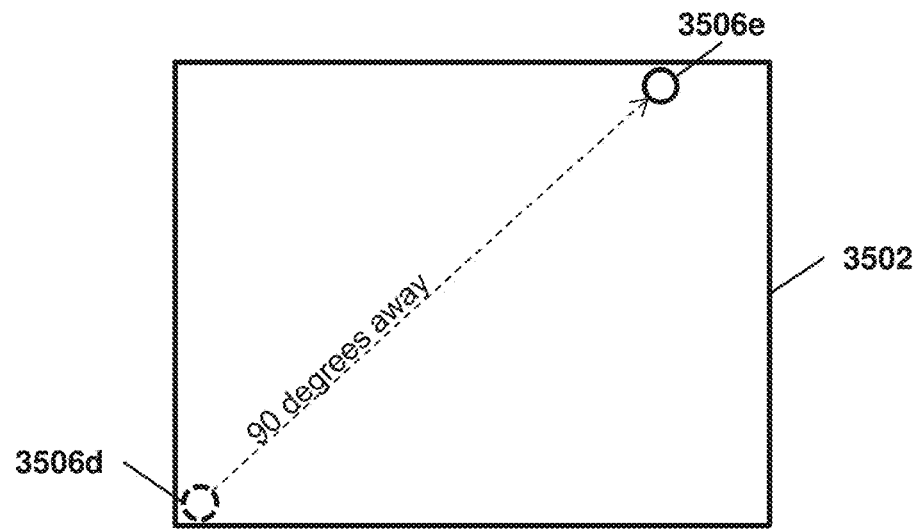
Figure 35E:
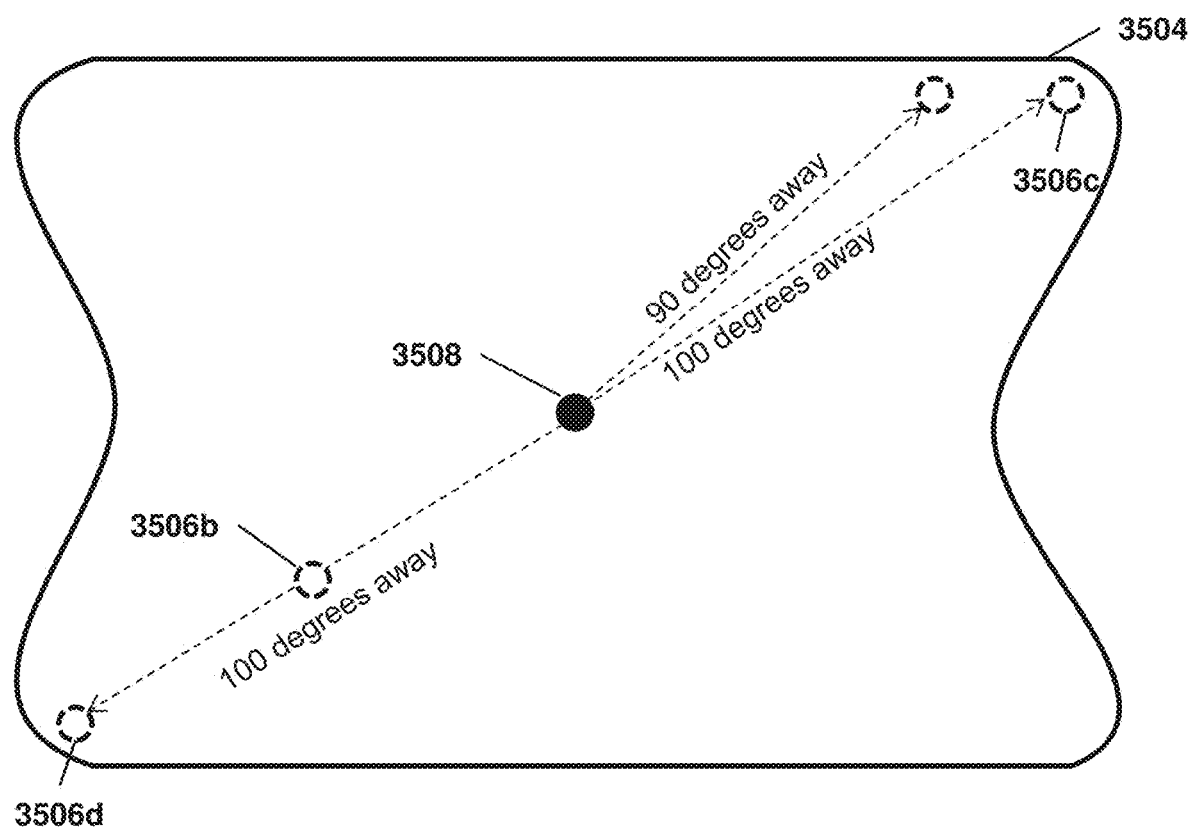
Figure 35F:
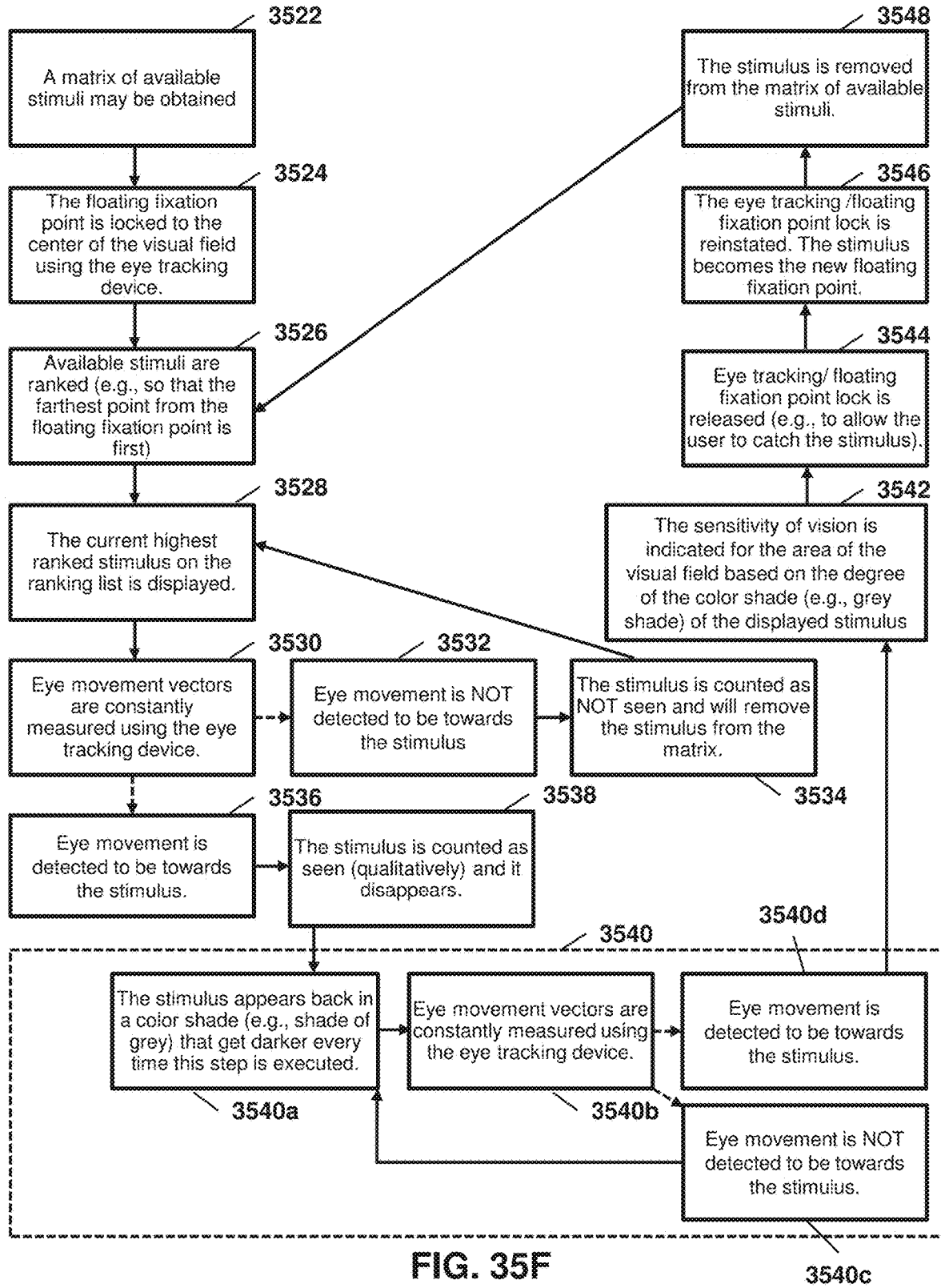
FIG. 35F illustrates a flowchart related to a process for facilitating a visual test presentation using a dynamic fixation point, in accordance with one or more embodiments.

In some embodiments, the fixation point may be locked, and one or more test stimuli may be displayed relative to that fixation point until the lock is released (e.g., FIG. 35F). Upon the lock being released, the current fixation point may be set to a location of the visual test presentation that the patient is currently looking at a particular instance. The new fixation point may then be locked, and one or more subsequent test stimuli may be displayed relative to that new fixation point. In some embodiments, while the fixation point remains the same, multiple stimuli may be displayed at one or more different locations on the visual test presentation. As an example, as the fixation point remains the same, one or more stimuli may be displayed after one or more other stimuli are displayed. In some embodiments, each of the multiple stimuli may be displayed and then deemphasized on or removed from the user interface on which the visual test presentation is provided. As an example, as the fixation point remains the same, one or more stimuli may be displayed and deemphasized/removed after one or more other stimuli are displayed and deemphasized/removed. In one use case, the brightness or other intensity level of a stimulus may be decreased (e.g., decreased by a predefined amount, decreased to a default "low" threshold level, decreased to a personalized threshold level at which it has been determined that the patient cannot see, etc.) to perform deemphasis of the stimulus. In another use case, the stimulus may be removed from the user interface (e.g., the stimulus is no longer being displayed by the user interface).

As discussed, in some embodiments, testing subsystem 122 may adjust a fixation point (e.g., for a visual test presentation) based on eye characteristic information related to a user (e.g., a patient's eye movement, gaze direction, or other eye-related characteristics, such as those occurring during the visual test presentation). In one use case, testing subsystem 122 may cause a first stimulus to be displayed at a first interface location on a user interface (e.g., of a wearable device or other device of the user) based on the fixation point. Testing subsystem 122 may adjust the fixation point based on the eye characteristic information and cause a second stimulus to be displayed at a second interface location on the user interface during the visual test presentation based on the adjusted fixation point. As discussed, in some embodiments, one or more stimuli may be displayed on the user interface (e.g., at different interface locations) between the display of the first stimulus and the display of the second stimulus. Testing subsystem 122 may obtain feedback information during the visual test presentation and generate visual defect information based on such feedback information. As an example, the feedback information may indicate feedback related to the first stimulus, feedback related to the second stimulus, feedback related to a third stimulus displayed during the visual test presentation, or feedback related to one or more other stimuli. Such feedback may indicate (i) a response of the user to a stimulus, (ii) a lack of response of the user to a stimulus, (iii) whether or an extent to which the user senses one or more stimuli, an extent of light sensitivity, distortion, or other aberration, or (iv) other feedback. The generated visual defect information may be used to (i) train one or more prediction models, (ii) determine one or more modification profiles for the user, (iii) facilitate live image processing to correct or modify images for the user, (iv) or perform other operations described herein.

In some embodiments, the use of a dynamic fixation point during a visual test presentation may facilitate greater coverage of a user's visual field than the dimensions of a view provided via a user interface. As an example, as indicated with respect to FIGS. 35A-35E, the user interface (e.g., of a wearable device or other device of the user) may be configured to display a view having one or more dimensions, where each of the dimensions correspond to a number of degrees (e.g., a width of 70 degrees, a height of 70 degrees, a width or height of another number of degrees, etc.). Through the use of the dynamic fixation point, however, testing subsystem 122 may generate visual defect information having coverage greater than the degrees with respect to one or more of the dimensions (e.g., a horizontal dimension for the user's visual field compared to the width of the user interface view, a vertical dimension for the user's visual field compared to the height of the user interface view, etc.). In one scenario, based on such techniques, the visual defect information may have coverage for up to a 2.85 times larger area than the overall user interface view, and the coverage area may be increased to a size that approaches 4 times the overall user interface view (e.g., if the distance between the wearable device and the eye of the user decreases or if the distance between two monitors of the wearable device increases). In addition, the visual defect information may have coverage for up to twice the width of the user's visual field area than the width of the user interface view, up to twice the height of the user's visual field area than the height of the user interface view, or other expanded area of the user's visual field. In another scenario, based on such techniques, the visual defect information may indicate whether or the extent to which defects exist at two or more visual field locations of the user's visual field, where the visual field locations are apart from one another by greater than the degrees of the user interface view dimensions with respect to one or more of the dimensions for the user's visual field.

In one use case, with respect to FIG. 35A, the use of a dynamic fixation point and user interface 3502 (e.g., which is configured to provide a 70-degree view) may facilitate the generation of a visual field map 3504 that has coverage greater than 70 degrees in both the horizontal and vertical dimensions. As an example, as indicated in FIG. 35A, stimulus 3506a may be displayed at a center of user interface 3502 to cause the user to look at the center of user interface 3502 to initially set the fixation point 3508 to the center of user interface 3502. Specifically, when the user's eye-related characteristics (e.g., as detected by eye tracking techniques described herein) indicate that the user looking at stimulus 3506a, the fixation point 3508 for the visual test presentation may currently be set to the location of user interface 3502 corresponding to stimulus 3506a. In some use cases, the fixation point "floats" on the user interface 3502 in accordance with where the user is currently looking.

In a further use case, as indicated in FIG. 35B, stimulus 3506b may be displayed at the bottom left-hand corner of user interface 3502 (e.g., 50 degrees away from the location of user interface 3502 at which stimulus 3506a was displayed). If the user's eye-related characteristics indicate that the user senses stimulus 3506b (e.g., the user's eye movement is detected as being toward stimulus 3506b), visual field map 3504 may be updated to indicate that the user is able to see the corresponding location in the user's visual field (e.g., 50 degrees away from the location of the fixation point in the visual field map 3504 in the same direction). When the user's eye-related characteristics indicate that the user is currently looking at stimulus 3506b, the fixation point 3508 for the visual test presentation may then be set to the location of the user interface corresponding to stimulus 3506b.

In another use case, as indicated in FIG. 35C, stimulus 3506c may be displayed at the top right-hand corner of user interface 3502 (e.g., 100 degrees away from the location of user interface 3502 at which stimulus 3506b was displayed). If the user's eye-related characteristics indicate that the user senses stimulus 3506c, visual field map 3504 may be updated to indicate that the user is able to see the corresponding location of the user's visual field (e.g., hundred degrees away from the location of the fixation point in the visual field map 3504 in the same direction). When the user's eye-related characteristics indicate that the user is currently looking at stimulus 3506c, the fixation point 3508 for the visual test presentation may then be set to the location of user interface 3502 corresponding to stimulus 3506c. As indicated in FIG. 35D, stimulus 3506d may be displayed at the bottom left-hand corner of user interface 3502 (e.g., 100 degrees away from the location of user interface 3502 at which stimulus 3506c was displayed). If the user's eye-related characteristics indicate that the user senses stimulus 3506d, visual field map 3504 may be updated to indicate that the user is able to see the corresponding location of the user's visual field (e.g., 100 degrees away from the location of the fixation point in the visual field map 3504 in the same direction). When the user's eye-related characteristics indicate that the user is currently looking at stimulus 3506d, and the fixation point 3508 for the visual test presentation may then be set to the location of user interface 3502 corresponding to stimulus 3506d. As indicated in FIG. 35E, stimulus 3506e may be displayed to the left of the top right-hand corner of user interface 3502 (e.g., 90 degrees away from the location of user interface 3502 at which stimulus 3506d was displayed). If the user's eye-related characteristics indicate that the user senses stimulus 3506e, visual field map 3504 may be updated to indicate that the user is able to see the corresponding location of the user's visual field (e.g., 90 degrees away from the location of the fixation point in the visual field map 3504 in the same direction). When the user's eye-related characteristics indicate that the user is currently looking at stimulus 3506b, the fixation point 3508 for the visual test presentation may then be set to the location of user interface 3502 corresponding to stimulus 3506e. In this way, for example, even though the user interface view was only 70 degrees in both the horizontal and vertical dimensions, the visual field map 3504 currently has coverage for 200 degrees of the user's visual field diagonally, 140 degrees of the user's visual field with respect to the horizontal dimension, and 140 degrees of the user's visual field with respect to the vertical dimension.

In another use case, with respect to FIG. 35B, if the user's eye-related characteristics indicates that the user did not see stimulus 3506b (e.g., there was no significant eye movement response to the display of stimulus 3506b, the user's gaze did not shift to an area proximate the location of stimulus 3506b on user interface 3502, etc.), visual field map 3504 may be updated to indicate that the user cannot see the corresponding location in the user's visual field. As such, in some scenarios, the visual field map may indicate vision defects and their corresponding locations in the user's visual field for an area greater than the size of the view of user interface 3502. As an example, even where the user interface view is only 70 degrees in the horizontal and vertical dimensions, the visual field map may indicate vision defects at visual field locations that are apart from one another by more than 70 degrees in each of the horizontal and vertical dimensions (e.g., the distances between such indicated visual defects may be up to 140 degrees apart with respect to the horizontal dimension, up to 140 degrees apart with respect to the vertical dimension, etc.).

In some embodiments, to facilitate greater coverage of a user's visual field (e.g., despite limitation of hardware/software components related to the user interface view), one or more locations on a user interface may be selected to display one or more stimuli based on the interface locations being farther from the current fixation point (e.g., for a visual test presentation). In some embodiments, testing subsystem 122 may select a first interface location on the user interface based on the first interface location being farther from the fixation point than one or more other interface locations on the user interface and cause a first stimulus to be displayed at the first interface location. In some embodiments, after the fixation point is adjusted (e.g., based on the user's eye-related characteristics), testing subsystem 122 may select a second interface location on the user interface based on the second interface location being farther from the adjusted fixation point than one or more other interface locations on the user interface and cause a second stimulus to be displayed at the second interface location.

As an example, the first stimulus may be selected to be added to a queue of stimuli to be displayed (e.g., a queue of stimuli to be displayed next) during the visual test presentation based on (i) the first stimulus being associated with a first visual field location of the user's visual field and (ii) the first visual field location corresponding to the first interface location (e.g., as determined by the fixation point and the location of the first visual field location relative to the fixation point). As further example, the second stimulus may be selected to be added to the queue during the visual test presentation based on (i) the second stimulus being associated with a second visual field location of the user's visual field and (ii) the second visual field location corresponding to the second interface location. By selecting "farther" stimuli/locations to be displayed next, testing subsystem 122 adjusts the fixation point farther away from the center of the user interface view, thereby increasing the coverage of the user's visual field. In one use case, with respect to FIG. 35B, stimulus 3506b and its corresponding location on user interface 3502 are selected to be the next stimulus/location to be displayed during the visual test presentation as a result of a determination that the corresponding interface location is one of the farthest locations on the user interface from the fixation point (located at the center of user interface 3502). In doing so, the fixation point is adjusted to the bottom left-hand corner of user interface 3502 (e.g., by causing the user to look there), thereby enabling the next stimulus to be displayed as far as 100 degrees away from the fixation point (e.g., the distance between stimulus 3506b and stimulus 3506c in FIG. 35C).

In some embodiment, one or more locations of a user's visual field may be included as part of a set of visual field locations to be tested during a visual test presentation. As an example, the test set of visual field locations may be represented by stimuli during the visual test presentation, and the determination of whether or the extent to which the user has visual defects at one or more of the visual field locations of the test set is based on whether or the extent to which the user senses one or more of the corresponding stimuli. In some embodiments, a visual field location may be removed from the test set based on a determination that the visual field location has been sufficiently tested (e.g., by displaying a stimulus at a corresponding location on a user interface and detecting whether or the extent to which the user senses the displayed stimulus). As an example, the removal of the visual field location may include labeling the visual field location in the test set as no longer being available to be selected from the test set during the visual test presentation. As such, in some scenarios, stimuli corresponding to the removed visual field location may not be subsequently displayed during the visual test presentation, and stimuli corresponding to one or more other visual field locations in the test set may be subsequently displayed during the visual test presentation. In further scenarios, the visual field location may subsequently be added to the test set (e.g., by labeling the visual field location in the test as being available to be selected during the visual test presentation, by removing the prior label specifying that the visual field location was not available to be selected during the visual test presentation, etc.).

In some embodiments, where a fixation point has been adjusted to a first user interface location on a user interface at which a first stimulus is displayed during a visual test presentation, testing subsystem 122 may cause one or more stimuli to be displayed on the user interface based on the fixation point at the first interface location. Testing subsystem 122 may also subsequently cause a second stimulus to be displayed at a second interface location on the user interface. As an example, the second stimulus may be displayed while the fixation point remains at the first interface location (e.g., the fixation point may be locked to the first interface location until just prior to the second stimulus being display, until the second stimulus is displayed, etc.). In some embodiments, testing subsystem 122 may detect that an eye of the user has fixated on the second interface location based on eye characteristic information related to the user, and testing subsystem 122 may adjust the fixation point to the second interface location based on the fixation detection.

In some embodiments, testing subsystem 122 may establish a lock of a fixation point for a visual test presentation to prevent adjustment (or readjustment) of the fixation point to a different interface location on the user interface while the lock remains established. In this way, for example, while the lock of the fixation point remains established, one or more stimuli may be displayed on the user interface to test one or more locations of the user's the visual field relative to the locked fixation point. Subsequently, when the lock of the fixation point is released, the fixation point may again be dynamically adjusted. As an example, testing subsystem 122 may cause a stimulus to be presented at a new interface location (different from the interface location to which the fixation point was set) on the user interface. Based on detecting that an eye of the user has fixated on the new interface location, and after the lock of the fixation point is released, testing subsystem 122 may adjust the fixation point to the new interface location. In one use case, as discussed above with respect to FIG. 35F, the fixation point lock may be released to allow the user to "catch" the stimulus (e.g., operation 3544), and the fixation point lock may then be reinstated to the new interface location based on the user looking at the stimulus (e.g., operation 3546). Specifically, if the user has "caught" the stimulus (and is still looking at the stimulus), the location of the stimulus becomes the new fixation point.

In some embodiments, while a fixation point remains at a first interface location on a user interface, testing subsystem 122 may cause multiple stimuli to be displayed at interface locations different from the first interface location. As an example, subsequent to one or more stimuli of the multiple stimuli being displayed on the user interface, one or more other stimuli of the multiple stimuli may be displayed on the user interface. As another example, a stimulus may be displayed on the user interface and then deemphasized on or removed from the user interface, and another stimulus may be subsequently displayed on the user interface and deemphasized on or removed from the user interface. In one use case, with respect to FIG. 35F, the fixation point may be locked to an interface location (at which a prior stimulus was displayed) (e.g., operation 3546), and one or more stimuli may be displayed on the user interface at a new interface location (e.g., operation 3528, operation 3540a, etc.) based on the fixation point.

In another use case, multiple locations of the user's visual field may be tested by displaying multiple stimuli at different interface locations while the fixation point remains locked. As an example, with respect to FIG. 35C, the fixation point may instead be locked to the interface location at which stimulus 3506b is displayed on user interface 3502, and the portion of the user's visual field corresponding to the top right hand corner of visual field map 3504 may be tested by displaying stimuli at different locations of user interface 3502 while the fixation point remains locked at the interface location of stimulus 3506b.

In some embodiment, one or more interface locations of a user interface may be predesignated to be a fixation point relative to which a user's visual field is tested. As an example, where the four corners of a user interface are predesignated to each be a fixation point during a visual test presentation, testing subsystem 122 may initially cause a stimulus to be displayed at the center of the user interface so that the user will initially fixate on the center stimulus (e.g., the initial fixation point). Testing subsystem 122 may then cause a stimulus to be displayed at the top right-hand corner of the user interface and, upon detecting that the user sees the top right stimulus (e.g., based on eye characteristics of the user), adjust and lock the fixation point to the top right-hand corner of the user interface. Testing subsystem 122 may subsequently test a portion of the user's visual field by causing stimuli to be displayed at different locations of on the user interface while the fixation point remains locked. In one use case, if the user interface is represented by user interface 3502 of FIG. 35A, and the user's visual field is represented by visual field map 3504 of FIG. 35A, by displaying the stimuli at different locations of the user interface while the fixation point remains locked to the top right-hand corner, the portion of the user's visual field corresponding to the bottom left-hand quarter of visual field map 3504 may be thoroughly tested. The foregoing process may then be repeated for the other corners of the user interface to test the portions of the user's visual field corresponding to the other parts of visual field map 3504.

In some embodiments, while a fixation point remains at a first interface location on a user interface (at which a first stimulus is displayed), testing subsystem 122 may cause multiple stimuli to be displayed and then deemphasized on or removed from the user interface while the first stimulus continues to be displayed at the first interface location on the user interface. As an example, where the first interface location is the top right-hand corner of the user interface, the first stimulus may continue to be displayed while a series of other stimuli are momentarily displayed on the user interface. As such, the visual change occurring at another interface location (from another stimulus appearing at that other interface location) will cause the user to look at the source of the visual change if the other interface location does not correspond to a defective portion of the user's visual field (e.g., a blind spot of the user's visual field). However, when the other stimulus disappears, the user will fixate back on the top right-hand corner because the first stimulus will be the primary (or only) source of visual simulation for the eye of the user.

In some embodiments, while a fixation point remains at a first interface location on a user interface (at which a first stimulus is displayed), testing subsystem 122 may cause the first stimulus to be deemphasized on or removed from the user interface and then emphasized or redisplayed at the first interface location on the user interface. In some embodiments, while the fixation point remains at the first interface location, testing subsystem 122 may cause multiple stimuli to be displayed on the user interface and, subsequent to the display of at least one stimulus of the multiple stimuli, cause the first stimulus to be emphasized or redisplayed at the first interface location on the user interface. In one use case, if the brightness of the first stimulus was decreased, the brightness of the first stimulus may be increased so that the eye of the user will detect the visual change (and the increased visual stimulation) and fixate back on the first interface location at which the first stimulus is displayed on the user interface. In another use case, if the first stimulus was removed from the user interface, the redisplay of the first stimulus will likewise cause the eye of the user to fixate back on the first interface location on the user interface.

In some embodiments, one or more portions of the process shown in FIG. 35F may be used to facilitate a visual test presentation using a dynamic fixation point. With respect to FIG. 35F, in operation 3522, a matrix of possible stimuli (e.g., all possible stimuli) in a visual field of a user is created or obtained. In operation 3524, an eye tracking device is used to lock a floating fixation point is locked to the center of the visual field. As an example, the eye coordinates obtained from the eye tracking device may be used to "float" the floating fixation point around with the eye. In operation 3526, the available stimuli of the matrix may be ranked (e.g., so that the farthest point from the floating fixed point is first). As an example, stimuli corresponding to locations of the user interface view that are at least as far from the fixation point as all other locations on the user interface (that correspond to an available stimulus of the matrix) may be ranked ahead of all the other available stimuli (or ranked with equal priority as other stimuli that are of equal distance from the floating fixation point). As an example, the ranking may be performed in real-time using the eye tracking device (e.g., pupil or eye tracker or other eye tracking device).

In operation 3528, subsequent to the ranking, the first stimulus on the ranking list (e.g., the stimulus with the highest priority) may the next stimulus to be displayed during the visual test presentation. As an example, the stimulus may be displayed in a color that highly contrasts with the background (e.g., the stimulus color may be black to contrast a black background). In operation 3530, eye movement vectors (or other representation of eye-related characteristics) may be consistently measured using the eye tracking device. If eye movement is not detected to be toward the stimulus (operation 3532), then, in operation 3534, the stimulus is counted as not being seen and will be removed from the matrix of available stimuli. Operations 3528-3530 will be repeated with the current highest ranked stimulus on the ranking list (that is in the matrix of available stimuli).

If eye movement is detected to be toward the stimulus (operation 3536) (e.g., thereby, indicating that the user senses the stimulus), then, in operation 3538, the stimulus is counted as being seen (qualitatively), and the stimulus disappears from the user interface. In operations 3540a-3540d, the visual test presentation may test the extent to which the user can sense a stimulus in the particular area of the visual field. As an example, in operation 3540*a*, the stimulus appears back in a color shade (e.g., grey shade) that gets darker every time this operation is executed. In one use case, the stimulus may initially appear back in a color that is similar to the background color (e.g., the stimulus color may initially be a light grey color when the background color is white). In operation 3540*b*, eye movement vectors (or other representation of eye-related characteristics) may be constantly measured using the eye tracking device. If eye movement is not detected to be toward the stimulus (operation 3540*c*), then the operations 3540*a* and 3540*b* will be repeated (e.g., with a darker color shade to further contrast the white background color). If eye movement is detected to be toward the stimulus, the sensitively of vision is indicated for the particular area of the visual field based on the degree of the color shade (e.g., the degree of the grey shade) of the displayed stimulus (operation 3542).

In operation 3544, the eye tracking/floating fixation point lock is released (e.g., to allow the user to catch the stimulus). In operation 3546, the eye tracking/floating fixation point lock is reinstated (e.g., based on where the user is currently looking). As an example, if the user has "caught" the stimulus (and is still looking at the stimulus), the location of the stimulus becomes the new floating fixation point. In operation 3548, the stimulus is removed from the matrix of available stimuli, and the process repeats with operation 3526 with respect to the other available stimulus of the matrix.

Figure 35G:
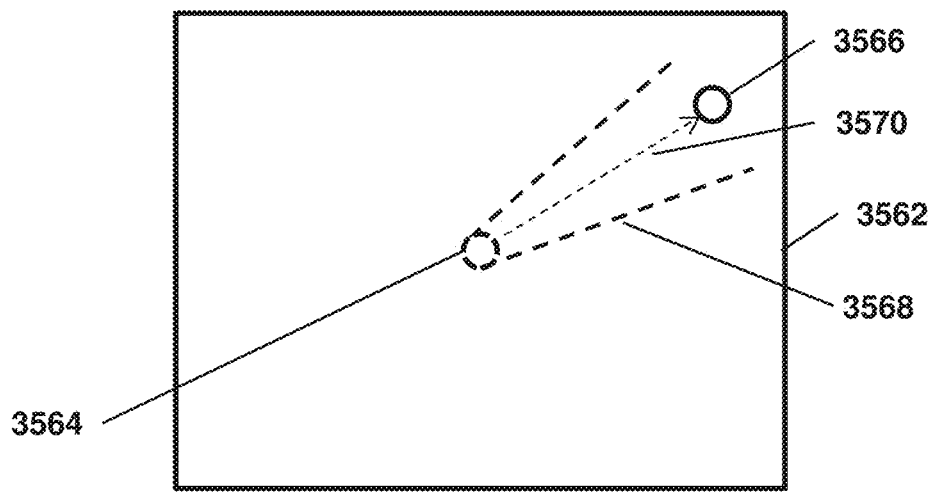
FIG. 35G-35I illustrate vision testing involving monitoring of whether eye movement remains within or occurs outside a bounding structure or region when a stimulus is presented, in accordance with one or more embodiments.

In some embodiments, testing subsystem 122 may determine or confirm that a user sees a stimulus (and, thus, has vision in a corresponding visual field location) on a user interface based on a determination that the user's eye movement is an intentional movement toward the stimulus. In some embodiments, one or more bounding boxes or other structures defining a region of a user interface may be used to determine or confirm that a user can see a stimulus. In some embodiments, the defined region may be a region within which a user's eye (e.g., the user's gaze direction) must remain while moving toward a displayed stimulus. In some embodiments, the defined region may be a region between lines equal to or less than a certain number of degrees (e.g., 35 degrees, 30 degrees, 25 degrees, 20 degrees, 15 degrees, 10 degrees, or other number of degrees) away from a straight, direct path from the fixation point to the stimulus. As an example, if testing subsystem 122 determines that the user's eye movement remained within the defined region when the stimulus is displayed until the user's eye has reached the particular location of the user interface at which the stimulus is displayed, such determination may be used as a confirmation that the user actually saw the stimulus. In one use case, with respect to FIG. 35G, when the user's eye is viewing user interface 3562 and fixated at fixation point 3564, stimulus 3566 may be presented near the top-right corner of user interface 3562. If the user's eye movement stays within region 3568 (e.g., between the boundary lines forming a cone-shaped boundary structure) until the eye reaches the location of the user interface at which stimulus 3566 is presented (e.g., as shown by gaze travel 3570), testing subsystem 122 may determine with high accuracy that the user actually saw stimulus 3566. In this way, for example, the amount of time required to detect that the user has seen may be significantly reduced via use of such determination. For example, the use of eye trackers typically requires additional confirmation time (e.g., ~400 ms for a 30 Hz eye tracker) to detect that an eye is fixating on a stimulus position. Through the use of such a bounding structure (or such region defined by the bounding structure), the foregoing additional confirmation time may be eliminated for each stimulus to be tested.

In addition, eye trackers are generally more accurate for tracking eye movement or fixation in a central region (e.g., the macular region of the user's visual field), but less accurate for tracking eye movements or fixation in the periphery. Thus, in some embodiments, such technical deficiencies of eye trackers with respect to tracking peripheral eye movements or fixation may be overcome via the foregoing use of the defined region. As indicated above, if testing subsystem 122 determines that user's eye movement remained within the defined region when the stimulus is displayed until the eye tracker has detected that the user's eye has reached the particular location of the user interface at which the stimulus is displayed, such determination may be used as a confirmation that the user actually saw the stimulus. In this way, for example, despite the greater error rate of eye trackers for tracking peripheral eye fixation, the confirmation from the foregoing determination may be used to decrease such errors.

Figure 35H:
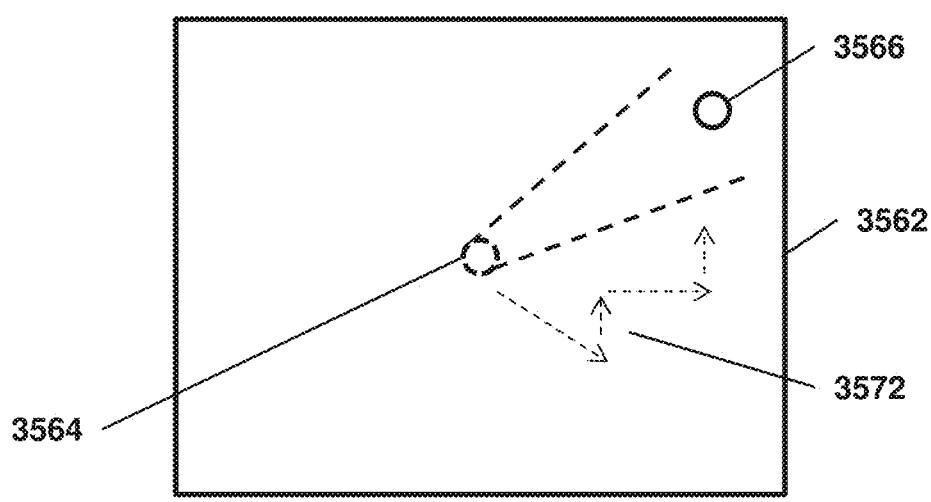

As another example, if testing subsystem 122 determines that the user's eye moved outside of a defined region (e.g., defined by a bounding structure) when a stimulus was displayed, such determination may be used to retest the particular location of the user interface at which the stimulus was displayed, invalidate an initial determination that the user can see the displayed stimulus at the particular location, or indicate that the user cannot see the displayed stimulus at the particular location. In one use case, with respect to FIG. 35H, when the user's eye is viewing user interface 3562 and fixated at fixation point 3564, the user may not see stimulus 3566 when it is presented near the top-right corner of user interface 3562 (e.g., due to a visual field defect at the corresponding location of the user's visual field). Because the user does not see stimulus 3566, the user's eye may start to wonder around. In some cases, however, by wondering around, the user's eye may unintentionally land on stimulus 3566, which may cause a typical vision testing system to determine that the user can see stimulus 3566. However, in this case, because the user's eye movement went outside of region 3568 (e.g., as shown by gaze travel 3572), testing subsystem 122 may determine that the user did not see stimulus 3566 or retest the corresponding location (e.g., by increasing the contrast level or adjusting another characteristic of stimulus 3566 at another time during the visual test) even if the user's eye eventually lands on stimulus 3566.

Figure 35I:
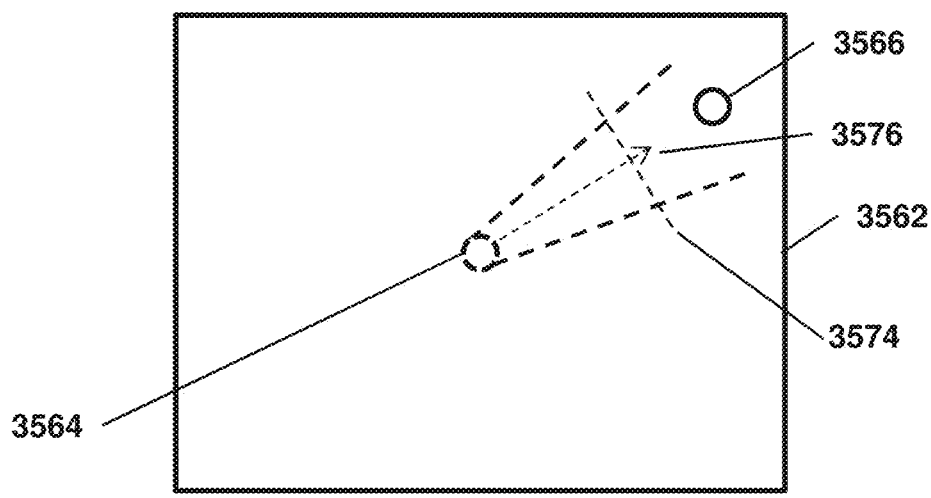

In some embodiments, testing subsystem 122 may determine or confirm that a user can see a stimulus based on a determination that the user's eye remained within a defined region (e.g., defined by a bounding structure) when the stimulus is displayed until the user's eye has moved at least a threshold distance toward the stimulus (or toward the location of the user interface at which the stimulus is displayed). As an example, with respect to FIG. 35I, when the user's eye is fixated at fixation point 3564, stimulus 3566 may be presented near the top-right corner of user interface 3562. If the user's eye movement stays within region 3568 (e.g., between the boundary lines forming a cone-shaped boundary structure) until the eye passes line 3574 (e.g., as shown by gaze travel 3576), testing subsystem 122 may determine that the user's eye movement was an intentional movement toward stimulus 3566 (and, thus, that the user saw stimulus 3566). As an example, line 3574 may represent 60% of the distance between the fixation point and location of the user interface at which stimulus 3566 is presented or other percentage of such distance (e.g., 50%, 70%, 80%, 90%, etc.). In this way, for example, the amount of time required to detect that the user has seen a stimulus may further be reduced via use of such determination. For example, the wait time for the eye movement may be ~200-400 ms (e.g., depending on how peripheral the stimulus is). Through the use of such a bounding structure (or such region defined by the bounding structure), accurate detection may be achieved without waiting for the eye to land on each stimulus, thereby reducing the wait time because the eye would not need to travel all the way to the location at which the stimulus is presented. Once it is determined that the eye movement is an intentional movement toward the stimulus, the vision test may move on to testing one or more other locations.

In some embodiments, the location of a fixation point or the locations of the stimuli to be displayed to the user may be static during a visual test presentation. As an example, testing subsystem 122 may display a stimulus in the center of the user interface (or the location corresponding to the static fixation point) to cause the user to look at the center of the user interface (or other such location corresponding to the static fixation point). Once the user is detected as looking at the static fixation point location, testing subsystem 122 may display the next stimulus of a set of stimuli for testing one or more areas of the user's visual field. Each time that the user is detected as not looking at the static fixation point location, testing subsystem 122 may repeat the display of a stimulus at the static fixation point location.

Figure 35J:
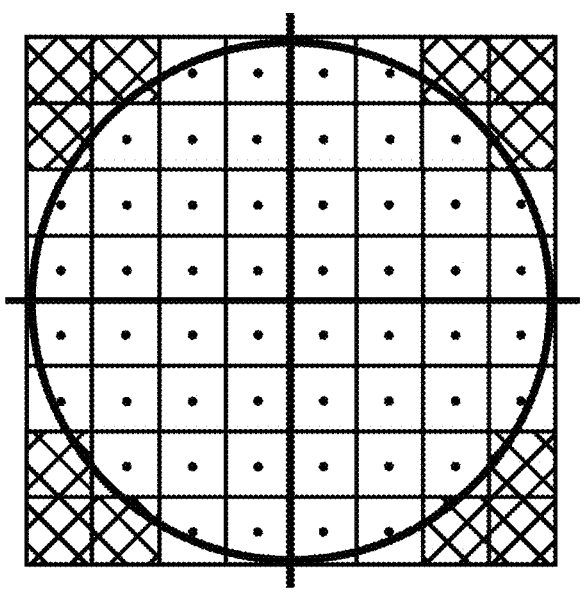
FIG. 35J illustrates a visual test presentation including multiple contrast staircase stimuli and stimuli sequences at predetermined locations, in accordance with one or more embodiments.

As another example, with respect to FIG. 35J, a visual test presentation applying a fast thresholding strategy may utilize four contrasting staircase stimuli covering the central 40 degrees' radius using 52 stimuli sequences at predetermined locations. In other examples, different numbers of contrast stimuli, coverage, and stimuli locations may be used. In this example, the stimuli was located at the center of each cell shown in the FIG. 35J. The twelve corner cells, where the stimuli are not visible because of the circular display's lens, were not tested. The spacing between each stimulus location was approximately 10 degrees apart. Each stimuli sequence contained four consecutive stimuli at different contrast levels with respect to the background. Stimuli contrast ranged between 33 dB down to 24 dB in steps of 3 dB in a descending order between each contrast level. Threshold values were recorded at the last seen stimulus. If the patient did not see any stimulus contrast at a specific location, the location is marked unseen and was given a value of 0 dB.

The background had a bright illumination (100 lux) while the stimuli were dark dots with different contrast degrees. Therefore, the test was a photopic test rather than a mesopic one. In some embodiments, the background may be dark, and the stimuli may comprise bright illumination dots. Each stimulus was presented for a time period of approximately 250 msec, followed by a response waiting time period of approximately 300 msec. These time periods were also made adjustable through a control program according to the subject's response speed, which, for example, may be adjusted prior to testing based on pre-test demonstration or dynamically during testing. Generally, a stimulus size of 0.44 degrees was used at the central 24 degrees' radius, which is equivalent to the standard Goldmann stimulus size III. The stimulus size at the periphery (between 24 and 40 degrees' radius) was doubled to be 0.88 degrees. The purpose of doubling the stimulus size in the peripheral vision was to overcome the degraded display lens performance at the periphery. This lens degradation effect was significant, as the normal human vision's acuity even deteriorates at the peripheral regions. The testing program also had the ability for the stimulus size to be changed for the different patient cases.

The fixation target (pattern) of FIG. 35J was located in the center of the screen for each eye tested. This target was designed as a multicolor point, rather than a unicolor fixation point as routinely used in the traditional Humphrey tests. This color changing effect helped grab the attention of the subject and made target focusing easier for them. The frequency of the color changes was asynchronous with the stimulus appearance, so that the subject would not relate both events together and falsely responds. The testing protocol also had the ability for the fixation target size to be changed according to the patient's condition. In addition, the eye/pupil tracking system may be used to check the subject's eye fixation at different time intervals. The eye tracking system transmits to the testing program the gaze vectors' direction, which informs the program if the subject is properly focused to the center or not.

Fixation checks were performed using the pupil/gaze data for each eye individually. Pupil/gaze data were acquired at different time instances and, if the gaze direction vectors were at approximately 0 degrees, then the subject is focusing on the center target, otherwise the program would pause waiting for fixation to restored. If the patient were out of fixation, no stimulus was shown and the test was halted until the participant gets back in fixation. Offset tolerance was allowed for minor eye movements at the fixation target. Fixation checks were performed for each stimuli's location at mainly two time events; before showing each stimulus in the stimuli sequence (e.g., prior to each stimulus contrast level of the four levels mentioned earlier), and before recording a response, whether the response was positive (e.g., patient saw the stimulus) or negative (e.g., patient did not see the stimulus). Negative responses were recorded at the end of the stimuli sequence interval in addition to the allowed response time. Checking fixation before showing the stimuli sequence was to ensure the patient was focusing on the fixation target. If the subjects were out of fixation, no stimulus was shown, and the test was halted until the participant gets back in fixation.

Figure 36:
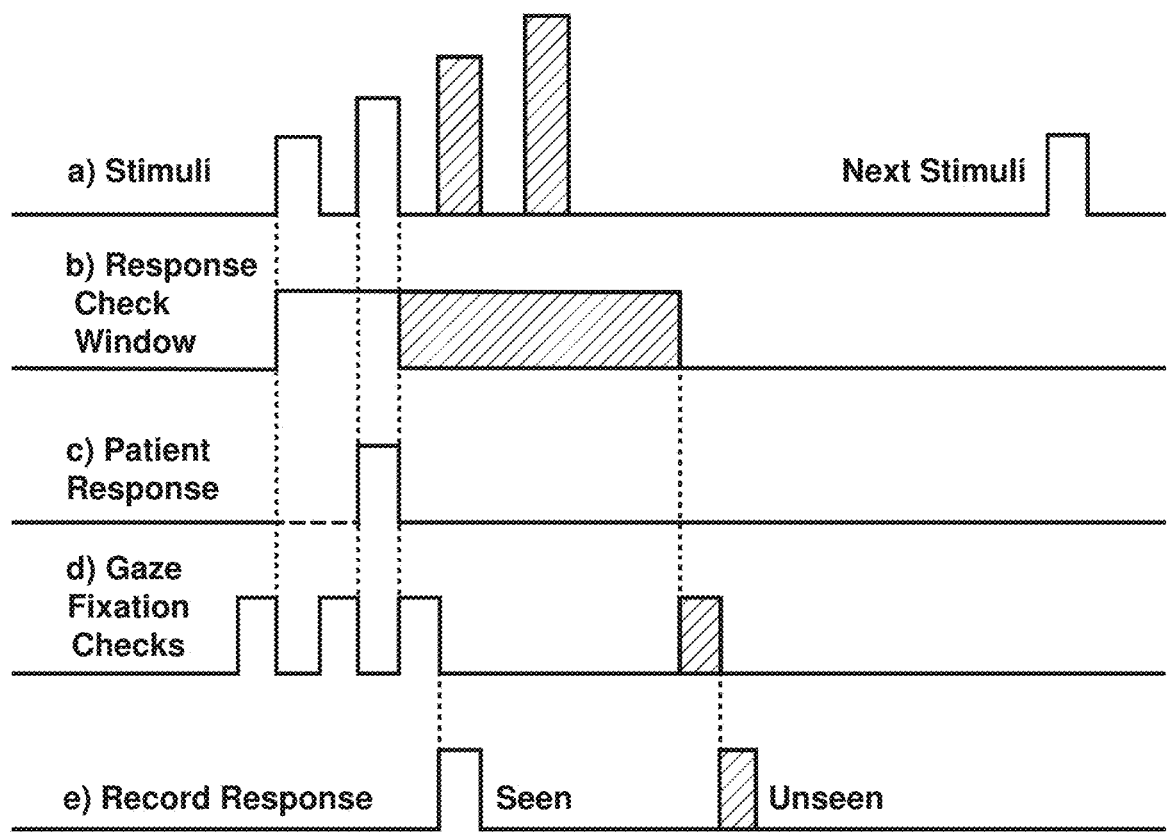
FIG. 36 illustrates a timing diagram showing operations of a testing sequence at one stimulus location, in accordance with one or more embodiments.

FIG. 36 shows a timing diagram showing operations of a testing sequence at one stimulus location. In one example, a pupil tracking device, which may be separate or a component of a vision system or device thereof, may include inward directed image sensors and be configured to provide data instructing the image display device, which may include a projector, to change the location of the stimulus being projected according to line of sight movement. In this way, even if the subject is looking around and not fixating, the stimuli may move with the eyes of the subject and will continue testing the desired location of the visual field. Therefore, rather than halting the stimuli sequence when the subject is determined to be focused outside of the fixation target, the stimuli sequence may continue with a modification of the stimuli to correspond with the intended location within the subject's visual field within the sequences as repositioned based on a determination of the subject's current fixation point.

For each subject, the visual field test started by orienting the subject of how the test goes. The spectacles device was fitted on the patient to ensure that the subject could see the fixation target clearly, and if necessary, target size was adjusted accordingly. Eye tracking calibration was performed at one point, the fixation target. Following that, a demonstration mode was presented to the subject. This mode follows the same sequence as the main test, but with only fewer locations, seven locations in this instance, and without recording any responses. The purpose of this mode was to train the subject on the test. Additionally, this training mode helps the program operator to check for the eye tracking system accuracy, patient response speed, and the patient eye's location with respect to the mounted headset, to make sure that no error or deviation would occur during the full test.

Normal blind spots were then scanned for, by showing suprathreshold stimuli at four different locations spaced by 1 degree in the 15-degree vicinity. This step was beneficial to avoid rotational misfits between the headset and the subject's eyes.

Next, the 52 stimuli sequences were presented to the patient at the pre-specified locations with random order. The subject indicated responses by either actuating an electronic clicker or gesturing in response to a stimuli. After recording the subject's responses at all locations, the "unseen" points' locations were temporarily stored. A search algorithm was then employed to find the locations of all "seen" points on the perimeter of the "unseen" points' locations. Those two sets of points were then retested, to eliminate random response errors by the participant, and ensure continuity of the visual field regions. False positive responses, false negative responses and fixation losses (if any) were calculated and reported by the end of the test. Consequently, all the 52 responses were interpolated using a cubic method to generate a continuous visual field plot of the tested participant.

The visual field test was tried on 20 volunteer subjects using simulated field defects, by covering parts of the inner display lens of the spectacles device. The results were assessed on point by point comparison basis with an image showing the covered areas of the display. The 52 responses were compared at the approximate corresponding locations in the covered headset's display image, as a measure of testing accuracy. Summary of the calculated errors are listed in Table 1.

TABLE 1

Error calculations for the 20 cases simulated defects visual field measurements.

|  | Left Eyes | | Right Eyes | | Total Error | |
| --- | --- | --- | --- | --- | --- | --- |
|  | Mean | SD | Mean | SD | Mean | SD |
| Error Points | 1.600 | 1.698 | 1.500 | 1.396 | 1.550 | 1.535 |
| Error Percentage | 3.137% | 3.329% | 2.941% | 2.736% | 3.039% | 3.009% |

On the other hand, visual field tests for the 23 clinical patients were compared with the most recent Humphrey Field Analyzer (HFA) test routinely made by the subject during their visits. The common 24 degrees central areas were matched and compared between the two field testing devices. The comparison and relative error calculations were based again on a point by point basis at the common central 24 degrees areas, where areas beyond this region were judged through continuity with the central area and lack of isolated response points. Summary of the calculated errors are listed in table 2.

TABLE 2

Error calculations for 23 patients visual field measurements.

|  | Left Eyes | | Right Eyes | | Total Error | |
| --- | --- | --- | --- | --- | --- | --- |
|  | Mean | SD | Mean | SD | Mean | SD |
| Error Points | 3.059 | 2.277 | 3.063 | 2.061 | 3.061 | 2.120 |
| Error Percentage | 7.647% | 5.692% | 7.656% | 5.039% | 7.652% | 5.301% |

An image remapping process was then performed, which involved finding new dimensions and a new center for the displayed images to be shown to the patient. The output image fits in the bright visual field of a subject's eye by resizing and shifting the original input image.

The visual field was binarized by setting all seen patient responses to ones, and keeping the unseen responses to zeros, this resulted in a small binary image of 8×8 size. In other embodiments, smaller or larger binary images sizes may be used. Small regions containing at most 4 connected pixels, were removed from the binary visual field image. The 4 connected pixels represented a predetermined threshold value for determination of small regions, although larger or smaller threshold values may be used in some embodiments. Those small regions were not considered in the image fitting process. The ignored small regions represent either the normal blind spots, insignificant defects, or any random erroneous responses that might have occurred during the subject's visual field test.

Based on this interpolated binary field image, the bright field's region properties were calculated. Calculated properties for the bright regions included: 1) bright areas in units of pixels, 2) regions' bounding box, 3) weighted area centroid, and 4) a list of all pixels constituting the bright regions of the visual field. A bounding box was taken as the smallest rectangle enclosing all pixels constituting the bright region. A region's centroid was calculated as the center of mass of that region calculated in terms of horizontal and vertical coordinates. The values of this property correspond to the output image's new center, which corresponds to an amount of image shift required for mapping.

Figure 37:
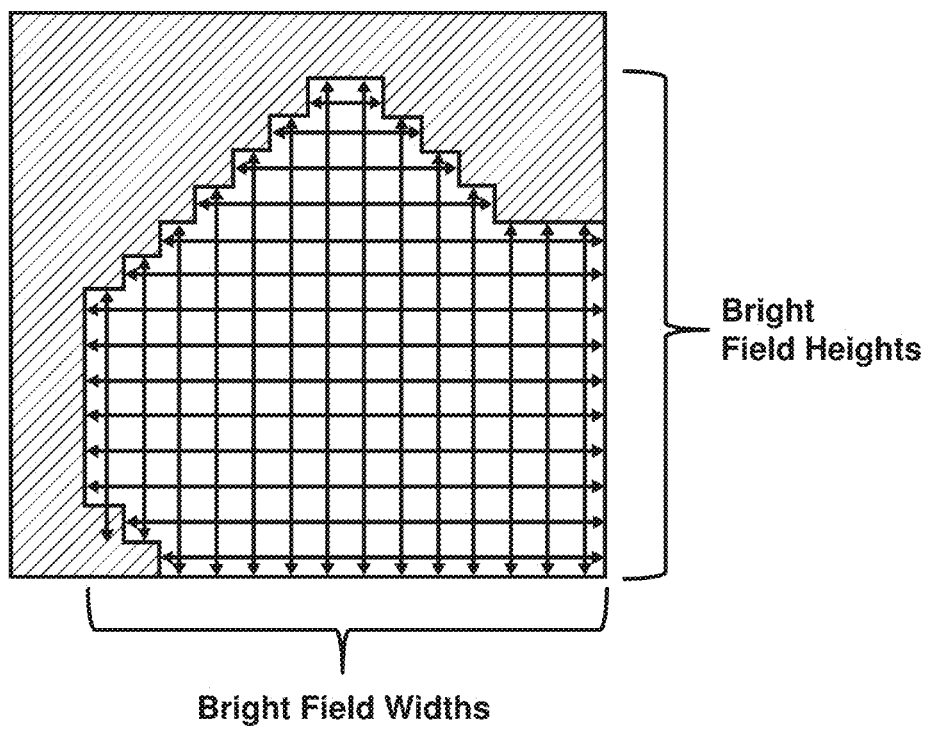
FIG. 37 illustrates calculation of widths and heights of pixels bounding the largest bright field, in accordance with one or more embodiments.

Using a list of pixels constituting the largest bright field, the widths and heights of all pixels bounding the bright field were calculated, as shown in FIG. 37. For each row in the bright field, the two bounding pixels were found, and their vertical coordinates were subtracted to get the field's width $BF_{widths}$ at that specific row. This width calculation was iterated for all rows establishing the considered bright field to calculate $BF_{widths}$. The same iteration process may be applied on a column basis to calculate $BF_{heights}$. Afterwards, either one of two scaling equations may be used to determine the new size of the mapped output image; $Width_{map}$ and $Height_{map}$, as shown in FIG. 37.

The $Width_{map}$ may be calculated using resizing equation:

$$Width_{map1} = \frac{median(BF_{widths})}{50},$$

$$Height_{map1} = median(BF_{hegiths}),$$

where $BF_{widths}$ and $BF_{heights}$ are the calculated bright field's bounding pixels' widths and heights, respectively. This scaling method calculates the new output image size as the median of the bright visual field size in each direction, centered at the new image center, found as above. The median measure was used rather than the mean value, to avoid any resizing skewness related to exceedingly large or small bright field dimensions. The mapping behavior of this method is to fit images within the largest possible bright area, but image stretching or squeezing could occur, as this method does not preserve the aspect ratio.

The $Height_{map}$ may be calculated using resizing equation:

$$Width_{map2} = \frac{\sum BF_{widths}}{Isize^2} \times BX_{Width},$$

$$Height_{map2} = \frac{\sum BF_{heights}}{Isize^2} \times BX_{height},$$

where $I_{size}$ is the interpolated image size (output image size), $BX_{widths}$, $BX_{heights}$ are the bounding box width and height. The summations in the numerators of the equation approximate the bright field area calculated with respect to the horizontal and vertical directions, respectively. Therefore, dividing those summations by the square of the output image's size provided an estimate of the proportional image areas to be mapped in each direction. These proportions are then multiplied by the corresponding bounding box dimension that was previously calculated. The mapping behavior of this method is to fit images in the largest bright visual field while trying to preserve the output image's aspect ratio. Incorporating the bounding box's dimensions into the calculations helped this effect to happen. Yet, preservation of the aspect ratio may not result in all defective visual field patterns.

In one embodiment, the AI system may utilize the two equations and tens if not hundreds of the different equations in a process of optimization to see which one will allow fitting more of the seeing visual field with the image. Based on the feedback of the operators the system may learn to prefer an equation more than the others based on the specific visual field to be corrected.

Figure 38:
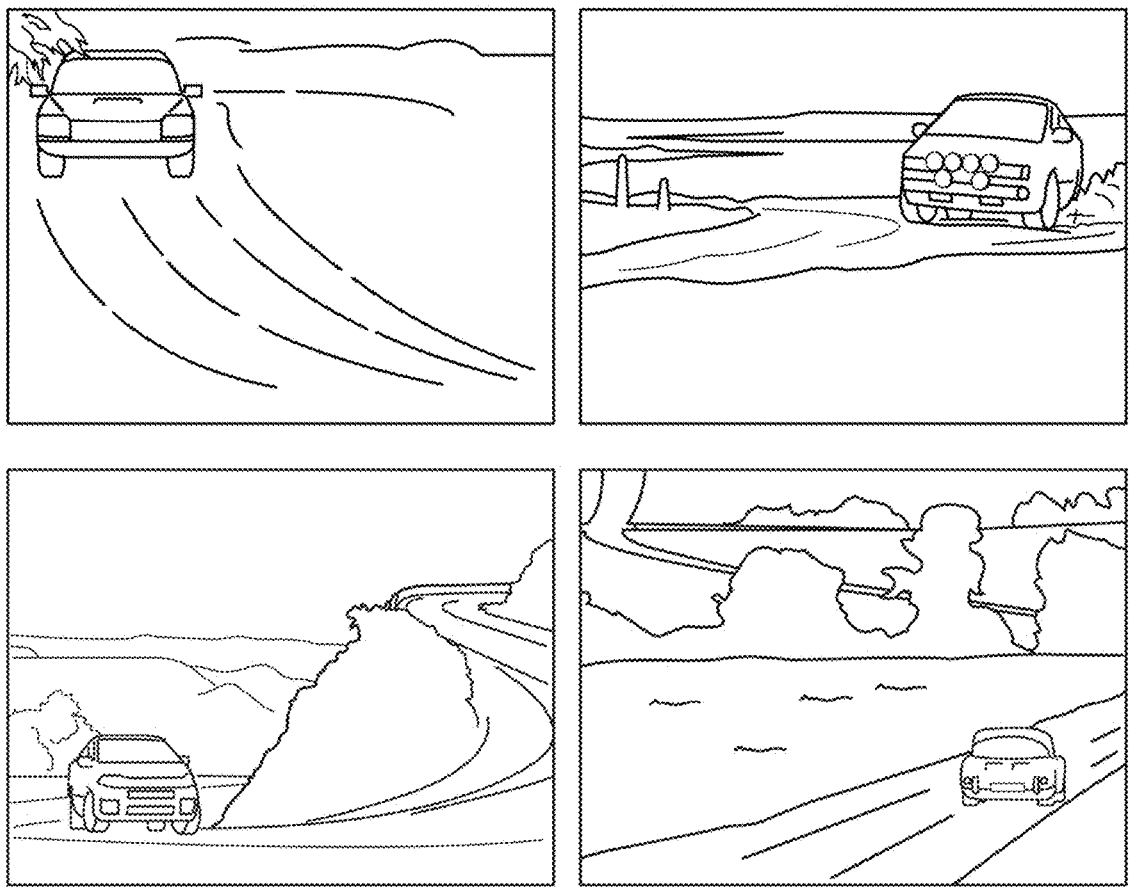
FIG. 38 illustrate test images used to test four main quadrants of a visual field, in accordance with one or more embodiments.
Figure 39A:
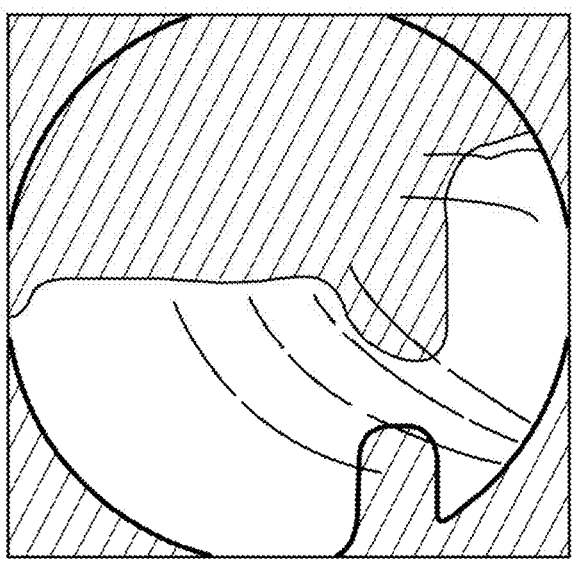
FIG. 39A illustrates an example visual field view prior to remapping, in accordance with one or more embodiments.
Figure 39B:
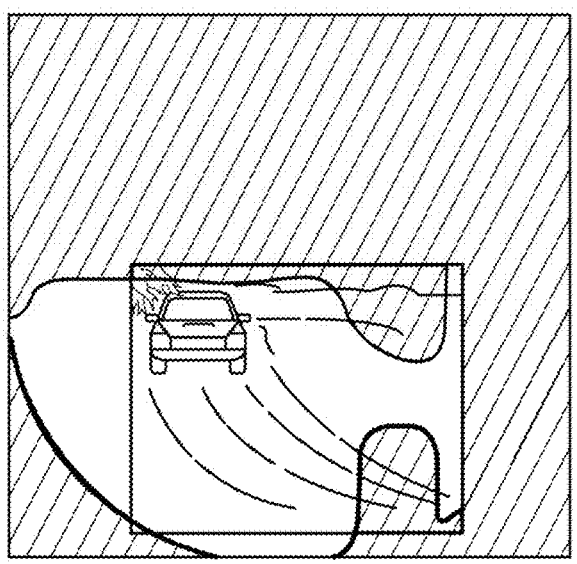
FIG. 39B illustrates an example visual field view following remapping, in accordance with one or more embodiments.

These remapping techniques were used in an identifying hazardous objects test. The remapping methods were tested on 23 subjects using test images that included a safety hazard, a vehicle in this test. The test images were chosen to test the four main quadrants of the visual field, as shown in FIG. 38. A visual field example was used to remap the test images for display to the subject. The subject was tested by showing an image of an incoming car. The subject could not see the car before being shown the remapped image, as shown in FIG. 39A illustrating the image as seen by the subject without remapping and in FIG. 39B illustrating the image as seen after remapping. Our preliminary study demonstrated that 78% subjects (18 out of 23) were able to identify safety hazards that they could not do without our aid. Some subjects were tested on both eyes individually, so 33 eye tests were available. It was found that in 23 out of 33 eyes the visual aid was effective in helping the subject identify the simulated incoming hazard (P=0.023).

As indicated, in some embodiments, with respect to FIG. 1A, testing subsystem 122 may determine one or more defective visual field portions of a visual field of a user based on a response of the user's eyes to a set of stimuli displayed to the user or lack of response of the user's eyes to the set of stimuli (e.g., eye movement response, pupil size response, etc.). In some embodiments, one or more moving stimuli may be dynamically displayed to the user as part of a visual test presentation, and the responses or lack of responses to a stimulus may be recorded and used to determine which part of the user's visual field is intact. As an example, in a kinetic part of the visual test presentation, recording of responses of a patient's eyes may begin after a stimulus is displayed in the visual test presentation and continues until the stimulus disappears (e.g., the stimulus may move from a starting point to a center point of the visual test presentation and then disappear). As another example, during the visual test presentation, the stimulus may be removed (e.g., disappear from the patient's view) when it is determined that the patient recognizes it (e.g., the patient's gaze direction changes to the current location of the stimulus). As such, the duration of the visual test presentation may be reduced and more interactive (e.g., the patient is provided with a feeling of playing a game rather than diagnosis of visual defects). Based on the foregoing indications (of responses or lack thereof to the set of stimuli), testing subsystem 122 may automatically determine the defective visual field portions of the user's visual field.

In some embodiments, testing subsystem 122 may determine one or more defective visual field portions of a visual field of a user, and visioning subsystem 124 may provide an enhanced image or cause an adjustment of one or more configurations of a wearable device based on the determination of the defective visual field portions. As an example, the enhanced image may be generated or displayed to the user such that one or more given portions of the enhanced image (e.g., a region of the enhanced image that corresponds to a macular region of the visual field of an eye of the user or to a region within the macular region of the eye) are outside of the defective visual field portion. As another example, a position, shape, or size of one or more display portions of the wearable device, a brightness, contrast, saturation, or sharpness level of such display portions, a transparency of such display portions, or other configuration of the wearable device may be adjusted based on the determined defective visual field portions.

Figure 4:
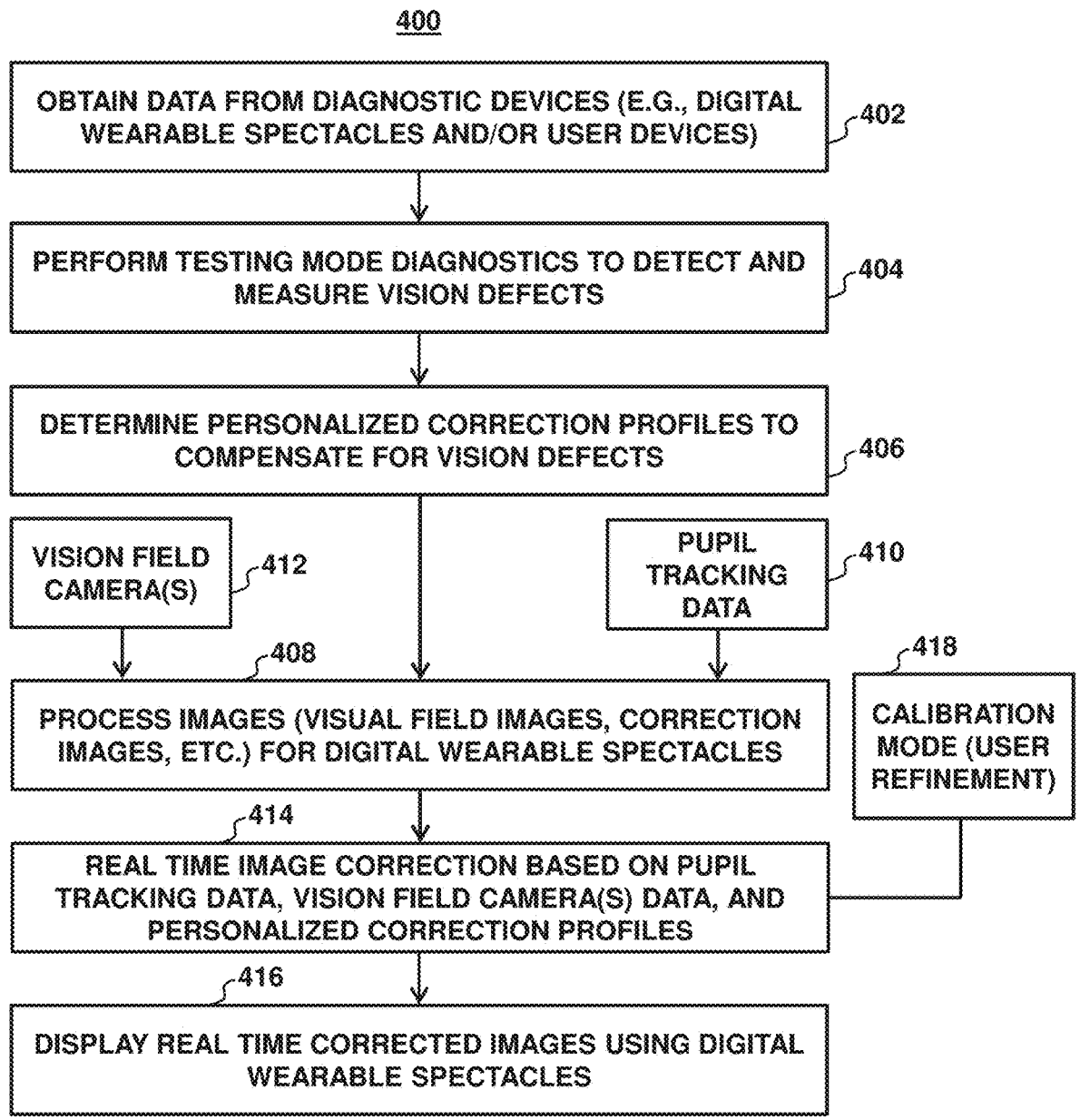
FIG. 4 illustrates an example process including a testing mode and a visioning mode, in accordance with one or more embodiments.

FIG. 4 illustrates a process 400 illustrating an example implementation of both a testing mode and a subsequent visioning mode. At a block 402, in a testing mode, data is obtained from diagnostic devices like image sensors embedded within spectacles device and other user input devices, such as a cellular phone or tablet PC. At a block 404, testing mode diagnostics may be performed to detect and measure ocular anomalies from the received data (e.g., visual field defects, eye misalignment, pupil movement and size, images of patterns reflected from the surface of the cornea or the retina, etc.). In an example, a control program and algorithms were implemented using MATLAB R2017b (MathWorks, Inc., Natick, Mass., USA). In various embodiments, a subject or tester may be provided with an option to select to test each eye individually, or test both eyes sequentially in one run. In some embodiments, the testing mode may include an applied fast thresholding strategy including contrast staircase stimuli covering central radius of 20 degrees or more using stimuli sequences at predetermined locations. As an example, the testing mode may include an applied fast thresholding strategy include four contrast staircase stimuli covering the central 40 degrees' radius using 52 stimuli sequences at predetermined locations, as discussed herein regarding FIGS. 35J and 36. As another example, the testing mode may include the automated determination of the visual defects (e.g., defective virtual field portions) based on one or more responses of the user's eyes to a set of stimuli displayed to the user or lack of such responses of the user's eyes to the set of stimuli (e.g., eye movement response, pupil size response, etc.) as described herein.

Figure 16:
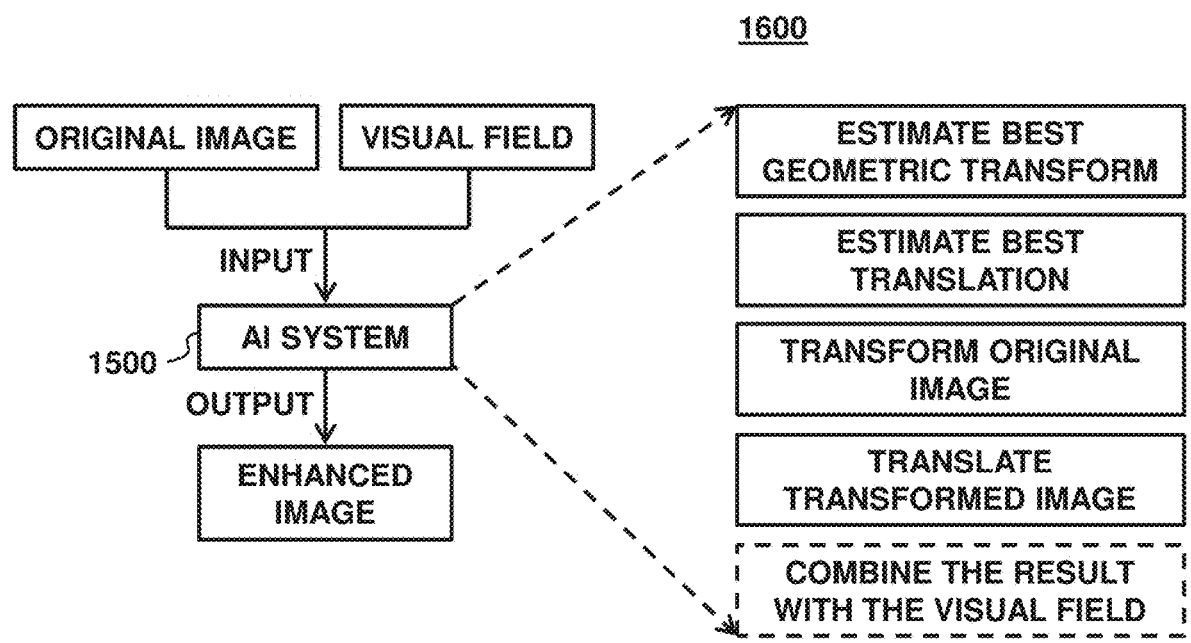
FIG. 16 illustrates a process of an AI system of a machine learning framework, in accordance with one or more embodiments.

At a block 406, the determined diagnostic data may be compared to a database or dataset that stores modification profiles for compensating for identifiable ocular pathologies (e.g., FIG. 16 and related discussions).

The identified modification profiles may then be personalized to the individual, for example, to compensate for differences in visual axis, visual field defects, light sensitivity, double vision, change in the size of the image between the two eyes, image distortions, decreased vision.

The personalized profiles may be used by a block 408, along with real-time data to process the images (e.g., using an image processor, scene processing module, and/or visioning module). The real-time data may include data detected by one or more inward directed image sensors 410, providing pupil tracking data, and/or from one or more outward directed image sensors comprising one or more visual field cameras 412 positioned to capture a visual field screen. At a block 414, real-time image correction may be performed and the images may be displayed (block 416) on the spectacles device, either as displayed recreated digital images, as augmented reality images passing through the spectacles device with corrected portions overlaid, or as images projected into the retinas of the subject. In some examples, the operation of block 414 is performed in combination with a calibration mode 418 in which the user can tune the image correction using a user interface such as an input device that allows a user to control image and modification profiles. For example, users can displace the image of one eye to the side, up and down or cyclotorted to alleviate double of vision. In the above or another example, a user may fine tune the degree of visual field transformation (e.g., fish eye, polynomial, or conformal) or translation to allow enlarging the field of vision without negatively impact the functional vision or cause unacceptable distortions, fine tune the brightness, and contrast, or invert colors.

Figure 5:
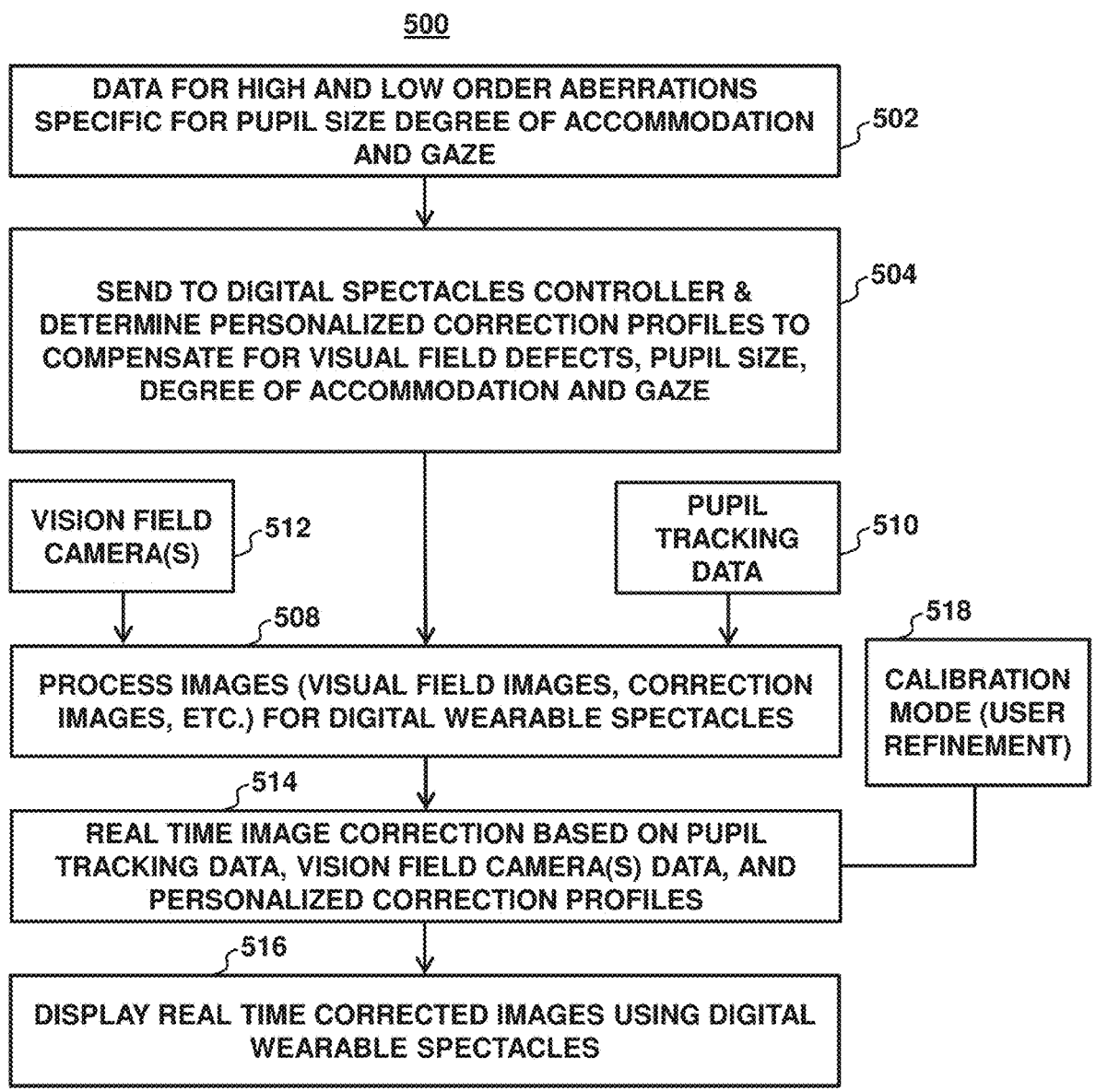
FIG. 5 illustrates an example process including a testing mode and a visioning mode, in accordance with one or more embodiments.

FIG. 5 illustrates another example process 500, similar to that of process 400, for implementation of a testing mode and visioning mode. At a block 502, data for high and low order aberrations for pupil size, degree of accommodation, and gaze, are collected. In some embodiments, all or a portion of the data may be collected from an aberrometer or by capturing the image of a pattern or grid projected on the cornea and/or retina and comparing it to the reference image to detect aberrations of the cornea or the total ocular optical system. The collected data may be sent to a vision correction framework, which, at a block 504, may determine personalized modification profiles similar to block 406 described above. Blocks 508-518 perform similar functions to corresponding blocks 408-418 in process 400.

Figure 8:
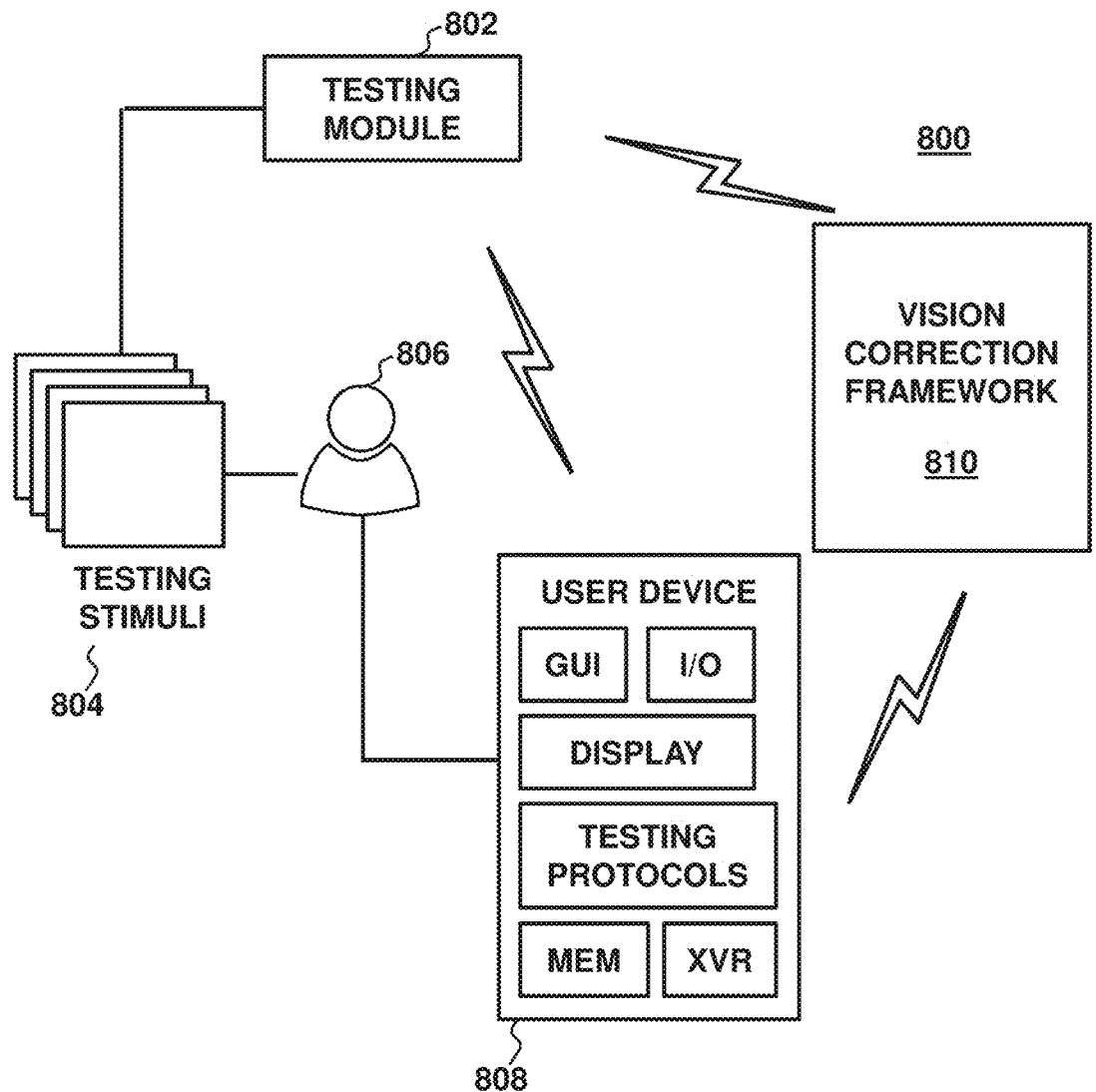
FIG. 8 illustrates a workflow including a testing module that generates and presents a plurality of visual stimuli to a user through a wearable spectacles device, in accordance with one or more embodiments.

FIG. 8 illustrates a workflow 800 showing a testing module 802 that generates and presents a plurality of visual stimuli 804 to a user 806 through the spectacles device. The user 806 has a user device 808 through which the user may interact to provide input response to the testing stimuli. In some examples, the user device 808 may comprise a joystick, electronic clicker, keyboard, mouse, gesture detector/motion sensor, computer, phone such as a smart phone, dedicated device, and/or a tablet PC through which that the user may interfaces to provide input response to the testing stimuli. The user device 808 may also include a processor and memory storing instructions that when executed by the processor generate display of a GUI for interaction by the user. The user device 808 may include a memory, a transceiver (XVR) for transmitting and receiving signals, and input/output interface for connecting wired or wirelessly with to a vision correction framework 810, which may be stored on an image processing device. The vision correction framework 810 may be stored on the spectacles device, on the user device, etc.—although in the illustrated example, the framework 810 is stored on an external image processing device. The framework 810 receives testing mode information from the testing module 802 and user input data from the user device 808.

Figure 9:
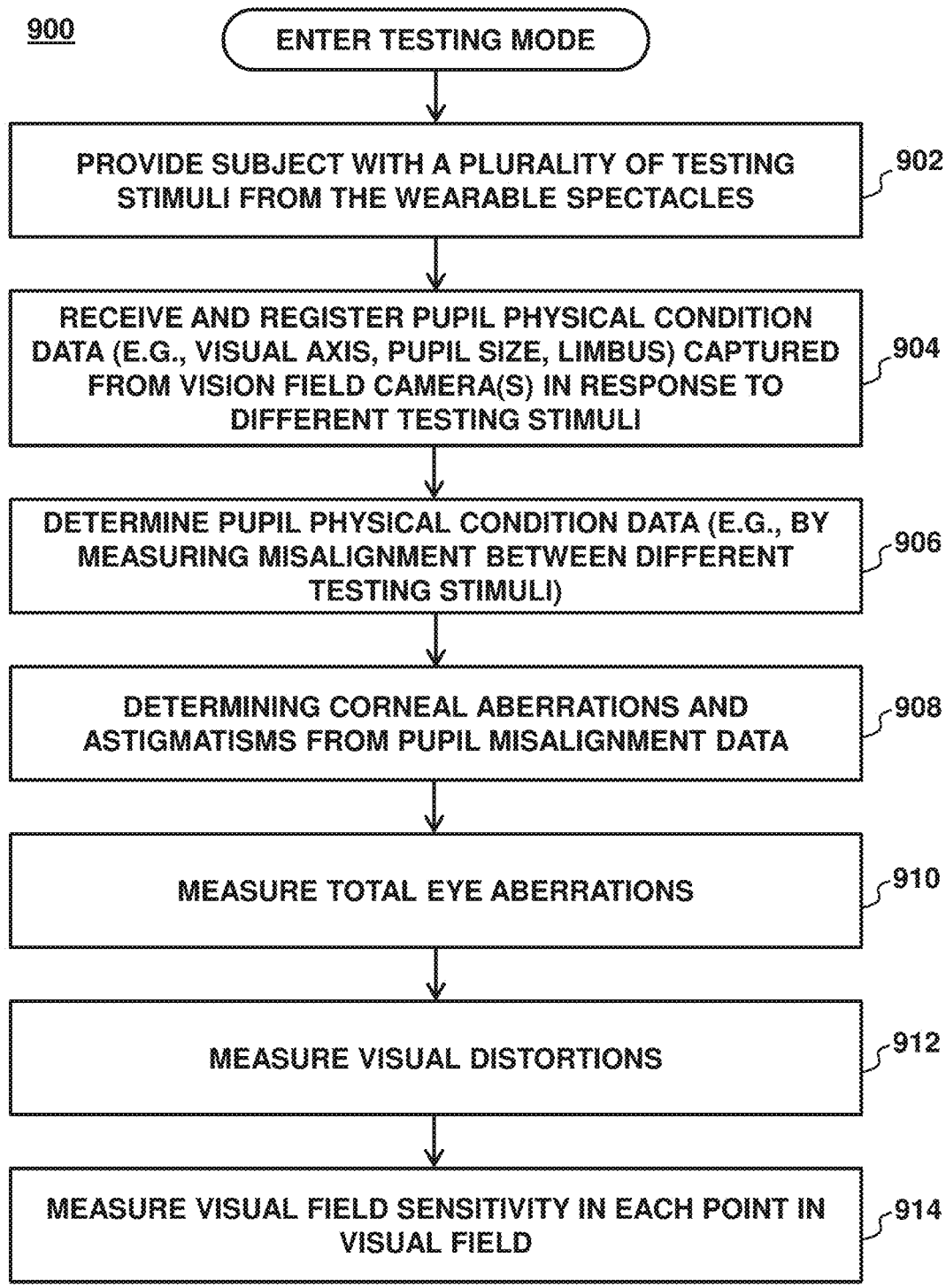
FIG. 9 illustrates a testing mode process, in accordance with one or more embodiments.

FIG. 9 illustrates a testing mode process 900, as may be performed by the workflow 800. At a block 902, a subject is provided a plurality of testing stimuli according to a testing mode protocol. That stimuli may include images of text, images of objects, flashes of light, patterns such as grid patterns. The stimuli may be displayed to the subject or projected onto the retina and/or cornea of the subject. At a block 904, a vision correction framework may receive detected data from one or more inward directed image sensors, such as data corresponding to a pupil physical condition (e.g., visual axis, pupil size, and/or limbus). The block 904 may further include receiving user response data collected from the user in response to the stimuli. At a block 906, the pupil position condition may be determined across different stimuli, for example, by measuring position differences and misalignment differences between different stimuli.

At a block 908, astigmatism determinations may be made throughout the field of vision, which may include analysis of pupil misalignment data and/or eye aberrations (e.g., projecting references images on the retina and cornea and comparing the reflected images from the retinal or corneal surfaces to reference images). At a block 910, total eye aberrations may be determined (e.g., by projecting reference images onto the retina and/or cornea and then comparing the reflected images from the retinal or corneal surfaces to reference images, such as described in FIGS. 31A, 32-34 and accompanying discussion). At a block 912, visual distortions, such as optical distortions such as coma, astigmatism, or spherical aberrations or visual distortions from retinal diseases, may be measured throughout the field of vision. At a block 914, the visual field sensitivity may be measured throughout the field of vision. In various embodiments of the process of FIG. 9, one or more of blocks 904-914 may be optional.

Figure 10:
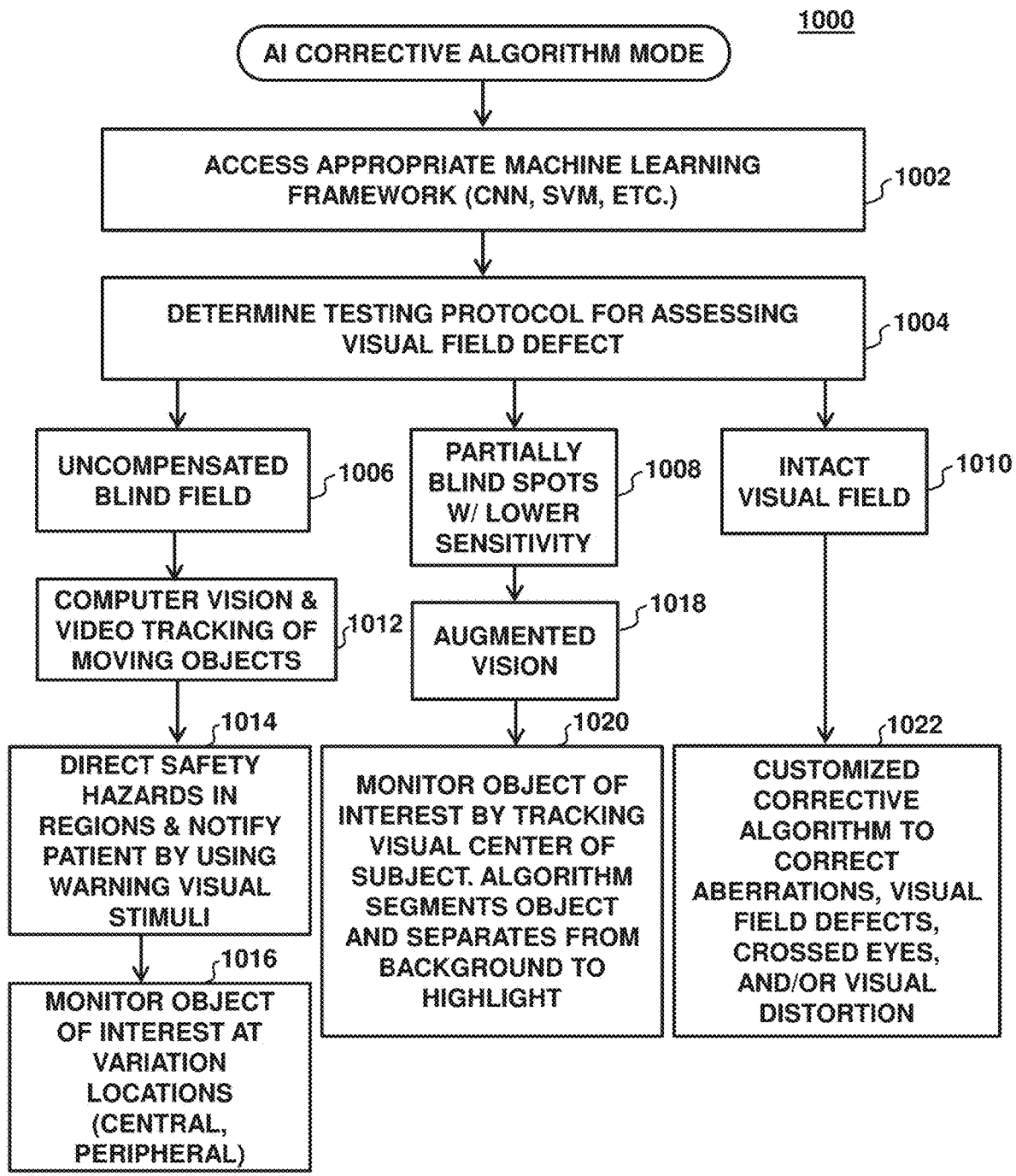
FIG. 10 illustrates a process for an artificial intelligence corrective algorithm mode that may be implemented as part of the testing mode, in accordance with one or more embodiments.

In some examples, the vision systems herein can assess the data from the testing mode and determine the type of ocular anomaly and the type of correction needed. For example, FIG. 10 illustrates a process 1000 comprising an artificial intelligence corrective algorithm mode that may be implemented as part of the testing mode. A machine learning framework is loaded at a block 1002, example frameworks may include, dimensionality reduction, ensemble learning, meta learning, reinforcement learning, supervised learning, Bayesian, decision tree algorithms, linear classifiers, unsupervised learning, artificial neural networks, association rule learning, hierarchical clustering, cluster analysis, deep learning, semi-supervised learning, etc.

At a block 1004, a visual field defect type is determined. Three example field defects are illustrated: uncompensated blind field 1006, a partially blind spot 1008 with lower sensitivity, and an intact visual field 1010. The block 1004 determines the visual field defect and then applies the appropriate correction protocol for the visioning mode. For example, for the uncompensated blind field 1006, at a block 1012, a vision correction framework tracks vision, such as through pupil tracking using inward directed image sensors and does video tracking of a moving object in the visual field (e.g., through outward directed image sensors such as external cameras). In the illustrated example, at a block 1014, safety hazards in regions of blind spots or that are moving into the regions of blind spots are detected by, for example, comparing the position of the safety hazard to a mapped visual field with defects as measured in the testing mode. At a block 1016, an object of interest may be monitored at various locations including a central location and a peripheral location.

In the example of a partially blind spot 1008, an augmented vision visioning mode may be entered at a block 1018, from which an object in the visual field is monitored by tracking a central portion of the visual field. At a block 1020, an image segmentation algorithm may be employed to separate the object from the visual field. An augmented outline may also be applied to the object and displayed to the user wherein the outline coincides with identified edges of the segmented object. With respect to the intact visual field 1010, at a block 1022, a customized corrective algorithm may be applied to correct aberrations, visual field defects, crossed eyes, and/or visual distortion.

In some embodiments, testing subsystem 122 may determine multiple modification profiles associated with a user (e.g., during a visual test presentation, while an enhanced presentation of live image data is being displayed to the user, etc.). In some embodiments, each modification profile may include a set of modification parameters or functions to be applied to live image data for a given context. As an example, the user may have a modification profile for each set of eye characteristics (e.g., a range of gaze directions, pupil sizes, limbus positions, or other characteristics). As further example, the user may additionally or alternatively have a modification profile for each set of environmental characteristics (e.g., a range of brightness levels of the environment, temperatures of the environment, or other characteristics).

Based on the eye-related or environment-related characteristics currently detected, the corresponding set of modification parameters or functions may be obtained and used to generate the enhanced presentation of the live image data. As an example, the corresponding set of modification parameters or functions may be obtained (e.g., to be applied to an image to modify the image for the user) based on the currently-detected eye-related characteristics matching a set of eye-related characteristics associated with the obtained set of modification parameters or functions (e.g., the currently-detected eye-related characteristics fall within the associated set of eye-related characteristics). In some embodiments, the set of modification parameters or functions may be generated based on the currently-detected eye characteristics or environmental characteristics (e.g., ad-hoc generation of modification parameters, adjustment of a set of modification parameters or functions of a currently-stored modification profile associated with the user for the given context, etc.).

In one use case, a wearable device (implementing the foregoing operations) may automatically adjust brightness of the enhanced presentation of the live image data for one or more eyes of the user based on the respective pupil sizes (e.g., where such adjustment is independent of the brightness of the surrounding environment). As an example, subjects with anisocoria have unequal pupil size, and those subjects have light sensitivity from a single eye, which cannot tolerate the light brightness tolerated by the healthy eye. In this way, the wearable device enables automatic adjustment of brightness for each eye separately (e.g., based on the detected pupil size of the respective eye).

In another use case, the wearable device may detect pupil size, visual axis, optical axis, limbus position, line of sight, or other eye accommodation state (e.g., including changes to the foregoing) and may change a modification profile based on the detected states. As an example, for subjects with higher order aberrations (e.g., errors of refraction that are not correctable by spectacles nor contact lenses), the subject's aberrations are dynamic and change according to the pupil size and the accommodation state of the eye. The wearable device may detect the state of accommodation by detecting the signs of the near reflex (e.g., miosis (decrease the size of the pupil) and convergence (inward crossing of the pupil)). Additionally, or alternatively, the wearable device may include a pupil and line of sight tracker to detect the direction of gaze. As another example, aberrations of the eye change according to the size and position of the aperture of the optical system and can be measured in relation to different pupil sizes and positions of the pupil and visual axis. The wearable device may, for example, measure the irregularities on the cornea to determine the higher order aberrations (e.g., based on the measurements) and calculate the modification profile to address the higher order aberrations. For different sizes and positions of the pupil and visual axis (or other eye accommodation states), different modification profiles may be created and stored for future use to provide real-time enhancements. One or more of these detected inputs enable the wearable device to use the appropriate modification profile (e.g., set of modification parameters or functions) to provide enhancements for the user.

As another example, the wearable device may be used to correct for presbyopia by automatically performing autofocus of the images displayed to the user to provide near vision. To further augment and enhance near vision, the wearable device may detect where the user is trying to look at a near target (e.g., by detecting the signs of the near reflex, such as miosis (decrease in pupil size and convergence (inward movement of the eye)) and perform autofocusing for a region of an image corresponding to the target that the user is looking (e.g., the portion of the display that the user is looking, the proximate area around an object at which the user is looking, etc.). Additionally, or alternatively, the wearable device may determine how far the target is (e.g., a target object or area) by quantifying the amount of the near reflex exerted by the subject and distance of the target from the eye (e.g., via sensors of the wearable device) and provide the adequate correction based on the quantified amount and target distance.

As another example, the wearable device may be used to correct for double vision (e.g., related to strabismus or other conditions). The wearable device may monitor the user's eyes and track the user's pupils to measure the angle of deviation to displace the images projected for each eye (e.g., in conjunction with detecting strabismus or other conditions). Because double vision is typically dynamic (e.g., the double vision increases or decreases towards one or more gazes), the wearable device may provide the appropriate correction by monitoring the user's pupils and the user's line of sight. For example, if the user has an issue in moving the user's right pupil away from the user's nose (e.g., toward to edge of the user's face), then the user's double vision may increase when the user is looking to the right and may decrease when the user is looking to the left. As such, the wearable device may display an enhanced presentation of live image data to each eye such that a first version of the enhanced presentation displayed to one of the user's eyes reflects a displacement from a second version of the enhanced presentation displayed to the user's other eye (e.g., where the amount of displacement is based on the pupil position and gaze direction) to dynamically compensate for the user's condition (e.g., strabismus or other condition) and, thus, prevent double vision for all potential gaze directions.

Although prisms can be applied to shift image in front of the crossed eye (e.g., caused by strabismus or other condition) to correct for double vision, prisms are unable to produce torsion of the image and, thus, not useful in correcting for double vision resulting from conditions that cause images to appear tilted or cyclotorted (e.g., cyclotropia is a form of strabismus which causes images received from both eyes to appear tilted or cyclotorted). In some use cases, the wearable device may monitor the user's eyes to measure the degree of strabismus (e.g., including cyclotorsion) by detecting the pupil, limbus, line of sight, or visual axis of both eyes in relation to each other. Additionally, or alternatively, the wearable device may perform such measurements by obtaining images of retinas of both eyes and comparing the structures of the retina and nerve in relation to each other.

In doing so, the wearable device may detect and measure the relative location of those eye structures and any torsion displacement. Such measurements may be provided to a prediction model to predict modification parameters for the live image processing to correct for the defect and alleviate the double vision. Continuous feedback may be obtained from sensors of the wearable device (e.g., pupil tracker, gaze tracker, tracker based on retina image, etc.) may be used to change the modification profile applied to live image data in real-time. In further use cases, the user may also fine tune the correction. As an example, an image may be displayed to the user on a user interface, and the user may move the image (or an object represented by the image) (e.g., using a joystick or other input device) until that image cross in front of one eye and rotate the object until the object overlaps with the image seen by the other eye. In some embodiments, upon detection of an indication of double vision, and without any user input explicitly indicating that the image should be moved or the amount or position of the movement, the wearable device may automatically move the image that is crossed in front of one eye (e.g., translate or rotate the image) to perform measurements or corrections related to the double vision.

As with other forms of strabismus, the resulting displacement caused by cyclotropia changes in real-time based on the intended direction of action of the paralyzed (or partially paralyzed) muscle associated with the cyclotropia and when such a patient is looking towards one side or the other. By tracking the eye characteristics, the wearable device can dynamically compensate for the user's condition by displaying an enhanced presentation of live image data to each eye such that a first version of the enhanced presentation displayed to one of the user's eyes reflects a displacement from a second version of the enhanced presentation displayed to the user's other eye (e.g., where the amount of displacement is based on the pupil position and gaze direction).

In some embodiments, with respect to FIG. 1A, upon obtaining feedback related to a set of stimuli (displayed to a user during a visual test presentation), feedback related to one or more eyes of the user, feedback related to an environment of the user, or other feedback, testing subsystem 122 may provide the feedback to a prediction model, and the prediction model may be configured based on the feedback. In some embodiments, testing subsystem 122 may obtain a second set of stimuli (e.g., during the visual test presentation). As an example, the second set of stimuli may be generated based on the prediction model's processing of the set of stimuli and the feedback related to the set of stimuli. The second set of stimuli may be additional stimuli derived from the feedback to further test one or more other aspects of the user's visual field (e.g., to facilitate more granular correction or other enhancements for the user's visual field). In one use case, testing subsystem 122 may cause the second set of stimuli to be displayed to the user (e.g., during the same visual presentation), and, in response, obtain further feedback related to the second set of stimuli (e.g., the further feedback indicating whether or how the user sees one or more stimuli of the second set). Testing subsystem 122 may then providing the further feedback related to the second set of stimuli to the prediction model, and the prediction model may be further configured based on the further feedback (e.g., during the visual test presentation). As an example, the prediction model may be automatically configured for the user based on (i) an indication of a response of the user to one or more stimuli (e.g., of the set of stimuli, the second set of stimuli, or other set of stimuli), (ii) an indication of a lack of response of the user to such stimuli, (iii) an eye image captured during the visual test presentation, or other feedback (e.g., the prediction model may be personalized toward the user based on the feedback from the visual test presentation). In one use case, for example, the feedback indicates one or more visual defects of the user, and the prediction model may be automatically configured based on the feedback to address the visual defects. As another example, the prediction model may be trained based on such feedback and other feedback from other users to improve accuracy of results provided by the prediction model (e.g., trained to provide modification profiles described herein, trained to generate an enhanced presentation of live image data, etc.).

In some embodiments, visioning subsystem 124 may provide live image data or other data (e.g., monitored eye-related characteristics) to the prediction model to obtain an enhanced image (derived from the live image data) and cause an enhanced image to be displayed. In some embodiments, the prediction model may continue to be configured during the display of the enhanced image (derived from the live image data) based on further feedback continuously provided to the prediction model (e.g., on a periodic basis, in accordance with a schedule, or based on other automated triggers). As an example, a wearable device may obtain a live video stream from one or more cameras of the wearable device and cause the enhanced image to be displayed on one or more displays of the wearable device (e.g., within less than a millisecond, less than a centisecond, less than a decisecond, less than a second, etc., of the live video stream being captured by the cameras of the wearable device). In some embodiments, the wearable device may obtain the enhanced image from the prediction model (e.g., in response to providing the live image data, monitored eye-related characteristics, or other data to the prediction model). In some embodiments, the wearable device may obtain modification parameters or functions from the prediction model (e.g., in response to providing the live image data, monitored eye-related characteristics, or other data to the prediction model). The wearable device may use the modification parameters or functions to generate the enhanced image from the live image data (e.g., parameters of functions used to transform or modify the live image data into the enhanced image). As a further example, the modification parameters may include one or more transformation parameters, brightness parameters, contrast parameters, saturation parameters, sharpness parameters, or other parameters.

In an example, a vision correction framework having a machine learning framework with an AI algorithm may be used to create automatic personalized modification profiles by applying transformation, translation, and resizing of the field of view to better fit it to the remaining functional visual field. The machine learning framework may include one or more of data collection, visual field classification, and/or regression models. To facilitate recording of participant responses, quantitative scores, and feedback, a graphical user interface (GUI) and data collection program may be used.

Figure 13:
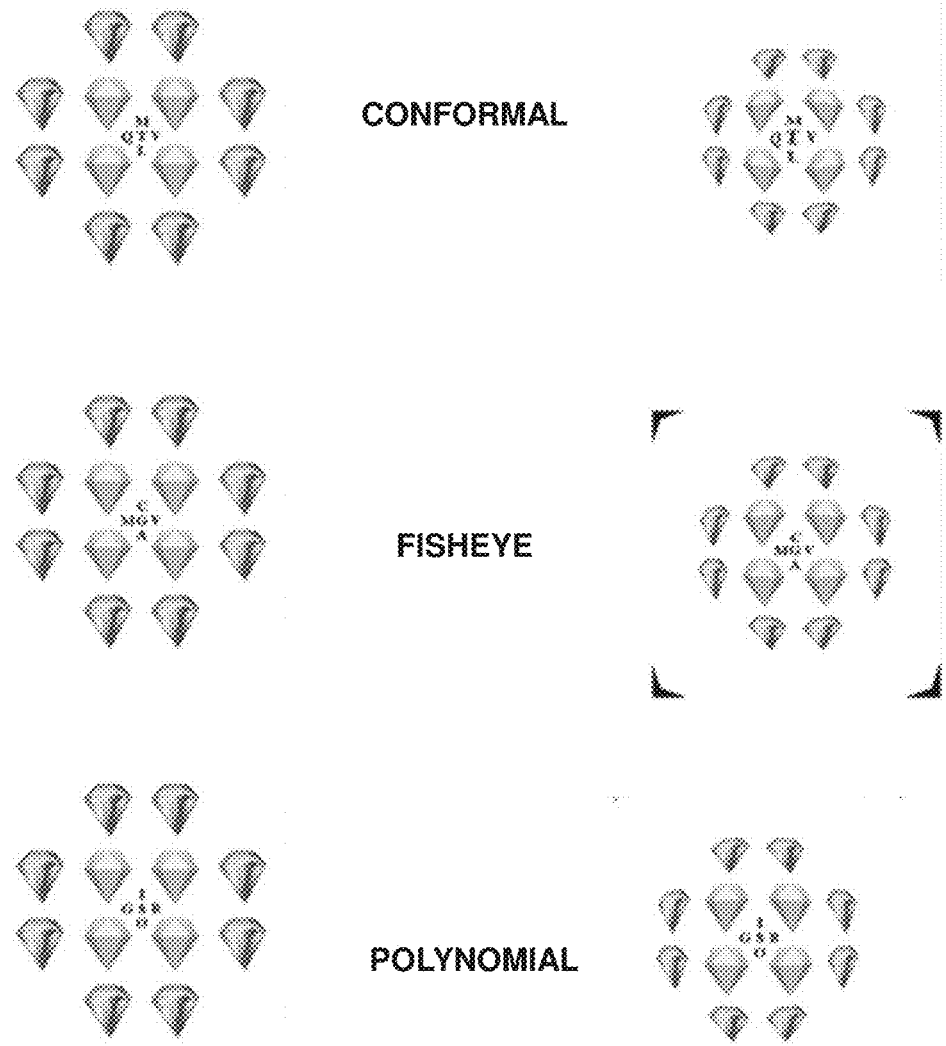
FIG. 13 illustrates examples of different correction transformations that may be applied to an image and presented to a subject, in accordance with one or more embodiments.

With respect to transformations applied to images in the visioning mode, example transformations of the machine learning framework may include one or more of: 1) conformal mapping, 2) fisheye, 3) custom 4th order polynomial transformation, 4) polar polynomial transformation (using polar coordinates), or 5) rectangular polynomial transformation (using rectangular coordinates) (e.g., FIG. 13).

With respect to translations applied to images in the visioning mode, examples may include one or more of the following. For the center detection, weighted averaged of the best center and the closest point to the center may be used. For example, the closest point may be determined by finding the nearest point to the center location. The best center may be determined by one or more of the following: 1) the centroid of the largest component, 2) the center of the largest inscribed circle, square, rhombus, and/or rectangle, or 3) the center of the local largest inscribed circle, square, rhombus, and/or rectangle (e.g., FIG. 14). For example, the framework may search for the largest shape but alliteratively to avoid getting far from the macular vision region, the framework may substitute this by the weighted average of the closest point with the methods.

In various embodiments, the AI algorithm may be initially trained using simulated visual field defects. For example, to train the AI algorithm, a dataset of visual field defects may be collected. For example, in one experimental protocol, a dataset of 400 visual field defects were obtained from patients with glaucoma. The dataset may be used to create simulated visual field defects on virtual reality glasses for presentation to normal subjects for grading. The resulting feedback obtained from the grading may then be used to train the algorithm.

For example, an AI algorithm that automatically fits an input image to areas corresponding to the intact visual field pattern for each patient individually may be used. In various embodiments, the algorithm may include at least three degrees of freedom to remap the images, although more or less degrees of freedom may be used. In one example, the degrees of freedom include transformation, shifting, and resizing. The added image transformation may preserve the quality of the central area of the image corresponding to the central vision, where acuity is highest, while condensing the peripheral areas with an adequate amount of image quality in the periphery. This may be applied such that the produced overall image content would be noticeable to the patient.

The image transformations included in the AI algorithm may include one or more of conformal, polynomial or fish eye transformations. In some embodiments, other transformations may be used. The machine learning techniques may be trained on a labeled dataset prior to performing their actual task. In one example, the AI algorithm may be trained on a visual field dataset that incorporates different types of peripheral defects. For example, in one experiment, the dataset included 400 visual field defect patterns. The training phase was then guided by normal participants to quantitatively score the remapped images generated by the AI algorithm.

Figure 11:
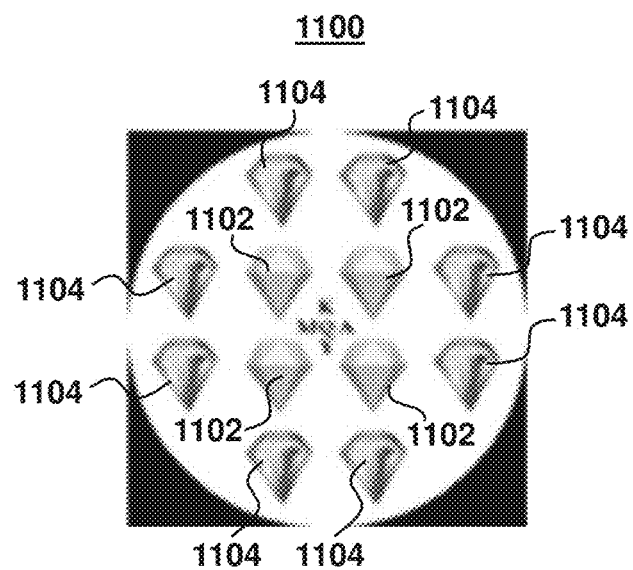
FIG. 11 illustrates a test image, in accordance with one or more embodiments.

FIG. 11 shows an image 1100 of a test image (stimuli) according to one example. The test image 1100 may be designed to measure the acuity, the paracentral vision and/or the peripheral vision. The illustrated test image displays five letters at the central region, four internal diamonds 1102 at the paracentral region, and eight external diamonds 1104 at the peripheral region as shown in FIG. 11.

Figure 12:
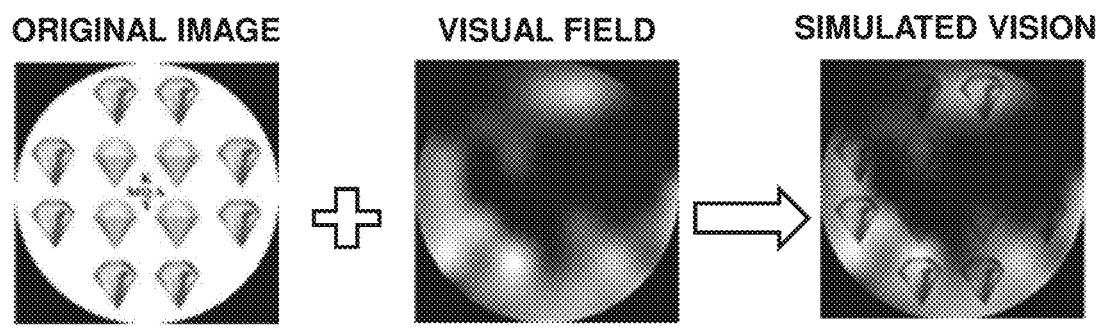
FIG. 12 illustrates development of a simulated vision image including overlaying an impaired visual field on a test image for presentation to a subject, in accordance with one or more embodiments.
Figure 14:
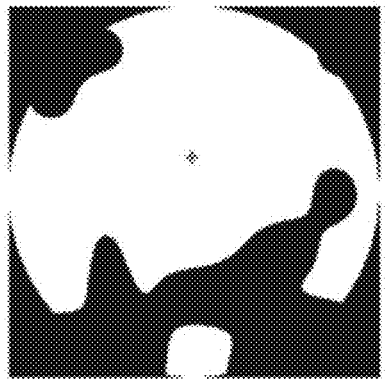
FIG. 14 illustrates example translation methods, in accordance with one or more embodiments.
Figure 14:
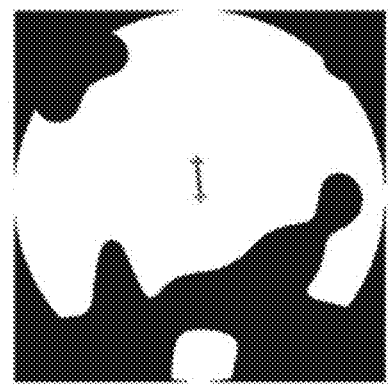
Figure 14:
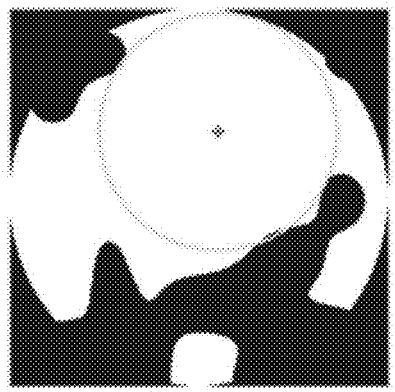
Figure 14:
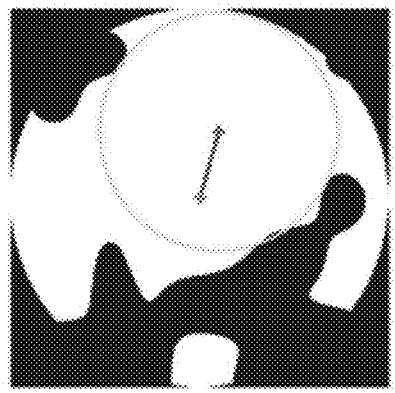
Figure 14:
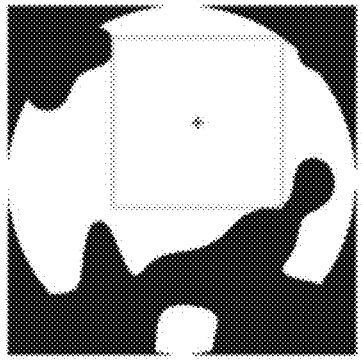
Figure 14:
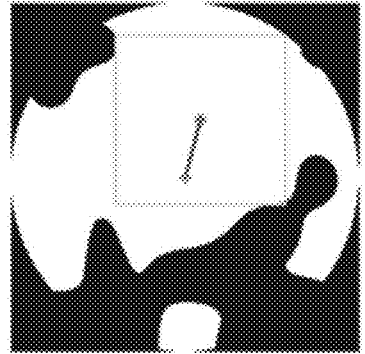

To be able to train the AI system, a volume of data is needed, as introduced above. As an initial step, defective binocular visual fields may be used to simulate binocular vision of patients as shown in FIG. 12. Next, the simulated vision may be presented to subjects through the spectacles device. In this way, the input image can be manipulated using different image manipulations then presented again to the subject to grade the modified vision. The corrected image may be further corrected and presented to the subject in a continually corrective process until an optimized corrected image is determined. FIG. 13 illustrates examples of different correction transformations that may be applied to the image and presented to the user. FIG. 14 illustrates an example of different translation methods (shifting the image to fit it in the intact visual field). The intact visual field is white and blind visual field is black.

Figure 15:
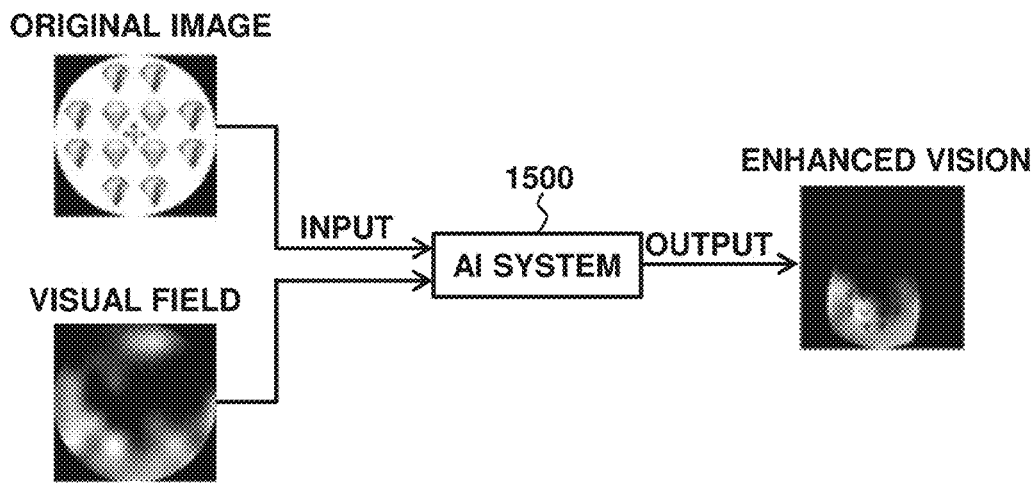
FIG. 15 illustrates an example of a machine learning framework, in accordance with one or more embodiments.

The AI system may be designed using machine learning models such as artificial neural networks and Support Vector Machines (SVM). In some examples, the AI system is designed to produce an output comprising an estimate of the best image manipulation methods (e.g., geometric transformation and translation) through an optimization AI system. The vision system, in a visioning mode, may presents images manipulated according to the output image manipulation methods to the patient through a headset such that the patient experiences the best possible vision based on his defective visual field. The machine learning framework (also termed herein "AI System") of the vision correction framework may trained using the collected data, (e.g., as described herein). A block diagram of an example AI system 1500 is shown in FIG. 15.

Figure 17:
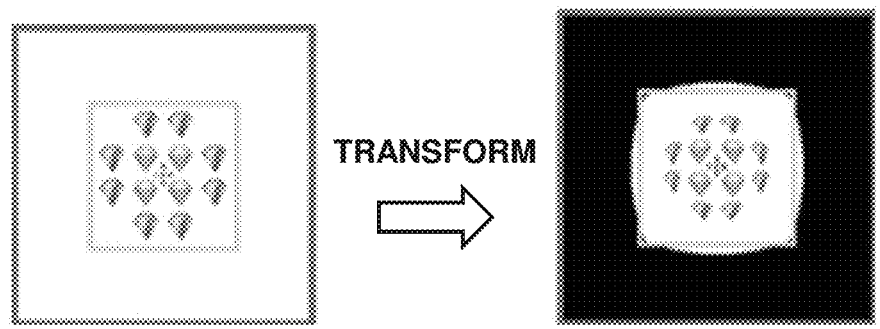
FIG. 17 illustrates an example transformation of a test image, in accordance with one or more embodiments.
Figure 18:
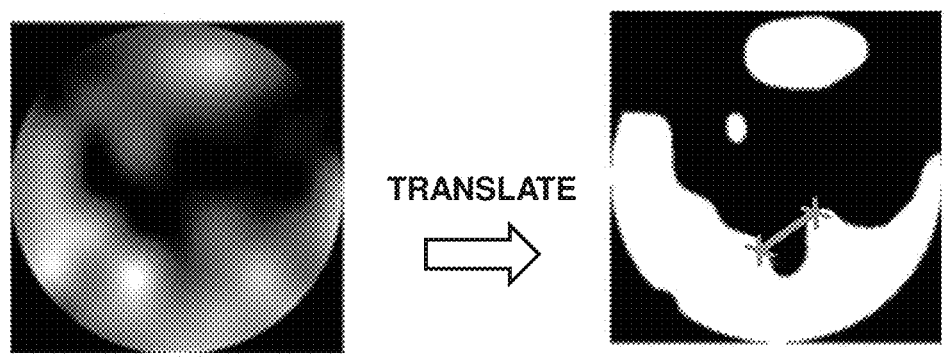
FIG. 18 illustrates an example translation of a test image, in accordance with one or more embodiments.
Figure 19:
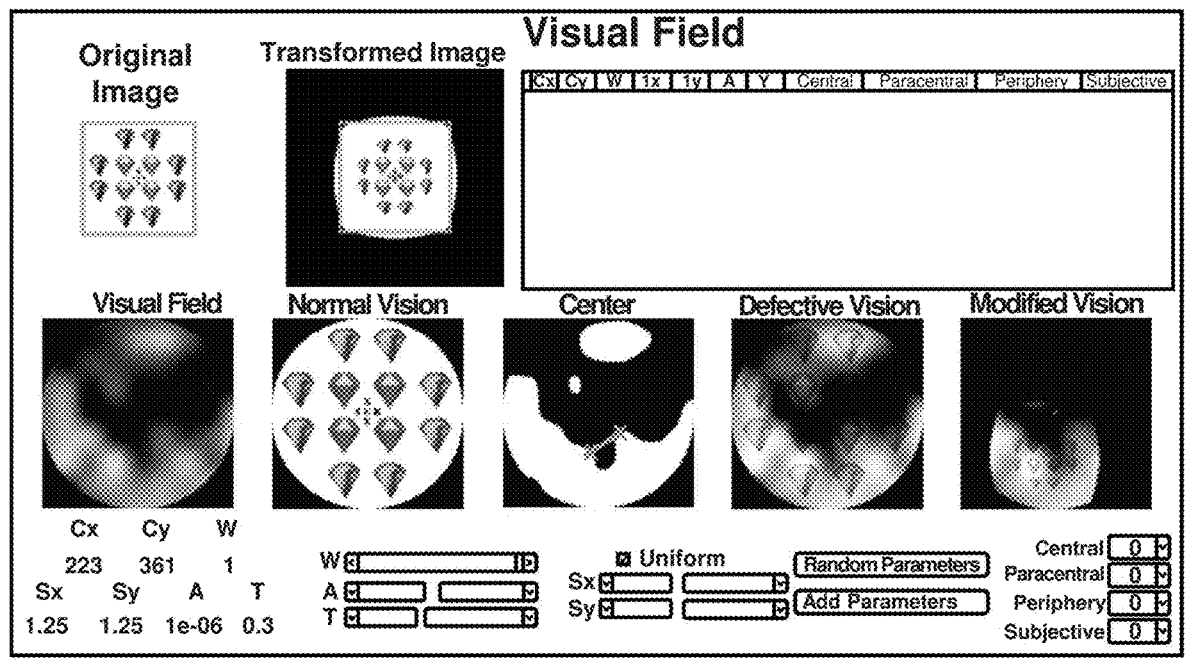
FIG. 19 is a graphical user interface illustrating various aspects of an implementation of an AI system, in accordance with one or more embodiments.

A process 1600 of the AI system 1500 is shown in FIG. 16. The input to the system 1500 includes a test image and a visual field image. The AI system 1500 estimates the best geometric transform for the test image such that more details can be presented through the visual field. Then, AI system 1500 estimates the best translation for the test image such that the displayed image covers major parts of the visual field. Then, the test image is transformed and translated as shown in FIG. 17. and FIG. 18, respectively. Finally, the image is combined with the visual field again in case of the training only for the simulation purpose, but it is displayed directly to the patient in the testing phase. A screenshot of graphical user interface presenting a summary of visual field analysis, which may include a final implementation of the visual field AI system including parameters of the image transformation and translation to be applied to the image, is shown in FIG. 19.

Figure 20:
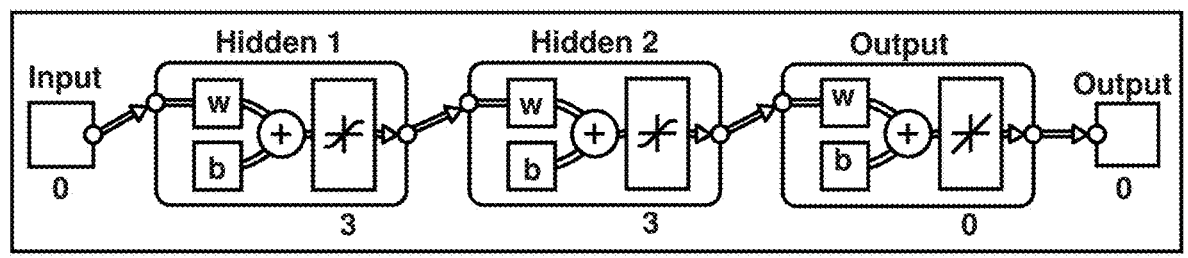
FIG. 20 illustrates a framework for an AI system including a feed-forward neural network, in accordance with one or more embodiments.
Figure 21:
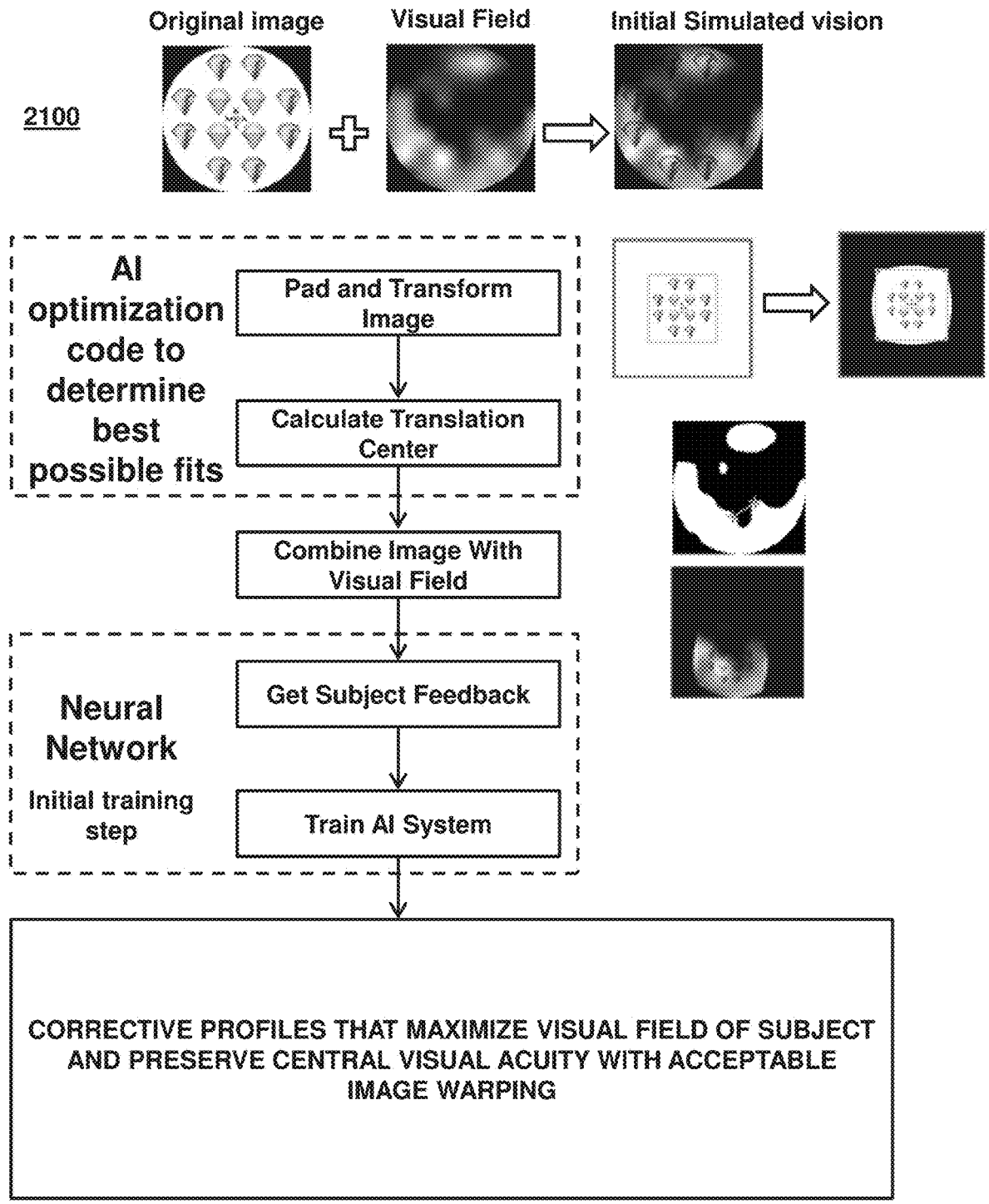
FIGS. 21-22 illustrate example testing mode processes of an AI system including a neural network and an AI algorithm optimization process, respectively, in accordance with one or more embodiments.
Figure 22:
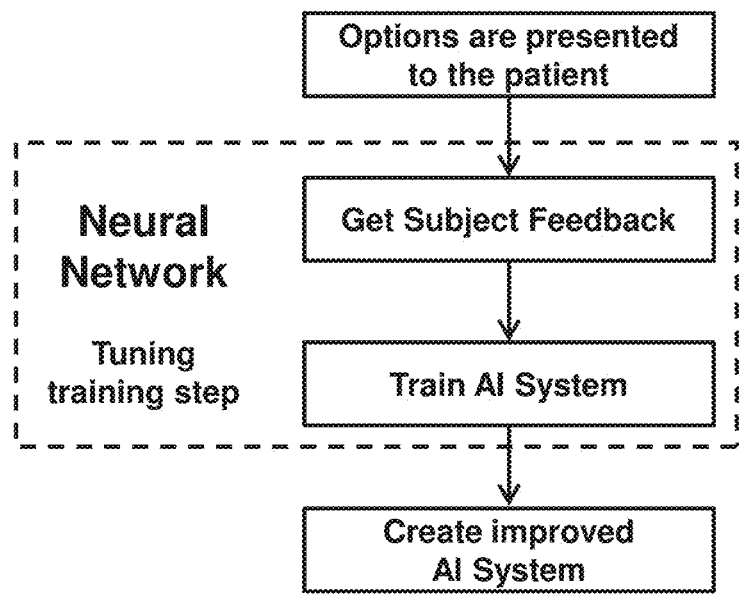

In example an implementation, an artificial neural network model was used to implement the machine learning framework ("AI system") on the vision correction framework. The AI system takes as the visual field image converted to a vector. The AI system gives as output the prediction of the parameters of the image transformation and the translation to be applied to the scene image. Then, the scene image is manipulated using these parameters. The AI system includes two hidden layers wherein each hidden layer includes three neurons (i.e., units) and one output layer. One such example AI system model is shown FIG. 20. This AI system may also extend to convolutional neural network model for even more accurate results, in other examples. FIGS. 21 and 22 illustrate example processes 2100 and 2200 of a testing mode application of a neural network and an AI algorithm optimization process using a neural network, respectively.

In some embodiments, with respect to FIG. 1A, upon obtaining feedback related to a set of stimuli (displayed to a user during a visual test presentation), feedback related to one or more eyes of the user, feedback related to an environment of the user, or other feedback, testing subsystem 122 may provide the feedback to a prediction model, and the prediction model may be configured based on the feedback. In some embodiments, further feedback may be continuously obtained and provided to the prediction model (e.g., on a periodic basis, in accordance with a schedule, or based on other automated triggers) to update the configuration of the prediction model. As an example, the configuration of the prediction model may be updated while one or more enhancements of live image data are being displayed to the user.

In some embodiments, visioning subsystem 124 may monitor characteristics related to one or more eyes of the user (e.g., gaze direction, pupil size or reaction, limbus position, visual axis, optical axis, eyelid position or movement, head movement, or other characteristics) and provide the eye characteristic information to the prediction model during an enhanced presentation of live image data to the user. Additionally, or alternatively, visioning subsystem 124 may monitor characteristics related to an environment of the user (e.g., brightness level of the environment, temperature of the environment, or other characteristics). As an example, based on the eye or environmental characteristic information (e.g., indicating the monitored characteristics), the prediction model may provide one or more modification parameters or functions to be applied to the live image data to generate the enhanced presentation of the live image data (e.g., the presentation of one or more enhanced images derived from the live image data to the user). In one use case, the prediction model may obtain the modification parameters or functions (e.g., stored in memory or at one or more databases) based on the currently-detected eye characteristics or environmental characteristics. In another use case, the prediction model may generate the modification parameters or functions based on the currently-detected eye characteristics or environmental characteristics.

In some embodiments, with respect to FIG. 1A, visioning subsystem 124 may facilitate enhancement of a field of view of a user via one or more dynamic display portions on one or more transparent displays (e.g., based on feedback related to a set of stimuli displayed to a user or other feedback). As an example, the dynamic display portions may include one or more transparent display portions and one or more other display portions (e.g., of a wearable device or other device). In some embodiments, visioning subsystem 124 may cause one or more images to be displayed on the other display portions (e.g., such that the images are not displayed on the transparent display portions). As an example, a user may see through the transparent display portions of a transparent display, but may not be able to see through the other display portions and instead sees the image presentation on the other display portions (e.g., around or proximate the transparent display portions) of the transparent display. That is, in some embodiments, a dynamic hybrid see-through/opaque display may be used. In this way, for example, one or more embodiments can (i) avoid the bulky and heavy weight of typical virtual reality headsets, (ii) make use of a user's intact vision (e.g., making use of the user's good acuity central vision if the user has intact central vision but a defective peripheral visual field, making use of the user's intact peripheral vision if the user has intact peripheral vision but a defective central visual field, etc.), and (iii) mitigate visual confusion that would otherwise be caused by typical augmented reality technology that has an overlap effect between the see-through scene with the internally displayed scene.

As an example, live image data may be obtained via the wearable device, and an enhanced image may be generated based on the live image data and displayed on the other display portions of the wearable device (e.g., display portions of a display of the wearable device that satisfy an opaque threshold or fail to satisfy a transparency threshold). In some embodiments, visioning subsystem 124 may monitor one or more changes related to one or more eyes of the user and cause, based on the monitoring, an adjustment of the transparent display portions of the transparent display. As an example, the monitored changes may include an eye movement, a change in gaze direction, a pupil size change, or other changes. One or more positions, shapes, sizes, transparencies, brightness levels, contrast levels, sharpness levels, saturation levels, or other aspects of the transparent display portions or the other display portions of the wearable device may be automatically adjusted based on the monitored changes.

Figure 24A:
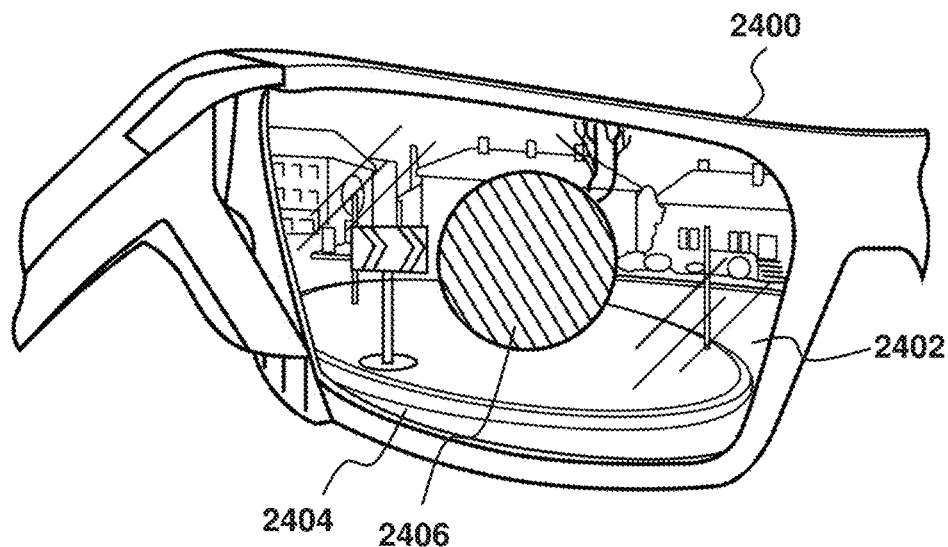
FIG. 24A illustrates a wearable spectacles device comprising custom reality wearable spectacles that allow an image from the environment to pass through a transparent portion of the wearable spectacles' display, where the transparent portion corresponds to a peripheral region of the user's visual field, and where other portions of the wearable spectacles' display are opaque portions, in accordance with one or more embodiments.

In one use case, with respect to FIG. 24A, a wearable device 2400 may include a transparent display 2402 dynamically configured to have a transparent peripheral portion 2404 and an opaque central portion 2406 such that the light from the user's environment can directly pass through the transparent peripheral portion 2404, but does not pass through the opaque central portion 2406. For patients with diagnosed central visual field anomalies 2306, the foregoing dynamic configuration enables such patients to use their intact peripheral visual field to view the actual un-corrected view of the environment and be presented with a corrected rendition of the central region on the opaque central portion 2406.

Figure 24B:
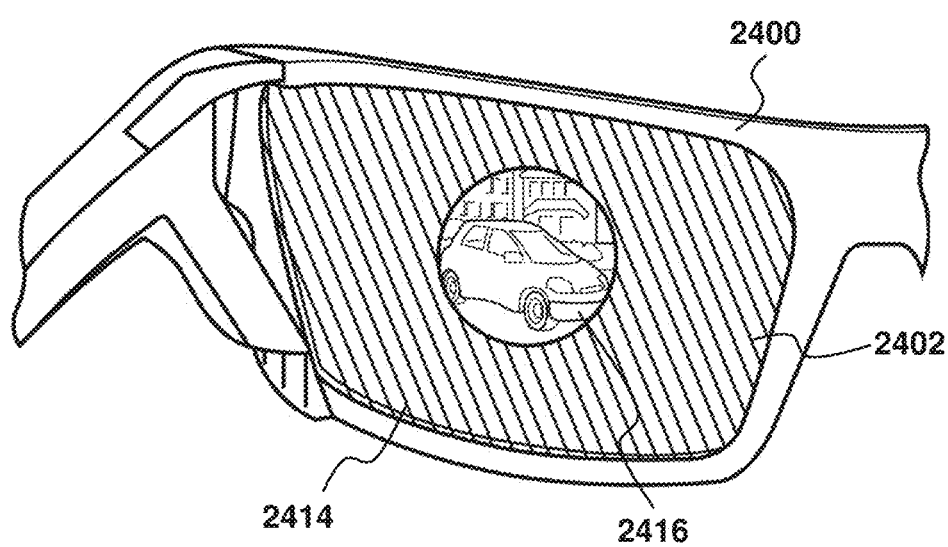
FIG. 24B illustrates a wearable spectacles device comprising custom reality wearable spectacles that allow an image from the environment to pass through a transparent portion of the wearable spectacles' display, where the transparent portion corresponds to a central region of the user's visual field, and where other portions of the wearable spectacles' display are opaque portions, in accordance with one or more embodiments.

In another use case, with respect to FIG. 24B, the wearable device 2400 may include the transparent display 2402 dynamically configured to have an opaque peripheral portion 2414 and a transparent central portion 2416 such that the light from the user's environment can directly pass through the transparent central portion 2416, but does not pass through the opaque peripheral portion 2414. For patients with peripheral visual field anomalies, the foregoing dynamic configuration enables such patients to use their intact central visual field to view the actual un-corrected view of the environment and be presented with a corrected rendition of the peripheral region on the opaque peripheral portion 2414. In each of the foregoing use cases, with respect to FIGS. 24A and 24B, one or more positions, shapes, sizes, transparencies, or other aspects of the transparent display portions 2404, 2416 or the opaque display portions 2406, 2414 may be automatically adjusted based on changes related to one or more eyes of the user that are monitored by the wearable device 2400 (or other component of system 100). Additionally, or alternatively, one or more brightness levels, contrast levels, sharpness levels, saturation levels, or other aspects of the opaque display portions 2406, 2414 may be automatically adjusted based on changes related to one or more eyes of the user that are monitored by the wearable device 2400. In some cases, for example, to dynamically accommodate for areas of the user's visual field that have reduced brightness, the user's pupil and line of sight (or other eye characteristics) may be monitored and used to adjust the brightness levels of parts of the opaque display portions 2406, 2414 (e.g., in addition to or in lieu of increasing the brightness levels of parts of the enhanced image that correspond to the reduced brightness areas of the user's visual field).

Figure 24C:
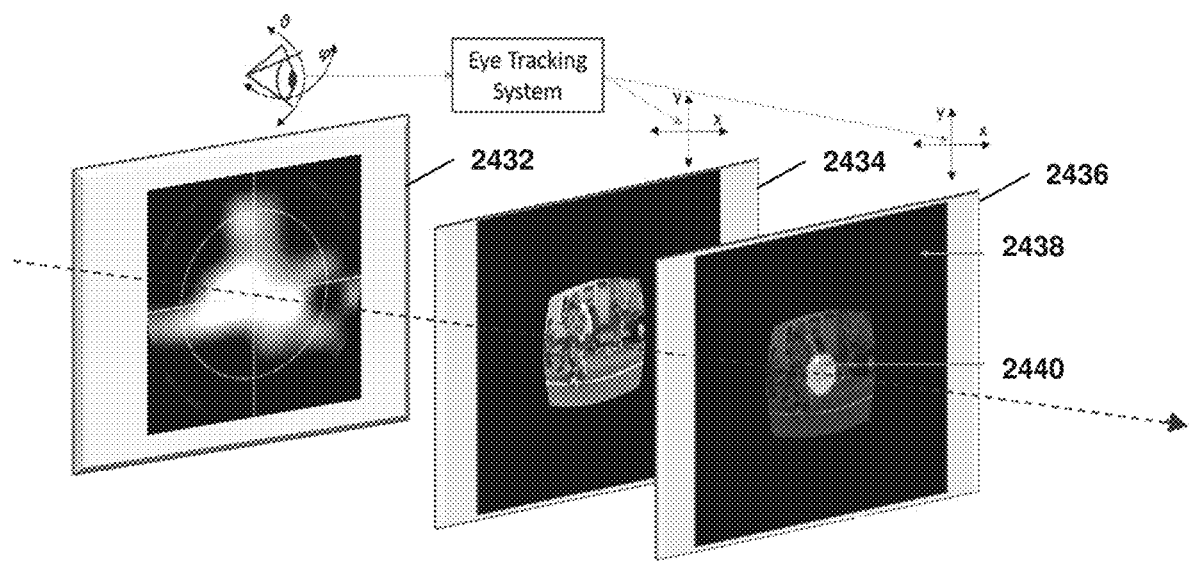
FIG. 24C illustrates an alignment between visual field plane, a remapped image plane, and a selective transparency screen plane using eye tracking, in accordance with one or more embodiments.

As an example, with respect to FIG. 24C, based on a determination of a user's visual field (e.g., including defective visual field portions, intact visual field portions, etc., as represented by visual field plane 2432), an enhanced image may be generated (e.g., as represented by the remapped image plane 2434) as described herein. The enhanced image may be displayed to the user on one or more opaque display portions in the opaque area 2438 of a display (e.g., as represented by selective transparency screen plane 2416) such that the displayed enhanced image augments the user's view of the environment through the transparent area 2440 of the display.

In one use case, with respect to FIG. 24C, the selective transparency screen plane 2436 may be aligned with the other planes 2432 and 2434 via one or more eye tracking techniques. As an example, an eye tracking system (e.g., of wearable device 2400 or other device) may be calibrated for a user to ensure proper image projections according to the user's personalized intact visual field. The eye tracking system may continuously acquire gaze coordinates (e.g., on a periodic basis, in accordance with a schedule, or other automated triggers). A coordinates transformation may be performed to convert the eye movements spherical coordinates (0, (p) into the display's Cartesian coordinates (x, y). As such, the device's controller may determine the central position of the images to be displayed. Camera images will be truncated and shifted to match the acquired gaze vector direction (e.g., FIG. 24C). The same Cartesian coordinates may be sent to the selective transparency screen controller to make the area corresponding to macular vision at the current gaze direction transparent and allow usage of the central visual acuity. In some cases, low pass filtering may be performed on the gaze data to remove micro-eye movements (e.g., micro-eye movements caused by incessantly moving and drafting that occur even at fixations because the eyes are never completely stationary) that may otherwise cause shaky images to be displayed to the user.

Figure 23:
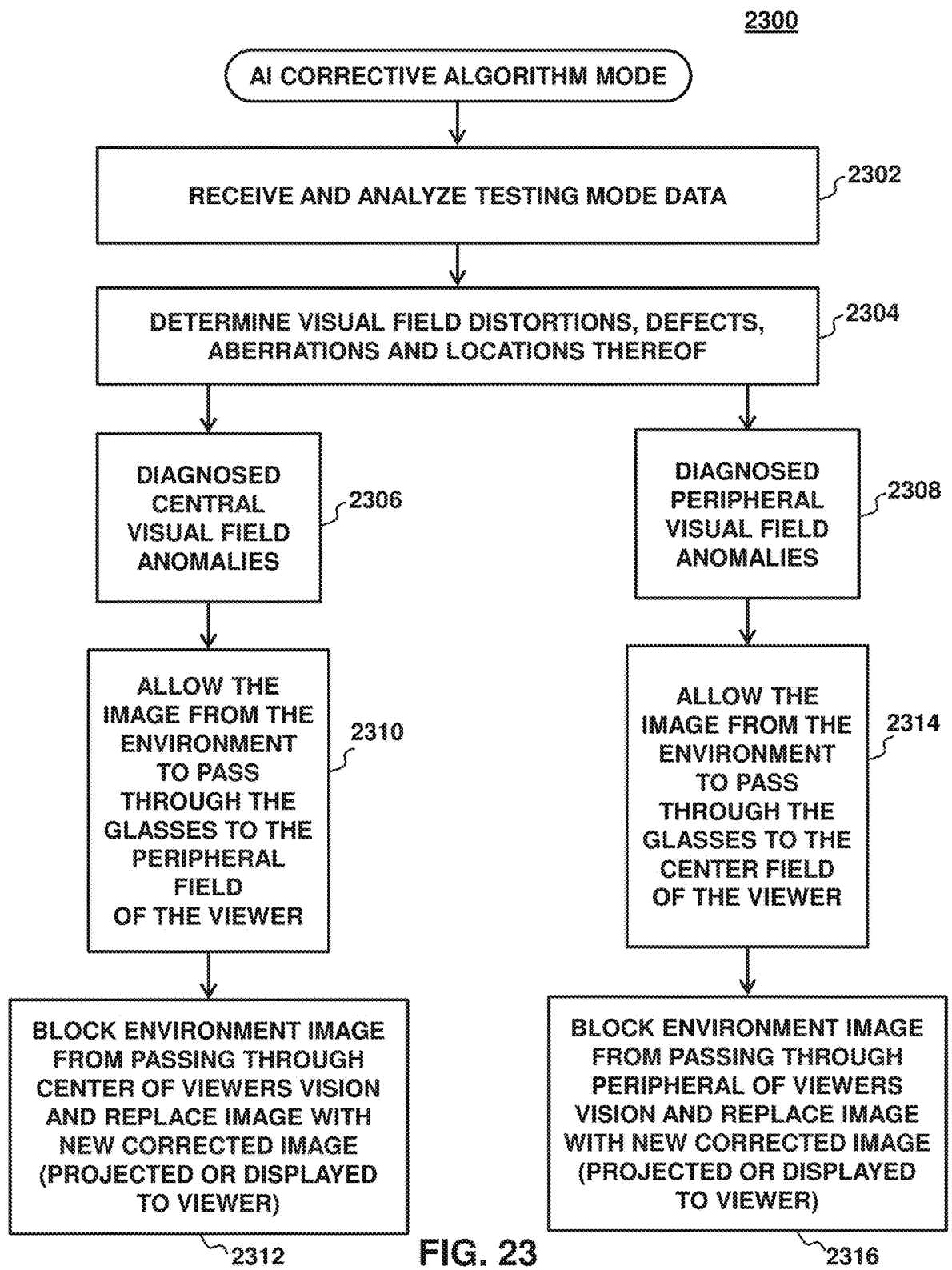
FIG. 23 illustrates an example process implementing testing and visioning modes, in accordance with one or more embodiments.

As indicated above, in some embodiments, the wearable device may be configured to selectively control transparency of a display area of a monitor, such as a screen, glass, film, and/or layered medium. FIG. 23 illustrates an example process 2300 implementing testing and visioning modes and the use of a custom-reality spectacles device, which may use a macular (central) versus peripheral vision manipulation.

In some examples, the custom reality spectacles device (e.g., FIGS. 40A-40C) include transparent glasses for overlaying corrected images onto a visible scene. The glasses may comprise a monitor comprising a screen having controllably transparency onto which images may be projected for display. In one example, the display comprises a heads-up display. In various embodiments, a custom reality spectacles device includes glasses having controllable layers for overlaying corrected images onto a scene visible through the glasses. The layers may comprise glass, ceramic, polymer, film, and/or other transparent materials arranged in a layered configuration. The controllable layers may include one or more electrically controlled layers that allow for adjusting the transparency over one or more portions of the visual field, for example, in pixel addressable manner. In one embodiment, may include pixels or cells that may be individually addressable (e.g., via an electric current, field, or light). The controllable layers may be layers that may be controlled to adjust contrast of one or more portions of the visual field, color filtering over portions, the zooming in/zooming out of portions, focal point over portions, transparency of the spectacles device surface that display the image to block or allow the light coming from the environment at a specific location of the visual field. If there is a portion of field of view (e.g., a portion of the peripheral vision or a portion of the macular vision or a portion, part of it is macular and part of it is peripheral) for manipulation to augment a subject's vision, then the transparency of that portion of the glass may be lowered to block the view of the environment through that portion of glass and to allow the patient to see more clearly the manipulated image displayed along that portion of the glass. In various embodiments, vision system or custom reality spectacles device may dynamically control transparency regions to allow a subject to naturally view the environment when redirecting eyes by eye movement rather than just head movement. For example, pupil tracking data (e.g., pupil and/or line of sight tracking) may be used to modify the portion of the glass having decreased transparency such that the decreased transparency region translates relative to the subject's eye.

Figures 40A, 40B, 40C:
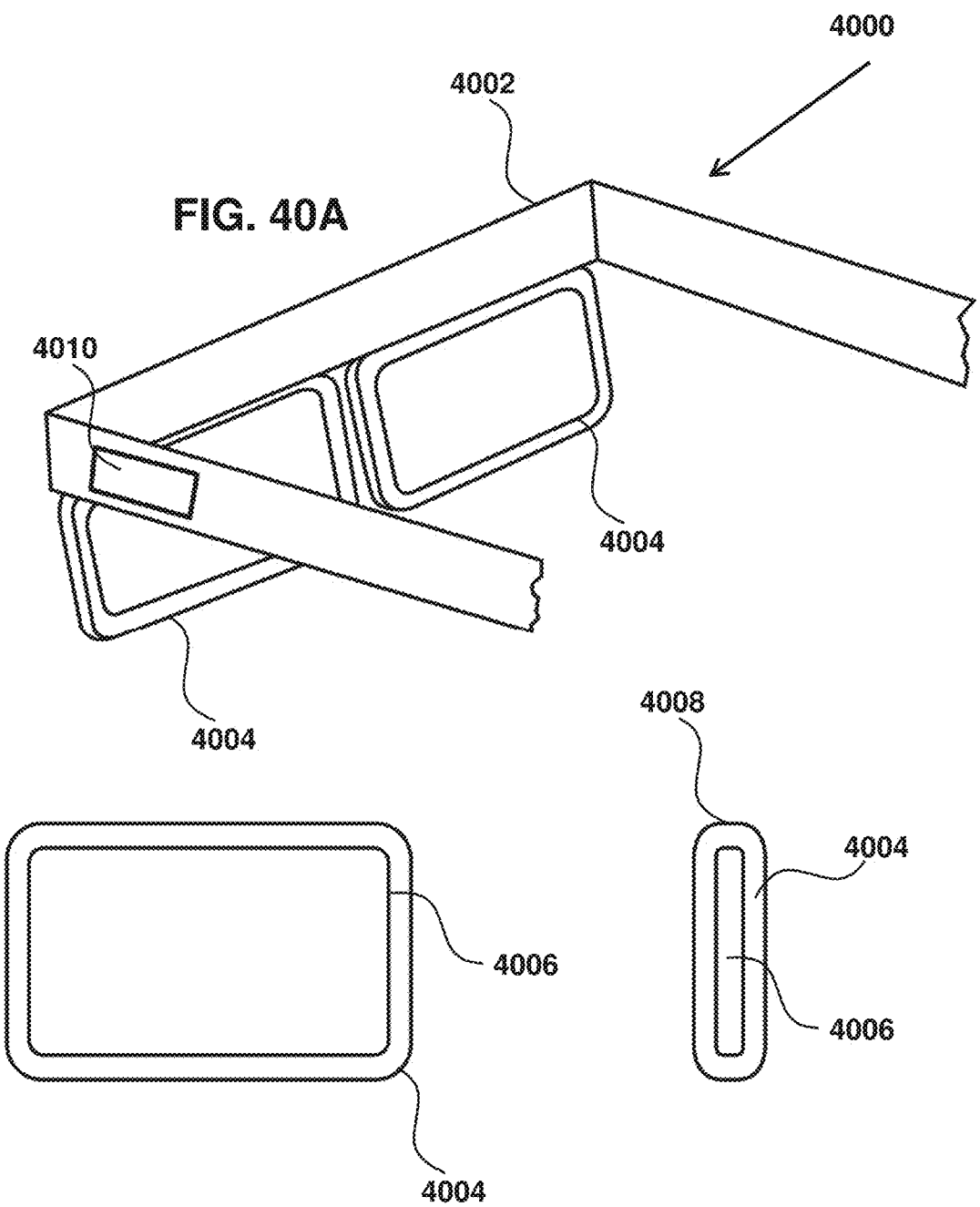
FIGS. 40A-40C illustrates an example custom reality spectacles device, in accordance with one or more embodiments.

For example, the transparency of the glass in the spectacles device comprising custom-reality glasses may be controllably adjusted to block light from that portion of the visual field corresponding to where image correction is performed (e.g., at a central region or a peripheral region). Otherwise subject may see the manipulated image and see through it and perceive the underling actual visual field in that region. Such light blocking can be achieved by a photochromic glass layer within the spectacles device. Moreover, the spectacles device may change the position of the area where the glass transparency is reduced by measuring for eye (pupil) movement using inward directed image sensors, and compensating based on such movement by processing in the vision correction framework. In one example, the display screen of the monitor includes pixels or cells including electric ink technology and that may be individually addressed to cause an electric field to modify the arrangement of ink within a cell to modify transparency and/or generate a pixel of the display. In an example implementation, FIG. 40A shows custom-reality glasses 4000 formed for a frame 4002 and two transparent glass assemblies 4004. As shown in FIGS. 40B and 40C, the transparent glass assemblies 4004 have embedded, electronically controllable correction layers 4006 that may be controllable from fully transparent to fully opaque, that may be digital layers capable of generating a correction image to overlay or supplant a portion of the field of view of the glasses 4000. The correction layers 4006 may be connected, through an electrical connection 4008, to an image processing device 4010 on the frame 4002.

With specific reference to the process 2300 of FIG. 23, at a block 2302 testing mode data may be received by a vision correction framework, and at a block 2304 visual field distortions, defects, aberrations, and/or other ocular anomalies may be determined, along with their locations.

For diagnosed central visual field anomalies 2306, at a block 2308 the custom reality spectacles device may allow the image from the environment to pass through the glass thereof to a peripheral field of the user (e.g., FIG. 24A). As shown, custom reality spectacles device 2400 may have a multi-layered glass viewfinder 2402. A peripheral region 2404 may be set as transparent to allow light passage there through, allowing the subject to view the actual un-corrected environment. At a block 2312, a central region 2406 of the environment may be made opaque by the spectacles device 2400 and a corrected rendition of the central region may be presented by display to the user, for example, using corrections such as those of FIGS. 13, 14, 17, and 18.

At block 2314, For diagnosed peripheral visual field anomalies (determined at block 2308), a central region 2416 (e.g., FIG. 24B) of the environment is allowed to pass through a transparent portion of the spectacles device 2400, and transparency of a peripheral region 2414 is modified to block such that a corrected peripheral version image may be displayed within peripheral region 2414, for example using the corrective transformations herein.

In some embodiments, with respect to FIG. 1A, visioning subsystem 124 may facilitate enhancement of a field of view of a user via projections onto selected portions of an eye of the user (e.g., based on feedback related to a set of stimuli displayed to a user or other feedback). As discussed herein, an enhanced presentation of live image data may be displayed to the user by projecting the enhanced presentation (e.g., modified images derived from the live image data) onto the user's eyes. In addition to or alternatively to the use of dynamic display portions on a screen (e.g., to enable the user to see-through one or more portions of the screen while the user sees modified live image data being displayed on one or more other portions of the screen), the modified image data may be projected onto one or more portions of an eye of the user (e.g., one or more portions of a retina of the user) while simultaneously avoiding projection of the modified image data onto one or more other portions of the user's eye (e.g., one or more other portions of the retina of the user).

In some embodiments, the modified image data may be projected onto one or more intact visual field portions of an eye of the user while simultaneously avoiding projection of the modified image data onto one or more other intact visual field portions of the user's eye. As an example, with respect to the other intact visual field portions where projection of the modified image data is avoided, light from the user's environment can pass through the user's retinas (e.g., without any significant interference from light being emitted by the projector), thereby allowing the user to see the environment via such other intact visual field portions. On the other hand, with respect to the intact visual field portions onto which the modified image data is being projected, the projected light prevents the user from seeing the environment via the projected-onto portions of the user's intact visual field. Nevertheless, by projecting the modified live image data onto those intact visual field portions of the user's eyes, the system allows the modified live image data to be used to augment the user's visual field (e.g., in a manner similar to the use of dynamic display portions to augment the user's visual field).

In some embodiments, visioning subsystem 124 may monitor one or more changes related to one or more eyes of the user and cause, based on the monitoring, an adjustment of one or more projecting portions of a projector (e.g., portions including laser diodes, LED diodes, etc., that are emitting a threshold amount of light visible to the user's eyes). As an example, as with the adjustment of a dynamic display portion on a screen, the monitored changes may include an eye movement, a change in gaze direction, a pupil size change, or other changes. One or more positions, shapes, sizes, brightness levels, contrast levels, sharpness levels, saturation levels, or other aspects of the projecting portions or other portions of the projector may be automatically adjusted based on the monitored changes.

In one use case, a wearable device may include a projector configured to selectively project an enhanced presentation (e.g., modified images derived from live image data) onto one or more portions of the user's eyes (e.g., one or more portions of each retina of the user that correspond to the user's intact visual field) while simultaneously avoiding projection of the modified image data onto one or more other portions of the user's eyes (e.g., one or more other portions of each retina of the user that correspond to the user's intact visual field). In some cases, alignment of such a selective projection plane may be aligned with the other planes (e.g., a visual field plane, a remapped image plane, etc.) via one or more eye tracking techniques (e.g., one or more techniques similar to those described in FIG. 24C with respect to the use of dynamic display portions on a screen).

With respect to FIG. 24A, a wearable device 2400 may include a transparent display 2402 dynamically configured to have a transparent peripheral portion 2404 and an opaque central portion 2406 such that the light from the user's environment can directly pass through the transparent peripheral portion 2404, but does not pass through the opaque central portion 2406. For patients with diagnosed central visual field anomalies 2306, the foregoing dynamic configuration enables such patients to use their intact peripheral visual field to view the actual un-corrected view of the environment and be presented with a corrected rendition of the central region on the opaque central portion 2406.

In another use case, with respect to FIG. 24B, the wearable device 2400 may include the transparent display 2402 dynamically configured to have an opaque peripheral portion 2414 and a transparent central portion 2416 such that the light from the user's environment can directly pass through the transparent central portion 2416, but does not pass through the opaque peripheral portion 2414. For patients with peripheral visual field anomalies, the foregoing dynamic configuration enables such patients to use their intact central visual field to view the actual un-corrected view of the environment and be presented with a corrected rendition of the peripheral region on the opaque peripheral portion 2414. In each of the foregoing use cases, with respect to FIGS. 24A and 24B, one or more positions, shapes, sizes, transparencies, or other aspects of the transparent display portions 2404, 2416 or the opaque display portions 2406, 2414 may be automatically adjusted based on changes related to one or more eyes of the user that are monitored by the wearable device 2400 (or other component of system 100). Additionally, or alternatively, one or more brightness levels, contrast levels, sharpness levels, saturation levels, or other aspects of the opaque display portions 2406, 2414 may be automatically adjusted based on changes related to one or more eyes of the user that are monitored by the wearable device 2400. In some cases, for example, to dynamically accommodate for areas of the user's visual field that have reduced brightness, the user's pupil and line of sight (or other eye characteristics) may be monitored and used to adjust the brightness levels of parts of the opaque display portions 2406, 2414 (e.g., in addition to or in lieu of increasing the brightness levels of parts of the enhanced image that correspond to the reduced brightness areas of the user's visual field).

In some embodiments, testing subsystem 122 may monitor one or more eye-related characteristics related to eyes of a user during visual test presentation via two or more user interfaces (e.g., on two or more displays) and determine visual defect information for one or more eyes of the user based on the eye-related characteristics occurring during the visual test presentation. As an example, testing subsystem 122 may cause one or more stimuli to be presented at one or more positions on at least one of the user interfaces and generate the visual defect information for an eye of the user based on one or more eye-related characteristics of the eye occurring upon the stimuli presentation. In some embodiments, a deviation measurement for the eye may be determined based on the eye-related characteristics (indicated by the monitoring as occurring upon the stimuli presentation) and used to provide corrections or other enhancements for the eye. As an example, the deviation measurement may indicate a deviation of the eye relative to the other eye, and the deviation measurement may be used to determine and correct for double vision or other vision defects. As an example, the amount of movement indicates the amount of eye crossing (e.g., strabismus), and the direction (or axis) of the movement indicates the type of strabismus. For example, if the eye movement was from "out" to "in," that means the strabismus is crossing out (e.g., exotropia). As such, in some embodiments, double vision may be autonomously determined and corrected via a wearable device.

In some embodiments, testing subsystem 122 may determine a deviation measurement or other visual defect information for a first eye of a user by (i) causing a stimulus to be presented at a position on a first user interface for the first eye while a stimuli intensity of a second user interface for a second eye of the user does not satisfy a stimuli intensity threshold and (ii) determining the visual defect information based on one or more eye-related characteristics of the first eye occurring upon the stimulus presentation. As an example, the stimulus presentation on the first user interface may occur while a stimulus is not presented on the second user interface. In one use case, if the first eye (e.g., right eye) is crossed outside immediately prior to such stimulus presentation on the first user interface (e.g., FIG. 25D), by presenting the stimulus in front of the first eye only (e.g., right eye only), the first eye will instinctively move toward and fixate on the stimulus position (e.g., within less than a second) because the second eye (e.g., left eye) will lose any dominance it had as a result of having nothing to look at. Testing subsystem 122 may measure the correction movement of the first eye (and other changes in the eye-related characteristics of the first eye) to determine the deviation measurement for the first eye. As an example, the amount of movement of the first eye that occur upon such stimulus presentation may correspond to the amount of the crossing of the first eye.

In some embodiments, testing subsystem 122 may determine a deviation measurement or other visual defect information for a first eye of a user by (i) causing a stimulus to be presented at a given time at the corresponding position on a first user interface for the first eye and at the corresponding position on a second user interface for the second eye and (ii) determining the visual defect information based on one or more eye-related characteristics of the first eye occurring upon the stimulus presentation. As an example, the target stimulus may be presented at the central position on both user interfaces or at another corresponding position on both user interfaces. In one use case, when presenting a stimulus in front of both eyes (e.g., FIG. 25B), the dominant eye (e.g., the left eye in FIG. 25B) will instinctively move to the corresponding position and fixate on the target stimulus (e.g., within less than a second). Although the other eye (e.g., the right eye in FIG. 25B) will also move, it will not instinctively fixate on the target stimulus because the other eye is crossed out, thereby causing the user to see double. For example, while the other eye will instinctively move, the instinctive movement will result in the other eye's gaze direction being toward a different position. However, when the user focuses on looking at the target stimulus with the user's other eye, the other eye will move and fixate on the target stimulus presented at the corresponding position on the other eye's user interface. Because the target stimulus is presented at the corresponding position on both user interfaces, the dominant eye will remain dominant and continue to fixate on the target stimulus presented at the corresponding position on the dominant eye's user interface. Testing subsystem 122 may measure the correction movement of the other eye (and other changes in the eye-related characteristics of the other eye) to determine the deviation measurement for the other eye (e.g., the amount of movement of the other eye may correspond to the amount of the crossing of the other eye).

In some embodiments, after obtaining a deviation measurement or other visual defect information for a first eye of a user by measuring changes in the eye-related characteristics of the first eye (e.g., the movement of the first eye occurring upon the presentation of a stimulus at a corresponding position on a first user interface for the first eye), testing subsystem may cause a stimulus to be presented at a modified position on the first user interface for the first eye display. As an example, the stimulus presentation at the modified position occurs while a stimulus is not presented on a second user interface for the second eye (or at least while a stimuli intensity of the second user interface does not satisfy a stimuli intensity threshold so that the second eye does not react to any stimuli on the second user interface). Based on one or more eye-related characteristics of the first eye or the second eye not changing beyond a change threshold upon the presentation at the modified position, testing subsystem 122 may confirm the deviation measurement or other visual defect information for the first eye. As an example, the deviation measurement for the first eye may be confirmed based on the first eye not moving beyond a movement threshold (e.g., no movement or other movement threshold) upon the presentation of a stimulus at the modified position. Additionally, or alternatively, the deviation measurement for the first eye may be confirmed based on the second eye not moving beyond the movement threshold.

In some embodiments, testing subsystem 122 may generate one or more modification profiles associated with a user based on one or more deviation measurements or other visual defect information for one or more eyes of the user (e.g., that are obtained via one or more visual test presentations). As an example, each of the modification profiles may include modification parameters or functions used to generate an enhanced image from live image data (e.g., parameters of functions used to transform or modify the live image data into the enhanced image). As such, in some embodiments, visioning subsystem 124 may generate modified video stream data to be displayed to the user based on (i) video stream data representing an environment of the user and (ii) the modification profiles associated with the user.

Figure 25A:
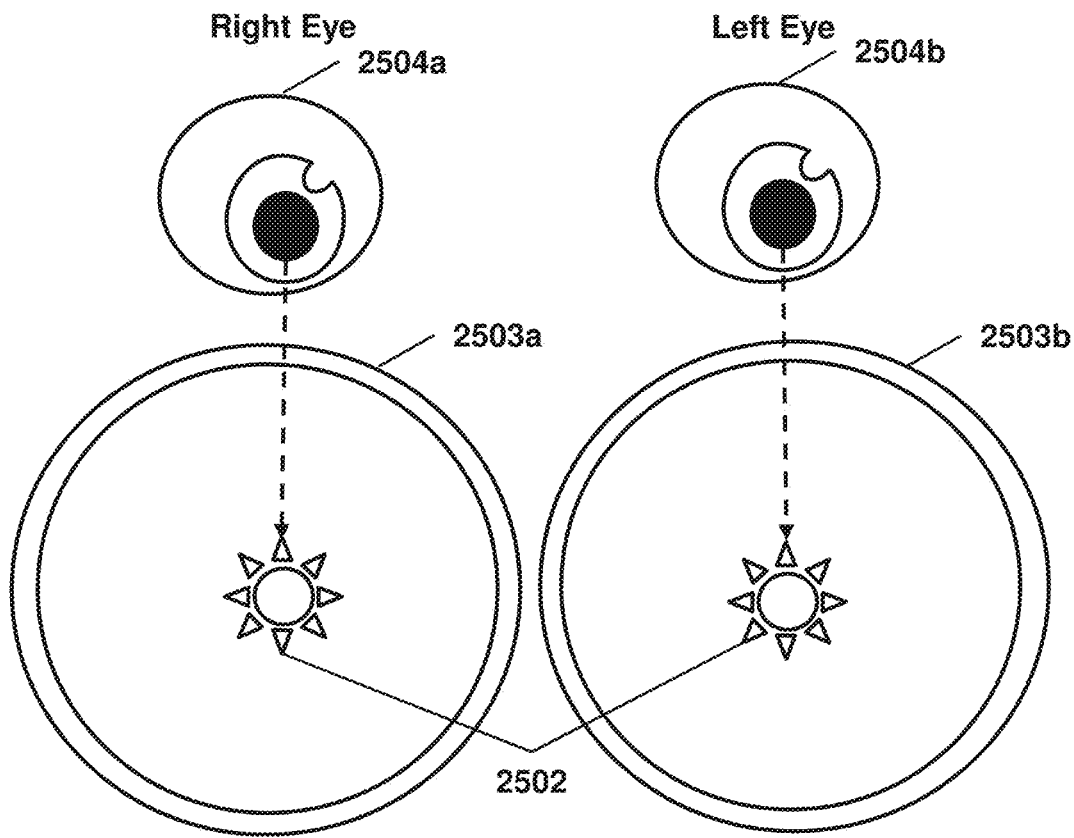
FIG. 25A illustrates a use case of a visual test presentation being displayed to a patient without crossed eyes, in accordance with one or more embodiments.

As an example, a visual test may be performed to determine whether a deviation of an eye of a user exists, measure a deviation of an eye of the user, or generate one or more modification profiles for an eye of the user. In one use case, with respect to FIG. 25A, when the target stimulus 2502 is presented at the central position on right and left displays 2503*a* and 2503*b* of a wearable device to a patient (e.g., patient with no crossed eyes), both eyes (e.g., right and left eyes 2504*a* and 2504*b*) will instinctively move and fixate on the target stimulus 2502 at the central position on each wearable display, and, thus, the patient only sees one target stimulus 2502. As such, based on the foregoing eye responses, testing subsystem 122 may determine that the user does not have double vision.

Figure 25B:
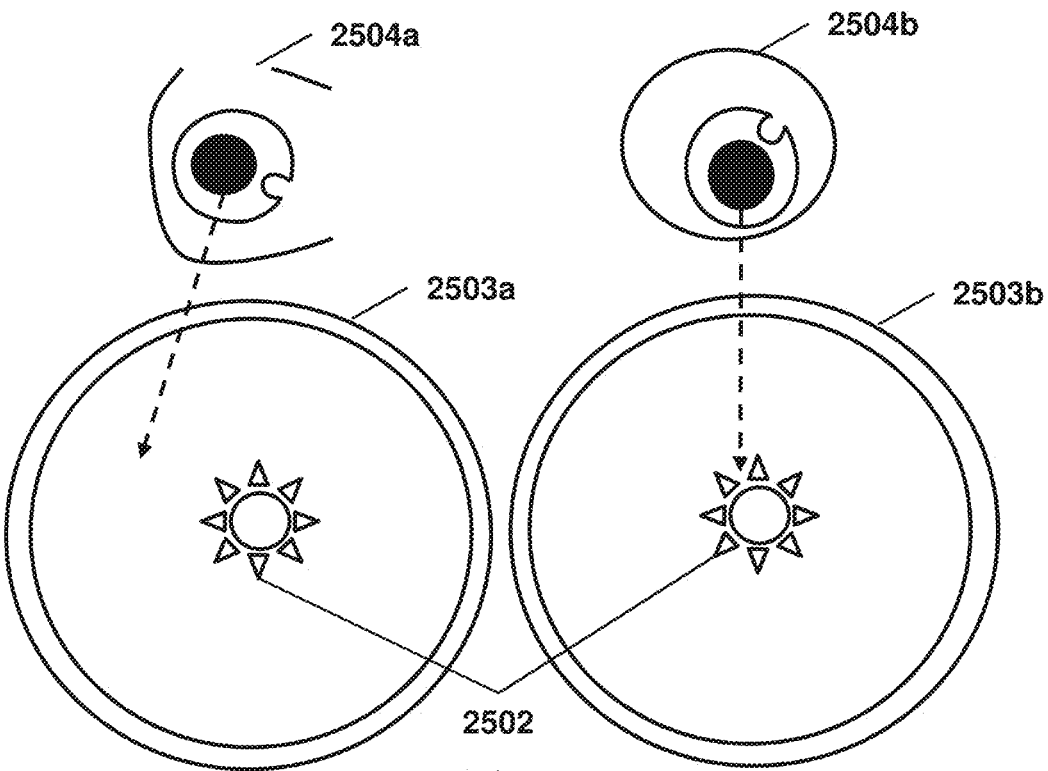
FIG. 25B illustrates a use case of a visual test presentation being displayed to a patient with crossed eyes, in accordance with one or more embodiments.

In another use case, with respect to FIG. 25B, when the target stimulus 2502 is presented at the central position on right and left displays of a wearable device to a patient with crossed eyes, one of the eyes (e.g., the dominant eye) will instinctively move to the central position and fixate on the target stimulus 2502 (e.g., the left eye 2504*b* instinctively fixated on the target stimulus 2502). Although the other eye (e.g., the right eye 2504*a*) will also move, it does not fixate on the target stimulus 2502 because the other eye is crossed out, thereby causing the user to see double (e.g., the user sees two target stimuli instead of one). For example, while the other eye will instinctively move, the instinctive movement will result in the other eye's gaze direction being toward a different position. Based on the foregoing eye responses, testing subsystem 122 may determine that the user has double vision. However, in a further use case, when the user focuses on looking at the target stimulus 2502 with the user's other eye (e.g., the crossed right eye 2504*a*), the other eye will move and fixate on the target stimulus 2502 presented at the central position on the other eye's user interface. Because the target stimulus 2502 is presented at the central position on both displays 2503*a* and 2503*b*, the dominant eye will remain dominant and continue to fixate on the target stimulus 2502 presented at the central position on the dominant eye's display. The correction movement of the other eye (and other changes in the eye-related characteristics of the other eye) may be measured to determine the deviation measurement for the other eye (e.g., the amount of movement of the other eye may correspond to the amount of the crossing of the other eye).

Figure 25C:
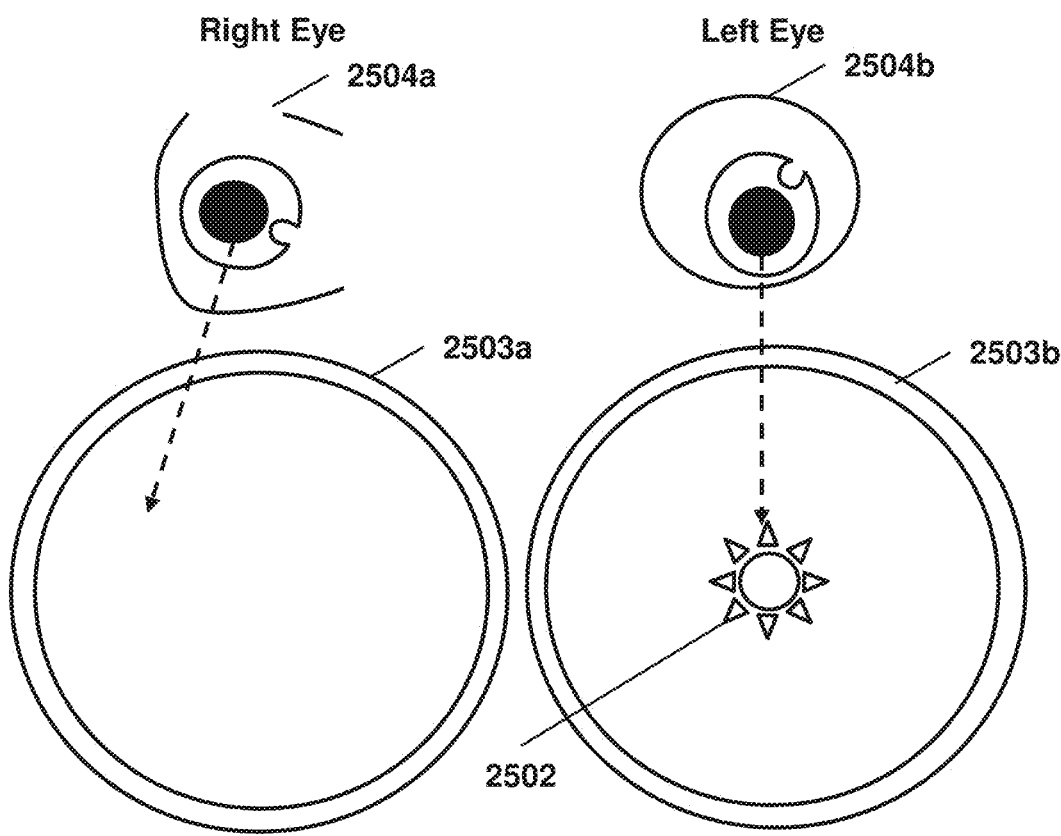
FIG. 25C-25I illustrate automated measurement and correction of double vision, in accordance with one or more embodiments.

In another use case, with respect to FIG. 25C, at time t1, a stimulus (e.g., the target stimulus 2502) may be presented at the central position only to the left eye 2504*b* by presenting the stimulus on the left display 2503*b* and not presenting a stimulus on the right display 2503*a*. If, for example, a stimulus was presented at the central position to both eyes 2504*a* and 2504*b* as shown in FIG. 25B immediately prior to the stimulus presentation to only the left eye 2504*b* (e.g., at time t0 immediately prior to the stimulus presentation at time t1), then the left eye 2504*b* will not move because the left eye 2504*b* is already fixated on the central position. If, however, the left eye 2504*b* is not already fixated on the central position, the stimulus presentation to only the left 2504*b* will cause the left eye 2504*b* to instinctively move to the central position and fixate on the target stimulus 2502.

Figure 25D:
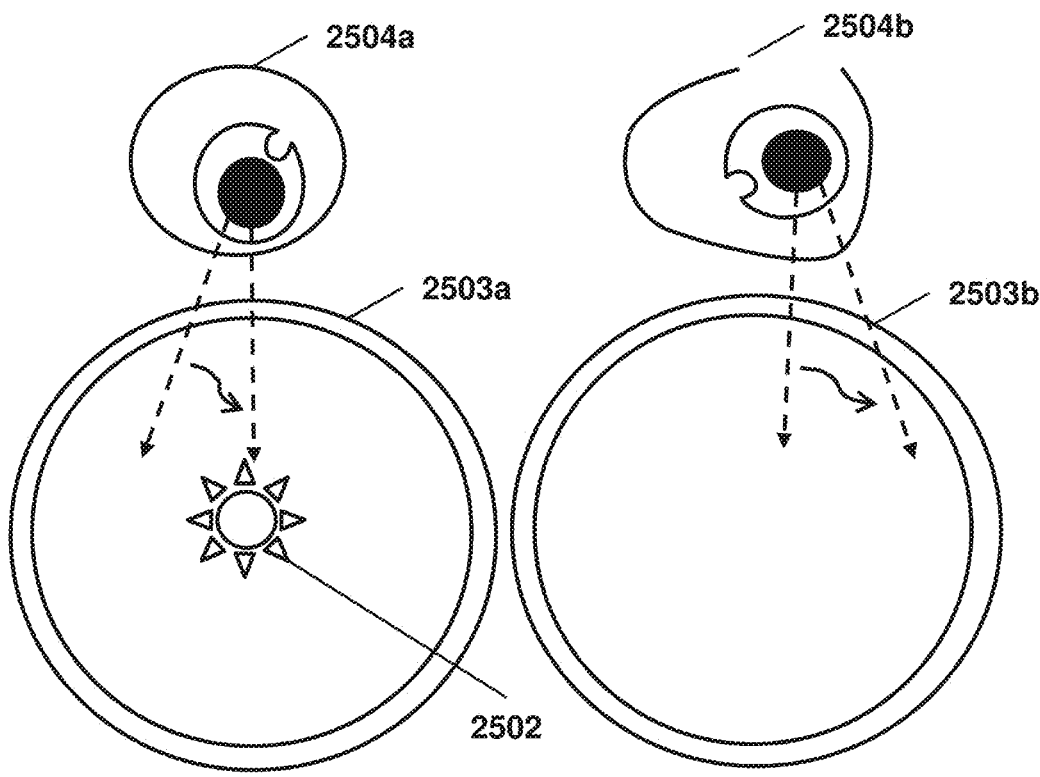

As indicated in FIG. 25D, a stimulus (e.g., the target stimulus 2502) may be presented at the central position only to the right eye 2504*a* (e.g., at time t2) by presenting the stimulus on the right display 2503*a* and not presenting a stimulus on the left display 2503*b*. Because the left eye 2504*b* is not being stimulated (e.g., has nothing to look at), the left eye 2504*b* will lose dominance and thus move to the outside as a result of the right eye 2504*a* taking over. Upon presenting the target stimulus 2502 only to the right eye 2504*a*, the right eye 2504*a* will instinctively take over and move to fixate on the central position. Testing subsystem 122 may measure the movement of the right eye 2504*a* to determine the deviation measurement for the right eye 2504*a* (e.g., the amount of movement may correspond to the amount of the crossing of the right eye 2504*a*).

Figure 25E:
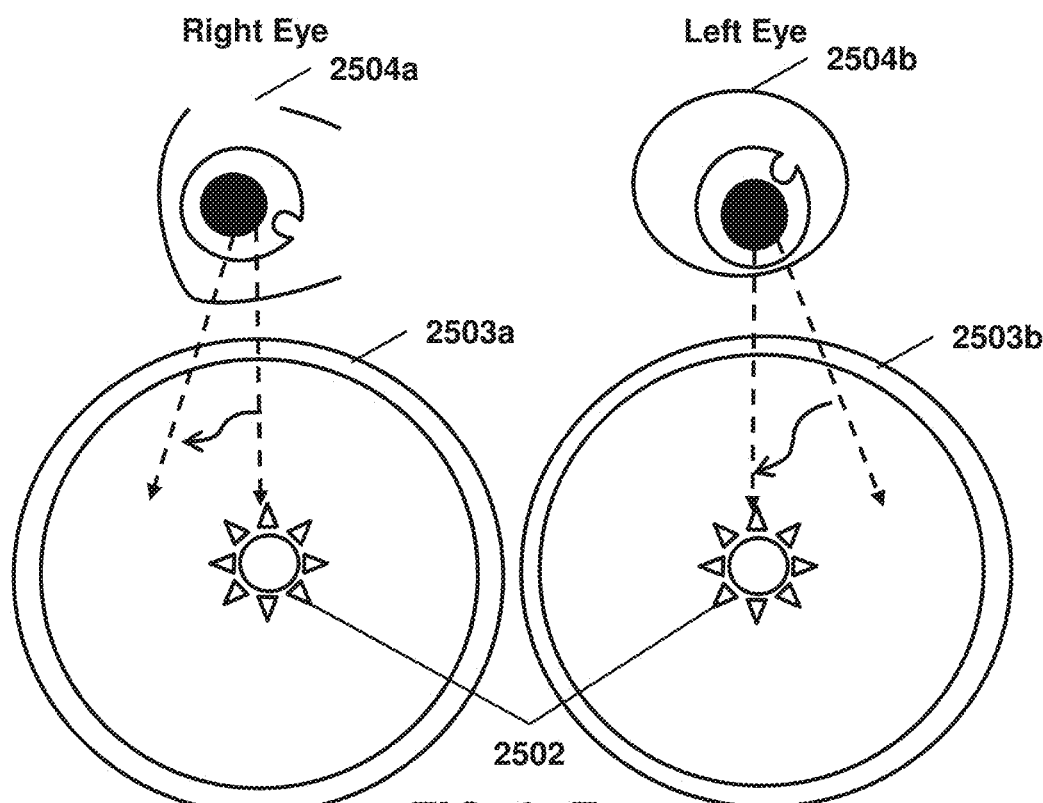

As indicated in FIG. 25E, a stimulus (e.g., the target stimulus 2502) may be presented at the central position to both eyes 2504*a* and 2504*b* (e.g., at time t3) by presenting the stimulus on the left display 2503*b* and on the right display 2503*a*. If crossing is alternating (no dominance of either eye), the right eye 2504*a* will stay fixating on the central position, and the left eye 2504*b* will stay crossed. If, however, the left eye 2504*b* is the dominant eye (as indicated in FIG. 25E), the left eye 2504*b* will instinctively move and fixate on the central position. The movement of the left eye 2504*b* will cause the right eye 2504*a* to be crossed, resulting the right eye 2504*a*'s gaze direction being toward a different position. Testing subsystem 122 may measure the movement of the left eye 2504*b* to determine or confirm the deviation measurement for the right eye 2504*a* (e.g., the amount of movement of the left eye 2504*b* may correspond to the amount of deviation of the right eye 2504*a*).

Figure 25F:
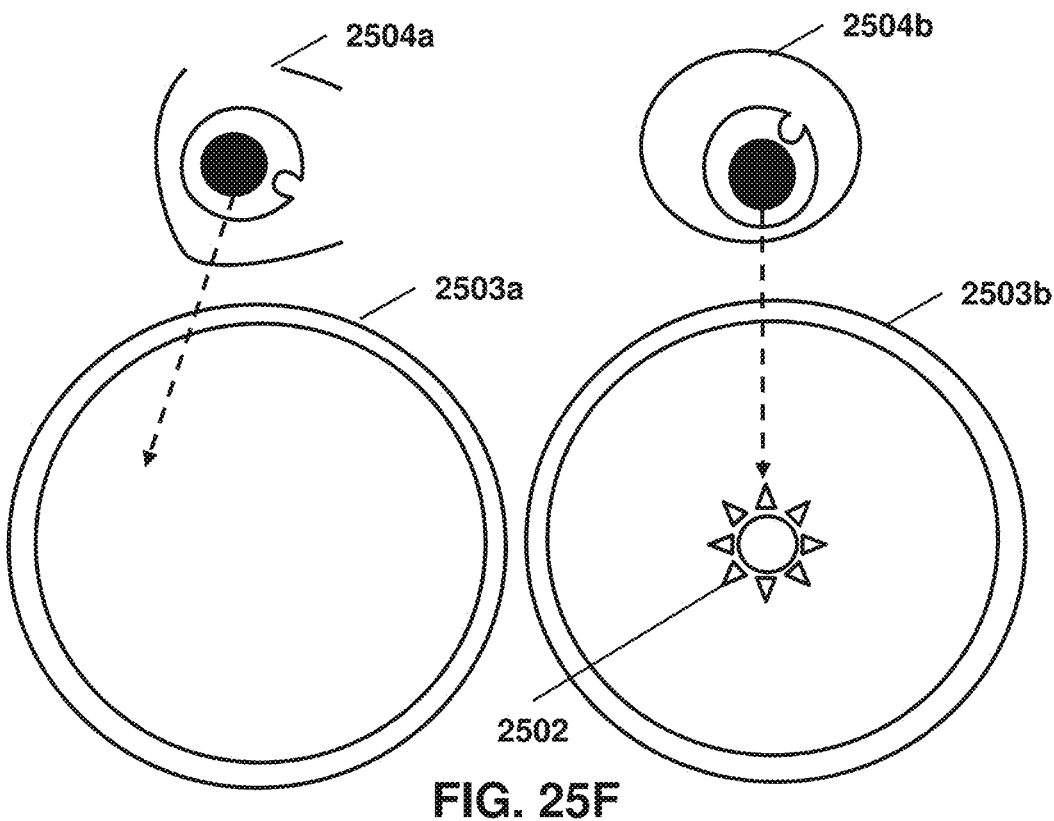
Figure 25G:
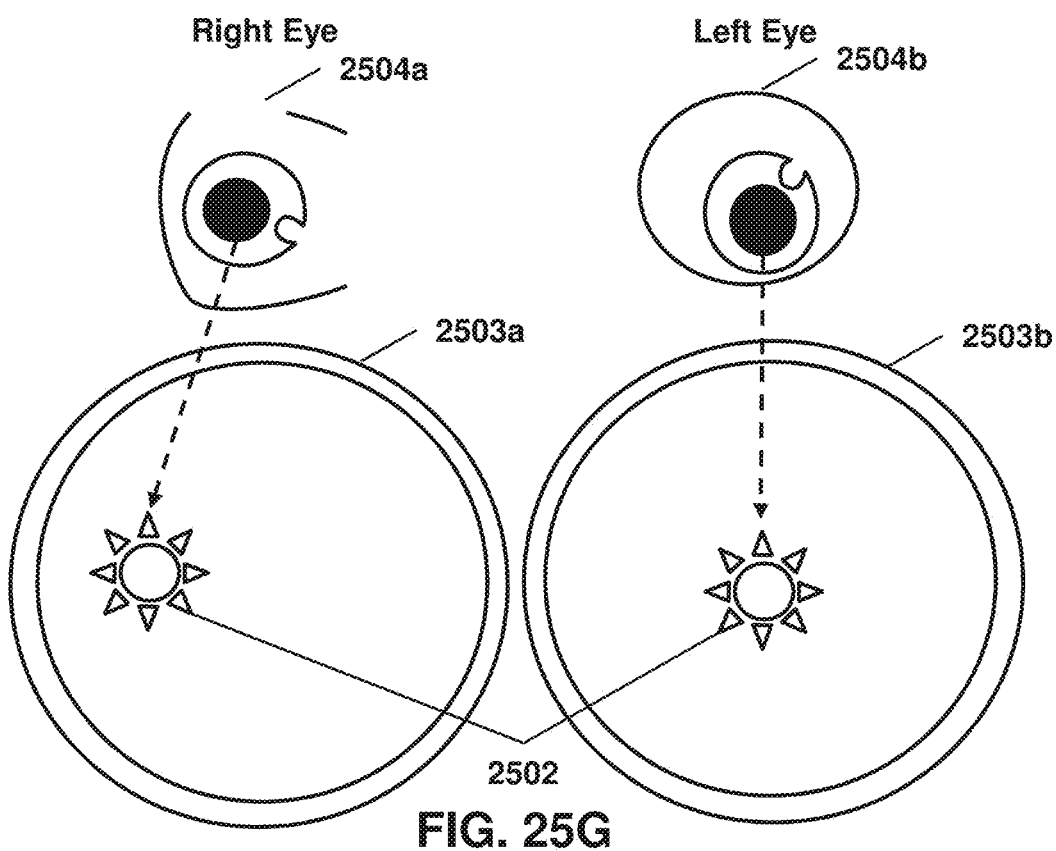

In a further use case, further testing may be performed to confirm the deviation measurement for the non-dominant eye. For example, as indicated in FIG. 25F, subsequent to one or more of the foregoing steps described with respect to FIGS. 25B-25E, a stimulus (e.g., the target stimulus 2502) may be presented at the central position only to the left eye 2504*b* (e.g., at time t4) by presenting the stimulus on the left display 2503*b* and not presenting a stimulus on the right display 2503*a*. To the extent that the left eye 2504*b* lost fixation (e.g., due to the presentation in FIG. 25E), the presentation in FIG. 25F will cause the left eye 2504*b* to instinctively move to gain fixation on the central position. The movement of the left eye 2504*b* will cause the right eye 2504*a* to be crossed, resulting in the right eye 2504*a*'s gaze direction being toward a different position. As indicated in FIG. 25G, based on the deviation measurement for the right eye 2504*a*, a modified position may be determined for presenting a stimulus to the right eye 2504*a*. As such, while the target stimulus 2502 is being presented at the central position on the left display 2503*b*, the target stimulus 2502 may be presented at the modified position on the right display 2503*a* (e.g., at time t5).

Figure 25H:
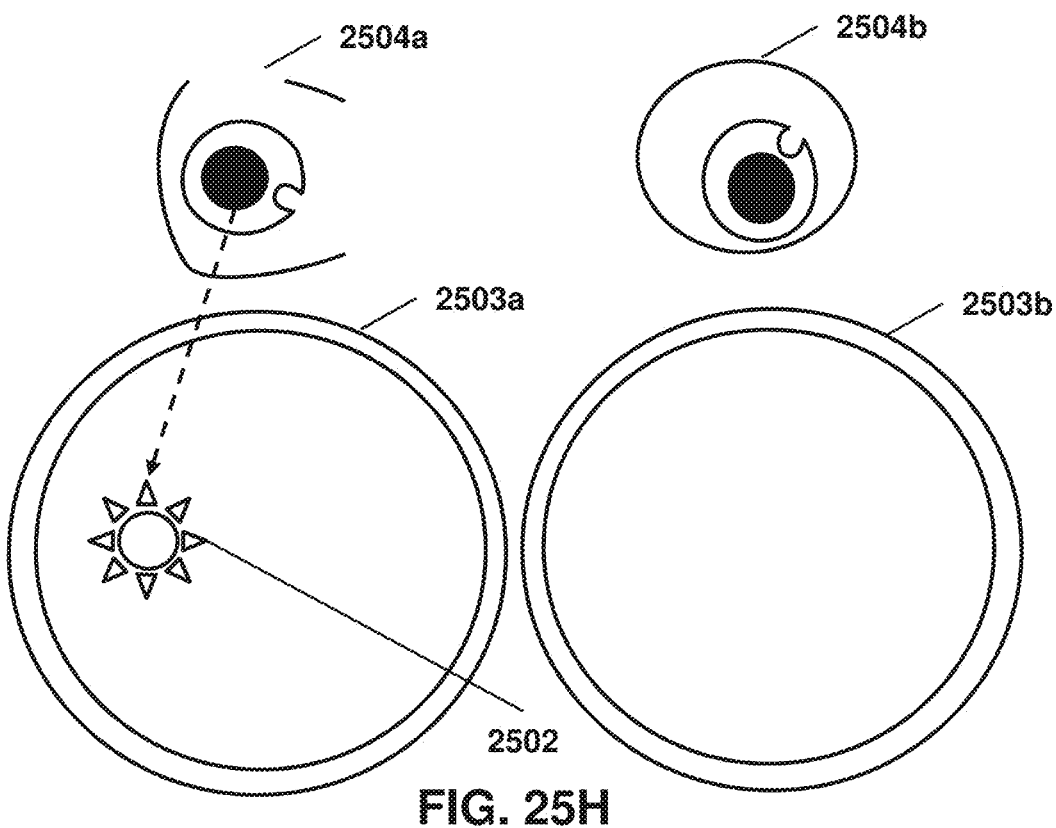
Figure 25I:
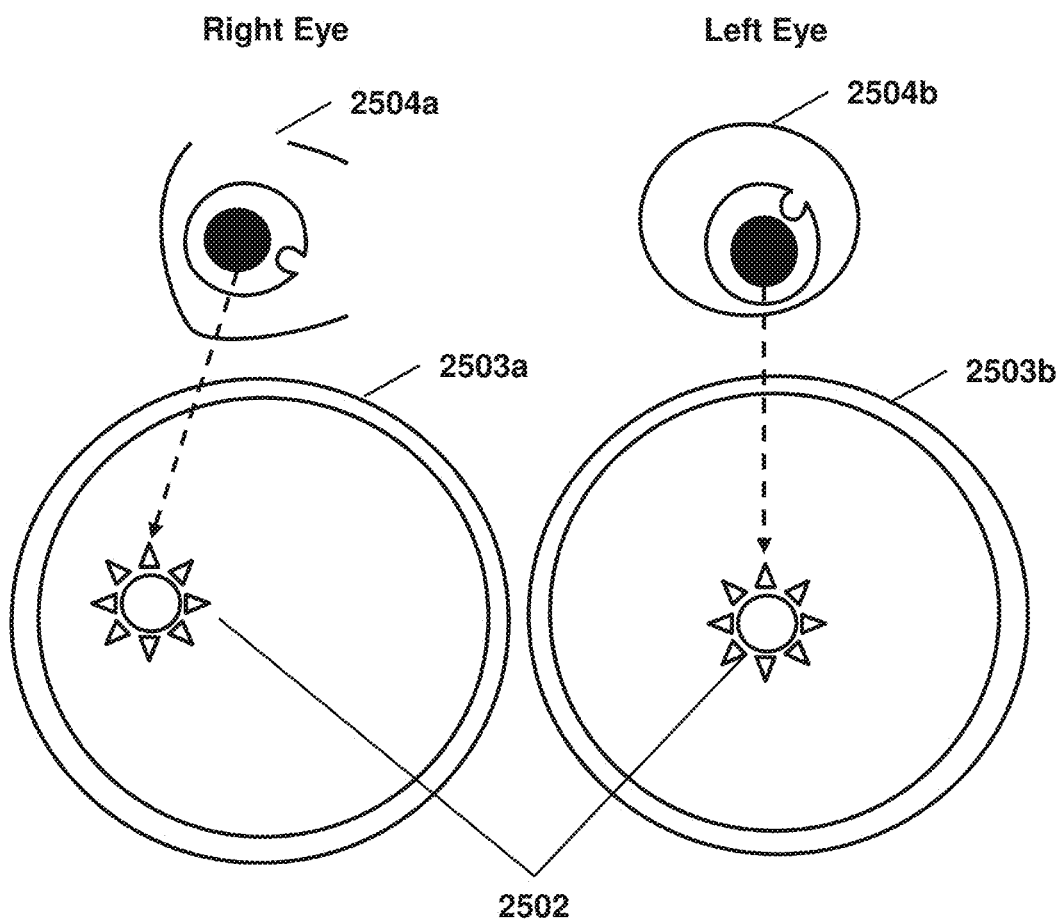

Subsequently, with respect to FIG. 25H, the target stimulus 2502 may only be presented to the right eye 2504*a* (e.g., at time t6) by presenting the target stimulus 2502 at the modified position on the right display 2503*a* and not presenting a stimulus on the left display 2503*b*. Specifically, for example, the target stimulus 2502 is deviated to the right by the same amount as the deviation measured in one or more of the foregoing steps described with respect to FIGS. 25B-25E. If the deviation measurement is accurate, the right eye 2504*a* will not move. If the deviation measurement is not accurate, the right eye 2504*a* will slightly move, and the amount of movement may be measured by the wearable device (e.g., the pupil tracker of the wearable device) and the measurement of the slight movement may be used to fine tune the deviation. As an example, the measurement and the modified position may be used to determine an updated modified position for presenting a stimulus to the right eye 2504*a*, and one or more of the steps described with respect to FIGS. 25F-25H may be repeated using the updated modified position. Additionally, or alternatively, one or more of the steps of FIGS. 25B-25E may be repeated to redetermine the deviation measurement for one or more eyes of the user (e.g., redetermining the deviation measurement for the right eye 2504*a*). With respect to FIG. 25I, the target stimulus 2502 may then be presented to both eyes 2504*a* and 2504*b* (e.g., at time t7) by presenting the target stimulus 2502 at the modified position on the right display 2503*a* and at the central position on the left display 2503*b*. Because the target stimulus 2502 in front of the right eye 2504*a* is deviated to the right in accordance with the deviation measurement (e.g., as determined or confirmed in one or more of the foregoing steps), the user is no longer seeing double, thereby providing autonomous correction for the patent's double vision.

In some embodiments, a visual test may be performed to determine which eye of a user is a deviating eye. Based on such determination, a deviation of the deviating eye may be measured, and the deviation measurement may be used to generate a modification profile to correct the deviation of the user's vision. As an example, testing subsystem 122 may cause a stimulus to be presented at a given time at a first position on a first user interface for a first eye and at the first position on a second user interface for a second eye. Testing subsystem 122 may detect lack of fixation of the first eye on the first position upon the stimulus presentation of a stimulus on the first user interface. Based on the detection of the lack of fixation of the first eye, testing subsystem 122 may determine the first eye of the user to be a deviating eye. As an example, with respect to FIG. 25B, when the target stimulus 2502 is presented at the central position on right and left displays of a wearable device to a patient with crossed eyes, one of the eyes (e.g., the dominant eye) will instinctively move to the central position and fixate on the target stimulus 2502 (e.g., the left eye 2504*b* instinctively fixated on the target stimulus 2502). Although the other eye (e.g., the right eye 2504*a*) will also move, it does not fixate on the target stimulus 2502 because the other eye is crossed out, thereby causing the user to see double (e.g., the user sees two target stimuli instead of one). Based on this detected lack of fixation, the other eye may be determined to be the deviating eye.

In some embodiments, a visual test may be performed while the eye is looking in different directions of gaze to detect how much is the double vision in each direction of gaze. In this way, diagnostics and correction may be performed for the specific type of strabismus (e.g., incomitant strabismus). For example, patient with paralysis of a muscle of the eye, the deviation between both eyes (angle of strabismus) is larger when the eye is looking towards the direction of action of that muscle. For example, if the muscle that takes the left eye out is paralyzed, then the left eye will be looking in (aka esotropia). The esotropia degree will be more if the left eye is trying to look out. This phenomenon happens with paralytic strabismus. By repeating the quantification test while the stimulus is presented in different areas of the field of vision, the wearable device (or other components in connection with the wearable device) may accurately measure the angle of deviation. Also, knowing the degree of deviation in different directions of gaze will enable dynamic correction for double vision. When such visual test presentation is provided via a wearable device, and when the pupil tracker of the wearable device detects that the eye at a specific gaze, the wearable device may provide the image displacement that corresponds to that gaze.

In some embodiments, such tests can be done while patient looking at a distance object and at a near object. In some embodiments, the wearable device may automatically test for the range of motion of the extraocular muscle by presenting a stimulus that moves around. As the patient follows it with his eyes, the wearable device (or other components in connection with the wearable device) measures the range of movement and determines information regarding the double vision of the user based on the range of movement measurement.

Thus, in some embodiments, multiple modification profiles may be generated for a user to correct for dynamic vision defects (e.g., double vision or other vision defects). As an example, a first modification profile associated with the user may include one or more modification parameters to be applied to modify an image for a first eye of the user in response to the second eye's gaze direction being directed at a first position, the second eye having a first torsion (e.g., first angle of torsion), or other characteristic of the second eye. A second modification profile associated with the user may include one or more modification parameters to be applied to modify an image for the first eye in response to the second eye's gaze direction being directed at a second position, the second eye having a second torsion (e.g., second angle of torsion), or other characteristic of the second eye. A third modification profile associated with the user may include one or more modification parameters to be applied to modify an image for the first eye in response to the second eye's gaze direction being directed at a third position, the second eye having a third torsion (e.g., third angle of torsion), or other characteristic of the second eye, and so on. In one use case, one or more of the steps described with respect to FIGS. 25B-25H may be repeated for one or more other positions (in addition or alternatively to the central position) to generate multiple modification profiles for the user.

In some embodiments, visioning subsystem 124 may monitor one or more eye-related characteristics of one or more eyes of the user and may generate modified video stream data to be displayed to the user based on (i) video stream data representing an environment of the user, (ii) the monitored eye-related characteristics, and (iii) the modification profiles associated with the user. As an example, if the monitoring indicates that the second eye's gaze direction is directed at the first position, the first modification profile (e.g., its modification parameters) may be used to modify the video stream data to generate the modified video stream data to be displayed to the user's first eye. As another example, if the monitoring indicates that the second eye's gaze direction is directed at the second position, the second modification profile (e.g., its modification parameters) may be used to modify the video stream data to generate the modified video stream data for the user's first eye, and so on. In this way, for example, the foregoing accounts for the typically dynamic nature of double vision (e.g., the double vision increases or decreases towards one or more gazes). For example, if the user has an issue in moving the user's right pupil away from the user's nose (e.g., toward to edge of the user's face), then the user's double vision may increase when the user is looking to the right and may decrease when the user is looking to the left. As such, the user's pupils, the user's line of sight, or other eye-related characteristics may be monitored to provide appropriate correction by applying the appropriate modification profile specific to the user's real-time eye-related characteristics to the live video stream data.

In some embodiments, a vision test may be performed to assess binocular vision of a user. In some embodiments, a wearable device may be used to perform the binocular vision test. As an example, one or more stimuli may be presented on a user interface of each wearable device display for an eye of the user, where the number or type of stimuli presented on one user interface is different from the number or type of stimuli presented on the other user interface (e.g., different number of stimuli on each user interface, at least one stimuli on one user interface having a different color or pattern than the stimuli in the other user interface, etc.). Alternatively, in some scenarios, the number or type of stimuli presented on both user interface is the same. Testing subsystem 122 may determine whether the user has double vision based on a user indication of the number or types of stimuli that the user sees.

Figure 25J:
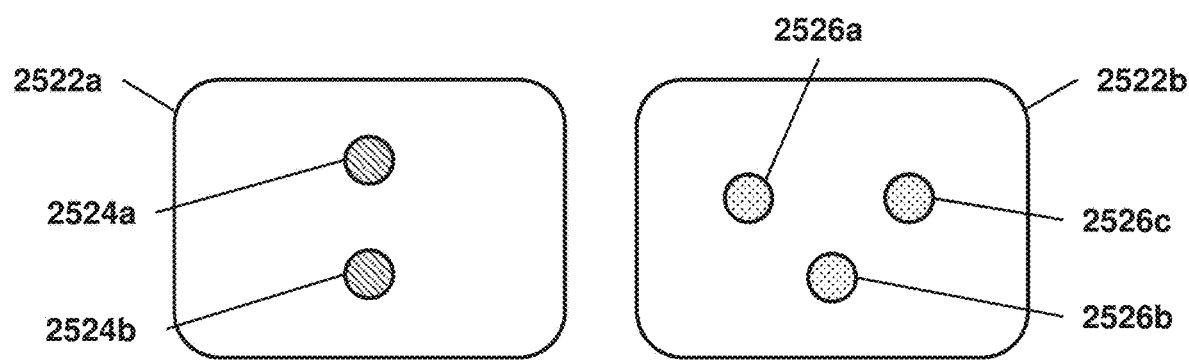
FIG. 25J-25L illustrate binocular vision testing and results of such testing, in accordance with one or more embodiments.
Figure 25K:
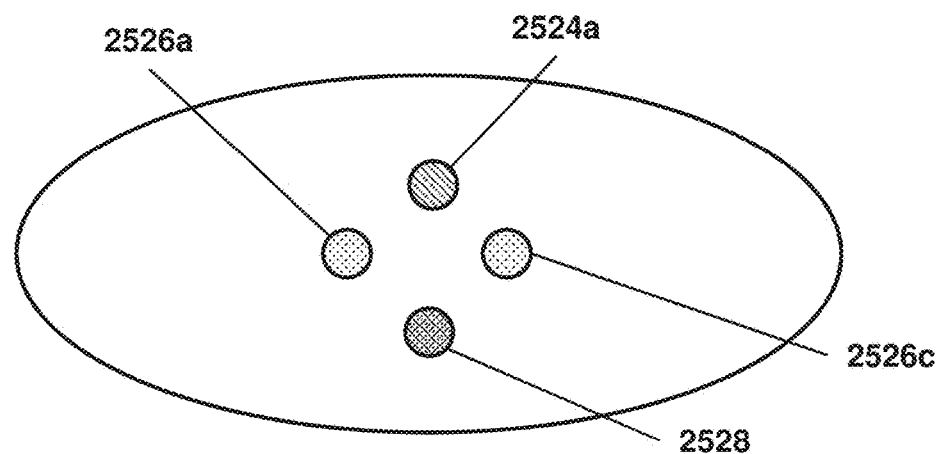
Figure 25L:
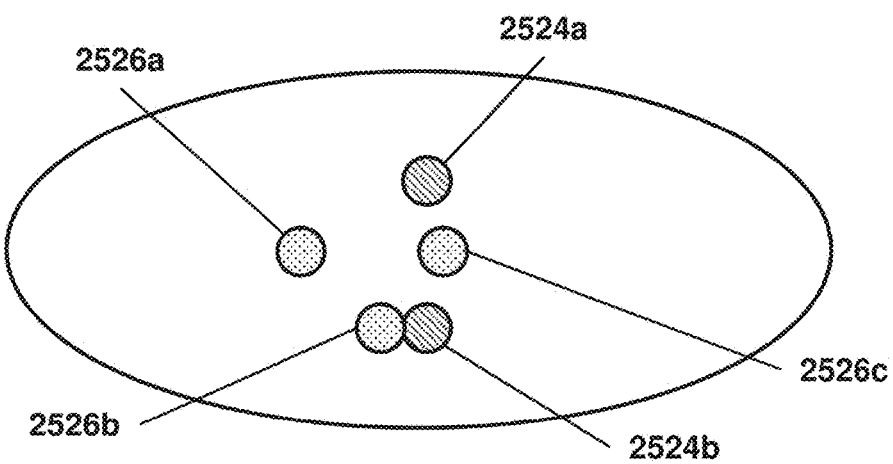

In one use case, with respect FIG. 25J, the binocular vision test may involve a user wearing a wearable device having displays 2522a and 2522b (or viewing such displays 2522a and 2522b via another device), where each display 2522 is configured to present one or more stimuli or other provide other presentations to a respective eye of the user. As an example, stimuli 2524a and 2524b (e.g., green dots) may be presented to one eye of the user on display 2522a, and stimuli 2526a, 2526b, and 2526c (e.g., red dots) may be presented to the other eye of the user on display 2522b. With respect to FIG. 25K, testing subsystem 122 may determine that the user is seeing binocular single vision (and, thus, does not have double vision) based on a user indication that the user sees 4 dots. Additionally, or alternatively, testing subsystem 122 may determine or confirm that the user is seeing binocular single vision based on a user indication that that the user is seeing one green dot (e.g., stimulus 2524a), two red dots (e.g., stimuli 2526a and 2526c), and one mixed color dot (e.g., mixed stimulus 2528 from the combination of stimuli 2524b and 2526b). On the other hand, with respect to FIG. 25L, testing subsystem 122 may determine that the user has double vision (e.g., diplopia) based on a user indication that the user sees 5 dots. Additionally, or alternatively, testing subsystem 122 may determine or confirm that the user has double vision based on a user indication that that the user is seeing two green dot (e.g., stimuli 2524a and 2524b) and three red dots (e.g., stimuli 2526a, 2526b, and 2526c).

In some embodiments, testing subsystem 122 may monitor one or more eye-related characteristics related to eyes of a user during visual test presentation via two or more user interfaces (e.g., on two or more displays) and determine whether the user has double vision based on the eye-related characteristics occurring during the visual test presentation in an autonomous manner. In some embodiments, testing subsystem 122 may determine an extent of the user's double vision based on such eye-related characteristics (e.g., by measuring the deviation of one or more eyes as described herein) and generate one or more modification profiles to correct for the double vision in an autonomous manner. As an example, a wearable device may include a pupil and line of sight tracker to detect the gaze direction of one or more eyes of the user or other eye-related characteristics. Based on the gaze direction (or the other eye-related characteristics, testing subsystem 122 may determine the number of points on which the user fixated (e.g., by using the detected gaze directions to see whether the user fixated on positions corresponding to the presented stimuli). In one use case, with respect to FIG. 25J, if it is determined that the user fixated on four points (e.g., points corresponding to stimuli 2524a, 2526a, 2526c, and 2528 shown in FIG. 25K), testing subsystem 122 may determine that the user does not have double vision. If it is determined that the user fixated on five points (e.g., points corresponding to stimuli 2524a, 2524b, 2526a, 2526b, and 2526c shown in FIG. 25L), testing subsystem 122 may determine that the user has double vision.

As a further example, in response to determining that the user has fixated on a particular point (e.g., corresponding to the presented stimuli or their respective display positions), testing subsystem 122 may mitigate the impact of the corresponding stimuli and increase the count of the number of stimuli that the user sees. As an example, the corresponding stimuli may be removed from the visual test presentation (e.g., the corresponding stimuli will disappear and the remaining stimuli may continue to be presented) or modified to reduce its impact (e.g., by decreasing the brightness or other intensity level of the stimuli). As another example, the other stimuli may be modified to increase its impact (e.g., by increasing the brightness or other intensity level of the other stimuli), thereby reducing the relative impact of the corresponding stimuli. As such, the user's eyes will instinctively move and fixate on one or more points corresponding to the remaining stimuli. With respect to FIG. 25K, for example, stimuli 2524b and 2526b (represented by mixed stimuli 2528) will be removed when the user's eyes fixate on the positions corresponding to stimuli 2524b and 2526b. On the other hand, with respect to FIG. 25L (where the user has double vision), stimuli 2524b and 2526b will be removed at two different times because the user will not fixate on the same relative position when the user is looking at stimuli 2524b or 2526b. Testing subsystem 122 may continue to remove stimuli and increase the count (of the number of stimuli that the user sees) in response to each of the user's fixations on the corresponding points. When all of the stimuli have been removed or other threshold has been satisfied, testing subsystem 122 may provide the number of stimuli that the user sees.

In some embodiments, based on eye-related characteristics occurring during a visual test presentation, testing subsystem 122 may determine whether the user has stereopsis or an extent of the user's stereopsis. As an example, testing subsystem 122 may cause one or more stimuli to be presented at one or more positions on one or more user interfaces and perform such stereopsis determinations or other visual defect information based on the eye-related characteristics in an autonomous manner. In one use case, with respect to FIG. 25M, the visual test presentation may involve a user wearing a wearable device having displays 2542a and 2542b (or viewing such displays 2542a and 2542b via another device), where each display 2542 is configured to present one or more stimuli or other provide other presentations to a respective eye of the user.

Figure 25M:
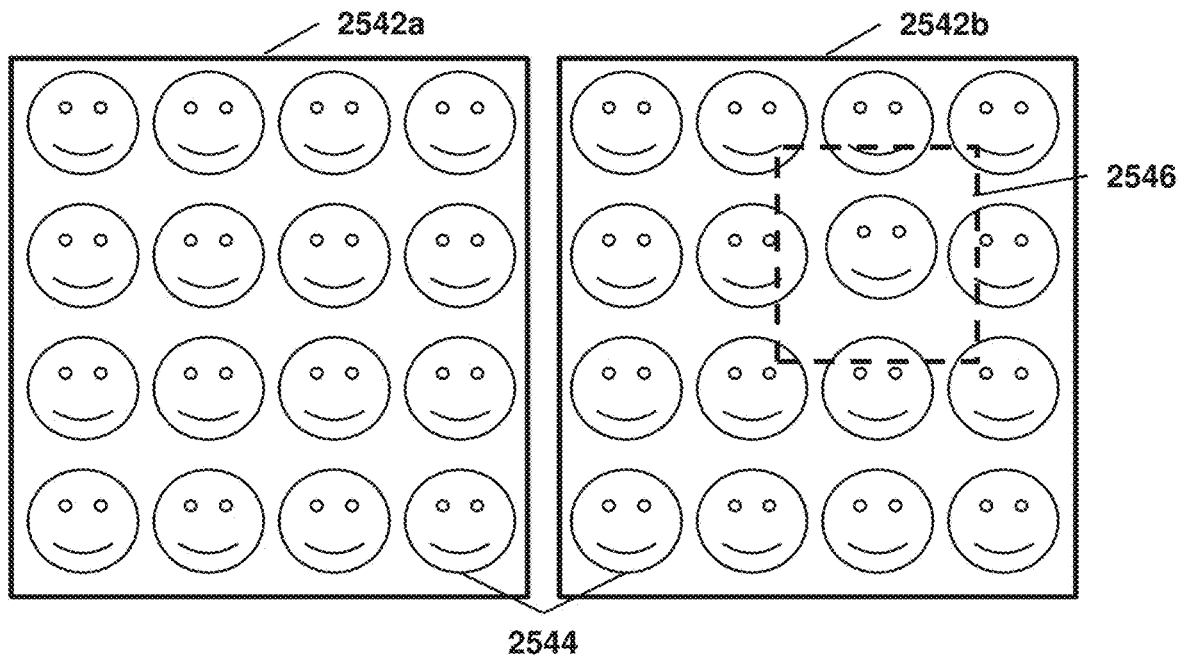
FIG. 25M-25N illustrate stereopsis testing, in accordance with one or more embodiments.

As shown in FIG. 25M, one or more icons 2544 or other stimuli may be presented on each display 2542, where one or more pairs of the icons 2544 are presented at corresponding positions on both displays 2542, and at least one pair of the icons 2544 is presented at slightly different positions on displays 2542a and 2542b. In particular, in FIG. 25M, the arrangement of the icons 2544 on both displays 2542 are the same, except that the icon 2544 in the second row and third column on display 2542b is shift slightly up and to the right (as shown by indicator 2546). To a user without binocular double vision and stereopsis, the slight difference will cause the icon pair to appear as a three-dimensional icon to the user, and all the other icons 2544 will appear as two-dimensional icons to the user. As such, the user will instinctively move and fixate on the three-dimensional icon. Based on a determination that the individual has fixated on the three-dimensional icon (e.g., within a predetermined threshold amount of time), testing subsystem 122 may determine that the user does not have stereopsis. As an example, testing subsystem 122 may detect that the gaze direction of one or more eyes of the user has changed upon the stimuli presentation and is currently directed toward the area at which the corresponding icons 2544 are presented on their respective displays 2542.

If, however, the user has stereopsis, the slight difference may not cause the icon pair to appear as a three-dimensional icon to the user, and the user likely will not fixate on the corresponding area at which the icon pair are presented on their respective displays 2542. Based on this lack of fixation (e.g., within the predetermined threshold amount of time), testing subsystem 122 may determine that the user has stereopsis.

In a further use case, with respect to FIG. 25M, the amount of the disparity between the two icons 2544 in the second row and third column icon 2544 may be modified to determine an extent of the user's stereopsis. As an example, the icon 2544 (in the area shown by indicator 2546) may be initially shifted up or to the right such that the disparity in the positions of the icon 2544 on display 2542b and its corresponding icon 2544 on display 2542a is a minimal amount. If the user does not fixate on the corresponding area at which the icon pair are presented, the icon 2544 on display 2542b may be shifted up or to the right again such that the disparity in the positions between the two icons 2544 is slightly greater. The positional disparity increase may be repeated until the user fixates on the corresponding area or until a positional disparity threshold has been reached. Testing subsystem 122 may use the positional disparity amount (or the number of times that the shifting operation is performed) to measure the extent of the user's stereopsis.

Figure 25N:
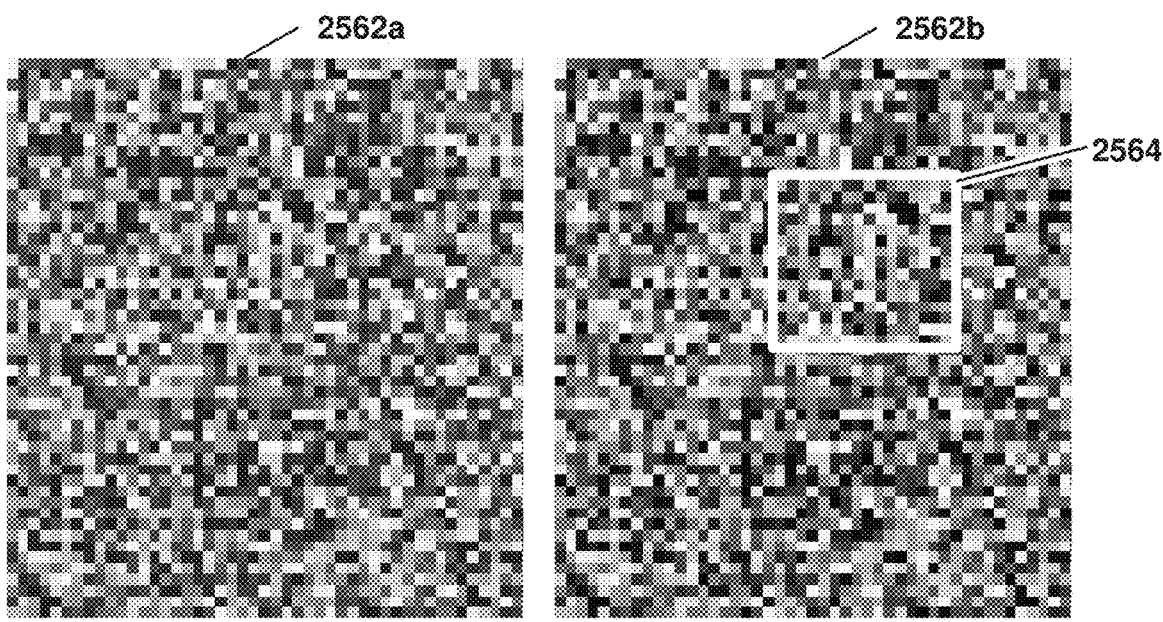

In another use case, with respect to FIG. 25N, the stimuli presentation during the visual test presentation may be provided in the form of randomly generated noise. In FIG. 25N, the stimuli presented on display 2562a and the stimuli presented on display 2562b are the same, except that the set of blocks (e.g., pixels) within the area shown by indicator 2564 is shifted to the right by five units (e.g., pixels) in display 2562b (as compared to the same set of blocks in display 2562a). As with the foregoing use case with respect to FIG. 25M, the slight difference will cause the set of blocks to appear as a three-dimensional object (or otherwise be noticeable) to a user without binocular double vision and stereopsis, resulting in the user quickly fixating on the three-dimensional object. Based on a determination that the individual has fixated on the three-dimensional object, testing subsystem 122 may determine that the user does not have stereopsis. If, however, the user has stereopsis, the slight difference may not cause the set of blocks to be noticeable to the user, and the user will not fixate on the corresponding area at which the set of blocks are presented on their respective displays 2562. Based on this lack of fixation, testing subsystem 122 may determine that the user has stereopsis.

Figure 26:
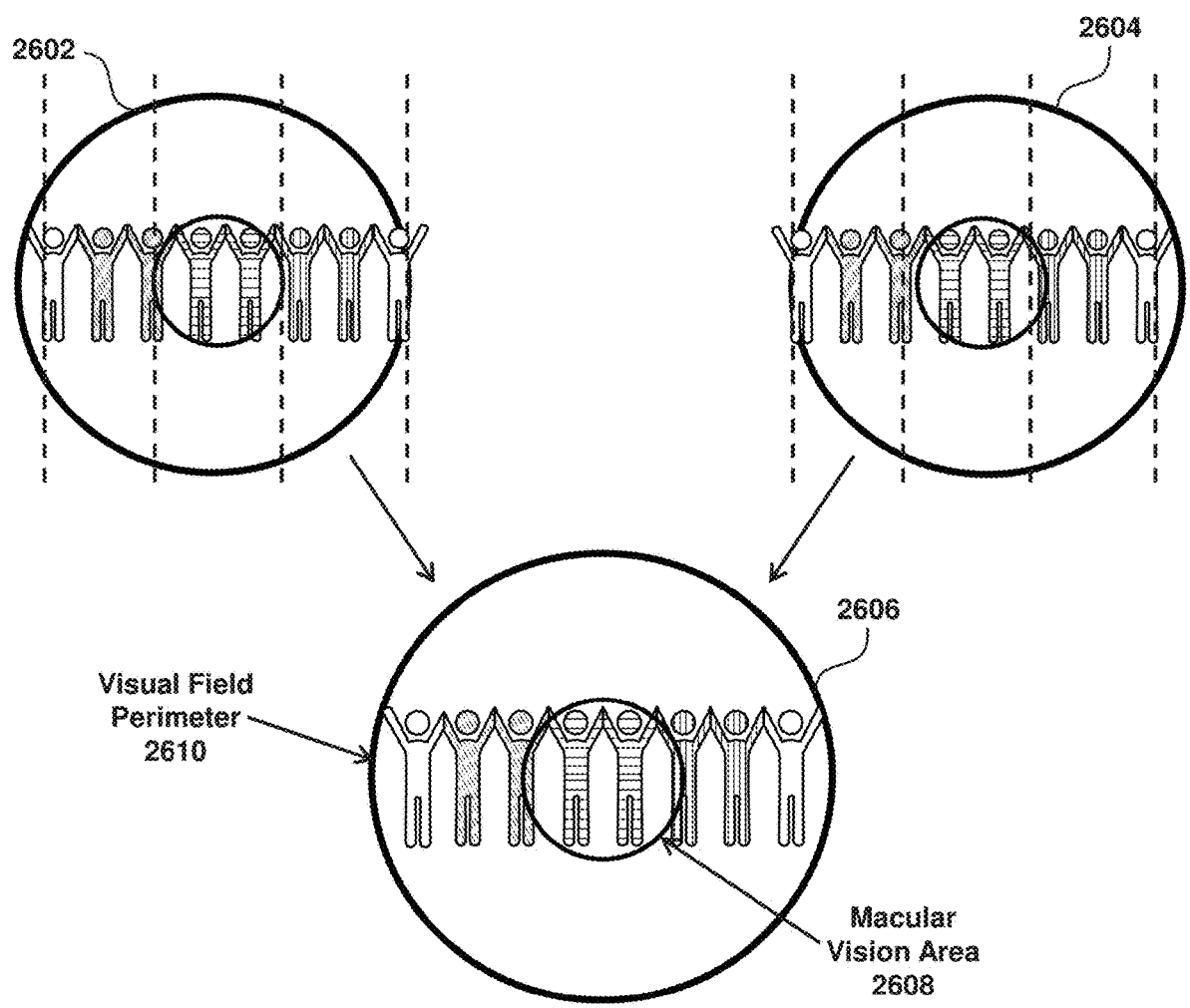
FIG. 26 illustrates a normal binocular vision for a subject where a monocular image from the left eye and from the right eye are combined into a single perceived image having a macular central area and a peripheral visual field area surrounding the central area.

In some embodiments, with respect to FIG. 1A, visioning subsystem 124 may facilitate an increase in a field of view of a user via combination of portions of multiple images of a scene (e.g., based on feedback related to a set of stimuli displayed to the user). As an example, FIG. 26 illustrates a representation of a normal binocular vision for a subject, where a monocular image from the left eye 2602 and from the right eye 2604 are combined into a single perceived image 2606 having a macular central area 2608 and a peripheral visual field area 2610 surrounding the central area 2608. In some cases, however, a subject may have a tunnel vision condition, wherein the peripheral area 2610 is not visible to the subject, as shown in the representation in FIG. 27. As shown, for these cases, one or more objects do not appear within a field of view, resulting in a peripheral defect 2612 in the area 2610, where objects within the area 2610 are not seen by the subject. Thus, for example, visioning subsystem 124 may combine portions of multiple images of a scene (e.g., common and divergent regions of such images) to increase the field of view of the subject.

In some embodiments, visioning subsystem 124 may obtain a plurality of images of a scene (e.g., images obtained via one or more cameras at different positions or orientations). Visioning subsystem 124 may determine a region common to the images, and, for each image of the images, determine a region of the image divergent from a corresponding region of at least another image of the images. In some embodiments, visioning subsystem 124 may generate or display an enhanced image to a user based on the common region and the divergent regions. As an example, the common region and the divergent regions may be combined to generate the enhanced image to include a representation of the common region and representations of the divergent regions. The common region may correspond to respective portions of the images that have the same or similar characteristics as one another, and each divergent region may correspond to a portion of one of the images that is distinct from all the other corresponding portions of the other images. In one scenario, a distinct portion of one image may include a part of the scene that is not represented in the other images. In this way, for example, the combination of the common region and the divergent region into an enhanced image increase the field of view otherwise provided by each of the images, and the enhanced image may be used to augment the user's visual field. In one use case, the common region may be any portion of at least one of the images of the left eye 2602 or the right eye 2604 between any of two of the four vertical dotted lines indicated in FIG. 27 for each such image. In another use case, with respect to FIG. 27, one of the divergent regions may be any portion of the image of the left eye 2602 to the left of the left-most vertical dotted line for that image. Another one of the divergent regions may be any portion of the image of the right eye 2604 to the right of the right-most vertical dotted line for that image.

In some embodiments, the common region is a region of at least one of the images that corresponds to a macular region of a visual field of an eye (or other central region of the visual field of the eye) or to a region within the macular region. In some embodiments, each of the divergent regions is a region of at least one of the images that corresponds to a peripheral region of a visual field of an eye or to a region within the peripheral region. As an example, with respect to FIG. 27, the common region may be (i) the portion of the image corresponding to the macular region of the left eye 2602 or (ii) the portion of the image corresponding to the macular region of the right eye 2604 (e.g., given that both such portions are common to both images). As another example, the common region may be the respective portions of the images corresponding to a common region within the macular regions of the left eye 2602 and right eye 2604. As a further example, based on the common region and the divergent regions, the image 2606 is generated to have the macular central area 2608 and the peripheral visual field area 2610 surrounding the central area 2608.

In some embodiments, visioning subsystem 124 may determine a region common to a plurality of images of a scene (e.g., captured via a wearable device of the user), and, for each image of the images, determine a region of the image divergent from a corresponding region of at least another image of the images. Visioning subsystem 124 may perform shifting of each image of the images and generate, subsequent to the performance of the shifting, an enhanced image based on the common region and the divergent regions. In some embodiments, the shifting of each of the images may be performed such that (i) a size of the common region is modified (e.g., increased or decreased) or (ii) a size of at least one of the divergent regions is modified (e.g., increased or decreased). In one scenario, the size of the common region may be increased as result of the shifting. In another scenario, the size of at least one of the divergent regions is decreased as a result of the shifting.

Figure 27:
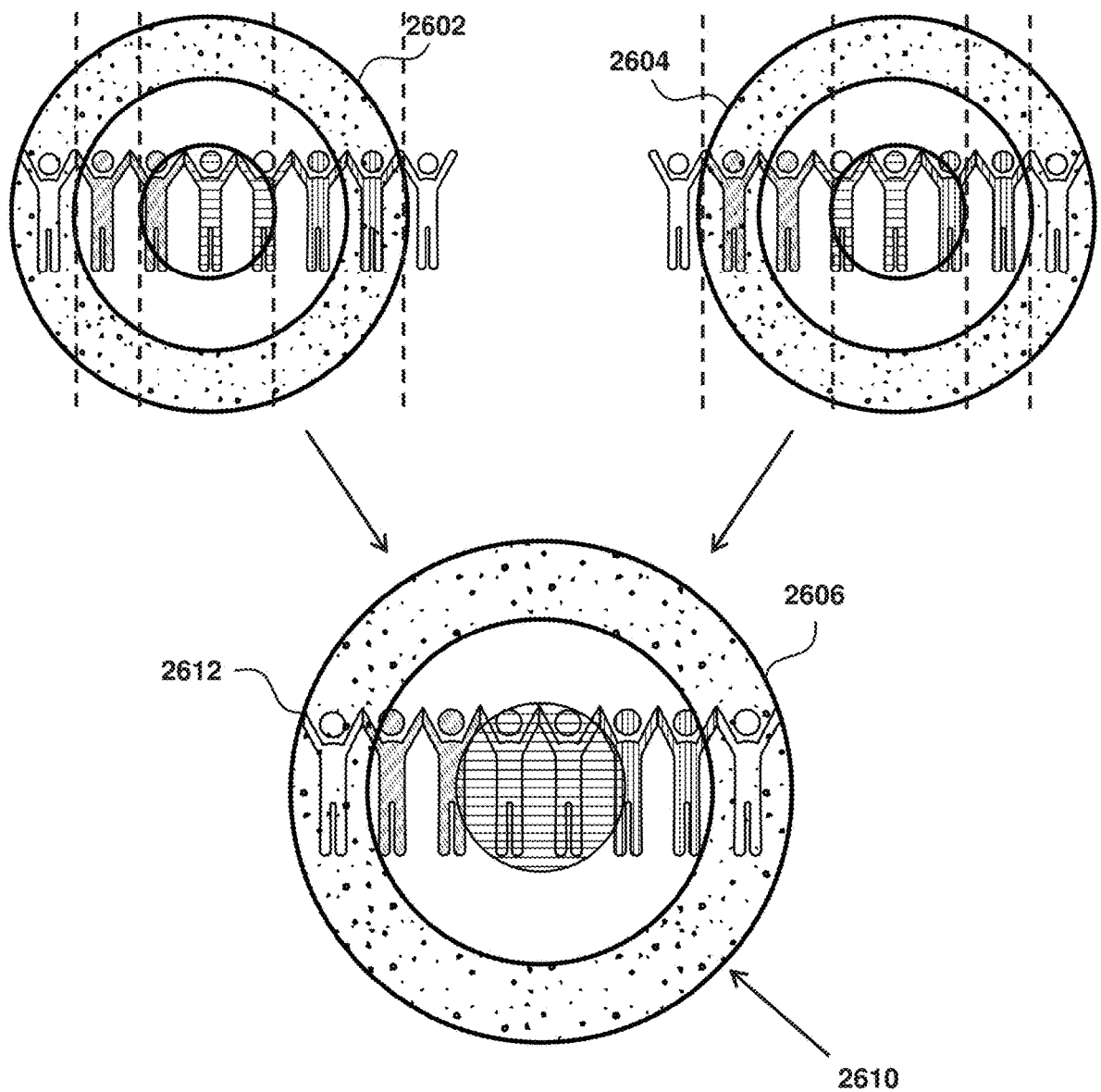
FIG. 27 illustrates a tunnel vision condition wherein a peripheral area is not visible to a subject.
Figure 28:
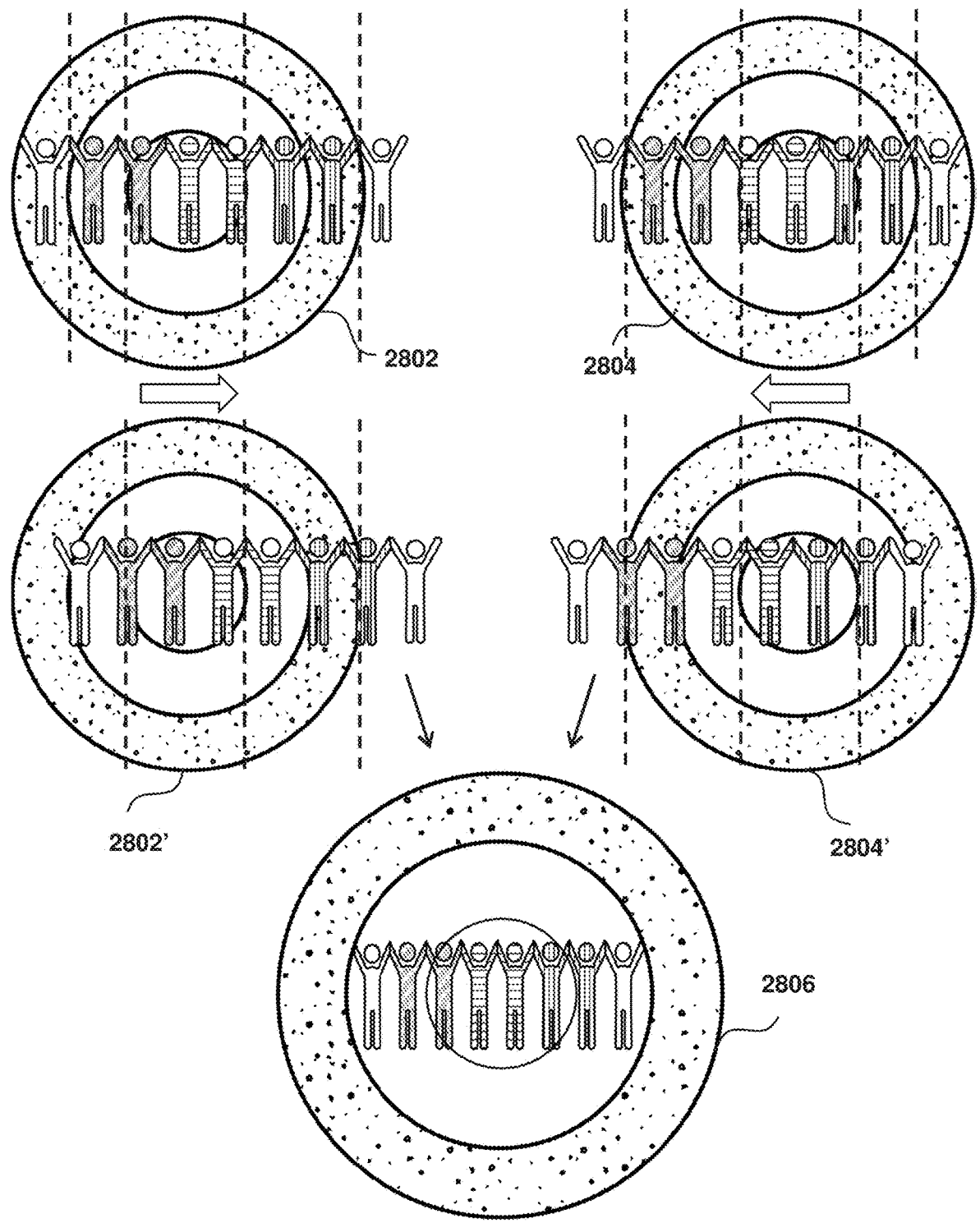
FIG. 28 illustrates an image shifting technique to enhance vision or to correct a tunnel vision condition, in accordance with one or more embodiments.

As an example, the defect in FIG. 27 may be corrected using a shifting image correction technique. In one use case, with respect to FIG. 28, each of two visual field cameras (e.g., of a wearable device) may capture a monocular image 2802 and 2804, respectively (e.g., where each monocular image is different as it's capturing the visual scene from a slightly different (offset) position). The two captured monocular images 2802, 2804 are then shifted toward each other in the vision correction framework resulting in images 2802' and 2804'. As shown in FIG. 28, the respective areas (e.g., a common region) of the two images 2802 and 2804 between the left-most vertical dotted line and the right-most vertical dotted line for each image 2802 and 2804 (is larger than the respective areas (e.g., a common region) between the two images 2802' and 2804' between the left-most vertical dotted line and the right-most vertical dotted line for each image 2802' and 2804'. As such, the common region is decreased in size subsequent the shifting. On the other hand, the divergent regions have increased in size subsequent the shifting (e.g., the area left of the left-most vertical dotted line for image 2802 vs. the area left of the left-most vertical dotted line for image 2802', and the area right of the right-most vertical dotted line for image 2804 vs. the area right of the right-most vertical dotted line for image 2804').

As a further example, these two shift images are then combined to generate a binocular image 2806 that captures the full periphery of the visual scene. For spectacles device having monitor displays, each display may display the corrected binocular image 2806 to the subject. In some use cases, for example, this shifting transformation can be used to increase the field of view of a subject by 5%, 10%, 15%, 20%, or more, without producing double vision effects for the subject.

In some embodiments, visioning subsystem 124 may determine a region common to a plurality of images of a scene (e.g., captured via a wearable device of the user), and, for each image of the images, determine a region of the image divergent from a corresponding region of at least another image of the images. Visioning subsystem 124 may perform resizing of one or more regions of the images and generate, subsequent to the performance of the resizing, an enhanced image based on the common region and the divergent regions. In some embodiments, visioning subsystem 124 may perform resizing of one or more regions of the images such that an extent of any resizing of the common region is different than an extent of any resizing of at least one of the divergent regions. In some embodiments, the resizing may be performed such that a percentage change in size of the common region represented in a first region of the enhanced image is greater than or less than a percentage change in size of at least one of the divergent regions represented in a second region of the enhanced image. As an example, the percentage change in size of at least one of the divergent regions may be zero, and the percentage change in size of the common region may be greater than zero. As another example, the percentage change in size of at least one of the divergent regions may be greater than zero, and the percentage change in size of the common region may be zero.

Figure 29:
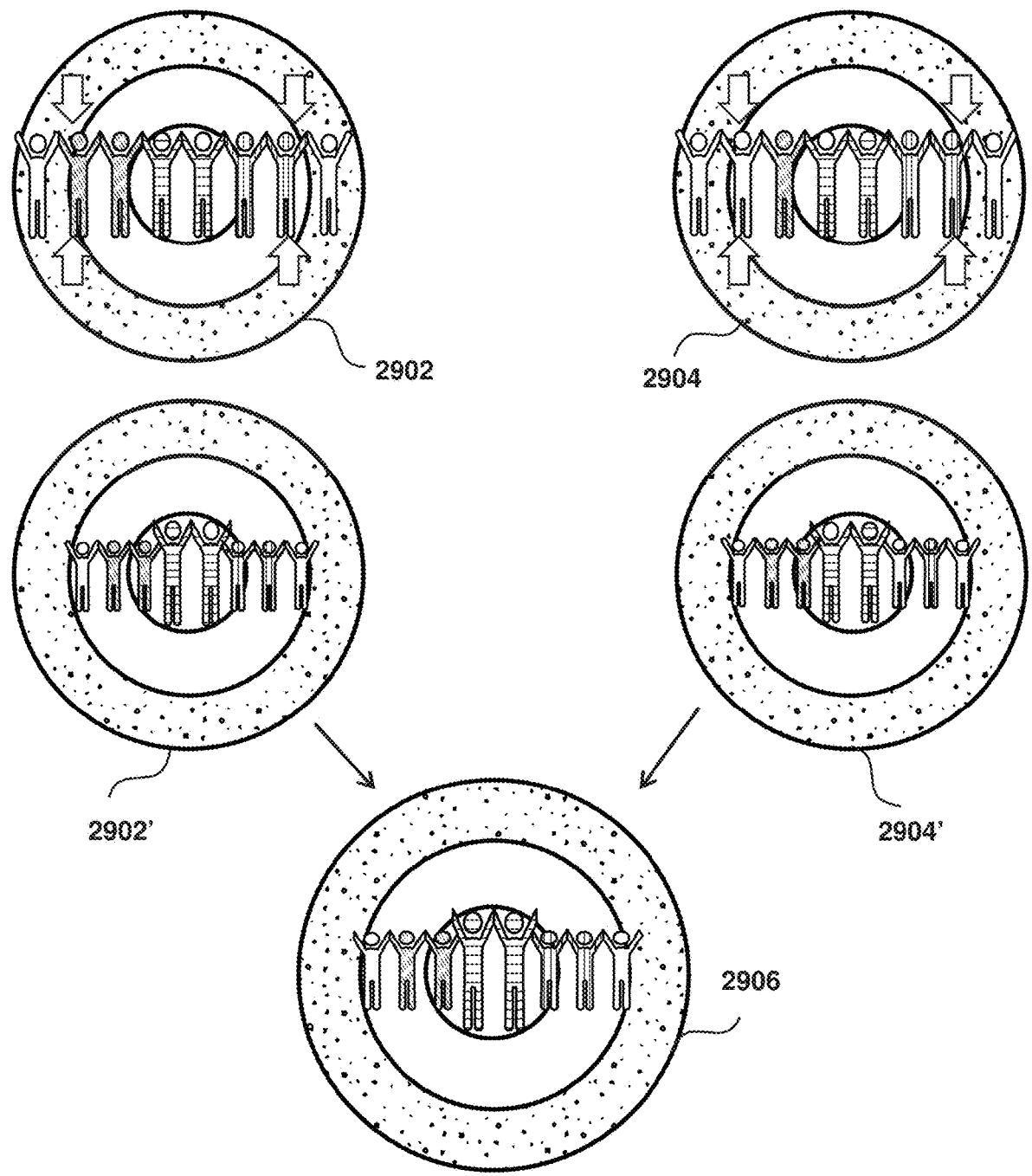
FIG. 29 illustrates an image resizing transformation technique to enhance vision or preserve central visual acuity while expanding the visual field, in accordance with one or more embodiments.

In one scenario, with respect to FIG. 29, captured monocular images 2902 and 2904 are resized only in peripheral areas, while keeping the macular central area (central 20 degrees) unchanged, resulting in corrected images 2902', 2904'. Such resizing transformation will preserve the visual acuity in the center while expanding the visual field. As shown in FIG. 29, a combined binocular image 2906 captures the objects in the periphery that were missed before, and at the same time, keeps the details of the central macular area. The peripheral objects are clearly noticed by the subject even after resizing them, as the peripheral vision is not as sensitive as the central one. In some use cases, for example, shrinking of up to 20% of the image size can be performed without producing double vision effects for the subject. In various embodiments, resizing of a peripheral region may be performed additionally or alternatively to resizing of a central area. For example, peripheral regions may be resized to the sizes of the peripheral regions while retaining the size of the macular central area (e.g., for glaucoma patients). In another scenario, for patients with macular degeneration, the peripheral vision may be left intact (e.g., with no resizing), and the central area may be resized to reduce the size of the central area. The enhanced image (e.g., the binocular image) may then be generated to include the resized central area.

In some embodiments, visioning subsystem 124 may determine a region common to a plurality of images of a scene (e.g., captured via a wearable device of the user), and, for each image of the images, determine a region of the image divergent from a corresponding region of at least another image of the images. Visioning subsystem 124 may perform a fisheye transformation, a conformal mapping transformation, or other transformation on the common region and generate, subsequent to the performance of the transformation, an enhanced image based on the common region and the divergent regions. In some embodiments, visioning subsystem 124 may perform the fisheye transformation, the conformal mapping transformation, or other transformation on a region of the enhanced image (that includes the common region).

As an example, the fisheye transformation may be performed on a region to modify a radical component of the images in accordance with:

$$r_{new}=r+\alpha r^3\text{, where }\alpha\text{ is a constant.}$$

As another example, the conformal mapping transformation may be performed on a region to modify a radial component of the images in accordance with:

$$r_{new}=r^\beta\text{, where }\beta\text{ is a constant power of the radial component and }\beta>1$$

Figure 30:
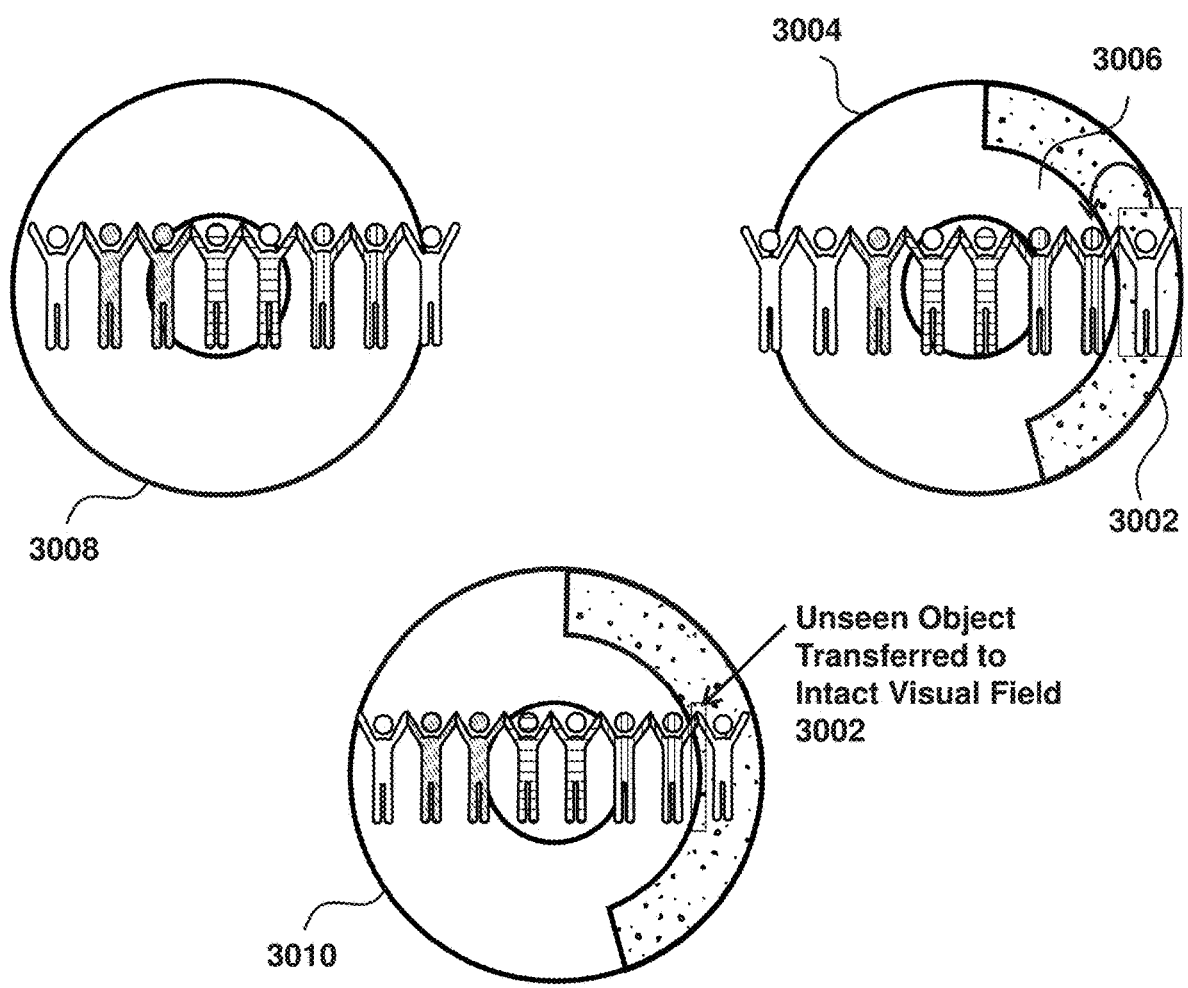
FIG. 30 illustrates a binocular view field expansion technique, in accordance with one or more embodiments.

In some embodiments, visioning subsystem 124 may modify at least one of a plurality of images of a scene by moving one or more objects in the image (e.g., prior to generating an enhanced image based on common and divergent regions of the images). As an example, with respect to FIG. 30, for patients with far peripheral defect in one eye, a missing object 3002 in a visual field 3004 of the defective eye can be transferred digitally to a mid-peripheral field region 3006 of the visual field 3004, while other visual field 3008, that of the healthy eye, would otherwise cover this area, meaning that the combined binocular image 3010 displays the missing object 3002 within an intact visual field. The subject may notice visual confusion in the area, but the subject can adapt to isolate information in this area of the visual field according to a moving object or the changing environment.

In some embodiments, visioning subsystem 124 may determine one or more defective visual field portions of a visual field of a user (e.g., in accordance with one or more techniques described herein). In some embodiments, visioning subsystem 124 may determine a region common to a plurality of images of a scene (e.g., captured via a wearable device of the user), and, for each image of the images, determine a region of the image divergent from a corresponding region of at least another image of the images. Visioning subsystem may generate an enhanced image based on the common and divergent regions of the images such that at least one of the common or divergent regions in the enhanced image do not overlap with one or more of the defective visual field portions.

In some embodiments, visioning subsystem 124 may detect an object in a defective visual field portion of a visual field of a user and cause an alert to be displayed. As an example, after correcting for defective visual field portion of a visual field of a user (e.g., via one or more techniques described herein), visioning subsystem 124 may monitor the remaining regions that were not corrected to detect one or more objects (e.g., safety hazards or other objects) and generate alerts (e.g., visual or audible alerts) indicating the objects, locations of the objects, the size of the objects, or other information related to the objects. In one use case, for a patient with irregular or multi-region defective visual field, the produced modification profile might still not be optimal in fitting the acquired field of view into the intact regions of the patient's visual field. Therefore, to maximize the patient's safety while moving, automatic video tracking algorithms may be implemented to detect objects that are in one of the detective visual field portions. Such objects may include moving objects (e.g., moving car) or other objects in the defective visual field portions of the patient's visual field.

In some embodiments, visioning subsystem 124 may generate a prediction indicating that an object will come in physical contact with a user and cause an alert to be displayed based on the physical contact prediction (e.g., an alert related to the object is displayed on a wearable device of the user). In some embodiments, visioning subsystem 124 may detect an object (e.g., in or predicted to be in a defective visual field portion of a visual field of a user) and cause the alert to be displayed based on (i) the object being in or predicted to be in the defective visual field portion, (ii) the physical contact prediction, or (iii) other information. In some embodiments, visioning subsystem 124 may determine whether the object is outside (or not sufficiently in) any image portion of an enhanced image (displayed to the user) that corresponds to at least one visual field portions satisfying one or more vision criteria. In one use case, no alert may be displayed (or a lesser-priority alert may be displayed) when the object is determined to be within (or sufficiently in) an image portion of the enhanced image that corresponds to the user's intact visual field portion (e.g., even if the object is predicted to come in physical contact with the user). On the other hand, if the object in the defective visual field portion is predicted to come in physical contact with the user, and it is determined that the object is outside (or not sufficiently in) the user's intact visual field portion, an alert may be displayed on the user's wearable device. In this way, for example, the user can rely on the user's own intact visual field to avoid incoming objects within the user's intact visual field, thereby mitigating the risk of dependence on the wearable device (e.g., through habit forming) for avoidance of such incoming objects. It should be noted, however, that, in other use cases, an alert related to the object may be displayed based on the physical contact prediction regardless of whether the object is within the user's intact visual field.

As an example, with respect to FIG. 10, for the uncompensated blind field 1006, at blocks 1012 and 1014, pupil tracking or other vision tracking (e.g., using inward directed image sensors) video tracking of a moving object in the visual field (e.g., through outward directed image sensors such as external cameras) may be used to detect safety hazards in regions of blind spots or that are moving into the regions of blind spots. In one use case, visioning subsystem 124 may compare the position of the safety hazard to a mapped visual field with defects (e.g., as measured in a testing mode) to detect when the safety hazard is in regions of blind spots or when the safety hazard is moving into such regions.

As another example, after correcting for defective visual field portion of a visual field of a user (e.g., via one or more techniques described herein), visioning subsystem 124 may monitor the remaining regions that were not corrected to detect any safety hazard (e.g., in real-time) approaching the user from such regions. If such detected safety hazards are predicted to come in physical contact with the user or come within a threshold distance of the user (e.g., one feet, two feet, or other threshold distance) (as opposed to passing by the user by at least the threshold distance of the user), visioning subsystem 124 may generate an alert related to the detected safety hazard (e.g., a visual alert displayed on a region seeable by the user, an audible alert, etc.).

In one use case, video signals (e.g., a live video stream) acquired from one or more cameras of a wearable device of a user will be preprocessed and filtered to remove residual noise effects. In some cases, the search region may be limited to the blind spots of the user or other defective visual field portions (e.g., that fail to satisfy one or more vision criteria). The limiting of the search region, for example, may reduce the amount of computational resources required to detect objects in the search region or generate related alerts or increase the speed of such detection or alert generation.

In some cases, two successive frames from a live video stream may be subtracted from one another to detect motion of one or more objects. As an example, occurrence of motion may be stored on a first delta frame (e.g., delta frame 1), and the first delta frame may be used to enable visualization of the moving objects and cancelling the stationary background. Another two successive frames from the live video stream may be subtracted from one another to produce a second delta frame (e.g., delta frame 2). The second delta frame may also be used to enable visualization of the moving objects and cancelling the stationary background. In further cases, comparison between the first and second delta frames may be performed. If a moving object is increasing in size as detected by subtracting the first delta frame and the second delta frame from one another, then the object may be determined to be getting closer. If the increase in size exceeds a predetermined threshold size, then the alert will be issued to the user (e.g., a visual alert displayed on a region seeable by the user, an audible alert, etc.).

In some embodiments, configuration subsystem 112 may store prediction models, modification profiles, visual defect information (e.g., indicating detected visual defects of a user), feedback information (e.g., feedback related to stimuli displayed to users or other feedback), or other information at one or more remote databases (e.g., in the cloud). In some embodiments, the feedback information, the visual defect information, the modification profiles, or other information associated with multiple users (e.g., two or more users, ten or more users, a hundred or more users, a thousand or more users, a million or more users, or other number of users) may be used to train one or more prediction models. In one use case, where a prediction model being trained is a neural network or other machine learning model, model manager subsystem 114 may provide as input to the machine learning model (i) stimuli information (e.g., indicating a set of stimuli and their associated characteristics, such as intensity levels, locations at which a stimuli is to be displayed, etc.) and (ii) feedback information (e.g., indicating feedback related to the set of stimuli) to cause the machine learning model to predict visual defect information, modification profiles, or other outputs. Model manager subsystem 114 may provide reference information (e.g., visual defect information or modification profiles determined to be accurate with respect to the provided stimuli and feedback information) to the machine learning model. The machine learning model may assess its predicted outputs (e.g., predicted visual defect information, predicted modification profiles, etc.) against the reference information and update its configurations (e.g., weights, biases, or other parameters) based on its assessment of its predicted outputs. The foregoing operations may be performed with additional stimuli information (e.g., displayed to other users), additional feedback information (e.g., the other users' feedback related to the stimuli displayed to them), and additional reference information to further train the machine learning model (e.g., by providing such information as input and reference feedback to train the machine learning model, thereby enabling the machine learning model to further update its configurations).

In another use case, where the machine learning model is a neural network, connection weights may be adjusted to reconcile differences between the neural network's prediction and the reference information. In a further use case, one or more neurons (or nodes) of the neural network may require that their respective errors be sent backward through the neural network to them to facilitate the update process (e.g., backpropagation of error). Updates to the connection weights may, for example, be reflective of the magnitude of error propagated backward after a forward pass has been completed.

In some embodiments, one or more prediction models may be trained or configured for a user or a type of device (e.g., a device of a particular brand, a device of a particular brand and model, a device having a certain set of features, etc.) and may be stored in association with the user or the device type. As an example, instances of a prediction model associated with the user or the device type may be stored locally (e.g., at a wearable device of the user or other user device) and remotely (e.g., in the cloud), and such instances of the prediction model may be automatically or manually synced across one or more user devices and the cloud such that the user has access to the latest configuration of the prediction model across any of the user devices or the cloud. In one use case, upon detecting that a first user is using a wearable device (e.g., when the first user logs into the user's account or is identified via one or more other techniques), configuration subsystem 112 may communicate with the wearable device to transmit the latest instance of a prediction model associated with the first user to the wearable device such that the wearable device has access to a local copy of the prediction model associated with the first user. In another use case, if a second user is later detected to be using the same wearable device, configuration subsystem 112 may communicate with the wearable device to transmit the latest instance of a prediction model associated with the second user to the wearable device such that the wearable device has access to a local copy of the prediction model associated with the second user.

In some embodiments, multiple modification profiles may be associated with the user or the device type. In some embodiments, each of the modification profiles may include a set of modification parameters or functions to be applied to live image data for a given context to generate an enhanced presentation of the live image data. As an example, the user may have a modification profile for each set of eye characteristics (e.g., a range of gaze directions, pupil sizes, limbus positions, or other characteristics). As further example, the user may additionally or alternatively have a modification profile for each set of environmental characteristics (e.g., a range of brightness levels of the environment, temperatures of the environment, or other characteristics). Based on the eye characteristics or environmental characteristics currently detected, the corresponding set of modification parameters or functions may be obtained and used to generate the enhanced presentation of the live image data. In one use case, upon detecting that a first user is using a wearable device (e.g., when the first user logs into the user's account or is identified via one or more other techniques), configuration subsystem 112 may communicate with the wearable device to transmit the modification profiles associated with the first user to the wearable device such that the wearable device has access to a local copy of the modification profiles associated with the first user. In another use case, if a second user is later detected to be using the same wearable device, configuration subsystem 112 may communicate with the wearable device to transmit the modification profiles associated with the second user to the wearable device such that the wearable device has access to a local copy the modification profiles associated with the second user.

In some embodiments, visual field locations of a user's field of view may be tested for visual defects. The visual field locations may be, for example, locations in a grid that covers the user's field of view or a portion of the user's field of view. For example, certain vision tests may test a certain number of visual field locations (e.g., 76 or other number of locations) of the user's field of view. The number of visual field locations may depend on a field of view of the user, a visual defect for which the user is being tested, the particular type of visual test being run, or any other factors. In some embodiments, stimuli may be presented at user interface locations of a wearable device (e.g., spectacles device 170, as shown in FIGS. 1C and 1D) that correspond to the visual field locations of the user's field of view. A stimulus at each visual field location may be tested over a series of characteristics (e.g., 50 different contrast levels) in order to determine a threshold characteristic under which the user can see the stimulus. In some embodiments, a threshold characteristic may be a characteristic above which a user can see the stimulus and below which the user cannot see the stimulus (or vice versa). For example, testing subsystem 122 may perform a test for each visual field location in a user's field of vision. In some embodiments, testing subsystem 122 may display each stimulus to the user in a descending or ascending order of characteristics (e.g., brightness levels, contrast levels, saturation levels, sharpness levels, or another range of characteristics). For example, testing subsystem 122 may present each stimulus at a range of contrast levels.

Testing every visual field location under each characteristic requires time and resources, which may be reduced via one or more techniques described herein. In some embodiments, a vision test (e.g., configured to test a plurality of visual field locations of a user) may be facilitated by obtaining a predicted characteristic with respect to each user interface location of a plurality of user interface locations (corresponding to the visual field locations) and setting an initial stimuli characteristic for each such user interface location based on the predicted characteristic for the user for the user interface location. As an example, the predicted characteristic for a given user interface location may be a characteristic under which the user is predicted to see a stimulus at the given user interface location. The initial stimulus characteristic for the given user interface location may be (i) the predicted characteristic (e.g., a threshold characteristic under which a user is predicted to see the stimulus at the given user interface location), (ii) a characteristic adjacent or proximate the predicted characteristic, or (iii) other characteristic. In this way, for example, such prediction-based setting of initial stimuli characteristics reduces the number of times a stimulus is required to be presented at each user interface location, thereby decreasing the amount of time of vision testing and the amount of resources related to such vision testing (e.g., computational or other resources).

In some embodiments, one or more prediction models may be used to determine a characteristic under which to initially present a stimulus at a given location. For example, a prediction model (e.g., neural network) may be trained on training sets and updated using feedback from users. Prediction models may increase the efficiency of vision testing by reducing the number of characteristics under which each stimulus must be tested. For example, predicted characteristics may allow each location to be tested with a minimal amount of testing time by presenting a stimulus at that location only twice under two different characteristics (e.g., at a contrast level below or at a threshold level, at a contrast level below and above the threshold level, etc.). As such, time and resources related to vision testing may be saved (e.g., computational resources or other resources).

In some embodiments, a prediction model (e.g., one or more instances of the prediction model) may be configured based on visual field datasets that incorporate different types of peripheral defects. For example, a training dataset may include visual field defect patterns so that the prediction model is trained to identify such visual field defect patterns during the testing process. In some embodiments, during a user's visual test, such a pre-configured prediction model (e.g., an instance of such prediction model) may additionally be trained using initial visual test results from the user to personalize the prediction model for the user. For example, several visual field locations and threshold characteristics under which the user saw stimuli at those visual field locations may be input into the training model. In this example, a sample of initial results from the vision test (e.g., for one or more stimuli) may improve the configuration of the prediction model to generate improved predictions. In this way, for example, even where the training dataset used to produce the initial pre-configured prediction model is relatively small, the use of the user's own initial visual test results to further train (and personalize) the prediction model will minimize the accuracy gap between the prediction model's predicted characteristics and those of a model created using a substantially larger training dataset.

Once the prediction model is configured (e.g., initially configured or further updated), the prediction model may generate one or more predictions for one or more visual field locations. In some embodiments, a prediction may be a first predicted characteristic (e.g., 43% contrast) under which the user is predicted to see a first stimulus at a first user interface location (that corresponds to a first visual field location). The vision test may then include presenting the first stimulus with the first predicted characteristic (e.g., 43% contrast) under which the user is predicted to see the first stimulus. In some embodiments, prior to presenting using the first predicted characteristic for the first stimulus, the vision test may include presenting the first stimulus with an adjacent characteristic (e.g., 42% contrast) under which the user is predicted to not see the first stimulus. In some embodiments, the generated prediction may be a characteristic which should be tested first during the vision test. For example, the generated prediction may be a characteristic adjacent to a characteristic (e.g., in the range of characteristics) under which the user is predicted to see the first stimulus at the first user interface location. The vision test may include presenting the first stimulus with the characteristic output by the prediction model (e.g., 42% contrast) under which the user is predicted to not see the first stimulus, followed by presenting the first stimulus with a characteristic adjacent to the characteristic output by the prediction model (e.g., 43% contrast) under which the user is predicted to see the stimulus.

In some embodiments, testing subsystem 122 may cause one or more stimuli to be presented to the user. As an example, the stimuli may be presented on a display (e.g., of a wearable device) or projected onto a retina or a cornea of the user to determine defects affecting the retina or the cornea. In some embodiments, each stimulus may be presented (e.g., via testing subsystem 122) under a range of characteristics relating to retinal sensitivity. For example, the range of characteristics may include brightness levels, contrast levels, saturation levels, sharpness levels, or another range of characteristics. For example, with respect to contrast levels, the stimuli may differ in contrast levels with respect to each other and with respect to a baseline contrast level by a certain amount (e.g., at least 20 dB). In some cases, the stimuli may differ in contrast levels with respect to each other and with respect to a baseline contrast level by a different amount (e.g., at least 30 dB). In some cases, testing subsystem 122 may, in the testing mode, instruct a wearable spectacles device to display the set of testing stimuli to the user in a descending or ascending contrast.

Figure 44A:
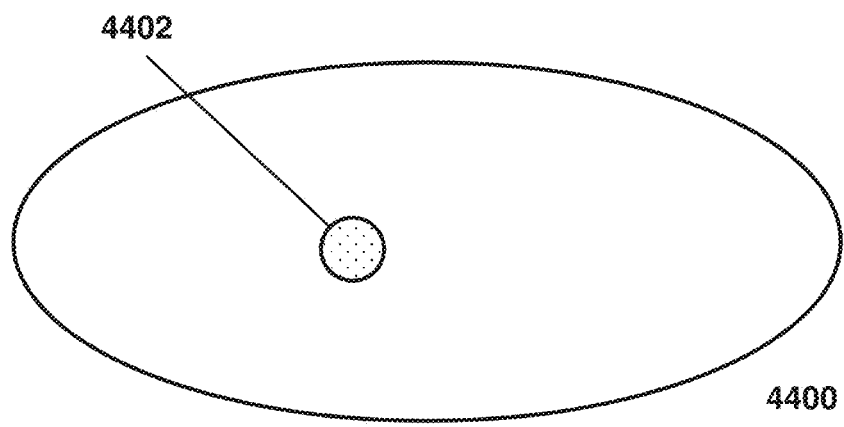
FIGS. 44A-44B show a stimulus presented at a visual field location at different times under two different characteristics, in accordance with one or more embodiments.
Figure 44B:
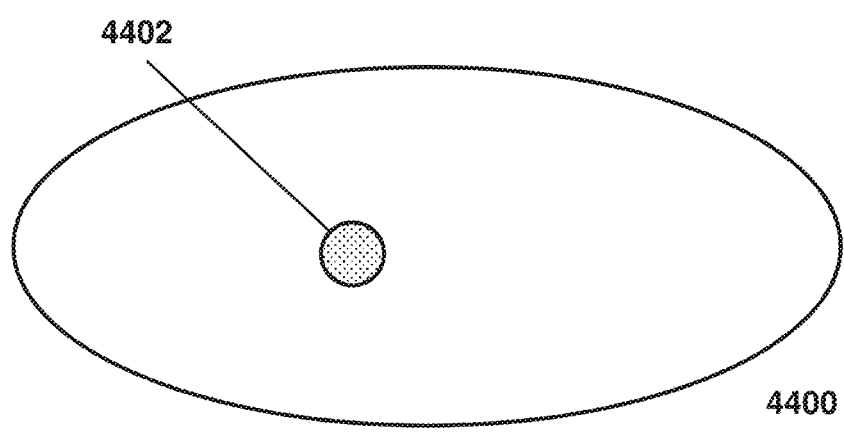

As an example, with respect to FIG. 44A, a stimulus 4402 (e.g., the first stimulus) is presented at a first user interface location under a first characteristic (e.g., 42% contrast) during a visual test presentation 4400. As shown in FIG. 44B, stimulus 4402 (e.g., the first stimulus) is presented at the first user interface location under a second characteristic (e.g., 43% contrast). As described above, FIG. 44B may show the stimulus presented under the first predicted characteristic, as output by the prediction model (e.g., a characteristic under which the user is predicted to see stimulus 4402). In this example, testing subsystem 122 may subsequently present stimulus 4402 as shown in FIG. 44A (e.g., which the user is predicted to not see) in order to confirm that the first predicted characteristic is the threshold characteristic for the first user interface location. In some embodiments, the stimulus may be presented under additional characteristics (e.g., 41% contrast, 40% contrast, etc.) until a threshold characteristic is reached.

In some embodiments, testing subsystem 122 may obtain feedback from a user in response to presentation of one or more stimuli to the user (e.g., the sets of stimuli 4402-4412, as shown in FIGS. 44A and 44B) and use such feedback to update the prediction model. As an example, the feedback may include an indication of a response of the user to one or more stimuli or an indication of a lack of response of the user to such stimuli. The response (or lack thereof) may relate to an eye movement, a gaze direction, a pupil size change, or a user modification of one or more stimuli, or other user input (e.g., the user's reaction or other response to the stimuli). As another example, the feedback may include an eye image captured during the visual test presentation. The eye image may be an image of a retina of the eye (e.g., the overall retina or a portion thereof), an image of a cornea of the eye (e.g., the overall cornea or a portion thereof), or another eye image. In some embodiments, the feedback may indicate a threshold characteristic of the range of characteristics under which the user sees each stimulus. For example, the threshold characteristic under which the user is able to see a stimulus at a given user interface location may be different from a predicted characteristic for the user interface location. The prediction model may thus update its configurations based on its assessment of its prediction (e.g., the predicted characteristic) and feedback information (e.g., threshold characteristic under which the user sees the stimulus at the user interface location, as indicated by the user feedback).

In some embodiments, testing subsystem 122 may use the updated prediction model to generate a second predicted characteristic under which the user is able to see a second stimulus at a second user interface location. In some embodiments, the second stimulus may be presented under the second predicted characteristic (e.g., second predicted contrast level), as output by the updated prediction model. Based on feedback from the user, testing subsystem 122 may present the second stimulus with a second characteristic (e.g., an adjacent contrast level, a higher contrast level, a lower contrast level, etc.) until feedback from the user indicates that a threshold characteristic is reached. In some embodiments, the prediction model may be continuously updated based on each predicted characteristic and reference feedback (e.g., feedback from the user).

In some embodiments, testing subsystem 122 may use the updated prediction model to obtain a pattern for a second set of locations of the user interface. For example, testing subsystem 122 may identify a visual field defect pattern (e.g., as described above) based on the feedback from the user in response to the first set of stimuli 4402, as shown in FIGS. 44A and 44B. The pattern for the second set of locations of the user interface may therefore be based on the identified visual field defect pattern. For example, the pattern may indicate predicted characteristics for user interface locations of the second set of locations. In some embodiments, the pattern for the second set of locations may be based on other aspects of the feedback from the user in response to the first set of stimuli 4402. In some embodiments, the second set of locations may include a different number of user interface locations than the first set of locations (e.g., a greater number of user interface locations).

Figure 44C:
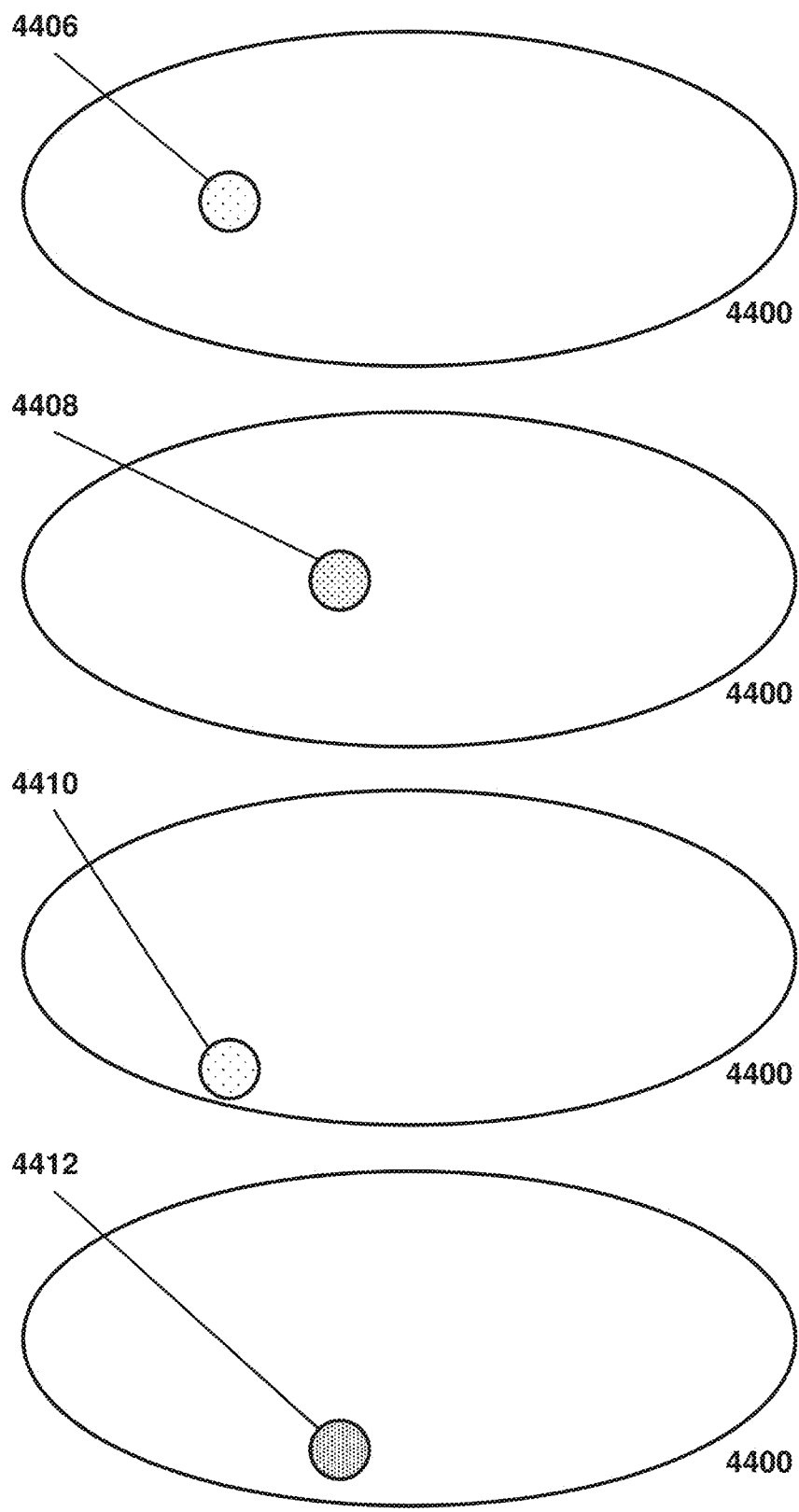
FIG. 44C shows a set of stimuli presented at a set of locations of a user interface, in accordance with one or more embodiments.

FIG. 44C shows a second set of stimuli presented at a second set of locations of the user interface 4400, in accordance with one or more embodiments. For example, the second set of stimuli may include stimulus 4406, stimulus 4408, stimulus 4410, and stimulus 4412. In some embodiments, each stimulus of the second set of stimuli 4402 may be presented under at least one characteristic of the range of characteristics. For example, the second set of stimuli 4402 may all be presented under the same characteristic or under different characteristics. In some embodiments, the pattern obtained by testing subsystem 122 may indicate a predicted characteristic for each stimulus of the second set of stimuli. In this example, testing subsystem 122 may present each stimulus of the second set of stimuli based on the pattern. For example, testing subsystem 122 may present stimulus 4406 at a first predicted characteristic (e.g., 79% contrast), as indicated by the pattern. Testing subsystem 122 may then present stimulus 4406 under a second characteristic (e.g., 78% contrast or 80% contrast, depending on whether the user was able to see stimulus 4406 under the first characteristic), and so on. Testing subsystem 122 may continue to test stimulus 4406 under various characteristics until a threshold characteristic is reached. For example, testing subsystem 122 may determine that the threshold characteristic for stimulus 4406 is 76% contrast.

In some embodiments, testing subsystem 122 may proceed with testing the next stimulus of the second set of stimuli (e.g., stimulus 4408) based on a predicted characteristic under which the user is predicted to see stimulus 4408 (e.g., based on the pattern). Testing subsystem 122 may subsequently present stimulus 4408 under a first characteristic, which may be the same as or different than the first characteristic used to present stimulus 4406. Testing subsystem 122 may continue testing stimulus 4408 under various characteristics until a threshold characteristic is reached for stimulus 4408. Testing subsystem 122 may repeat this process with the remaining stimuli of the second set of stimuli (e.g., stimulus 4410 and stimulus 4412).

In some embodiments, each stimulus of the second set of stimuli 4402 may be presented based on the pattern that was previously obtained. For example, the pattern may indicate threshold characteristics under which the user is predicted to see second set of stimuli presented at the second set of locations. In some embodiments, the prediction model may be continuously updated based on each predicted characteristic and reference feedback (e.g., feedback from the user) for each stimulus. For example, testing subsystem 122 may use the feedback received in response to the testing of each stimulus of the second set of stimuli in order to update the prediction model prior to testing subsequent stimuli of the second set of stimuli. In some embodiments, testing subsystem 122 may update the prediction model after feedback is received for each stimulus, after feedback is received for several stimuli, after feedback is received for each set of stimuli, or at another time.

In some embodiments, based on feedback related to the stimuli (displayed to a user during the visual test) or other feedback, testing subsystem 122 may determine light sensitivity, distortions, or other aberrations related to one or more eyes of the user. In some embodiments, visioning subsystem 124 may generate visual defect information for the user based on feedback received from the user with respect to each stimulus presented by testing subsystem 122. Testing subsystem 122 may determine one or more defective visual field portions of a visual field of a user (e.g., an automatic determination based on feedback related to the stimuli displayed to the user or other feedback). As an example, a defective visual field portion may be one of the visual field portions of the user's visual field that fails to satisfy one or more vision criteria (e.g., whether or an extent to which the user senses one or more stimuli, an extent of light sensitivity, distortion, or other aberration, or other criteria). In some cases, the stimuli may include a grid of stimuli corresponding to visual field locations within the user's field of view. In some embodiments, a defective visual field portion may be a portion of the user's visual field which matches a visual field defect pattern. Defective visual field portions may include regions of reduced vision sensitivity, regions of higher or lower optical aberrations, regions of reduced brightness, or other defective visual field portions.

In some embodiments, a neural network may be used as at least part of a prediction model for facilitating vision testing. In some embodiments, visioning subsystem 124 may train a neural network to improve efficiency and speed of vision testing. For example, visioning subsystem 124 may provide a first user interface location as input to a neural network (e.g., machine learning model 162, as shown in FIG. 1B). In some embodiments, the neural network may generate a first predicted characteristic under which the user is predicted to see a first stimulus at the first user interface location. In some embodiments, testing subsystem 122 may present the first stimulus to the user under a range of characteristics. For example, testing subsystem 122 may present the first stimulus (e.g., corresponding to the first visual field location) with the first predicted characteristic (e.g., first predicted contrast level). Based on feedback from the user, testing subsystem 122 may present the first stimulus with a second characteristic (e.g., a higher or lower contrast level) until feedback from the user indicates that a threshold characteristic is reached. In some embodiments, visioning subsystem 124 may provide the user feedback indicating that the threshold characteristic has been reached as reference feedback to the neural network discussed above.

In some embodiments, the neural network may update its configurations (e.g., weights, biases, or other parameters) based on its assessment of its prediction (e.g., first predicted threshold characteristic) and reference feedback information (e.g., threshold characteristic under which the user sees the first stimulus, as indicated by the user feedback). As discussed herein, in some embodiments, connection weights may be adjusted to reconcile differences between the neural network's prediction and the reference feedback. In some embodiments, the neural network may additionally or alternatively be trained on a visual field dataset that incorporates different types of peripheral defects. For example, training datasets may include visual field defect patterns so that the neural network is trained to identify such visual field defect patterns during the testing process. In this way, for example, the neural network may be trained to generate better predictions.

In some embodiments, predictions of the neural network may be based upon recognized visual field defect patterns. For example, the neural network may match initial results of a vision test to a pattern present in certain visual field defects. This may allow the neural network to predict characteristics under which the user will see stimuli to be tested. In some embodiments, the updated neural network may generate predicted characteristics that are similar to characteristics under which the user sees adjacent stimuli.

In some embodiments, multiple sets of predicted characteristics (e.g., each set corresponding to a set of locations of the user interface) may be obtained via a prediction model, and at least one set of the multiple sets may be selected to perform a vision test based on the predicted characteristics of the selected set(s) (e.g., via one or more techniques described herein).

In some embodiments, during one or more portions of a visual test, one or more locations may be tested with one or more default starting characteristics (e.g., default starting contrast levels, brightness levels, contrast levels, sharpness levels, saturation levels, etc.) under which one or more stimuli may initially be presented to a user (e.g., after which the stimuli characteristic for a location may be dynamically adjusted if it is detected that the user is unable to see a stimulus presented at the location). In this way, for example, initial visual defect information or additional visual defect information may be determined and provided to a prediction model to obtain one or more predicted characteristics for one or more additional locations to be tested. As an example, when it is known that additional visual defect information is needed to increase accuracy of predictions for a visual field region to a sufficient accuracy level, one or more default starting characteristics may be used to initially present stimuli at one or more locations (e.g., corresponding to locations in the visual field region) to obtain and provide the visual defect information for those locations to the prediction model to increase the prediction model's accuracy when predicting characteristics for one or more other locations.

In some embodiments, a default starting characteristic may be a starting characteristic configured to be used for every user in one or more portions of the visual test. In some embodiments, a default starting characteristic may include (i) a starting characteristic specific to a left eye or to a right eye, a starting characteristic specific to a virtual field region (e.g., central, paracentral, near-peripheral, mid-peripheral, far-peripheral, or other region), (ii) a starting characteristic specific to a demographic characteristic (e.g., age, sex, ethnicity, or other demographic), (iii) a starting characteristic specific to a disease or other health condition (e.g., a particular heart disease, diabetes, or other health condition that the user is known to have or known to be predisposed to have), or (iv) other starting characteristic. In one use case, based on one or more known characteristics of the user (e.g., the particular eye to be tested, the visual field regions to be tested, the demographic characteristics of the user, the health conditions of the user, etc.), the starting characteristics may be predetermined for a vision test prior to conducting the visual testing presentation of one or more stimuli for deriving (i) the threshold characteristics under which the user is able to see such stimuli at the respective locations of the user interface (e.g., corresponding to locations of the user's visual field) or (ii) other visual defect information. In this way, for example, by beginning testing of locations with such user-specific default starting characteristics, the number of times a stimulus is required to be presented at each of the locations will be reduced overall, thereby decreasing the amount of time of vision testing and the amount of resources related to such vision testing (e.g., computational or other resources).

As an example, during a first portion of a visual test presentation, an initial set of locations of a user interface may be tested using one or more default starting characteristics (e.g., one or more default contrast levels) to determine threshold characteristics (e.g., minimum contrast levels) under which the user is able to see stimuli presented at respective locations of the initial set. Feedback (e.g., indicating such threshold characteristics) from the first portion of the visual test presentation may be provided to a neural network, and the neural network may output one or more predicted characteristics for one or more additional locations to be tested. As a further example, during a second portion of the visual test presentation, the predicted characteristics for the additional locations may then be used to test the user (e.g., via one or more techniques described herein). The feedback (e.g., indicating the respective threshold characteristics) from the second portion of the visual test presentation may be provided a neural network (e.g., the same or different instance of the neural network from the first portion of the visual test presentation, a different neural network, etc.), and the neural network may output one or more predicted characteristics for one or more further locations to be tested. The predicted characteristics for the further locations may then be used to test the user during a third portion of the visual test presentation. The foregoing operations may be repeated for subsequent portions of the vision test until a threshold number of locations have been tested or all locations of a test set have been tested.

Figure 46A:
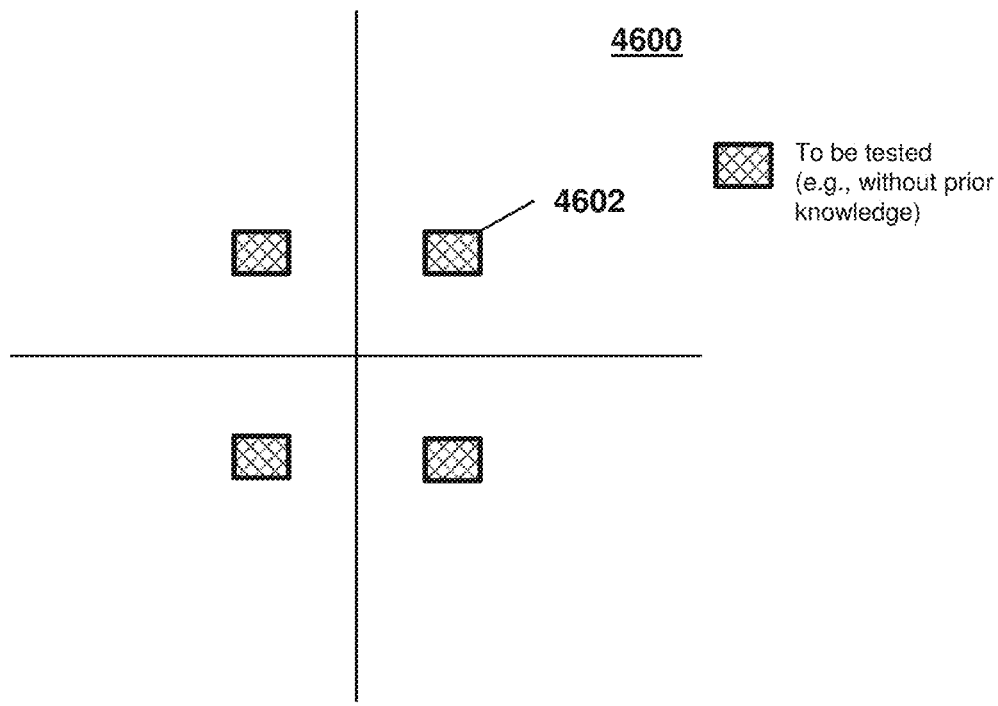
FIGS. 46A-46F shows portions of a vision test facilitated by prediction-based setting of initial stimuli characteristics, in accordance with one or more embodiments.
Figure 46B:
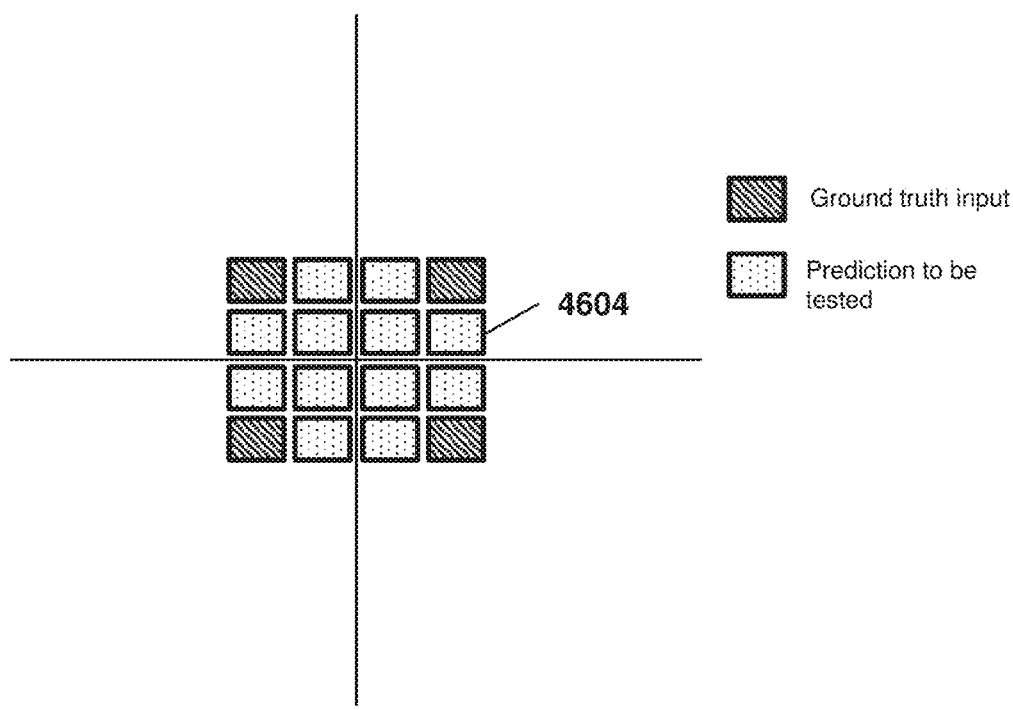

In one use case, with respect to FIGS. 46A-46B, during a first portion of a vision test, four locations 4602 on user interface 4600 (e.g., corresponding to a location in each central quadrant of a visual field of a user) may be initially tested (e.g., without prior knowledge) with one or more default starting characteristics (e.g., a default starting contrast level or other default starting characteristics), and feedback for the locations 4602 (e.g., indicating threshold characteristics under which the user is able to see stimuli at the respective locations 4602) may be obtained during the first portion of the vision test. Such feedback may be provided as a ground truth input to a neural network, and the neural network may output predicted characteristics for twelve locations 4604 on user interface 4600. During a second portion of the vision test, the predicted characteristics for the locations 4604 may be used to test the user. The feedback for the locations 4604 (e.g., indicating the respective threshold characteristics from the second portion of the vision test) may be obtained during the second portion of the vision test. Such feedback may be provided as a ground truth input to a neural network, and the neural network may output one or more predicted characteristics for one or more further locations to be tested during a subsequent portion of the vision test. The neural network used for the second portion of the vision test may, for example, be the same instance of the neural network from the first portion of the vision test or a different instance of the same neural network (or otherwise a different neural network) to accommodate or optimize for different input/output configurations.

Figure 46C:
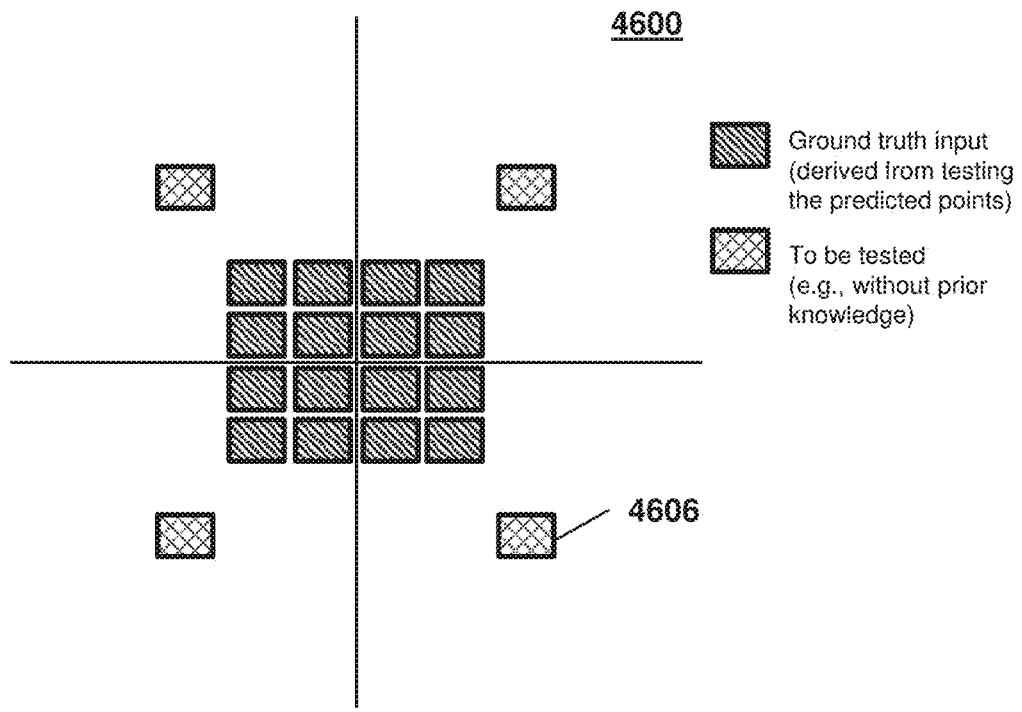
Figure 46D:
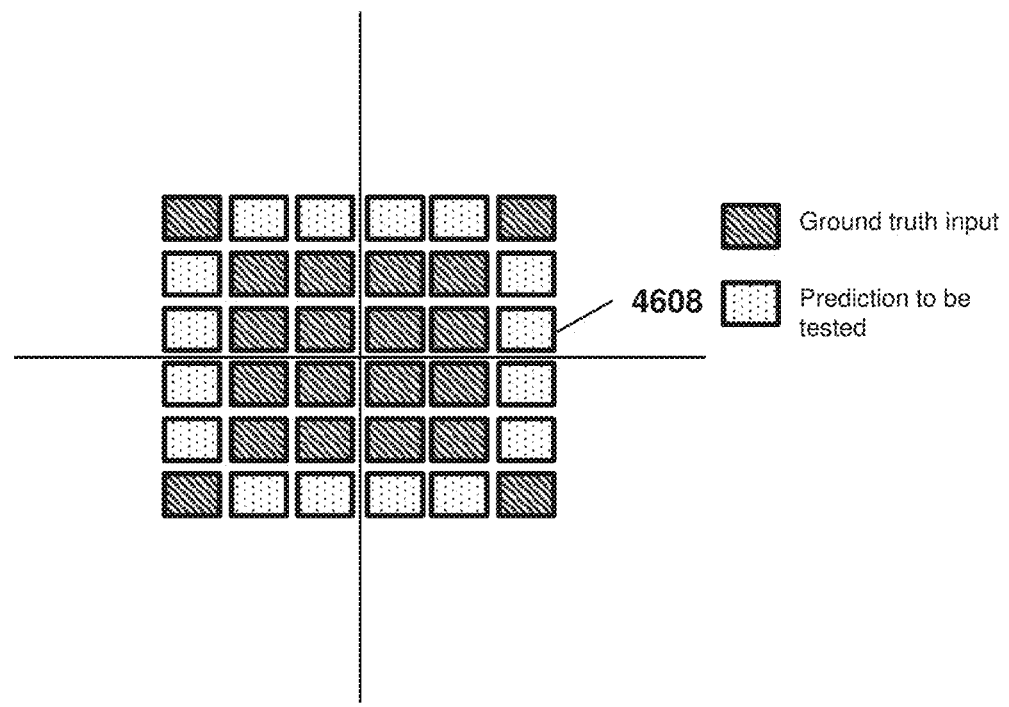

In another use case, with respect to FIGS. 46C-46D, during a third portion of the vision test, four locations 4606 on user interface 4600 (e.g., corresponding to a location in each paracentral quadrant of a visual field of a user) may be tested with one or more default starting characteristics, and feedback for the locations 4606 may be obtained. Such feedback for the locations 4606 along with the prior feedback (e.g., for one or more of the locations 4602, the locations 4604, etc.) may be provided as a ground truth input to a neural network, and the neural network may output predicted characteristics for twelve locations 4608 on user interface 4600. During a fourth portion of the vision test, the predicted characteristics for the locations 4608 may be used to test the user, and the feedback for the locations 4608 may be obtained. Such feedback for the locations 4608 along with the prior feedback (e.g., for one or more of the locations 4602, the locations 4604, the locations 4606, etc.) may be provided as a ground truth input to a neural network, and the neural network may output one or more predicted characteristics for one or more further locations to be tested during a subsequent portion of the vision test. The neural network used for the third or fourth portion of the vision test may, for example, be the same instance of the neural network from the first or second portion (or the other one of the third or fourth portion) of the vision test or a different instance of the same neural network (or otherwise a different neural network) to accommodate or optimize for different input/output configurations.

Figure 46E:
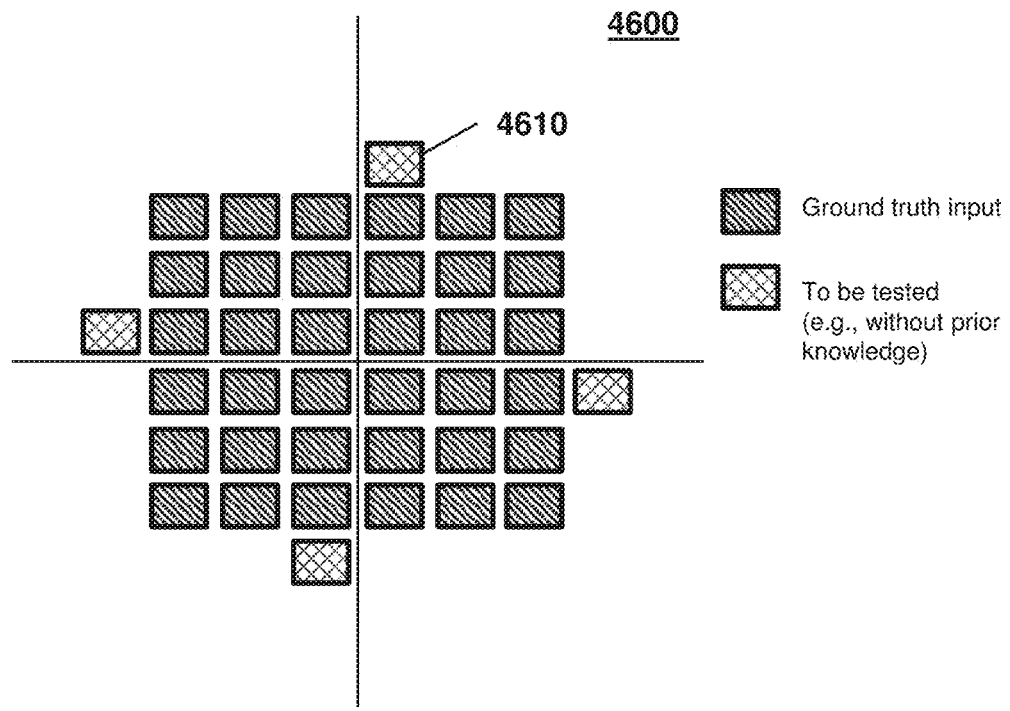
Figure 46F:
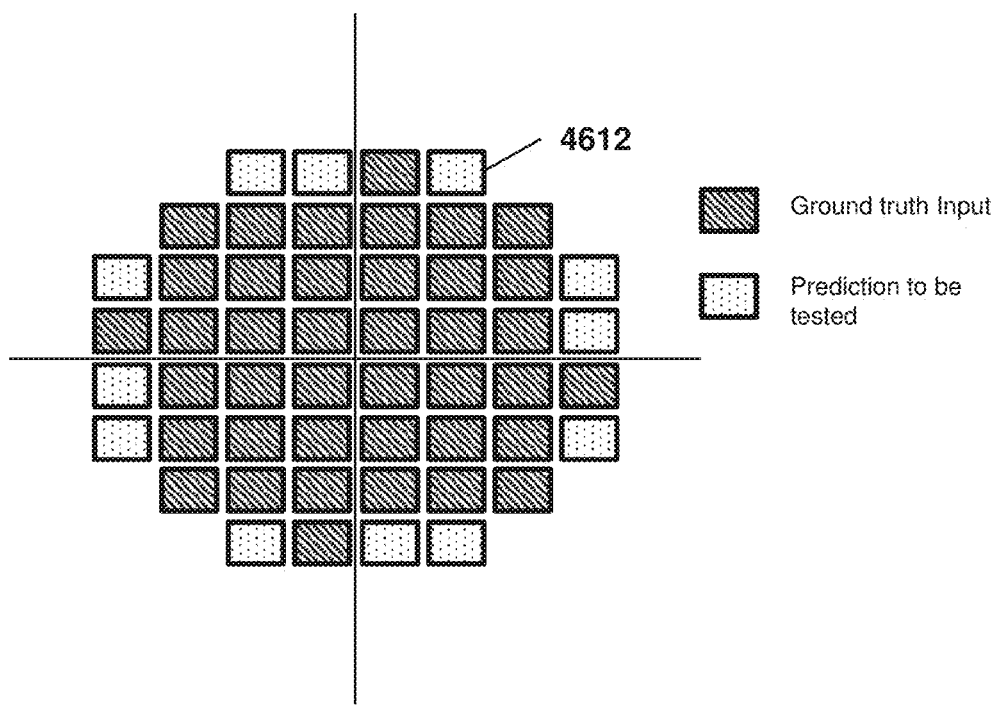

In a further use case, with respect to FIGS. 46E-46F, during a fifth portion of the vision test, four locations 4610 on user interface 4600 (e.g., corresponding to a location in each near-peripheral quadrant of a visual field of a user) may be tested with one or more default starting characteristics, and feedback for the locations 4610 may be obtained during the fifth portion of the vision test. Such feedback for the locations 4610 along with the prior feedback (e.g., for one or more of the locations 4602-4608) may be provided as a ground truth input to a neural network, and the neural network may output predicted characteristics for twelve locations 4612 on user interface 4600. During a sixth portion of the vision test, the predicted characteristics for the locations 4612 may be used to test the user, and the feedback for the locations 4612 may be obtained. Such feedback for the locations 4612 along with the prior feedback (e.g., for one or more of the locations 4602-4610) may be provided as a ground truth input to a neural network, and the neural network may output one or more predicted characteristics for one or more further locations to be tested during a subsequent portion of the vision test. The neural network used for the fifth or sixth portion of the vision test may, for example, be the same instance of the neural network from the first, second, third, or fourth portion (or the other one of the fifth or sixth portion) of the vision test or a different instance of the same neural network (or otherwise a different neural network) to accommodate or optimize for different input/output configurations. In additional use cases, the foregoing operations may be performed with respect to one or more other regions (e.g., mid-peripheral regions, far-peripheral regions, or other defined regions to be tested). It should be noted that, although the foregoing use cases with respect to FIGS. 46A-46F begin with testing locations of the central region of the visual field and involve assessing regions in order from their proximity to the center of the visual field, other use cases that begin testing locations in other regions (e.g., near-peripheral, mid-peripheral, far-peripheral, etc.) or assess in a different order are contemplated.

In some embodiments, a set of predicted characteristics may be selected to perform one or more portions of the vision test based on a confidence score associated with the set of predicted characteristics. As an example, the set of predicted characteristics may be selected over one or more other sets of predicted characteristics (of the multiple sets) based on the confidence scores associated with the respective sets of predicted characteristics (e.g., selected for a given round or portion of the visual test presentation). In one use case, a pattern (e.g., corresponding to the set of predicted characteristics) may be selected based on the confidence score associated with the pattern being greater than or equal to confidence scores associated with one or more other patterns (e.g., corresponding to the other sets of predicted characteristics). In another use case, the pattern may be selected based on the confidence score associated with the pattern satisfying a threshold score (e.g., a predefined threshold score, a dynamic threshold score, etc.), and the other patterns may not be selected based on the confidence scores associated with the other patterns failing to satisfy the threshold score.

Figure 45:
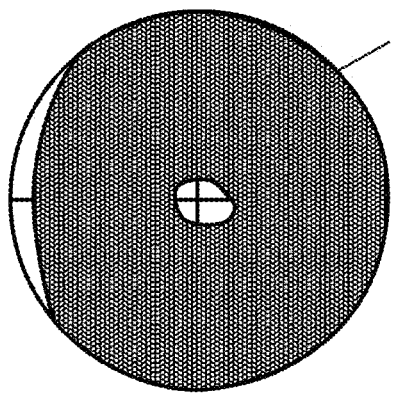
FIG. 45 shows examples of common patterns of visual defects reflecting data used to train or configure one or more prediction models, in accordance with one or more embodiments.
Figure 45:
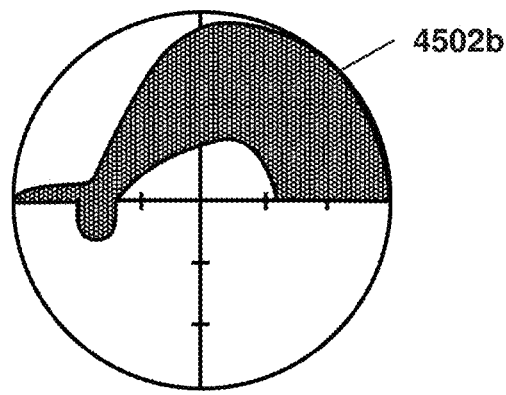
Figure 45:
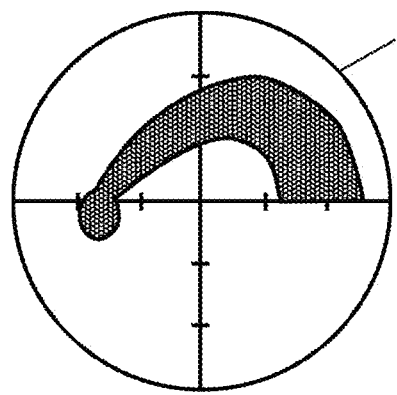
Figure 45:
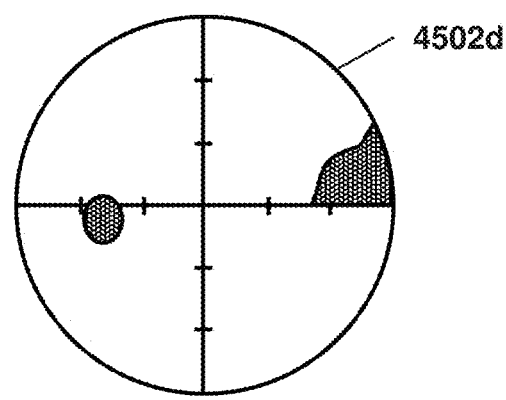
Figure 45:
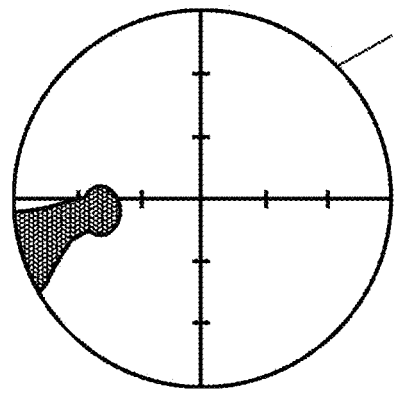
Figure 45:
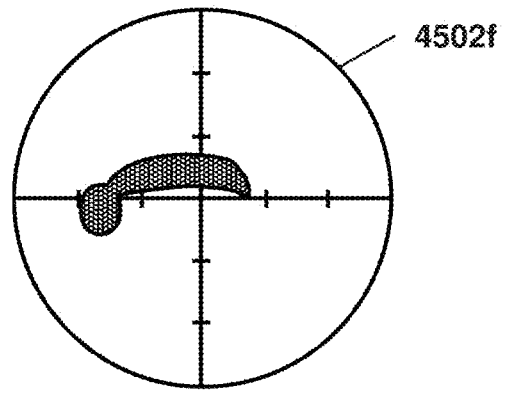

As shown in FIG. 45, for example, patterns 4502*a*-4502*f* are examples of common visual defect patterns, such as (a) tunnel vision defect with temporal crescent sparing, (b) superior arcuate with peripheral breakthrough and early inferior defect, (c) established superior arcuate defect, (d) nasal step, (e) temporal wedge, and (f) superior, fixation-threatening paracentral defect. With respect to FIG. 45, the dark areas of patterns 4502*a*-4502*f* represent locations of a user's visual field that have defects, and the white areas of patterns 4502*a*-4502*f* represent locations of the user's visual field without visual defects (e.g., as determined in accordance with a visual field testing standard). It should be noted that, for convenience, other common visual defect patterns (e.g., complete field loss, early superior paracentral defect, etc.) or details regarding additional characteristics necessary for a user to see a stimulus at a visual defect location (along with further patterns) are not shown in FIG. 45 (e.g., details indicating a contrast level necessary for the user to see the stimulus), but are contemplated. In one use case, a neural network (or one or more instances of the neural network) may be trained to predict one or more patterns (e.g., where each pattern corresponds to a set of predicted characteristics for a set of user interface locations corresponding to locations of the user's visual field). In a first portion of a visual test presentation, an initial set of locations of a user interface may be tested to determine threshold characteristics (e.g., minimum contrast levels) under which the user is able to see stimuli presented at respective locations of the initial set. Feedback (e.g., indicating such threshold characteristics) from the first portion of the visual test presentation may be provided to the neural network, and the neural network may output a first pattern of predicted characteristics (e.g., for all locations of the test set). As an example, the first pattern may be outputted by the neural network based on the first pattern being associated with a confidence score satisfying a threshold score, the confidence score being greater than or equal to confidence scores for other patterns predicted by the neural network, etc. During a second portion of the visual test presentation, one or more predicted characteristics for locations of the outputted first pattern may then be used to test the user (e.g., via one or more techniques described herein).

In some use cases, only a subset of the locations of the outputted pattern are selected to be tested during the second portion of the visual test presentation, and the feedback (e.g., indicating threshold characteristics under which the user is able to see stimulus presented at the respective selected locations) from the second portion of the visual test presentation may be provided to a neural network (e.g., the same or different instance of the neural network from the first portion of the visual test presentation, a different neural network, etc.), and the neural network may output a second pattern of predicted characteristics (e.g., for all locations of the test set). One or more predicted characteristics for locations of the outputted second pattern may then be used to test the user during a third portion of the visual test presentation. The foregoing operations may be repeated for subsequent portions of the visual test presentation until a threshold number of locations have been tested or all locations of a test set have been tested.

In one use case, with respect to FIGS. 46A-46B, during a first portion of a vision test, four locations 4602 on user interface 4600 (e.g., corresponding to a location in each central quadrant of a visual field of a user) may be initially tested (e.g., without prior knowledge) with one or more default starting characteristics, and feedback for the locations 4602 (e.g., indicating threshold characteristics under which the user is able to see stimuli at the respective locations 4602) may be obtained during the first portion of the vision test. Such feedback may be provided as a ground truth input to a neural network, and the neural network may output a first pattern of predicted characteristics (e.g., for all locations of the test set). During a second portion of the vision test, predicted characteristics for the twelve locations 4604 of the outputted first pattern (e.g., a subset of the locations of the first pattern) may then be used to test the user. The feedback for the locations 4604 (e.g., indicating the respective threshold characteristics from the second portion of the vision test) may be obtained during the second portion of the vision test. Such feedback may be provided to a neural network, and the neural network may output a second pattern of predicted characteristics to be used to test the user during a subsequent portion of the vision test. The neural network used for the second portion of the vision test may, for example, be the same instance of the neural network from the first portion of the vision test or a different instance of the same neural network (or otherwise a different neural network) to accommodate or optimize for different input/output configurations.

In another use case, with respect to FIGS. 46C-46D, during a third portion of the vision test, four locations 4606 on user interface 4600 (e.g., corresponding to a location in each paracentral quadrant of a visual field of a user) may be tested with one or more default starting characteristics, and feedback for the locations 4606 may be obtained. Such feedback for the locations 4606 along with the prior feedback (e.g., for one or more of the locations 4602, the locations 4604, etc.) may be provided as a ground truth input to a neural network, and the neural network may output the second pattern of predicted characteristics (e.g., for all locations of the test set). During a fourth portion of the vision test, predicted characteristics for the twelve locations 4608 of the outputted second pattern (e.g., a subset of the locations of the second pattern) may be used to test the user, and the feedback for the locations 4608 may be obtained. Such feedback for the locations 4608 along with the prior feedback (e.g., for one or more of the locations 4602, the locations 4604, the locations 4606, etc.) may be provided as a ground truth input to a neural network, and the neural network may output a third pattern of predicted characteristics to be used to test the user during a subsequent portion of the vision test. The neural network used for the third or fourth portion of the vision test may, for example, be the same instance of the neural network from the first or second portion (or the other one of the third or fourth portion) of the vision test or a different instance of the same neural network (or otherwise a different neural network) to accommodate or optimize for different input/output configurations.

In a further use case, with respect to FIGS. 46E-46F, during a fifth portion of the vision test, four locations 4610 on user interface 4600 (e.g., corresponding to a location in each near-peripheral quadrant of a visual field of a user) may be tested with one or more default starting characteristics, and feedback for the locations 4610 may be obtained during the fifth portion of the vision test. Such feedback for the locations 4610 along with the prior feedback (e.g., for one or more of the locations 4602-4608) may be provided as a ground truth input to a neural network, and the neural network may output the third pattern of predicted characteristics (e.g., for all locations of the test set). During a sixth portion of the vision test, predicted characteristics for the locations 4612 of the outputted third pattern (e.g., a subset of the locations of the third pattern) may be used to test the user, and the feedback for the locations 4612 may be obtained. Such feedback for the locations 4612 along with the prior feedback (e.g., for one or more of the locations 4602-4610) may be provided as a ground truth input to a neural network, and the neural network may output a fourth pattern of predicted characteristics to be used to test the user during a subsequent portion of the vision test. The neural network used for the fifth or sixth portion of the vision test may, for example, be the same instance of the neural network from the first, second, third, or fourth portion (or the other one of the fifth or sixth portion) of the vision test or a different instance of the same neural network (or otherwise a different neural network) to accommodate or optimize for different input/output configurations. In additional use cases, the foregoing operations may be performed with respect to one or more other regions (e.g., mid-peripheral regions, far-peripheral regions, or other defined regions to be tested). It should be noted that, although the foregoing use cases with respect to FIGS. 46A-46F begin with testing locations of the central region of the visual field and involve assessing regions in order from their proximity to the center of the visual field, other use cases that begin testing locations in other regions (e.g., near-peripheral, mid-peripheral, far-peripheral, etc.) or assess in a different order are contemplated.

In some embodiments, a set of predicted characteristics (for a set of locations of a user interface) and a set of confidence scores associated with the set of locations may be obtained via a prediction model (e.g., one or more instances of the prediction model). Based on the set of confidence scores, one or more locations of the set of locations may be selected to be tested during a visual test presentation. As an example, the locations may be selected over one or more other locations of the set of locations based on the set of confidence scores (e.g., selected for a given round or portion of the visual test presentation). In one use case, the locations may be selected based on confidence scores associated with the locations being greater than or equal to confidence scores associated with the other locations. In another use case, the locations may be selected based on confidence scores associated with the locations satisfying a threshold score (e.g., a predefined threshold score, a dynamic threshold score, etc.), and the other locations may not be selected based on confidence scores associated with the locations failing to satisfy the threshold score. Additionally, or alternatively, the locations may be selected (e.g., over the other locations) based on an amount of locations to be tested (e.g., a fixed number or percentage of locations outputted by the prediction model that are to be tested during a given round or portion of the visual test presentation), a bounding box or other structure defining a region of a user's visual field to be tested, or other criteria.

After the foregoing locations are selected, one or more stimuli may then be presented at the selected locations during the visual test presentation based on one or more predicted characteristics associated with the selected locations. As an example, the predicted characteristics may include predictions of a threshold characteristic under which a user (taking the visual test) will see a stimulus at the respective selected locations (e.g., one or more predicted brightness levels, contrast levels, saturation levels, sharpness levels, etc.). A first stimulus may, for example, initially be presented at a first location of the locations based on a first predicted characteristic associated with the first location. In one use case, the first stimulus may initially be presented at the first location under the first predicted characteristic (e.g., a first contrast level under which the user is predicted to see the first stimulus). In another use case, the first predicted characteristic may be used to determine at least one characteristic that is adjacent to the first predicted characteristic in a range of characteristics, and the first stimulus may be initially presented at the first location under the adjacent characteristic.

In some embodiments, feedback indicating one or more threshold characteristics (under which a user sees one or more stimuli presented on a user interface) may be provided to a prediction model. Based on the feedback, a set of predicted characteristics (for a set of locations of the user interface) and a set of confidence scores associated with the set of locations may be obtained via the prediction model. As discussed above, locations of the set of locations may be selected based on the confidence scores, and stimuli may be presented at the selected locations based on predicted characteristics associated with the selected locations. From such stimuli presentation, additional feedback indicating threshold characteristics (under which the user sees the stimuli at the selected locations, respectively) may be obtained. Based on the foregoing feedback(s), visual defect information may be generated for the user (e.g., in accordance with one or more techniques described herein).

In some embodiments, a ground truth input for a prediction model may be initialized, and a set of predicted characteristics (for a set of locations of the user interface) and a set of confidence scores associated with the set of locations may be obtained via the prediction model based on the ground truth input. As an example, the ground truth input may include initial feedback related to an initial set of stimuli presented at an initial set of locations of the user interface under a range of characteristics (e.g., initial feedback indicating threshold characteristics of the range of characteristics under which a user sees each stimulus of the initial set of stimuli). As discussed above, locations of the set of locations may be selected based on the confidence scores (e.g., selected for a given round or portion of the visual test presentation), and stimuli may be presented at the selected locations (e.g., during the given round/portion) based on predicted characteristics associated with the selected locations. From such stimuli presentation (e.g., during the given round/portion), additional feedback indicating threshold characteristics (under which the user sees the stimuli at the selected locations, respectively) may be obtained. Based on the additional feedback, the ground truth input may be updated for a subsequent round or portion of the visual test presentation. As an example, the ground truth input may be updated to include the initial feedback, the additional feedback, or other input information.

Figure 47A:
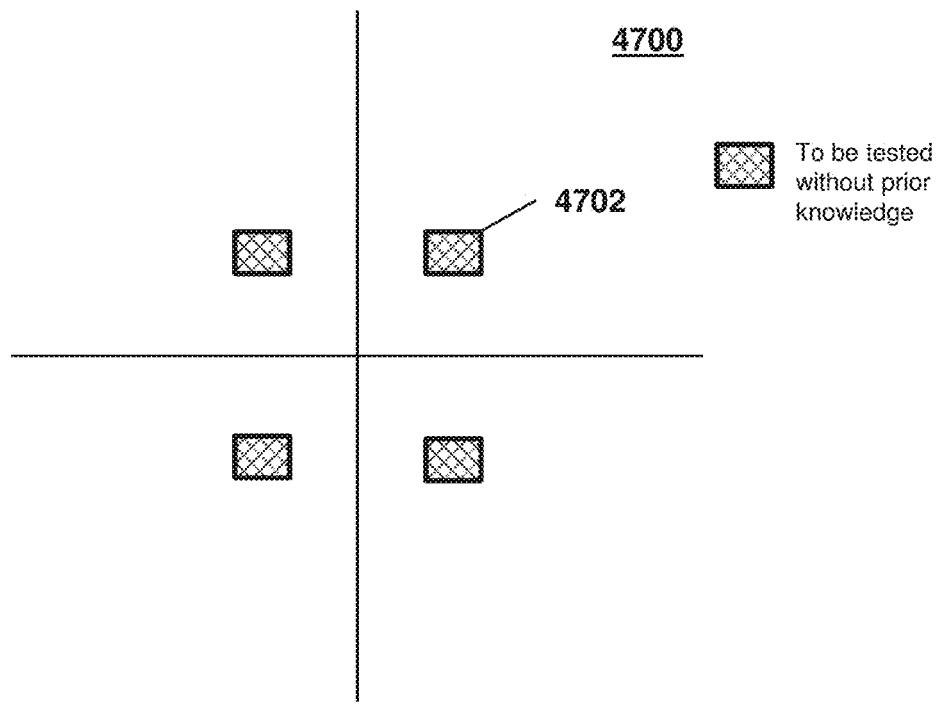
FIGS. 47A-47F shows portions of a vision test facilitated by prediction-based setting of initial stimuli characteristics and confidence-based selection of a testing location subset, in accordance with one or more embodiments.
Figure 47B:
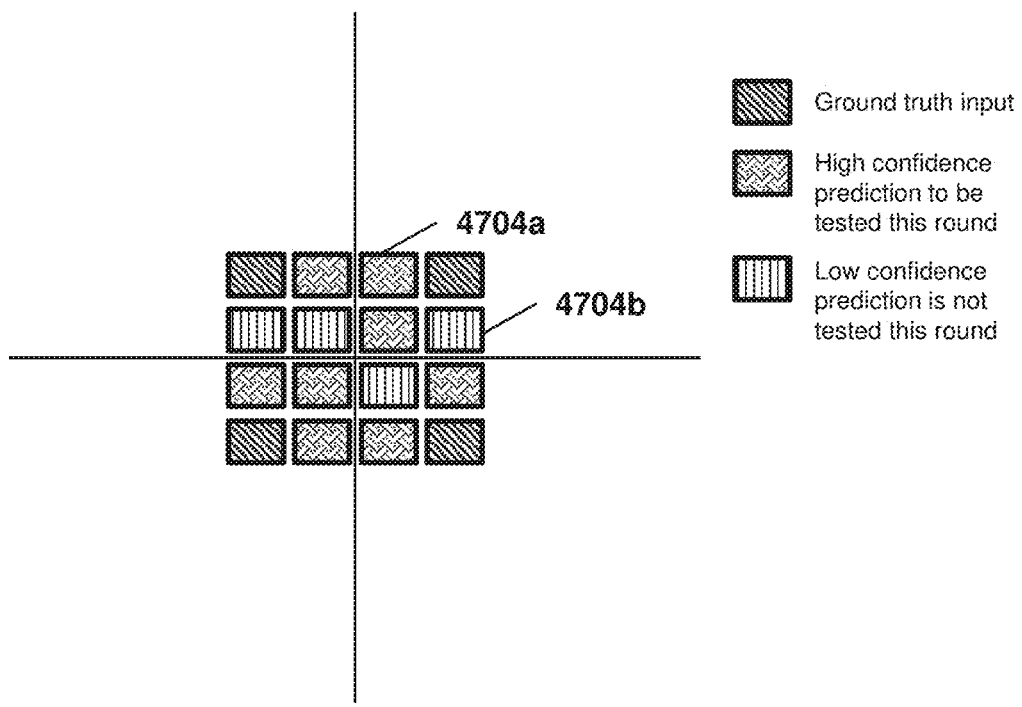

In one use case, with respect to FIGS. 47A-47B, during a first portion of a vision test, four locations 4702 on user interface 4700 (e.g., corresponding to a location in each central quadrant of a visual field of a user) may be initially tested (e.g., without prior knowledge) with one or more default starting characteristics, and feedback for the locations 4702 (e.g., indicating threshold characteristics under which the user is able to see stimuli at the respective locations 4702) may be obtained during the first portion of the vision test. Such feedback may be provided as a ground truth input to a neural network, and a first set of predicted characteristics for a first set of locations 4704 (e.g., at least part of a first pattern of predicted characteristics) and a first set of confidence scores associated with the first set of locations 4704 may be obtained via the neural network (e.g., via one or more hidden or output layers of the neural network). Locations 4704a may be selected to be tested during a second portion of the vision test over locations 4704b based on the predictions for locations 4704a being high confidence predictions and the predictions for locations 4704b being low confidence predictions. As such, for example, the predicted characteristics for the locations 4704a may be used to test the user during the second portion of the vision test, while the locations 4704b are not tested during the second portion of the vision test. The feedback for the locations 4704a (e.g., indicating the respective threshold characteristics from the second portion of the vision test) may be obtained during the second portion of the vision test, and such feedback may be provided as a ground truth input to a neural network to obtain one or more predicted characteristics for one or more further locations to be tested during a subsequent portion of the vision test. The neural network used for the second portion of the vision test may, for example, be the same instance of the neural network from the first portion of the vision test or a different instance of the same neural network (or otherwise a different neural network) to accommodate or optimize for different input/output configurations.

Figure 47C:
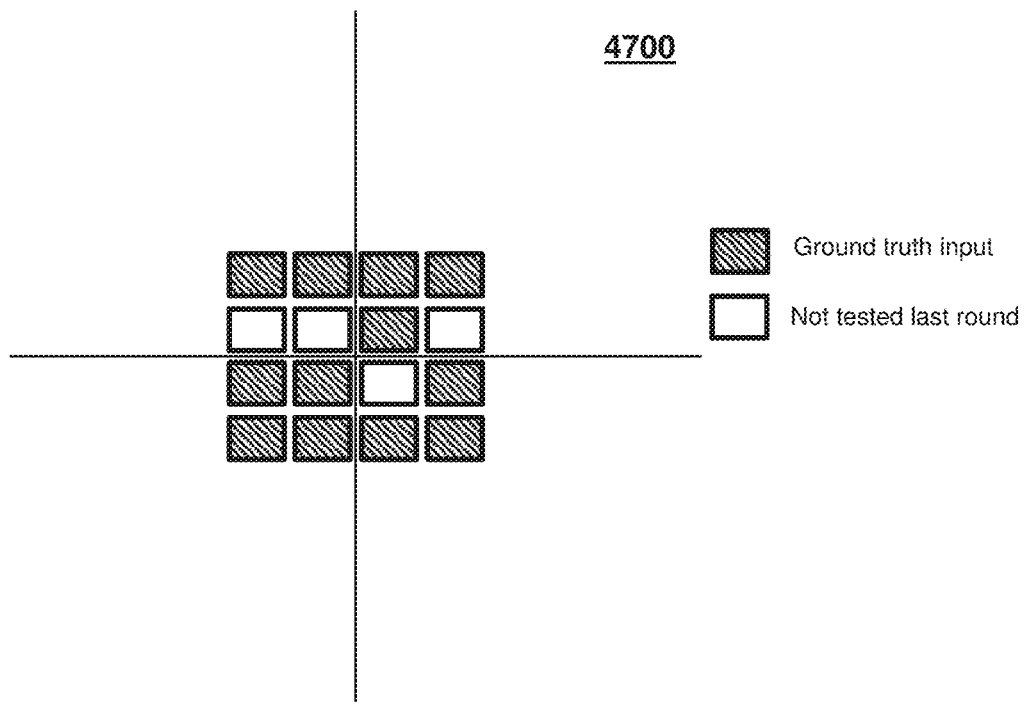
Figure 47D:
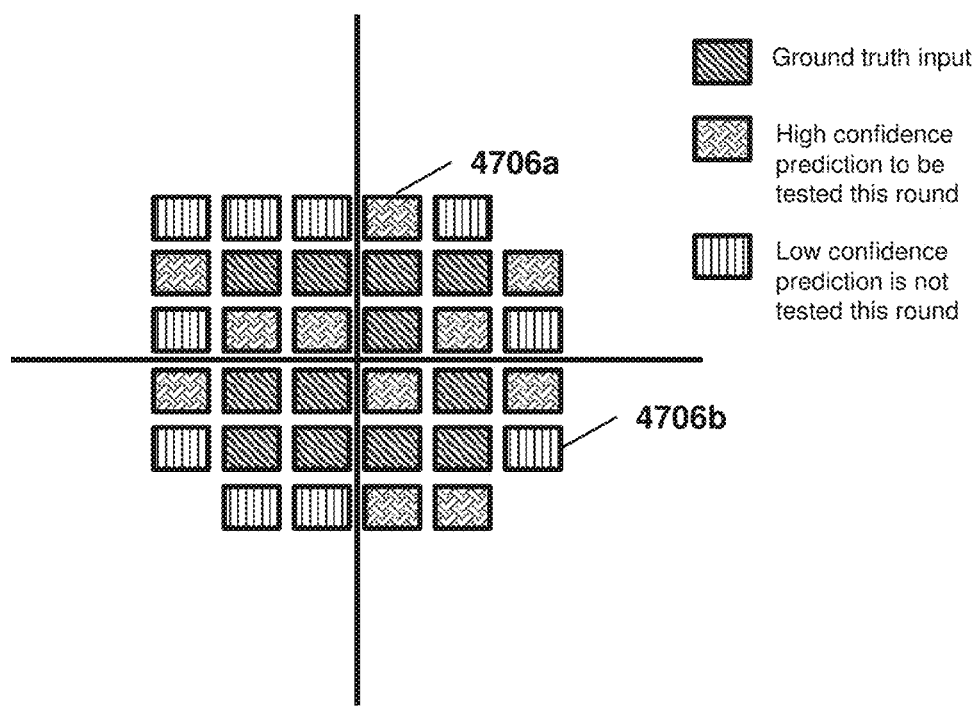

In another use case, with respect to FIGS. 47C-47D, during a third portion of the vision test, the feedback for the locations 4704a along with the prior feedback (e.g., for one or more of the locations 4702) may be provided as a ground truth input to a neural network, and a second set of predicted characteristics for a second set of locations 4706 (e.g., at least part of a second pattern of predicted characteristics) and a second set of confidence scores associated with the second set of locations 4706 may be obtained via the neural network (e.g., via one or more hidden or output layers of the neural network). Locations 4706a (e.g., which includes location 4704b) may be selected to be tested during a fourth portion of the vision test over locations 4706b based on the predictions for locations 4706a being high confidence predictions and the predictions for locations 4706b being low confidence predictions. As such, for example, the predicted characteristics for the locations 4706a may be used to test the user during the fourth portion of the vision test, while the locations 4706b are not tested during the fourth portion of the vision test. The feedback for the locations 4706a may be obtained during the fourth portion of the vision test, and such feedback may be provided as a ground truth input to a neural network to obtain one or more predicted characteristics for one or more further locations to be tested during a subsequent portion of the vision test. The neural network used for the third or fourth portion of the vision test may, for example, be the same instance of the neural network from the first or second portion (or the other one of the third or fourth portion) of the vision test or a different instance of the same neural network (or otherwise a different neural network) to accommodate or optimize for different input/output configurations.

Figure 47E:
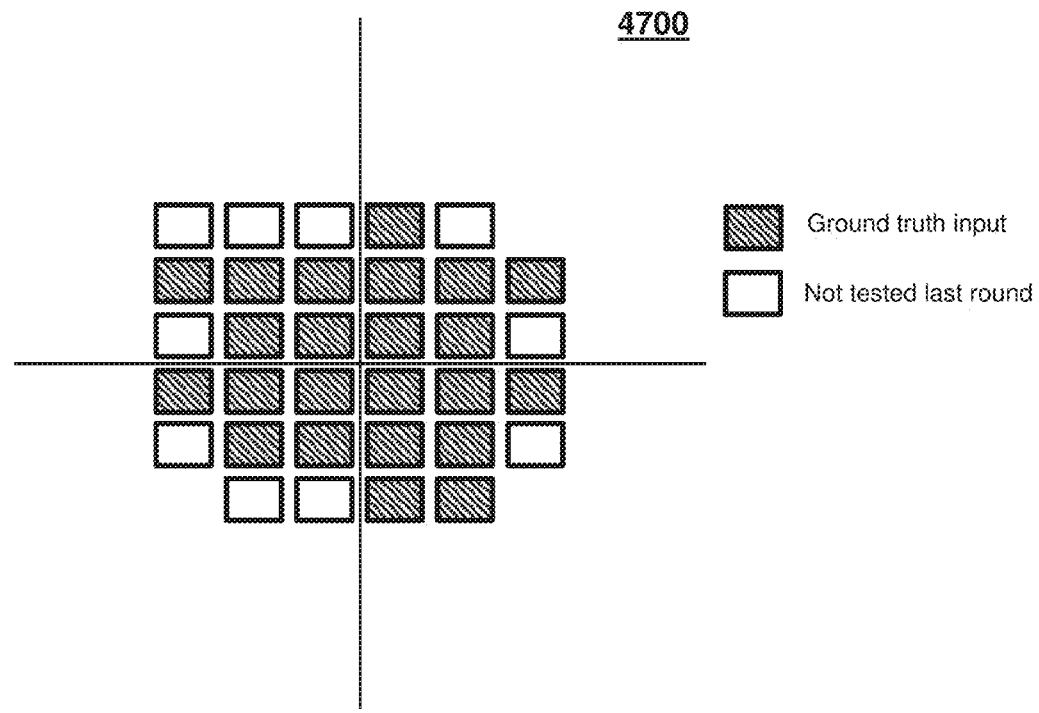
Figure 47F:
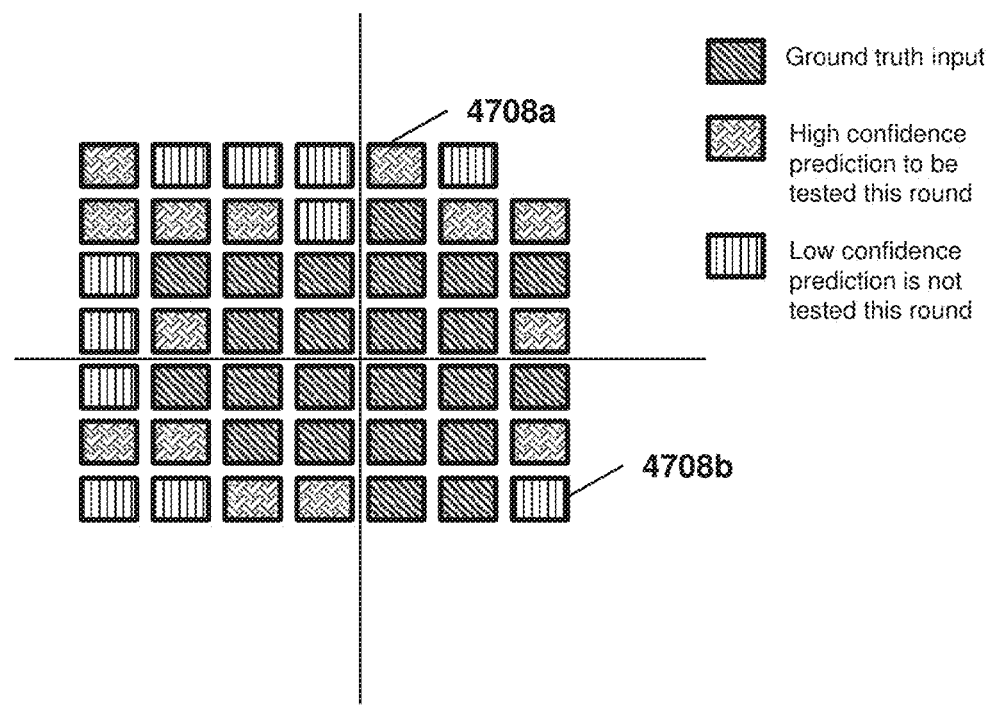

In a further use case, with respect to FIGS. 47E-47F, during a fifth portion of the vision test, the feedback for the locations 4706a along with the prior feedback (e.g., for one or more of the locations 4702 and 4704a) may be provided as a ground truth input to a neural network, and a third set of predicted characteristics for a third set of locations 4708 (e.g., at least part of a third pattern of predicted characteristics) and a third set of confidence scores associated with the third set of locations 4708 may be obtained via the neural network (e.g., via one or more hidden or output layers of the neural network). Locations 4708a (e.g., which includes location 4706b) may be selected to be tested during a sixth portion of the vision test over locations 4708b based on the predictions for locations 4708a being high confidence predictions and the predictions for locations 4708b being low confidence predictions. As such, for example, the predicted characteristics for the locations 4708a may be used to test the user during the sixth portion of the vision test, while the locations 4708b are not tested during the sixth portion of the vision test. The feedback for the locations 4708a may be obtained during the sixth portion of the vision test, and such feedback may be provided as a ground truth input to a neural network to obtain one or more predicted characteristics for one or more further locations to be tested during a subsequent portion of the vision test. In additional use cases, the foregoing operations may be performed with respect to one or more other regions (e.g., mid-peripheral regions, far-peripheral regions, or other defined regions to be tested). It should be noted that, although the foregoing use cases with respect to FIGS. 47A-47F begin with testing locations of the central region of the visual field and involve assessing regions in order from their proximity to the center of the visual field, other use cases that begin testing locations in other regions (e.g., near-peripheral, mid-peripheral, far-peripheral, etc.) or assess in a different order are contemplated.

FIGS. 41-43 and 48-49 are example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

Figure 41:
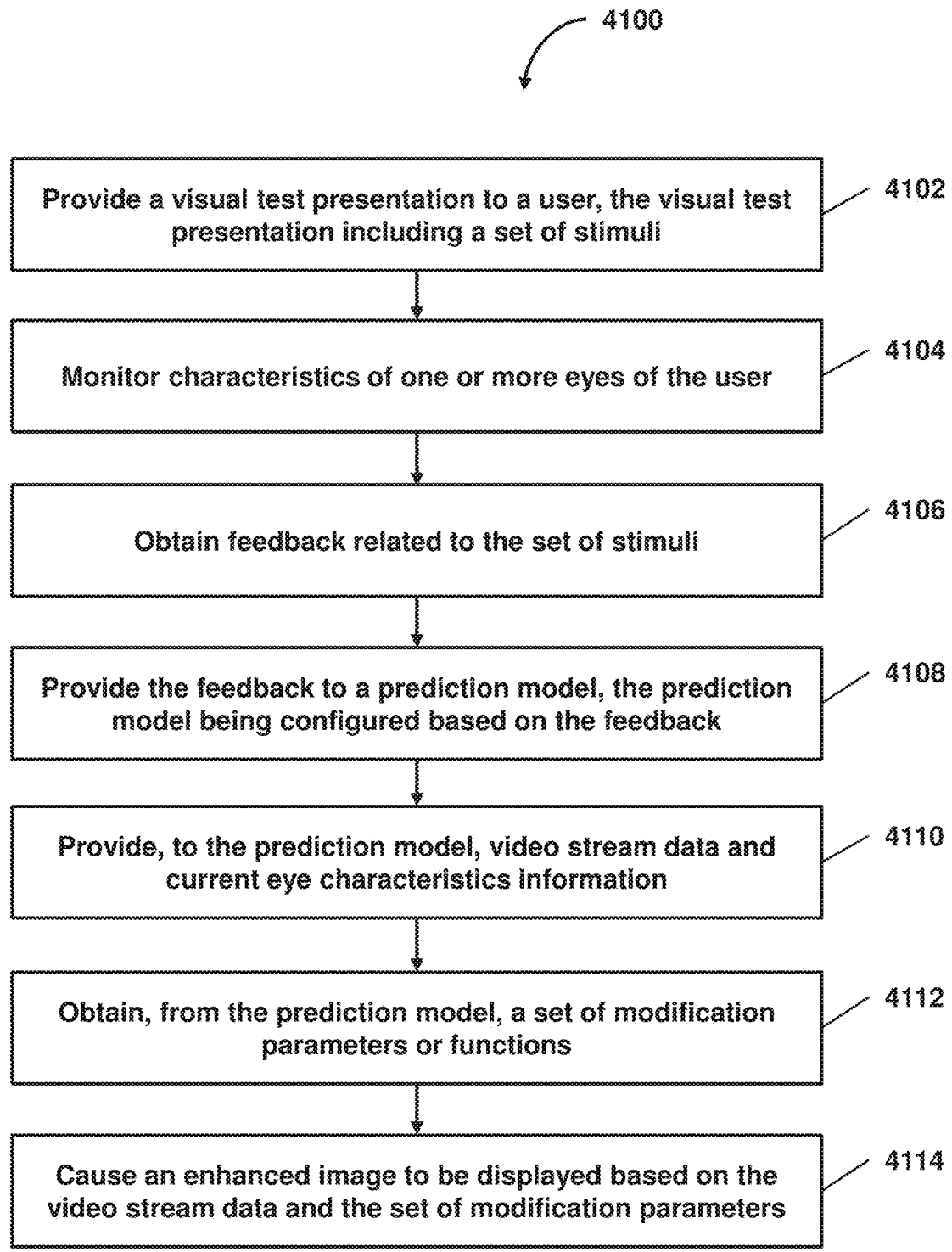
FIG. 41 shows a flowchart of a method of facilitating modification related to a vision of a user via a prediction model, in accordance with one or more embodiments.

FIG. 41 shows a flowchart of a method 4100 of facilitating modification related to a vision of a user via a prediction model, in accordance with one or more embodiments.

In an operation 4102, a visual test presentation may be provided to a user. As an example, the visual test presentation may include a set of stimuli. The set of stimuli may include light stimuli, text, or images displayed to the user. Operation 4102 may be performed by a subsystem that is the same as or similar to testing subsystem 122, in accordance with one or more embodiments.

In an operation 4104, one or more characteristics of one or more eyes of the user may be monitored. As an example, the eye characteristics may be monitored during the visual test presentation. The eye characteristics may include gaze direction, pupil size, limbus position, visual axis, optical axis, or other characteristics (e.g., during the visual test presentation). Operation 4104 may be performed by a subsystem that is the same as or similar to testing subsystem 122, in accordance with one or more embodiments.

In an operation 4106, feedback related to the set of stimuli may be obtained. As an example, the feedback may be obtained during the visual test presentation, and the feedback may indicate whether or how the user sees one or more stimuli of the set. Additionally, or alternatively, the feedback may include one or more characteristics related to the eyes occurring when the stimuli are displayed. Operation 4106 may be performed by a subsystem that is the same as or similar to testing subsystem 122, in accordance with one or more embodiments.

In an operation 4108, the feedback related to the set of stimuli may be provided to a prediction model. As an example, the feedback may be provided to the prediction model during the visual test presentation, and the prediction model may be configured based on the feedback and the eye characteristic information. As another example, based on the feedback, the prediction model may be configured to provide modification parameters or functions to be applied to image data (e.g., live video stream) to generate an enhanced presentation related to the image data. Operation 4108 may be performed by a subsystem that is the same as or similar to testing subsystem 122, in accordance with one or more embodiments.

In an operation 4110, video stream data and the user's current eye characteristics information (e.g., indicating the user's current eye characteristics) may be provided to the prediction model. As an example, the video stream data may be a live video stream obtained via one or more cameras of a wearable device of the user, and the live video stream and the current eye characteristics information may be provided to the prediction model in real-time. Operation 4110 may be performed by a subsystem that is the same as or similar to visioning subsystem 124, in accordance with one or more embodiments.

In an operation 4112, a set of modification parameters or functions may be obtained from the prediction model. As an example, the set of modification parameters or functions may be obtained from the prediction model based on the video stream and the current eye characteristics information being provided to the prediction model. As another example, the set of modification parameters or functions may be configured to be applied to the video stream to generate an enhanced image (e.g., that accommodates for dynamic aberrations of the user). Additionally, or alternatively, the set of modification parameters or functions may be configured to be applied to dynamically adjust one or more display portions of a display. Operation 4112 may be performed by a subsystem that is the same as or similar to visioning subsystem 124, in accordance with one or more embodiments.

In an operation 4114, an enhanced image may be caused to be displayed to the user based on the video stream data and the set of modification parameters or functions. Operation 4114 may be performed by a subsystem that is the same as or similar to visioning subsystem 124, in accordance with one or more embodiments.

Figure 42:
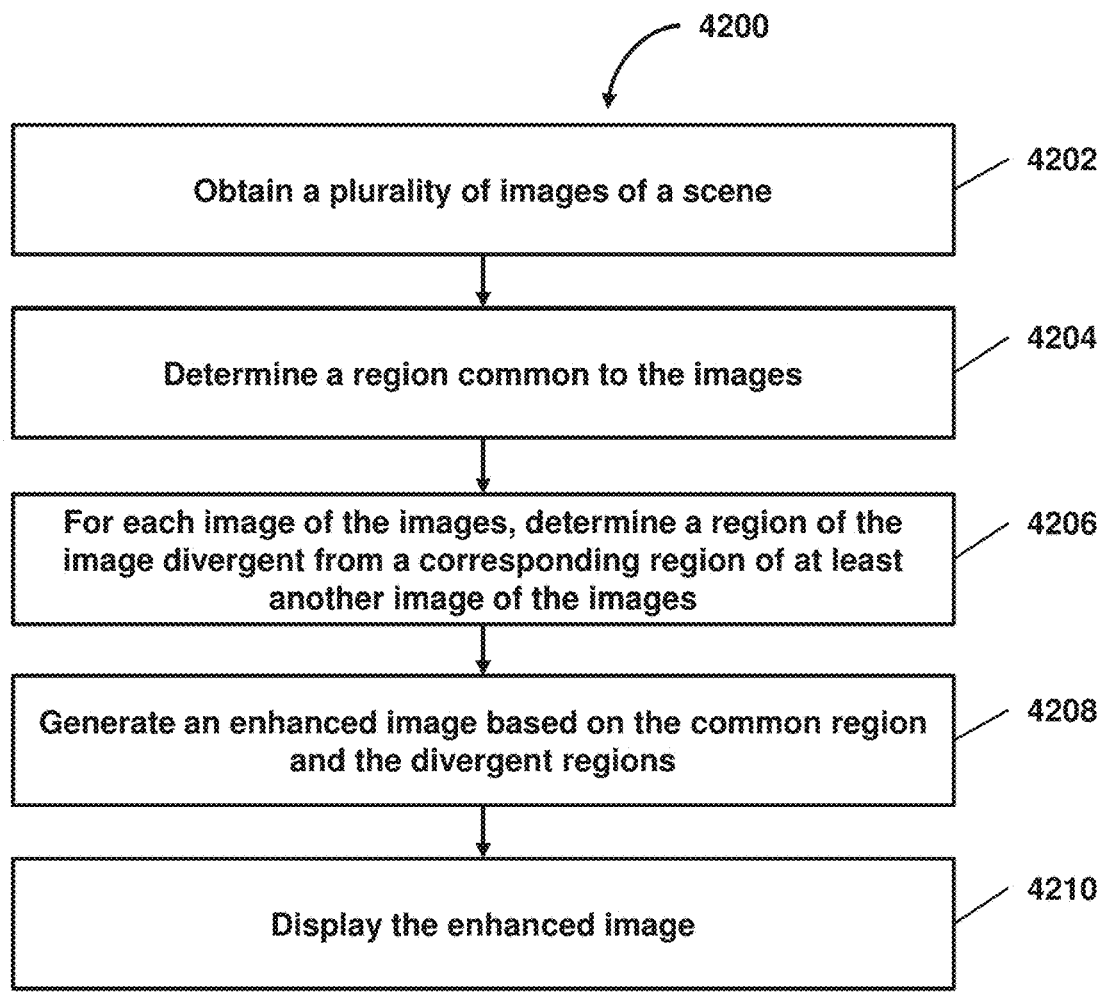
FIG. 42 shows a flowchart of a method of facilitating an increase in a field of view of a user via combination of portions of multiple images of a scene, in accordance with one or more embodiments.

FIG. 42 shows a flowchart of a method 4200 of facilitating an increase in a field of view of a user via combination of portions of multiple images of a scene, in accordance with one or more embodiments.

In an operation 4202, a plurality of images of a scene may be obtained. As an example, the images may be obtained via one or more cameras (e.g., of a wearable device) at different positions or orientations. Operation 4202 may be performed by a subsystem that is the same as or similar to visioning subsystem 124, in accordance with one or more embodiments.

In an operation 4204, a region common to the images may be determined. As an example, the common region may correspond to respective portions of the images that have the same or similar characteristics as one another. Operation 4204 may be performed by a subsystem that is the same as or similar to visioning subsystem 124, in accordance with one or more embodiments.

In an operation 4206, for each image of the images, a region of the image divergent from a corresponding region of at least another image (of the images) may be determined. As an example, each divergent region may correspond to a portion of one of the images that is distinct from all the other corresponding portions of the other images. Operation 4206 may be performed by a subsystem that is the same as or similar to visioning subsystem 124, in accordance with one or more embodiments.

In an operation 4208, an enhanced image may be generated based on the common region and the divergent regions. As an example, the enhanced image may be generated such that (i) a first region of the enhanced image includes a representation of the common region and (ii) a second region of the enhanced image comprises representations of the divergent regions. As another example, the enhanced image may be generated such that the second region is around the first region in the enhanced image. Operation 4208 may be performed by a subsystem that is the same as or similar to visioning subsystem 124, in accordance with one or more embodiments.

In an operation 4210, the enhanced image may be displayed. As an example, the enhanced image may be displayed via one or more displays of a wearable device of the user. Operation 4210 may be performed by a subsystem that is the same as or similar to visioning subsystem 124, in accordance with one or more embodiments.

Figure 43:
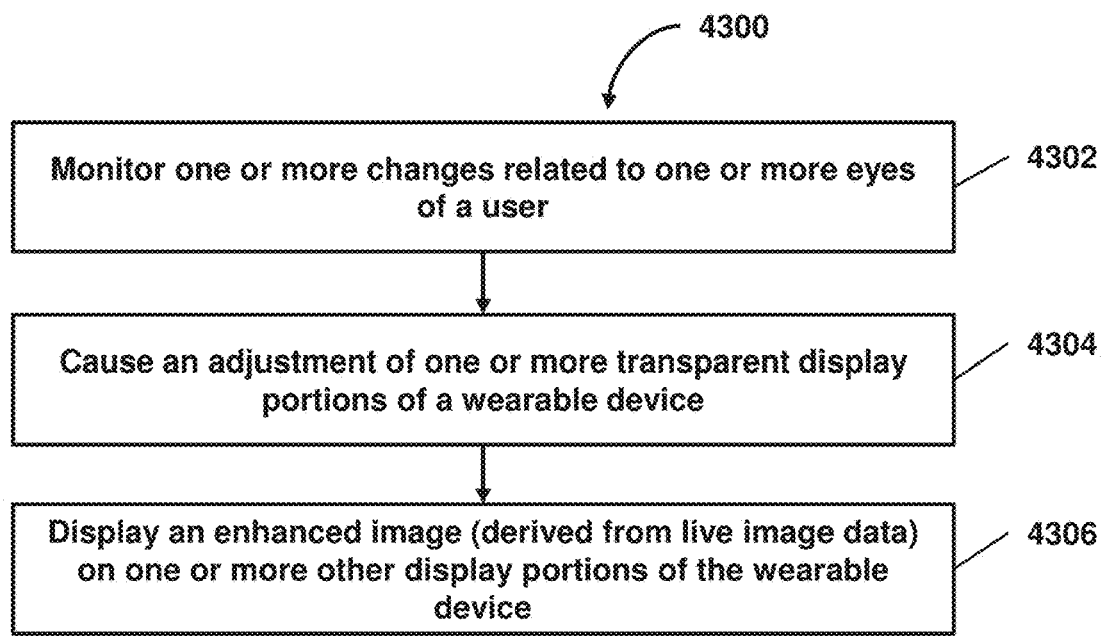
FIG. 43 shows a flowchart of a method of facilitating enhancement of a field of view of a user via one or more dynamic display portions on one or more transparent displays, in accordance with one or more embodiments.

FIG. 43 shows a flowchart of a method 4300 of facilitating enhancement of a field of view of a user via one or more dynamic display portions on one or more transparent displays, in accordance with one or more embodiments.

In an operation 4302, one or more changes related to one or more eyes of a user may be monitored. As an example, the eye changes may include an eye movement, a change in gaze direction, a pupil size change, or other changes. Operation 4302 may be performed by a subsystem that is the same as or similar to visioning subsystem 124, in accordance with one or more embodiments.

In an operation 4304, an adjustment of one or more transparent display portions of a wearable device may be caused based on the monitored changes. As an example, one or more positions, shapes, or sizes of the transparent display portions of the wearable device may be adjusted based on the monitored changes. Operation 4304 may be performed by a subsystem that is the same as or similar to visioning subsystem 124, in accordance with one or more embodiments.

In an operation 4306, an enhanced image (e.g., derived from live image data) may be displayed on one or more other display portions of the wearable device. As an example, at least one of the other display portions may be around at least one of the transparent display portions of the wearable device such that the enhanced image is displayed around the transparent display portion (e.g., and not within the transparent display portions). Operation 4306 may be performed by a subsystem that is the same as or similar to visioning subsystem 124, in accordance with one or more embodiments.

Figure 48:
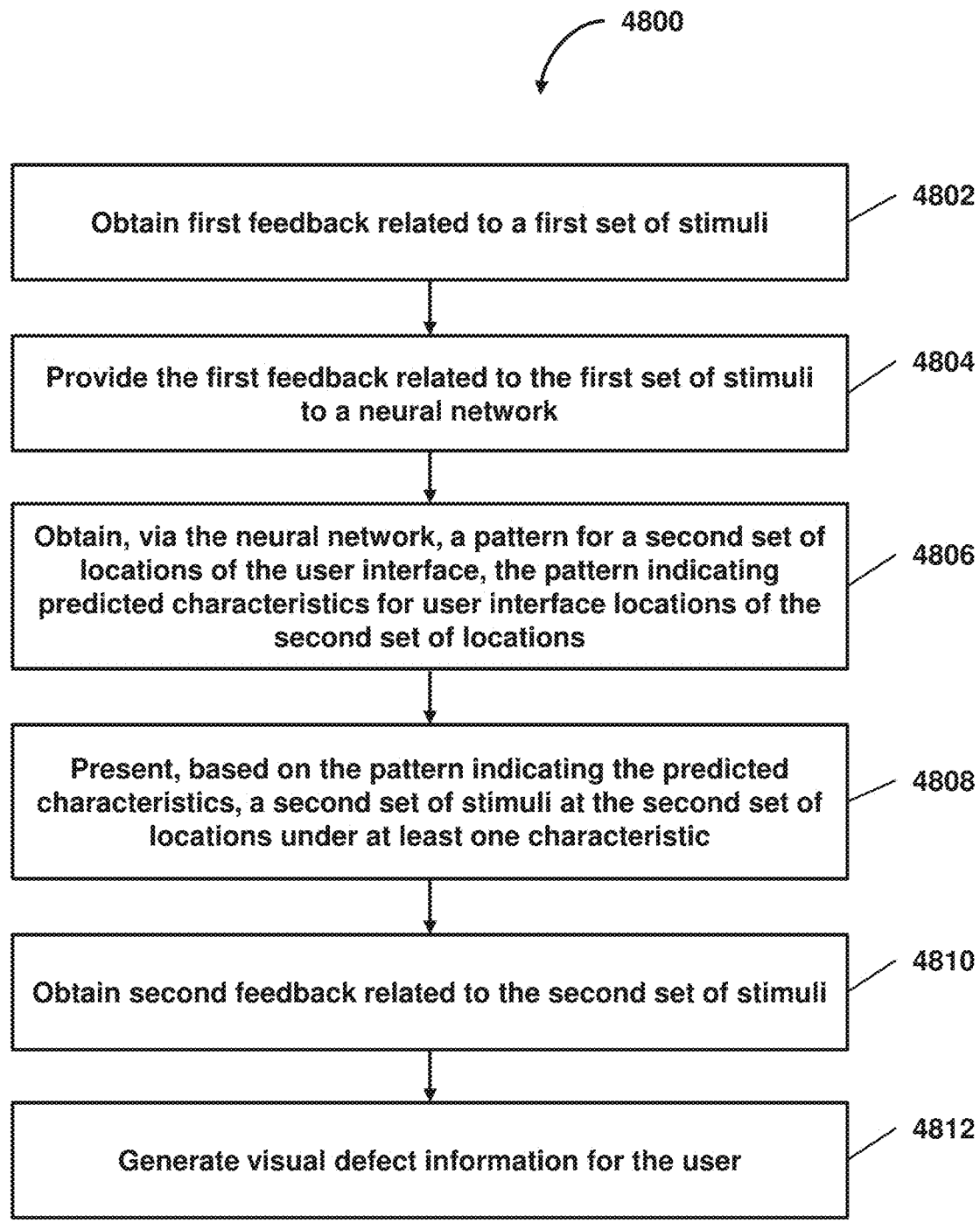
FIG. 48 shows a flowchart of a method of facilitating vision testing via pattern-based selection of a testing location, in accordance with one or more embodiments.

FIG. 48 shows a flowchart of a method 4800 of facilitating vision testing via pattern-based selection of a testing location, in accordance with one or more embodiments.

In an operation 4802, first feedback related to a first set of stimuli (presented at a first set of locations of a user interface) may be obtained. In some embodiments, the first set of stimuli may be presented under a range of characteristics. Operation 4802 may be performed by a subsystem that is the same as or similar to testing subsystem 122, in accordance with one or more embodiments.

In an operation 4804, the first feedback related to the first set of stimuli may be provided to a neural network. In some embodiments, the neural network may be configured based on the first feedback. Operation 4802 may be performed by a subsystem that is the same as or similar to testing subsystem 122, in accordance with one or more embodiments.

In an operation 4806, a pattern for a second set of locations of the user interface may be obtained. In some embodiments, the pattern may indicate predicted characteristics for user interface locations of the second set of locations. In some embodiments, the second set of locations may include a greater number of user interface locations than the first set of locations. Operation 4806 may be performed by a subsystem that is the same as or similar to testing subsystem 122, in accordance with one or more embodiments.

In an operation 4808, a second set of stimuli may be presented at the user interface location under at least one characteristic of the range of characteristics. For example, the second set of stimuli may be presented based on the pattern indicating the predicted characteristics. In some embodiments, the second set of stimuli may be presented such that (i) a first stimulus is initially presented at a user interface location of the second set of locations based on a first predicted characteristic indicated by the pattern and (ii) a second stimulus is initially presented at another user interface location of the second set of locations based on a second predicted characteristic indicated by the pattern. Operation 4808 may be performed by a subsystem that is the same as or similar to testing subsystem 122, in accordance with one or more embodiments.

In an operation 4810, second feedback related to the second set of stimuli may be obtained. For example, the second feedback may indicate a threshold characteristic of the range of characteristics under which the user sees each stimulus of the second set of stimuli. Operation 4810 may be performed by a subsystem that is the same as or similar to testing subsystem 122, in accordance with one or more embodiments.

In an operation 4812, visual defect information may be generated for the user. For example, the visual defect information may be generated based on the first feedback related to the first set of stimuli and the second feedback related to the second set of stimuli. Operation 4812 may be performed by a subsystem that is the same as or similar to testing subsystem 122, in accordance with one or more embodiments.

Figure 49:
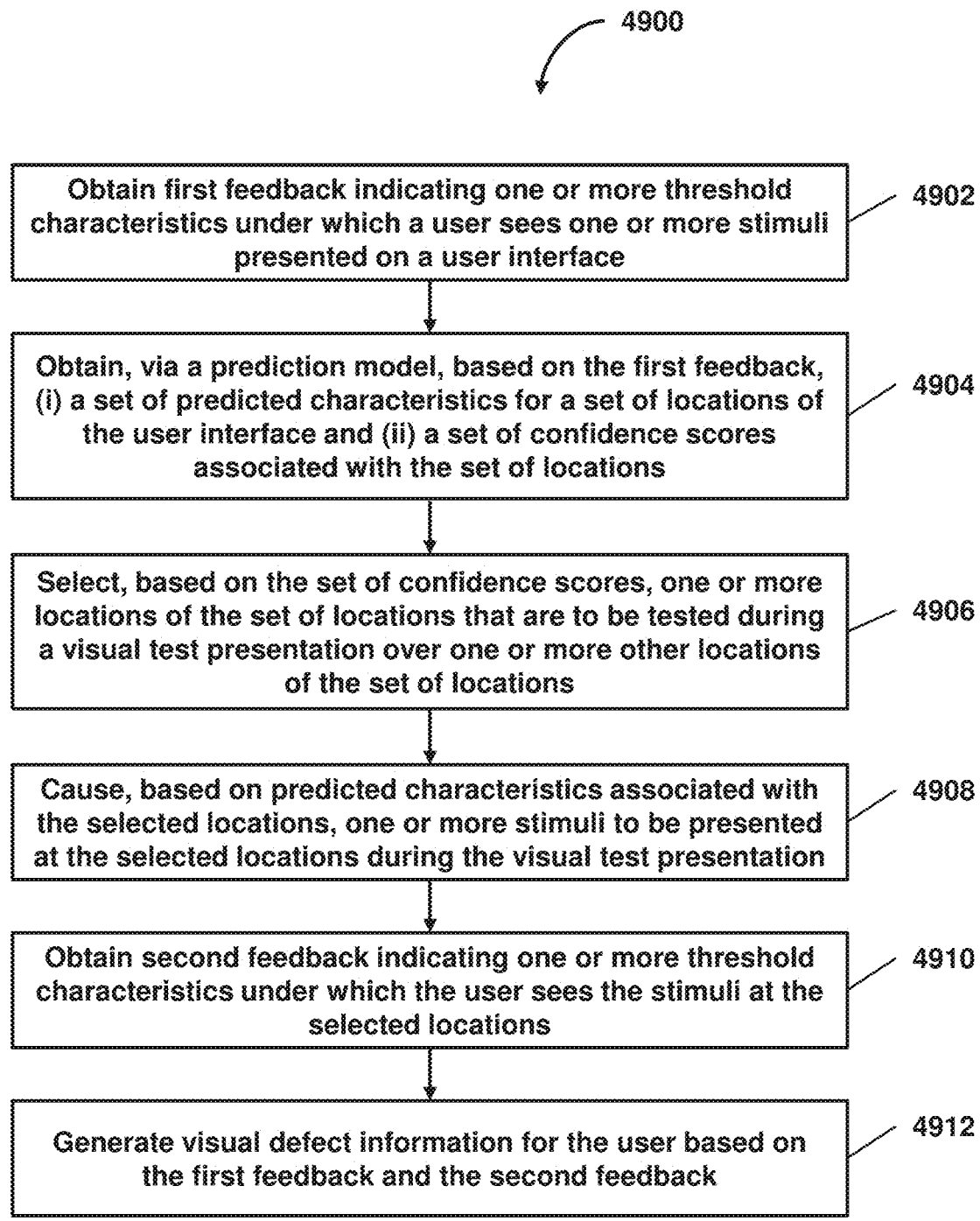
FIG. 49 shows a flowchart of a method of facilitating vision testing via confidence-based selection of a testing location subset, in accordance with one or more embodiments.

FIG. 49 shows a flowchart of a method 4900 of facilitating vision testing via confidence-based selection of a testing location subset, in accordance with one or more embodiments.

In an operation 4902, first feedback indicating one or more threshold characteristics (under which a user sees one or more stimuli presented on a user interface) may be obtained. As an example, each such stimulus may be presented to the user in a descending or ascending order of characteristics (e.g., brightness levels, contrast levels, saturation levels, sharpness levels, or another range of characteristics) at a given user interface locations that correspond to a given visual field locations of the user's field of view. A threshold characteristic may be a characteristic above which a user can see the stimulus and below which the user cannot see the stimulus (or vice versa). Operation 4902 may be performed by a subsystem that is the same as or similar to testing subsystem 122, in accordance with one or more embodiments.

In an operation 4904, a set of predicted characteristics for a set of locations of the user interface and a set of confidence scores associated with the set of locations may be obtained via a prediction model based on the first feedback. As an example, the first feedback may be provided as input to the prediction model, and the prediction model may output (i) a first predicted characteristic for a first location and a first confidence score associated with the first location and its prediction, (ii) a second predicted characteristic for a second location and a second confidence score associated with the second location and its prediction, (iii) a third predicted characteristic for a third location and a third confidence score associated with the third location and its prediction, and (iv) so on. As an example, such confidence scores may be probabilities related to the accuracy of the predictions of threshold characteristics under which the user is able to see a stimulus at the respective locations (e.g., user interface locations corresponding to locations of the user's visual field). Operation 4904 may be performed by a subsystem that is the same as or similar to testing subsystem 122, in accordance with one or more embodiments.

In an operation 4906, one or more locations of the set of locations (that are to be tested during a visual test presentation) may be selected based on the set of confidence scores. As an example, the locations may be selected over one or more other locations of the set of locations based on the set of confidence scores (e.g., selected for a given round or portion of the visual test presentation). In one use case, the locations may be selected based on (i) confidence scores associated with the locations being greater than or equal to confidence scores associated with the other locations, (ii) the confidence scores associated with the locations satisfying a threshold score (e.g., a predefined threshold score, a dynamic threshold score, etc.), (iii) an amount of locations to be tested (e.g., a fixed number or percentage of locations outputted by the prediction model that are to be tested during a given round or portion of the visual test presentation), (iv) a bounding box or other structure defining a region of a user's visual field to be tested, or (v) other criteria. Operation 4906 may be performed by a subsystem that is the same as or similar to testing subsystem 122, in accordance with one or more embodiments.

In an operation 4908, one or more stimuli may be caused to be presented at the selected locations during the visual test presentation based on one or more predicted characteristics associated with the selected locations. As an example, the predicted characteristics may include predictions of a threshold characteristic under which a user (taking the visual test) will see a stimulus at the respective selected locations (e.g., one or more predicted brightness levels, contrast levels, saturation levels, sharpness levels, etc.). In one use case, a first stimulus may initially be presented at the first location of the locations under a first predicted contrast level associated with the first location. If it is determined that the user sees the first stimulus under the first predicted contrast level, such determination may be stored as feedback indicating the first predicted contrast level as a threshold contrast level for the first location. On the other hand, if it is determined that the user cannot see the first stimulus under the first predicted contrast level, the contrast level may be increased to the next contrast level. Such process may be repeated for the first location until the user sees the first stimulus or a maximum contrast level is reached (e.g., the first stimulus is presented at the highest contrast level of a set of available contrast levels). Operation 4908 may be performed by a subsystem that is the same as or similar to testing subsystem 122, in accordance with one or more embodiments.

In an operation 4910, second feedback indicating one or more threshold characteristics (under which the user sees the stimuli at the selected locations) may be obtained. As indicated above, if it is determined that the user sees a given stimulus at a selected location under a predicted contrast level, such determination may be stored as part of the second feedback (e.g., indicating that the predicted contrast level is a threshold contrast level for the user to see the stimulus at the selected location). Such feedback may also indicate one or more selected locations for which it is determined that the user was not able to see stimuli (e.g., the user was not able to see stimuli at those selected locations when the stimuli were presented at the highest contrast level of a set of available contrast levels). Operation 4910 may be performed by a subsystem that is the same as or similar to testing subsystem 122, in accordance with one or more embodiments.

In an operation 4912, visual defect information may be generated for the user based on the first feedback and the second feedback. As an example, the visual defect information may include information indicating defective visual field portions, such as (i) locations of the user's visual field where the user is determined to have no vision (e.g., the user did not see stimuli presented at the highest contrast level), (ii) locations of the user's visual field where the user is determined to have reduced vision (e.g., the user was able to see stimuli at respective contrast levels greater than a particular threshold contrast level), (iii) the amount of vision reduction or sensitivities for each of such locations where the user is determined to have reduced vision, (iv) etc. Operation 4912 may be performed by a subsystem that is the same as or similar to testing subsystem 122, in accordance with one or more embodiments.

In some embodiments, the various computers and subsystems illustrated in FIG. 1A may include one or more computing devices that are programmed to perform the functions described herein. The computing devices may include one or more electronic storages (e.g., prediction database(s) 132, which may include training data database(s) 134, model database(s) 136, etc., or other electric storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other technologies). The computing devices may include a plurality of hardware, software, and/or firmware components operating together. For example, the computing devices may be implemented by a cloud of computing platforms operating together as the computing devices.

The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-124 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-124 described herein is for illustrative purposes, and is not intended to be limiting, as any of subsystems 112-124 may provide more or less functionality than is described. For example, one or more of subsystems 112-124 may be eliminated, and some or all of its functionality may be provided by other ones of subsystems 112-124. As another example, additional subsystems may be programmed to perform some or all of the functionality attributed herein to one of subsystems 112-124.

The present techniques may be used in any number of applications, including for example for otherwise healthy subjects frequently affected by quick onset of optical pathologies, subjects such as soldiers and veterans. Loss of visual field compromises the ability of soldiers, veterans, other affected patients to perform their essential tasks as well as daily life activities. This visual disability compromises their independence, safety, productivity and quality of life and leads to low self-esteem and depression. Despite recent scientific advances, treatment options to reverse existing damage of the retina, optic nerve or visual cortex are limited. Thus, treatment relies on offering patients with visual aids to maximize their functionality. Current visual aids fall short in achieving those goals. This underlines the need for having better visual aids to improve visual performance, quality of life and safety. The techniques herein, integrated into spectacles device, are able to diagnose and mitigate common quick onset eye injuries, such as military-related eye injuries and diseases, that cause visual field defects, in austere or remote, as well as general, environments. The techniques herein are able to diagnose and quantify visual field defects. Using this data, the devices process, in real-time, patients' field of view and fits and projects corrected images on their remaining functional visual field. Thus, minimizing the negative effect of the blind (or reduced) part of visual field on patients' visual performance. Moreover, the fact that the spectacles device does not rely on another clinical device to diagnose visual field defects make them specifically useful in austere and remote environments. Similarly, the present techniques may be used to augment the visual field of normal subjects to have a better than normal visual field or vision.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The present techniques will be better understood with reference to the following enumerated embodiments:

A1. A method comprising: providing a presentation (e.g., a visual test presentation or other presentation) comprising a set of stimuli to a user; obtaining feedback related to the set of stimuli (e.g., the feedback indicating whether or how the user senses one or more stimuli of the set); providing the feedback related to the set of stimuli to a model (e.g., a machine learning model or other model), the model being configured based on the feedback related to the set of stimuli.

A2. The method of embodiment A1, further comprising: providing live image data, eye characteristic information, or environment characteristic information to the model to obtain an enhanced image derived from the live image data; and causing an enhanced image to be displayed to the user, the eye characteristic information indicating one or more characteristics of one or more eyes of the user that occurred during a live capture of the live image data, the environment characteristic information indicating one or more characteristics of the environment that occurred during the live capture of the live image data.

A3. The method of embodiment A2, further comprising: obtaining the enhanced image from the model based on the live image data, eye characteristic information, or environment characteristic information being provided to the model.

A4. The method of embodiment A2, further comprising: obtaining one or more modification parameters from the model based on the live image data, eye characteristic information, or environment characteristic information being provided to the model; and generating the enhanced image based on the live image data or the one or more modification parameters to obtain the enhanced image.

A5. The method of embodiment A4, wherein the one or more modification parameters comprises one or more transformation parameters, brightness parameters, contrast parameters, saturation parameters, or sharpness parameters.

A6. The method of any of embodiments A1-A5, wherein obtaining the feedback related to the set of stimuli comprises obtaining an eye image captured during the presentation, the eye image being an image of an eye of the user, and wherein providing the feedback related to the set of stimuli comprises providing the eye image to the model.

A7. The method of any of embodiment A5, wherein the eye image is an ocular image, an image of a retina of the eye, or an image of a cornea of the eye.

A8. The method of any of embodiments A1-A7, wherein obtaining the feedback related to the set of stimuli comprises obtaining an indication of a response of the user to one or more stimuli of the set of stimuli or an indication of a lack of response of the user to one or more stimuli of the set of stimuli, and wherein providing the feedback related to the set of stimuli comprises providing the indication of the response or the indication of the lack of response to the model.

A9. The method of embodiment A8, wherein the response comprises an eye movement, a gaze direction, a pupil size change, or a user modification of one or more stimuli via user input of the user.

A10. The method of embodiment A9, wherein the user modification comprises a movement of one or more stimuli via user input of the user or supplemental data provided via user input of the user over one or more stimuli displayed to the user.

A11. The method of any of embodiments A1-A10, further comprising: obtaining a second set of stimuli, the second set of stimuli being generated based on the model's processing of the set of stimuli and the feedback related to the set of stimuli; causing the second set of stimuli to be displayed to the user; obtaining feedback related to the second set of stimuli (e.g., the feedback indicating whether or how the user sees one or more stimuli of the second set); and providing the feedback related to the second set of stimuli to the model, the model being further configured based on the feedback related to the second set of stimuli.

A12. The method of any of embodiments A1-A11, further comprising: determining, via the model, a defective visual field portion of a visual field of the user based on the feedback related to the set of stimuli, the visual field of the user comprising visual field portions, the defective visual field portion being one of the visual field portions that fails to satisfy one or more vision criteria.

A13. The method of embodiment A12, wherein the enhanced image is based on one or more transformations corresponding to the defective visual field portion of the live image data such that an image portion of the live image data is represented in an image portion of the enhanced image outside of the defective visual field portion.

A14. The method of any of embodiments A12-A13, wherein the enhanced image is based on one or more brightness or contrast modifications of the live image data such that (i) a brightness, contrast, or sharpness level increase is applied to an image portion of the live image data corresponding to the defective visual field portion to generate a corresponding image portion of the enhanced image and (ii) the brightness, contrast, or sharpness level increase is not applied to another image portion of the live stream data to generate a corresponding image portion of the enhanced image.

A15. The method of any of embodiments A12-A14, further comprising: detecting an object (e.g., in the defective visual field portion or predicted to be in the defective visual field portion); determining that the object is not sufficiently in any image portion of the enhanced image that corresponds to at least one of the visual field portions satisfying the one or more vision criteria; generating a prediction indicating that the object will come in physical contact with the user; and causing an alert to be displayed (e.g., over the enhanced image) based on (i) the prediction of physical contact and (ii) the determination that the object is not sufficiently any image portion of the enhanced image that corresponds to at least one of the visual field portions satisfying the one or more vision criteria, wherein the alert indicates an oncoming direction of the object.

A16. The method of any of embodiments A1-15, wherein one or more of the foregoing operations are performed by a wearable device.

A17. The method of embodiment A16, wherein the wearable device comprises one or more cameras configured to capture the live image data and one or more display portions configured to display one or more enhanced images.

A18. The method of any of embodiments A16-A17, wherein the one or more display portions comprise first and second display portions of the wearable device.

A19. The method of embodiment A18, wherein the wearable device comprises a first monitor comprising the first display portion and a second monitor comprising the second display portion.

A20. The method of any of embodiments A16-A19, wherein the one or more display portions comprise one or more dynamic display portions on one or more transparent displays of the wearable device, and wherein one or more enhanced images are displayed on the one or more display portions.

A21. The method of any of embodiments A1-A20, further comprising: monitoring one or more changes related to one or more eyes of the user.

A22. The method of embodiment 21, further comprising: providing the one or more changes as further feedback to the model; and obtaining one or more modification parameters from the model based on the live image data, eye characteristic information, or environment characteristic information being provided to the model; and generating the enhanced image based on the live image data and the one or more modification parameters to obtain the enhanced image.

A23. The method of any of embodiments A21-A22, further comprising: causing, based on the monitoring, an adjustment of one or more positions, shapes, sizes, or transparencies of the first or second display portions on one or more transparent displays of the wearable device, wherein causing the enhanced image to be displayed comprises causing the enhanced image to be displayed on the first or second display portions.

A24. The method of any of embodiments A1-A23, wherein the model comprises a neural network or other machine learning model.

A25. The method of any of embodiments A1-A24, wherein the presentation comprises presenting each stimulus of the set of stimuli under a set of characteristics (e.g., under a range of characteristics in ascending or descending order).

A26. The method of any of embodiments A1-A25, wherein the feedback related to the set of stimuli comprises a threshold characteristic of the set of characteristics under which the user sees each stimulus of the set of stimuli.

A27. The method of any of embodiments A1-A26, further comprising: subsequent to the configuration of the model, obtaining, via the model, a predicted characteristic with respect to a user interface location of a user interface; presenting, based on the predicted characteristic, a stimulus at the user interface location under at least one characteristic of the set of characteristics; obtaining second feedback related to the stimulus, the second feedback related to the stimulus indicating a threshold characteristic of the set of characteristics under which the user sees the stimulus; and generating visual defect information for the user based on the first feedback related to the set of stimuli and the second feedback related to the stimulus.

A28. The method of embodiment A27, wherein the predicted characteristic comprises a prediction of the threshold characteristic of the set of characteristics under which the user sees the stimulus.

A29. The method of any of embodiments A27-A28, wherein the stimulus is initially presented at the user interface location under the predicted characteristic.

A30. The method of embodiment A29, wherein the stimulus is initially presented at the user interface location under at least one characteristic that is adjacent, in the set of characteristics, to the predicted characteristic.

A31. The method of any of embodiments A27-A30, wherein the one or more user interface locations of the user interface correspond to visual field locations.

A32. The method of embodiment A31, wherein the visual defect information describes one or more visual field locations at which the user has visual defects.

A33. The method of embodiment A32, wherein the one or more visual field locations at which the user has visual defects correspond to one or more user interface locations at which one or more threshold characteristics under which the user sees corresponding stimuli breach a predetermined level.

A34. The method of any of embodiments A27-A33, wherein the set of characteristics comprise contrast levels, saturation levels, or sharpness levels.

B1. A method comprising: obtaining a plurality of images of a scene; determining a region common to the images; for each image of the images, determining a region of the image divergent from a corresponding region of at least another image of the images; generating an enhanced image based on the common region and the divergent regions; and causing the enhanced image to be displayed.

B2. The method of embodiment B1, wherein generating the enhanced image comprises generating the enhanced image based on the common region and the divergent regions such that (i) a first region of the enhanced image comprises a representation of the common region (ii) a second region of the enhanced image comprises representations of the divergent regions, and (iii) the second region is around the first region in the enhanced image.

B3. The method of embodiment B2, wherein generating the enhanced image comprises generating the enhanced image based on the common region, the divergent regions, and a second region common to the images such that (i) the first region of the enhanced image comprises the representation of the common region and a representation of the second common region and (ii) the second region of the enhanced image comprises representations of the divergent regions.

B4. The method of any of embodiments B1-B3, wherein the common region is a region of at least one of the images that corresponds to a macular region of a visual field of an eye or to a region within the macular region of the visual field.

B5. The method of any of embodiments B1-B4, wherein each of the divergent regions is a region of at least one of the images that corresponds to a peripheral region of a visual field of an eye or to a region within the peripheral region of the visual field.

B6. The method of any of embodiments B1-B5, further comprising: performing shifting of each image of the images, wherein generating the enhanced image comprises generating the enhanced image based on the common region and the divergent regions subsequent to the performance of the shifting.

B7. The method of embodiment B6, wherein performing the shifting comprises performing shifting of each image of the images such that a size of the common region is decreased and a size of at least one of the divergent regions is increased.

B8. The method of any of embodiments B1-B7, further comprising: performing resizing of one or more regions of the images, wherein generating the enhanced image comprises generating the enhanced image based on the common region and the divergent regions subsequent to the performance of the resizing.

B9. The method of embodiment B8, wherein performing the resizing comprises performing resizing of one or more regions of the images such that an extent of any resizing of the common region is different than an extent of any resizing of at least one of the divergent regions.

B10. The method of any of embodiments B8-B9, wherein performing the resizing comprises performing the resizing of one or more regions of the images such that a percentage change in size of the common region represented in the first region of the enhanced image is greater than or less than a percentage change in size of at least one of the divergent regions represented in the second region of the enhanced image.

B11. The method of embodiment B10, wherein the percentage change in size of at least one of the divergent regions is zero, and wherein the percentage change in size of the common region is greater than zero.

B12. The method of embodiment B10, wherein the percentage change in size of at least one of the divergent regions is greater than zero, and wherein the percentage change in size of the common region is zero.

B13. The method of any of embodiments B1-B12, further comprising: performing a fisheye transformation, a conformal mapping transformation, or other transformation on the common region, wherein generating the enhanced image comprises generating the enhanced image based on the common region and the divergent regions subsequent to the performance of the foregoing transformation(s).

B14. The method of any of embodiments B1-B13, further comprising: determining a defective visual field portion of a visual field of the user, wherein the visual field of the user comprises visual field portions, the defective visual field portion being one of the visual field portions that fails to satisfy one or more vision criteria, and wherein generating the enhanced image based on the determined defective visual field portion such that at least one of the common region or the divergent regions in the enhanced image do not overlap with the defective visual field portion of the visual field of the user.

B15. The method of any of embodiments B1-B14, further comprising: determining a visual field portion of the user's visual field that satisfies (i) one or more vision criteria, (ii) one or more position criteria, and (iii) one or more size criteria, and wherein generating the enhanced image based on the visual field portion such that at least one of the common region or the divergent regions in the enhanced image is within the visual field portion.

B16. The method of embodiment B15, wherein the one or more size criteria comprises a requirement that the visual field portion be a largest visual field portion of the user's visual field that satisfies the one or more vision criteria and the one or more position criteria.

B17. The method of any of embodiments B15-B16, wherein the one or more position criteria comprises a requirement that a center of the visual field portion correspond to a point within a macular region of an eye of the user.

B18. The method of any of embodiments B1-B17, wherein one or more of the foregoing operations are performed by a wearable device.

B19. The method of embodiment B18, further comprising: causing one or more display portions of the wearable device to be transparent, wherein causing the enhanced image to be displayed comprises causing an enhanced image to be displayed on one or more other display portions of the wearable device other than the one or more transparent display portions.

B20. The method of embodiment B19, further comprising: causing an adjustment of the one or more transparent display portions and the one or more other display portions of the wearable device.

B21. The method of embodiment B20, further comprising: monitoring one or more changes related to one or more eyes of the user, wherein causing the adjustment comprises causing, based on the monitoring, the adjustment of the one or more transparent display portions and the one or more other display portions of the wearable device.

B21. The method of embodiment B20, further comprising: monitoring one or more changes related to one or more eyes of the user, wherein causing the adjustment comprises causing, based on the monitoring, the adjustment of the one or more transparent display portions and the one or more other display portions of the wearable device.

B22. The method of any of embodiments B20-B21, wherein causing the adjustment comprises causing an adjustment of one or more positions, shapes, sizes, or transparencies of the one or more transparent display portions of the wearable device based on the monitoring.

B23. The method of any of embodiments B20-B22, wherein the enhanced image or the adjustment is based on the one or more changes.

B24. The method of any of embodiments B18-B23, wherein causing the enhanced image to be displayed comprises causing one or more of the common region or the divergent regions to be displayed on the one or more other display portions of the wearable device such that at least one of the common region or the divergent regions are not displayed on the one or more transparent display portions of the wearable device.

B25. The method of any of embodiments B18-B24, wherein the wearable device comprises first and second cameras, and wherein obtaining the images comprises obtaining at least one of the images via the first camera of the wearable device and obtaining at least another one of the images via the second camera of the wearable device.

B26. The method of any of embodiments B18-B25, wherein the one or more monitors of the wearable device comprises first and second monitors, and wherein causing the enhanced image to be displayed comprises causing the enhanced image to be displayed via the first and second monitors.

B27. The method of any of embodiments B18-B26, wherein the wearable device comprises a wearable spectacles device.

B28. The method of any of embodiments B1-B27, wherein the enhanced image or the adjustment is based on feedback related to a set of stimuli (e.g., the feedback indicating whether or how the user senses one or more stimuli).

C1. A method comprising: monitoring one or more changes related to one or more eyes of a user; causing, based on the monitoring, an adjustment of one or more transparent display portions or one or more other display portions of a wearable device; and causing an enhanced image to be displayed on the one or more other display portions of the wearable device, wherein the enhanced image is based on live image data obtained via the wearable device.

C2. The method of embodiment C1, wherein causing the adjustment comprises causing, based on the monitoring, an adjustment of one or more positions, shapes, sizes, brightness levels, contrast levels, sharpness levels, or saturation levels of the one or more transparent display portions of the wearable device or the one or more other display portions of the wearable device.

C3. The method of any of embodiments C1-C2, further comprising: determining a defective visual field portion of a visual field of the user, wherein the visual field of the user comprises visual field portions, the defective visual field portion being one of the visual field portions that fails to satisfy one or more vision criteria, and wherein causing the adjustment comprises causing an adjustment of one or more positions, shapes, or sizes of the one or more transparent display portions of the wearable device such that the one or more transparent display portions do not overlap with the defective visual field portion.

C4. The method of embodiment C3, further comprising: detecting an object (e.g., in the defective visual field portion or predicted to be in the defective visual field portion); determining that the object is not sufficiently in any image portion of the enhanced image that corresponds to at least one of the visual field portions satisfying one or more vision criteria; generating a prediction indicating that the object will come in physical contact with the user; and causing an alert to be displayed (e.g., over the enhanced image) based on (i) the prediction of physical contact and (ii) the determination that the object is not sufficiently any image portion of the enhanced image that corresponds to at least one of the visual field portions satisfying the one or more vision criteria, wherein the alert indicates an oncoming direction of the object.

C5. The method of any of embodiments C1-C4, further comprising: providing information related to the one or more eyes to a model, the model being configured based on the information related to the one or more eyes; subsequent to the configuring of the model, providing the one or more monitored changes related to the one or more eyes to the model to obtain a set of modification parameters, wherein causing the adjustment of the one or more transparent display portions comprises causing the adjustment of the one or more transparent display portions based on one or more modification parameters of the set of modification parameters.

C6. The method of embodiment C5, wherein the information related to the one or more eyes comprises one or more images of the one or more eyes.

C7. The method of any of embodiments C5-C6, wherein the information related to the one or more eyes comprises feedback related to a set of stimuli (e.g., the feedback indicating whether or how the user senses one or more stimuli).

C8. The method of any of embodiments C1-C7, wherein the one or more changes comprises an eye movement, a change in gaze direction, or a pupil size change.

C9. The method of any of embodiments C1-C8, wherein the enhanced image or the adjustment is based on feedback related to a set of stimuli (e.g., the feedback indicating whether or how the user senses one or more stimuli).

C10. The method of any of embodiments C1-C9, wherein the enhanced image or the adjustment is based on the one or more changes.

C11. The method of any of embodiments C1-C10, wherein the adjustment is performed simultaneously with the display of the enhanced image.

C12. The method of any of embodiments C1-C11, wherein one or more of the foregoing operations are performed by the wearable device.

C13. The method of any of embodiments C1-C12, wherein the wearable device comprises a wearable spectacles device.

D1. A method comprising: monitoring one or more eyes of a user (e.g., during a first monitoring period in which a set of stimuli are displayed to the user); obtaining feedback related to the set of stimuli (e.g., during the first monitoring period); and generating a set of modification profiles associated with the user based on the feedback related to the set of stimuli, each modification profile of the set of modification profiles (i) being associated with a set of eye-related characteristics and (ii) comprising one or more modification parameters to be applied to an image to modify the image for the user when eye-related characteristics of the user match the associated set of eye-related characteristics.

D2. The method of embodiment D1, wherein the feedback related to the set of stimuli indicates whether or how the user sees one or more stimuli of the set of stimuli.

D3. The method of any of embodiments D1-D2, wherein the feedback related to the set of stimuli comprises one or more characteristics related to the one or more eyes occurring when the one or more stimuli are displayed (e.g., during the first monitoring period).

D4. The method of any of embodiments D1-D3, further comprising: monitoring the one or more eyes of the user (e.g., during a second monitoring period); obtaining image data representing an environment of the user (e.g., during the second monitoring period); obtaining one or more modification profiles associated with the user based on (i) the image data or (ii) characteristics related to the one or more eyes (e.g., from the second monitoring period); and causing modified image data to be displayed to the user (e.g., during the second monitoring period) based on (i) the image data and (ii) the one or more modification profiles.

D5. The method of embodiment D4, wherein the characteristics related to the one or more eyes comprises gaze direction, pupil size, limbus position, visual axis, optical axis, or eyelid position or movement.

D6. The method of any of embodiments D1-D5, wherein obtaining the feedback related to the set of stimuli comprises obtaining an eye image captured during the first monitoring period, the eye image being an image of an eye of the user, and wherein generating the set of modification profiles comprises generating the set of modification profiles based on the eye image.

D7. The method of embodiment D6, wherein the eye image is an image of a retina of the eye or an image of a cornea of the eye.

D8. The method of any of embodiments D1-D7, wherein obtaining the feedback related to the set of stimuli comprises obtaining an indication of a response of the user to the one or more stimuli or an indication of a lack of response of the user to the one or more stimuli, and wherein generating the set of modification profiles comprises generating the set of modification profiles based on the indication of the response or the indication of the lack of response.

D9. The method of embodiment D8, wherein the response comprises an eye movement, a gaze direction, or a pupil size change.

D10. The method of any of embodiments D1-D9, wherein one or more of the foregoing operations are performed by a wearable device.

D11. The method of embodiment D10, wherein the wearable device comprises a wearable spectacles device.

E1. A method comprising: causing a first stimulus to be displayed at a first interface location on a user interface of a user based on a fixation point for a visual test presentation; adjusting, during the visual test presentation, the fixation point for the visual test presentation based on eye characteristic information related to the user, the eye characteristic information indicating one or more characteristics related to one or more eyes of the user that occurred during the visual test presentation; causing a second stimulus to be displayed at a second interface location on the user interface based on the adjusted fixation point for the visual test presentation; obtaining feedback information indicating feedback related to the first stimulus and feedback related to the second stimulus, the feedback related to the first or second stimulus indicating a response of the user or lack of response of the user to the first or second stimulus; and generating visual defect information associated with the user based on the feedback information.

E2. The method of embodiment of E1, the user interface is configured to display a view having a horizontal dimension corresponding to a first number of degrees or a vertical dimension corresponding the first number of degrees, and wherein the visual defect information is generated such that the visual defect information has coverage for greater than the first number of degrees with respect to the horizontal dimension for the visual field of the user or with respect to the vertical dimension for the visual field of the user.

E3. The method of any of embodiments E1-E2, wherein the user interface is configured to display a view having a given dimension corresponding to a first number of degrees, and wherein the visual defect information is generated such that (i) the visual defect information indicates at least two defects existing at visual field locations of a visual field of the user and (ii) the visual field locations are greater than the first number of degrees apart with respect to the given dimension for the visual field of the user.

E4. The method of any of embodiments E1-E3, wherein the user interface is configured to display a view having a given dimension corresponding to a first number of degrees, wherein the feedback information further indicates feedback related to a third stimulus displayed on the user interface during the visual test presentation, further comprising: determining whether a vision defect exists at visual field locations of the visual field of the user based on the feedback information such that at least two of the visual field locations are apart from one another by more than the first number of degrees with respect to the given dimension for the visual field; and generating the visual defect information based on the determination of whether a vision defect exists at the visual field locations.

E5. The method of any of embodiments E1-E4, further comprising: determining the first interface location for the first stimulus based on the fixation point for the visual test presentation and a first relative location associated with the first stimulus; and determining the second interface location for the second stimulus based on the adjusted fixation point for the visual test presentation and a second relative location associated with the second stimulus, wherein causing first stimulus to be displayed comprises causing, during the visual test presentation, the first stimulus to be displayed at the first interface location on the user interface based on the determination of the first interface location, and wherein causing second stimulus to be displayed comprises causing, during the visual test presentation, the second stimulus to be displayed at the second interface location on the user interface based on the determination of the second interface location.

E6. The method of any of embodiments E1-E5, further comprising: selecting, during the visual test presentation, the first interface location for the first stimulus based on the first interface location being farther from the fixation point than one or more other interface locations on the user interface, the one or more other interface locations corresponding to one or more other visual field locations of the test set, wherein causing first stimulus to be displayed comprises causing, during the visual test presentation, the first stimulus to be displayed at the first interface location on the user interface based on the selection of the first interface location.

E7. The method of embodiment E6, further comprising: removing the first visual field location from the test set.

E8. The method of embodiment E7, wherein removing the first visual field location comprises removing the first visual field location from the test set such that the first visual field location is no longer available to be selected from the test set during the visual test presentation.

E9. The method of any of embodiments E7-E8, further comprising: selecting, subsequent the removal of the first visual field location from the test set, the second interface location for the second stimulus based on the second interface location being farther from the adjusted fixation point than the one or more other interface location, wherein causing second stimulus to be displayed comprises causing, during the visual test presentation, the second stimulus to be displayed at the second interface location on the user interface based on the selection of the second interface location.

E10. The method of any of embodiments E6-E9, wherein selecting the first interface location comprises selecting the first interface location for the first stimulus based on the first interface location being at least as far from the fixation point than all other interface locations on the user interface that correspond to a visual field location of the test set other than the first visual field position with respect to a given dimension.

E11. The method of any of embodiments E6-E10, wherein selecting the second interface location comprises selecting the second interface location for the second stimulus based on the second interface location being as least as far from the adjusted fixation point than all other interface locations on the user interface that correspond to a visual field location of the test set other than the second visual field position with respect to a given dimension.

E12. The method of any of embodiments E1-E11, further comprising: establishing a lock of the adjusted fixation point such that fixation point readjustment is avoided while the lock of the adjusted fixation point remains established; causing, while the lock of the adjusted fixation point remains established, one or more stimuli to be displayed on the user interface based on the adjusted fixation point; and releasing the lock of the adjusted fixation point prior to the display of the second stimulus.

E13. The method of any of embodiments E1-E12, further comprising: causing, while the adjusted fixation point remains the same (e.g., at the first interface location), multiple stimuli to be displayed on the user interface and then deemphasized on or removed from the user interface, wherein at least one stimulus of the multiple stimuli is displayed on the user interface subsequent to at least one other stimuli of the multiple stimuli being displayed on the user interface.

E14. The method of embodiment E13, wherein the multiple stimuli are displayed and then deemphasized or removed while the first stimulus continues to be displayed at the first interface location on the user interface.

E15. The method of any of embodiments E13-E14, further comprising: causing the first stimulus to be deemphasized on or removed from the user interface and then emphasized or redisplayed at the first interface location on the user interface subsequent to at least one stimulus of the multiple stimuli being displayed on the user interface.

E16. The method of any of embodiments E1-E15, wherein the eye characteristic information indicates one or more gaze directions, pupil size changes, eyelid movements, head movements, or other eye-related characteristics of the user that occurred during the visual test presentation.

F1. A method comprising: monitoring eye-related characteristics related to eyes of a user during visual test presentation via two or more user interfaces (e.g., on two or more displays) that are provided to the respective eyes, the eyes comprising first and second eyes of the user; causing one or more stimuli to be presented at one or more positions on at least one of the user interfaces; and determining visual defect information for the first eye based on one or more eye-related characteristics (e.g., of the first eye) occurring upon the stimulus presentation.

F2. The method of embodiment F1, wherein determining the visual defect information comprises determining a deviation measurement for the first eye based on one or more eye-related characteristics of the first eye occurring upon the stimulus presentation.

F3. The method of embodiment F2, wherein deviation measurement indicates a deviation of the first eye relative to the second eye.

F4. The method of any of embodiments F1-F3, wherein causing the stimulus presentation comprises causing a stimulus to be presented at a first time at a position on a first user interface for the first eye such that the stimulus presentation occurs while a stimulus is not presented on a second user interface for the second eye.

F5. The method of any of embodiments F1-F4, wherein causing the stimulus presentation comprises causing a stimulus to be presented at a position on the first user interface while a stimuli intensity of the second user interface does not satisfy a stimuli intensity threshold.

F6. The method of any of embodiments F4-F5, further comprising: causing a stimulus to be presented at the position on the second user interface at a prior time (prior to the first time) while a stimulus is not presented on the first user interface.

F7. The method of any of embodiments F4-F6, further comprising: causing a stimulus to be presented at the first position on the first display and a stimulus to be presented at the first position on the second display at a prior time prior to the first time; detecting lack of fixation of the first eye on the first position upon the presentation of a stimulus on the first display at the prior time; and determining the first eye of the user to be a deviating eye based on the detection of the lack of fixation of the first eye.

F8. The method of any of embodiments F4-F7, further comprising: causing, based on the visual defect information (e.g., the deviation measurement), a stimulus to be presented at a modified position on the first display at a subsequent time subsequent to the first time such that the presentation at the subsequent time occurs while a stimulus is not presented on the second display, the modified position being different from the first position; and confirming the visual defect information (e.g., the deviation measurement) based on one or more eye-related characteristics of the first eye or the second eye not changing beyond a change threshold upon the presentation at the subsequent time.

F9. The method of embodiment F8, further comprising: determining, based on the visual defect information (e.g., the deviation measurement), the modified position as a position at which a stimulus is to be presented on the first display at the subsequent time.

F10. The method of any of embodiments F1-F2, wherein causing the stimulus presentation comprises causing a stimulus to be presented at a given time at a position on a first user interface for the first eye and at the corresponding position on a second user interface for the second eye.

F11. The method of any of embodiments F1-F10, further comprising: generating a modification profile associated with the user based on the visual defect information (e.g., the deviation measurement), the modification profile comprising one or more modification parameters to be applied to modify an image for the user.

F12. The method of embodiment F11, further comprising: causing modified video stream data to be displayed to the user based on (i) video stream data representing an environment of the user and (ii) the modification profile associated with the user.

F13. The method of embodiment F12, wherein the modification profile comprises a translation or rotation parameter to be applied to modify an image for the first eye when the second eye's gaze direction is directed at the first position, wherein causing the modified video stream data to be displayed comprises: detecting the second eye's gaze direction being directed at the first position; using the translation or rotation parameter to modify the video stream data based on the detection of the second eye's gaze direction to generate the modified video stream data; and causing the modified video stream data to be displayed to the first eye of the user.

F14. The method of any of embodiments F1-F13, further comprising: generating a first modification profile associated with the user based on the deviation measurement, the first modification profile comprising one or more modification parameters to be applied to modify an image for the first eye in response to the second eye's gaze direction being directed at the first position; and generating a second modification profile based on a second deviation measurement for the first eye, the second modification profile comprising one or more modification parameters to be applied to modify an image for the first eye in response to the second eye's gaze direction being directed at a second position different from the first position.

F15. The method of any of embodiments F1-F14, wherein determining the visual defect information comprises determining whether the user has double vision or an extent of the double vision based on a number or type of stimuli seen by the user.

F16. The method of embodiment F15, further comprising: determining the number or type of stimuli seen by the user based on a user input indicating the number or type of stimuli that the user sees.

F17. The method of any of embodiments F15-F16, further comprising: determining the number or type of stimuli seen by the user based on one or more eye-related characteristics occurring upon the stimulus presentation.

F18. The method of any of embodiments F1-F17, wherein determining the visual defect information comprises determining whether the user has stereopsis or an extent of the stereopsis based on one or more eye-related characteristics occurring upon the stimulus presentation.

F19. The method of any of embodiments F1-F18, wherein the eye-related characteristics comprises one or more gaze directions, pupil size changes, or other eye-related characteristics.

G1. A method comprising: obtaining, via a model, (i) a set of predicted characteristics for a set of locations of a user interface and (ii) a set of confidence scores associated with the set of locations; selecting, based on the set of confidence scores, one or more locations of the set of locations that are to be tested during a visual test presentation, the one or more locations being selected over one or more other locations of the set of locations based on the set of confidence scores; and causing, based on one or more predicted characteristics associated with the selected locations, one or more stimuli to be presented at the selected locations during the visual test presentation.

G2. The method of embodiment G1, further comprising: obtaining feedback indicating one or more threshold characteristics under which a user sees the one or more stimuli at the selected locations; and generating visual defect information for the user based on the feedback.

G3. The method of embodiment G2, further comprising: obtaining, based on the feedback, (i) a second set of predicted characteristics for a second set of locations of the user interface and (ii) a second set of confidence scores associated with the second set of locations; selecting, based on the second set of confidence scores, one or more second locations of the second set of locations that are to be tested during the visual test presentation; causing, based on one or more predicted characteristics associated with the selected second locations, one or more second stimuli to be presented at the selected second locations during the visual test presentation.

G4. The method of embodiment G3, further comprising: obtaining additional feedback indicating one or more threshold characteristics under which the user sees the one or more second stimuli; and generating the visual defect information based on the feedback and the additional feedback.

G5. The method of any of embodiments G3-G4, wherein the second set of locations comprises the one or more other locations of the set of locations and one or more additional locations.

G6. The method of any of embodiments G1-G5, further comprising: obtaining prior feedback indicating one or more threshold characteristics under which a user sees one or more prior stimuli presented on a user interface; and providing the prior feedback to the model to obtain the set of predicted characteristics and the set of confidence scores.

G7. The method of any of embodiments G1-G6, wherein presenting the one or more stimuli at the selected second locations comprises initially presenting a first stimulus at a first location of the selected locations based on a first predicted characteristic associated with the first location, and wherein the first predicted characteristic comprises a prediction of a threshold characteristic of a range of characteristics under which a user sees the first stimulus or a characteristic adjacent the threshold characteristic within the range of characteristics.

G8. The method of any of embodiments G1-G6, wherein presenting the one or more stimuli at the selected locations comprises initially presenting a first stimulus at a first location of the selected locations under a first predicted characteristic associated with the first location, and wherein the first predicted characteristic comprises a prediction of a threshold characteristic of the range of characteristics under which a user sees the first stimulus.

G9. The method of any of embodiments G1-G6, wherein presenting the one or more stimuli at the selected locations comprises initially presenting a first stimulus at a first location of the selected locations under at least one characteristic that is adjacent, in the range of characteristics, to a first predicted characteristic associated with the first location, and wherein the first predicted characteristic comprises a prediction of a threshold characteristic of the range of characteristics under which a user sees the first stimulus.

G10. The method any of embodiments G1-G9, wherein selecting the one or more locations comprises selecting the one or more locations over the one or more other locations based on one or more confidence scores associated with the one or more locations being greater than one or more confidence scores associated with the one or more other locations.

G11. The method any of embodiments G1-10, wherein the one or more predicted characteristics associated with the selected locations comprises a predicted contrast level, a predicted saturation level, or a predicted sharpness level.

G12. The method of any of embodiments G1-G11, further comprising: initializing a ground truth input for the model, the ground truth input comprising initial feedback related to an initial set of stimuli presented at an initial set of locations of a user interface under a range of characteristics, the initial feedback indicating threshold characteristics of the range of characteristics under which a user sees each stimulus of the initial set of stimuli; and providing the ground truth input to the model to obtain the set of predicted characteristics and the set of confidence scores.

H1. A tangible, non-transitory, machine-readable medium storing instructions that, when executed by a data processing apparatus, cause the data processing apparatus to perform operations comprising those of any of embodiments A1-A34, B1-B28, C1-C13, D1-D11, E1-E16, F1-F19, or G1-G12.

H2. A system comprising: one or more processors; and memory storing instructions that, when executed by the processors, cause the processors to effectuate operations comprising those of any of embodiments A1-A34, B1-B28, C1-C13, D1-D11, E1-E16, F1-F19, or G1-G12.

What is claimed is:

1. A system for facilitating vision testing via predicted-pattern-based selection of a testing location subset, the system comprising:

a computer system that comprises one or more processors executing computer program instructions that, when executed, cause the computer system to perform operations comprising:

initializing, during a visual test presentation comprising multiple test rounds, a ground truth input for a neural network, the ground truth input comprising initial feedback related to an initial set of stimuli presented at an initial set of locations of a user interface of a wearable device under a range of characteristics, the initial feedback indicating threshold characteristics of the range of characteristics under which a user sees each stimulus of the initial set of stimuli;

performing the following during each round of the multiple test rounds:

providing, during the round of the visual test presentation, the ground truth input to the neural network to cause the neural network to generate a pattern of predicted characteristics, the pattern of predicted characteristics corresponding to a set of predicted characteristics for a set of locations of the user interface;

presenting, based on the pattern of predicted characteristics, stimuli at locations of the set of locations during the round such that:

(i) a first stimulus is initially presented at a first location of the locations based on a first predicted characteristic associated with the first location; and (ii) a second stimulus is initially presented at second location of the locations based on a second predicted characteristic associated with the second location;

obtaining feedback related to the stimuli during the round, the feedback related to the stimuli indicating threshold characteristics of the range of characteristics under which the user sees each stimulus of the stimuli; and updating, based on the feedback related to the stimuli, the ground truth input for a next round of the visual test presentation such that the updated ground truth input comprises the initial feedback and the feedback related to the stimuli; and generating visual defect information for the user based on the initial feedback and the feedback from the multiple test rounds of the visual test presentation.

2. The system of claim 1, wherein the first stimulus is initially presented at the first location under the first predicted characteristic.

3. The system of claim 1, wherein the first stimulus is initially presented at the first location under at least one characteristic that is adjacent, in the range of characteristics, to the first predicted characteristic.

4. The system of claim 1, wherein the range of characteristics comprises contrast levels, saturation levels, or sharpness levels.

5. A method comprising:

initializing a ground truth input for a prediction model, the ground truth input comprising initial feedback related to an initial set of stimuli presented at an initial set of locations of a user interface under a range of characteristics, the initial feedback indicating threshold characteristics of the range of characteristics under which a user sees each stimulus of the initial set of stimuli;

obtaining, via the prediction model, based on the ground truth input, a pattern of predicted characteristics, the pattern of predicted characteristics corresponding to a set of predicted characteristics for a set of locations of the user interface;

presenting, based on the pattern of predicted characteristics, one or more stimuli at one or more locations of the set of locations during a portion of a visual test presentation;

obtaining feedback related to the one or more stimuli during the portion of the visual test presentation, the feedback indicating one or more threshold characteristics of the range of characteristics under which the user sees each stimulus of the one or more stimuli;

updating, based on the feedback related to the one or more stimuli, the ground truth input for a subsequent portion of the visual test presentation such that the updated ground truth input comprises the feedback related to the one or more stimuli; and generating visual defect information for the user based on the initial feedback, the feedback from the portion of the visual test presentation, and additional feedback from the subsequent portion of the visual test presentation.

6. The method of claim 5, wherein presenting the one or more stimuli comprises initially presenting a first stimulus at a first location of the set of locations based on a first predicted characteristic associated with the first location, and wherein the first predicted characteristic comprises a prediction of a threshold characteristic of the range of characteristics under which the user sees the first stimulus or a characteristic adjacent the threshold characteristic within the range of characteristics.

7. The method of claim 5, wherein presenting the one or more stimuli comprises initially presenting a first stimulus at a first location of the set of locations under a first predicted characteristic associated with the first location, and wherein the first predicted characteristic comprises a prediction of a threshold characteristic of the range of characteristics under which the user sees the first stimulus.

8. The method of claim 5, wherein presenting the one or more stimuli comprises initially presenting a first stimulus at a first location of the set of locations under at least one characteristic that is adjacent, in the range of characteristics, to a first predicted characteristic associated with the first location, and wherein the first predicted characteristic comprises a prediction of a threshold characteristic of the range of characteristics under which the user sees the first stimulus.

9. The method of claim 5, further comprising:

obtaining, via the prediction model, based on the ground truth input, (i) a set of patterns of predicted characteristics and (ii) a set of confidence scores associated with the set of patterns, wherein each pattern of the set of patterns indicates a predicted characteristic for a same location on the user interface that is different from a predicted characteristic for the same location indicated by another pattern of the set of patterns; and selecting, based on the set of confidence scores, the pattern to be used for the portion of the visual test presentation, the pattern being selected over one or more other patterns of the set of patterns based on a confidence score associated with the pattern being greater than one or more confidence scores associated with the one or more other patterns, wherein the presentation of the one or more stimuli is based on the selection of the pattern.

10. The method of claim 9, wherein obtaining the set of patterns of predicted characteristics and the set of confidence scores comprises obtaining the set of patterns of predicted characteristics and the set of confidence associated with the set of patterns from the prediction model subsequent to providing the ground truth input to the prediction model.

11. The method of claim 9, further comprising:
obtaining, based on the updated ground truth input, (i) a second pattern of predicted characteristics for a second set of locations of the user interface and (ii) a second set of confidence scores associated with the second pattern of predicted characteristics;
presenting, based on the second pattern of predicted characteristics, one or more second stimuli at one or more second locations during the subsequent portion of the visual test presentation; and
obtaining the additional feedback during the subsequent portion of the visual test presentation, the additional feedback indicating one or more threshold characteristics of the range of characteristics under which the user sees each stimulus of the one or more second stimuli.

12. The method of claim 5, wherein the range of characteristics comprises contrast levels, saturation levels, or sharpness levels.

13. The method of claim 5, wherein the prediction model comprises one or more neural networks.

14. A non-transitory computer-readable media storing instructions that, when executed by one or more processor, cause operations comprising:
obtaining first feedback indicating one or more threshold characteristics under which a user sees one or more first stimuli presented on a user interface;
obtaining, via a prediction model, based on the first feedback, a pattern of predicted characteristics, the pattern of predicted characteristics corresponding to a set of predicted characteristics for a set of locations of the user interface;
presenting, based on the pattern of predicted characteristics, one or more stimuli at one or more locations of the set of locations during a visual test presentation;
obtaining second feedback indicating one or more threshold characteristics under which the user sees the one or more stimuli; and
generating visual defect information for the user based on the first feedback and the second feedback.

15. The media of claim 14, wherein presenting the one or more stimuli comprises initially presenting a first stimulus at a first location of the set of locations based on a first predicted characteristic associated with the first location, and wherein the first predicted characteristic comprises a prediction of a threshold characteristic of a range of characteristics under which the user sees the first stimulus or a characteristic adjacent the threshold characteristic within the range of characteristics.

16. The media of claim 14, wherein presenting the one or more stimuli comprises initially presenting a first stimulus at a first location of the set of locations under a first predicted characteristic associated with the first location, and
wherein the first predicted characteristic comprises a prediction of a threshold characteristic of a range of characteristics under which the user sees the first stimulus.

17. The media of claim 14, wherein presenting the one or more stimuli comprises initially presenting a first stimulus at a first location of the set of locations under at least one characteristic that is adjacent, in a range of characteristics, to a first predicted characteristic, and
wherein the first predicted characteristic comprises a prediction of a threshold characteristic of the range of characteristics under which the user sees the first stimulus.

18. The media of claim 14, the operations further comprising:
obtaining, via the prediction model, based on the first feedback, (i) a set of patterns of predicted characteristics and (ii) a set of confidence scores associated with the set of patterns, wherein each pattern of the set of patterns indicates a predicted characteristic for a same location on the user interface that is different from a predicted characteristic for the same location indicated by another pattern of the set of patterns; and
selecting, based on the set of confidence scores, the pattern to be used for the visual test presentation, the pattern being selected over one or more other patterns of the set of patterns based on a confidence score associated with the pattern being greater than one or more confidence scores associated with the one or more other patterns,
wherein the presentation of the one or more stimuli is based on the selection of the pattern.

19. The media of claim 14, the operations further comprising:
obtaining, based on the second feedback, (i) a second pattern of predicted characteristics for a second set of locations of the user interface and (ii) a second set of confidence scores associated with the second pattern of predicted characteristics;
presenting, based on the second pattern of predicted characteristics, one or more second stimuli at one or more second locations of the second set of locations during the visual test presentation; and
obtaining additional feedback during the visual test presentation, the additional feedback indicating one or more threshold characteristics of a set of characteristics under which the user sees each stimulus of the one or more second stimuli.

20. The media of claim 14, wherein the set of characteristics comprises contrast levels, saturation levels, or sharpness levels.

* * * * *